United States Patent
Shi et al.

(10) Patent No.: US 9,938,222 B2
(45) Date of Patent: Apr. 10, 2018

(54) CYCLOPROPANECARBOXYLIC ACID GPR120 MODULATORS

(71) Applicant: BRISTOL-MYERS SQUIBB COMPANY, Princeton, NJ (US)

(72) Inventors: Yan Shi, Flourtown, PA (US); Peter T. W. Cheng, Princeton, NJ (US); Ying Wang, Belle Mead, NJ (US); Sutjano Jusuf, Ardmore, PA (US); Shiwei Tao, Hillsborough, NJ (US); Hao Zhang, Belle Mead, NJ (US); Shung C. Wu, Princeton, NJ (US); Jeffrey A. Robl, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/509,214

(22) PCT Filed: Sep. 8, 2015

(86) PCT No.: PCT/US2015/048781
§ 371 (c)(1),
(2) Date: Mar. 7, 2017

(87) PCT Pub. No.: WO2016/040222
PCT Pub. Date: Mar. 17, 2016

(65) Prior Publication Data
US 2017/0253554 A1    Sep. 7, 2017

Related U.S. Application Data

(60) Provisional application No. 62/047,698, filed on Sep. 9, 2014.

(51) Int. Cl.
| | |
|---|---|
| *C07C 62/34* | (2006.01) |
| *C07C 59/64* | (2006.01) |
| *C07D 307/79* | (2006.01) |
| *C07D 277/30* | (2006.01) |
| *C07D 213/55* | (2006.01) |
| *C07D 231/12* | (2006.01) |
| *C07D 213/65* | (2006.01) |

(52) U.S. Cl.
CPC .............. *C07C 62/34* (2013.01); *C07C 59/64* (2013.01); *C07D 213/55* (2013.01); *C07D 213/65* (2013.01); *C07D 231/12* (2013.01); *C07D 277/30* (2013.01); *C07D 307/79* (2013.01); *C07C 2601/02* (2017.05)

(58) Field of Classification Search
CPC ................................................... C07C 62/34
See application file for complete search history.

(56) References Cited

U.S. PATENT DOCUMENTS

| | | | |
|---|---|---|---|
| 8,962,660 B2 | 2/2015 | Zhang et al. | |
| 9,518,000 B2 | 12/2016 | Shi et al. | |
| 9,598,390 B2 | 3/2017 | Shi et al. | |
| 2003/0149103 A1* | 8/2003 | Linderman | A01N 37/10 514/531 |

FOREIGN PATENT DOCUMENTS

| | | |
|---|---|---|
| WO | WO2009/058237 A1 | 5/2009 |
| WO | WO2012/124744 A1 | 9/2012 |
| WO | WO2014/151247 A1 | 9/2014 |
| WO | WO2014/159794 A2 | 10/2014 |
| WO | WO2014/159802 A1 | 10/2014 |
| WO | WO2016/040223 A1 | 3/2016 |
| WO | WO2016/040225 A1 | 3/2016 |
| WO | WO 2016105118 A2 * | 6/2016 ......... A61K 31/4725 |

OTHER PUBLICATIONS

U.S. Appl. No. 15/509,225, filed Mar. 7, 2017, Shi et al.
U.S. Appl. No. 15/509,237, filed Mar. 7, 2017, Cheng et al.
Arbeeny, C. et al., "The Metabolic Syndrome: From Pathophysiology to Novel Treatment Strategies", Current Med. Chem—Imm. Endoc. & Metab. Agents, vol. 1, pp. 1024 (2001).
Barlind, J., et al., "Identification and design of a novel series of MGAT2 inhibitors", Bioorganic & Medicinal Chemistry Letters, vol. 23, pp. 2721-26 (2013).
Ford, Earl et al., "Prevalence of the Metabolic Syndrome Among Us Adults", JAMA, vol. 287(3), pp. 356-359 ( 2002).
Ichimura, A. et al., "Dysfunction of lipid sensor GPR120 leads to obesity in both mouse and human", Nature, vol. 483, pp. 350-354 (2012).
Im, Dong-Soon, "Omega-3 fatty acids in anti-inflammation (pro-resolution) and GPCRs", Progress in Lipid Research, vol. 51, pp. 232-237 (2012).
Miyauchi, S., "Distribution and regulation of protein expression of the free fatty acid receptor GPR120", Naunyn-Schmied Arch Pharmacol, vol. 379, pp. 427-434 (2009).
(Continued)

*Primary Examiner* — Matthew P Coughlin
(74) *Attorney, Agent, or Firm* — Jing G. Sun

(57) ABSTRACT

The present invention provides compounds of Formula (I):

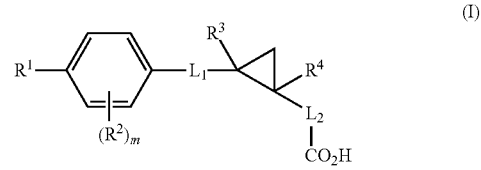

or a stereoisomer, or a pharmaceutically acceptable salt thereof, wherein all of the variables are as defined herein. These compounds are GPR120 G protein-coupled receptor modulators which may be used as medicaments.

18 Claims, No Drawings

(56) References Cited

OTHER PUBLICATIONS

Oh, Da Young, et al., "GPR120 is an Omega-3 Fatty Acid Receptor Mediating Potent Anti-inflammatory and Insulin-Sensitizing Effects", Cell, vol. 142, pp. 687-698 (2010).

\* cited by examiner

CYCLOPROPANECARBOXYLIC ACID GPR120 MODULATORS

CROSS-REFERENCE TO RELATED APPLICATIONS

This application claims priority to U.S. Provisional Application Ser. No. 62/047,698, filed Sep. 9, 2014; the entire content of which is incorporated herein by reference.

FIELD OF THE INVENTION

The present invention provides novel cyclopropanecarboxylic acid compounds, and their analogues thereof, which are GPR120 G protein-coupled receptor modulators, compositions containing them, and methods of using them, for example, for the treatment or prophylaxis of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Polyunsaturated fatty acids (PUFAs) such as omega-3 fatty acids are known to improve sensitivity to insulin. Insulin sensitivity can be improved by exerting anti-inflammatory effects in monocytes and/or macrophages and/or by enhancing glucose uptake in adipose and muscle. GPR120 is a membrane-bound receptor responsive to PUFAs which is preferentially expressed in adipose tissue and monocytes/macrophages. To decrease the medical burden of type 2 diabetes through enhanced glycemic control, GPR120 modulator compounds hold the promise of exerting a sensitizing effect to insulin as well as potential combination with a broad range of anti-diabetic drugs.

The present invention relates to novel phenylcycloalkyl and phenyl-azacycloalkyl carboxylic acid compounds which have the ability to modulate GPR120. Such compounds are therefore potentially useful for the treatment or prophylaxis of diabetes and related conditions.

SUMMARY OF THE INVENTION

The present invention provides cyclopropanecarboxylic acid compounds, and their analogues thereof, which are useful as GPR120 modulators, including stereoisomers, tautomers, pharmaceutically acceptable salts, polymorphs, or solvates thereof.

The present invention also provides processes and intermediates for making the compounds of the present invention or stereoisomers, tautomers, pharmaceutically acceptable salts, polymorphs, or solvates thereof.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The compounds of the invention may be used in the treatment of multiple diseases or disorders associated with GPR120, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment of multiple diseases or disorders associated with GPR120.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

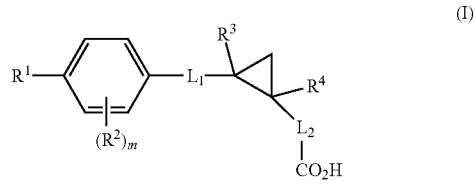

(I)

or a stereoisomer, a tautomer, a pharmaceutically acceptable salt, a polymorph, or a solvate thereof, wherein:

$R^1$ is independently selected from: phenyl and a 5- to 6-membered heteroaryl comprising carbon atoms and 1-4 heteroatoms selected from N, $NR^b$, O, and $S(O)_p$; wherein said phenyl and heteroaryl are substituted with 0-4 $R^5$;

$L_1$ is independently —$CH_2CH_2$—, —$CH_2OCH_2$—, —$CH_2O$— or —$OCH_2$—;

$L_2$ is independently a bond or —$CH_2$—;

$R^2$, at each occurrence, is independently selected from: halogen, $C_{1-6}$ alkyl substituted with 0-1 $R^a$, $C_{1-4}$ alkoxy, $C_{1-4}$ alkylthio, $C_{1-4}$ haloalkyl, and $C_{1-4}$ haloalkoxy;

$R^3$ and $R^4$, at each occurrence, are independently selected from the group consisting of H, halogen, $C_{1-4}$ alkyl, $C_{1-4}$ alkoxy, and $C_{1-4}$ haloalkyl;

$R^5$ at each occurrence, is independently selected from: halogen, $C_{1-6}$ alkyl, $C_{1-6}$ alkoxy, $C_{1-6}$ alkylthio, $C_{1-6}$ haloalkyl, $C_{1-6}$ haloalkoxy, —O—$C_{2-6}$ alkenyl, $SO_2(C_{1-4}$ alkyl), and —$(O)_{0-1}$—$(CH_2)_{0-2}$—$R^6$;

alternatively, two $R^5$ groups, when they are attached to two adjacent carbon atoms and together with the carbon atoms to which they are attached, combine to form a 5- to 6-membered carbocyclic or heterocyclic ring comprising carbon atoms and 0-3 heteroatoms selected from N, $NR^b$, O, and $S(O)_p$; wherein said heterocycle is substituted with 0-2 $R^c$;

$R^6$ is independently selected from: $C_{3-6}$ carbocycle and a 5- to 6-membered heterocycle comprising carbon atoms and 1-4 heteroatoms selected from N, $NR^b$, O, and S; wherein said carbocycle and heterocycle are substituted with 0-3 $R^c$;

$R^a$, at each occurrence, is independently selected from: $C_{1-4}$ alkoxy and C(=O)H;

$R^b$, at each occurrence, is independently selected from: H, $C_{1-4}$ alkyl, and —$(CH_2)_{0-2}$-phenyl;

$R^c$, at each occurrence, is independently selected from: halogen, $C_{1-6}$ alkyl, $C_{1-4}$ alkoxy, $C_{1-4}$ alkylthio, $C_{1-4}$ haloalkyl, $C_{1-4}$ haloalkoxy, $CO_2(C_{1-4}$ alkyl), and COPh;

m is independently 0, 1, or 2; and p is, independently at each occurrence, selected from 0, 1, and 2.

In a second aspect, the present invention includes a compound of Formula (IIa), (IIb), (IIc), (IId) or (IIe):

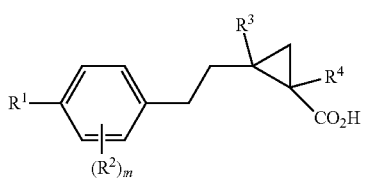
(IIa)

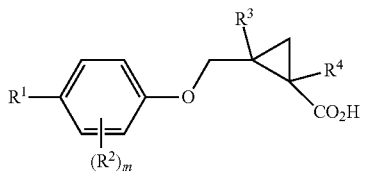
(IIb)

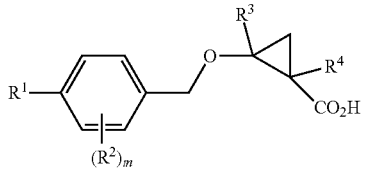
(IIc)

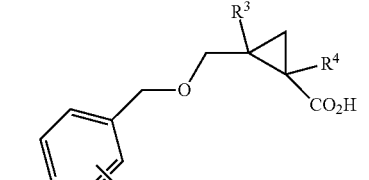
(IId)

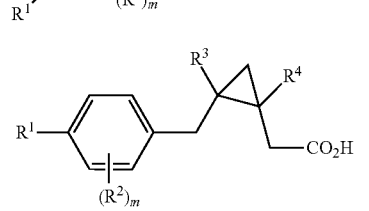
(IIe)

or a stereoisomer, a tautomer, a pharmaceutically acceptable salt, a polymorph, or a solvate thereof, within the scope of the first aspect.

In a third aspect, the present invention includes a compound of Formula (I), (IIa), (IIb), (IIc), (IId) or (IIe), or a stereoisomer, a tautomer, a pharmaceutically acceptable salt, a polymorph, or a solvate thereof, within the scope of any of the above aspects, wherein:

$R^2$ is independently selected from: halogen and $C_{1-4}$ alkyl;
$R^3$ is independently H or halogen;
$R^4$ is independently H or $C_{1-4}$ alkyl; and
m is independently 0 or 1.

In a fourth aspect, the present invention includes a compound of Formula (I), (IIa), (IIb), (IIc), (IId) or (IIe), or a stereoisomer, a tautomer, a pharmaceutically acceptable salt, a polymorph, or a solvate thereof, within the scope of any of the above aspects, wherein:

$R^1$ is independently selected from: phenyl substituted with 0-3 $R^5$, pyridyl substituted with 0-2 $R^5$, thiazolyl substituted with 0-2 $R^5$,

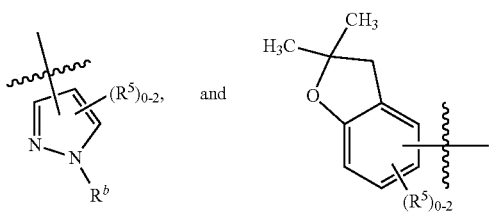

and $R^5$ at each occurrence, is independently selected from: halogen, $C_{1-6}$ alkyl, $C_{1-6}$ alkoxy, $C_{1-4}$ alkylthio, $C_{1-4}$ haloalkyl, $C_{1-4}$ haloalkoxy, —O—$C_{2-6}$ alkenyl, —O($C_{3-6}$ cycloalkyl), —OCH$_2$($C_{3-6}$ cycloalkyl), —(O)$_{0-1}$-(phenyl substituted with 0-2 $R^c$), and —(O)$_{0-1}$-(pyridyl substituted with 0-2 $R^c$).

In a fifth aspect, the present invention includes a compound of Formula (I), (IIa), (IIb), (IIc), (IId) or (IIe), or a stereoisomer, a tautomer, a pharmaceutically acceptable salt, a polymorph, or a solvate thereof, within the scope of any of the above aspects, wherein:

$R^3$ is independently H or F; and
$R^4$ is independently H or Me.

In another aspect, the present invention includes a compound of Formula (IIa), (IIb), (IIc), (IId) or (IIe), or a stereoisomer, a tautomer, a pharmaceutically acceptable salt, or a solvate thereof, within the scope of any of the above aspects, wherein:

$R^3$ and $R^4$ are H.

In a sixth aspect, the present invention provides a compound selected from the exemplified Examples 1 to 18, 20, 22 to 27, 30 to 133 within the scope of the first aspect, or a stereoisomer, a tautomer, a pharmaceutically acceptable salt, or a solvate thereof.

In another aspect, the present invention provides a compound selected from any subset list of the exemplified examples or a single exemplified example within the scope of the sixth aspect.

In another embodiment, the compounds of the present invention have hGPR120 EC$_{50}$ values<10 μM.

In another embodiment, the compounds of the present invention have hGPR120 EC$_{50}$ values<5 μM.

In another embodiment, the compounds of the present invention have hGPR120 EC$_{50}$ values<1 μM.

In another embodiment, the compounds of the present invention have hGPR120 EC$_{50}$ values<0.5 μM.

In another aspect, within the scope of any of the above aspects, wherein: X is CH$_2$O.

In another aspect, within the scope of any of the above aspects, wherein: X is OCH$_2$.

In another aspect, within the scope of any of the above aspects, wherein: L$_2$ is O.

In another aspect, within the scope of any of the above aspects, wherein: L$_2$ is S.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-pancreatitis agents, lipid lowering agents, anorectic agents and appetite suppressants.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin and alogliptin), a sodium-glucose transporter-2 (SGLT2) inhibitor (for example a member selected from dapagliflozin, canagliflozin, empagliflozin and remagliflozin), a GPR40/FFAR1 (Free fatty acid receptor 1) agonist (for example, TAK-875), and/or an MGAT2 (monoacylglycerol transferase 2) inhibitor (for example, compounds from WO 2012/124744, or compound (S)-10 from *Bioorg. Med. Chem. Lett.* (2013), DOI: http://dx.doi.org/10.1016/j.bmcl.2013.02.084).

In another embodiment, the present invention provides a method for the treatment and/or prophylaxis of multiple diseases or disorders associated with GPR120, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the GPR120 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases such as NASH (Non-Alcoholic SteatoHepatitis), NAFLD (Non-Alcoholic Fatty Liver Disease) and liver cirrhosis.

In another embodiment, the present invention provides a method for the treatment and/or prophylaxis of diabetes, hyperglycemia, gestational diabetes, obesity, dyslipidemia and hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hyperglycemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with GPR120.

In another embodiment, the present invention also provides the use of a compound of the present invention for the manufacture of a medicament for the treatment and/or prophylaxis of multiple diseases or disorders associated with GPR120.

In another embodiment, the present invention provides a method for the treatment and/or prophylaxis of multiple diseases or disorders associated with GPR120, comprising administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, linagliptin, vildagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with GPR120.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR120 receptor modulator of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin, alogliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, peliglitazar, tesaglitazar and aleglitazar), glucokinase activators (for example, PF-04937319 and AMG-151), GPR119 receptor modulators (for example, MBX-2952, PSN821, and APD597), sodium-glucose transporter-2 (SGLT2) inhibitors (for example, dapagliflozin, canagliflozin, empagliflozin and remagliflozin), GPR40 receptor agonists (e.g., TAK-875), amylin analogs such as pramlintide, and/or insulin.

The GPR120 receptor modulator of the present invention may also be optionally employed in combination with agents for treating complication of diabetes. These agents include PKC inhibitors and/or AGE inhibitors.

The GPR120 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 inhibitors and the like. The GPR120 receptor modulator of the present invention may also be employed in combination with an agonist of the glucagon-like peptide-1 receptor (GLP-1 R), such as exenatide, liraglutide, GLP-1(1-36) amide, GLP-1(7-36) amide, GLP-1(7-37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of stereoisomeric forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S-.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S-, and pentafluoroethyl-S-.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienooxazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium ($Ca^{2+}$) ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed.; *Remington: The Science and Practice of Pharmacy,* 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988);

e) Kakeya, N. et al., *Chem. Pharm. Bull.,* 32:692 (1984);

f) Rautio, J. et al., *Nature Rev. Drug Discovery,* 7:255-270 (2008), and g) Rautio, J., ed., *Prodrugs and Targeted Delivery (Methods and Principles in Medicinal Chemistry),* Vol 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. isotopes include those atoms having the same atomic number but different mass numbers. By way of general example and without limitation, isotopes of hydrogen include deuterium and tritium. isotopes of carbon include $^{13}C$ and $^{14}C$. isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography and mass spectrometry, "HPLC" for high pressure liquid chromatography, "[M–H]" for parent mass minus a proton, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
n-BuLi n-butyllithium
s-BuLi sec-butyllithium
t-BuLi tert-butyllithium
n-Bu$_4$NI tetra-n-butylammonium iodide
BH$_3$.THF borane-tetrahydrofuran complex
DIBALH or DIBAL-H diisobutylaluminium hydride
CDCl$_3$ deutero-chloroform
CHCl$_3$ chloroform
(COCl)$_2$ oxalyl chloride
cDNA complimentary DNA
DEAD diethyl azodicarboxylate
DIAD diisopropyl azodicarboxylate
DMAP 4-dimethylaminopyridine
DMF N,N-dimethylformamide
DMSO dimethyl sulfoxide
DMSO-d$_6$ hexadeutero-dimethyl sulfoxide
EDC or EDCI 1-ethyl-3-(3-dimethylaminopropyl)carbodiimide hydrochloride
EDTA ethylenediaminetetraacetic acid
EtOAc ethyl acetate
Et$_2$O diethyl ether
AgOTf silver trifluoromethanesulfonate
Boc tert-butyloxycarbonyl
CH$_2$Cl$_2$ or DCM dichloromethane
CH$_3$CN or MeCN Acetonitrile
Grubbs II catalyst (1,3-bis(2,4,6-trimethylphenyl)-2 imidazolidinylidene) dichloro(phenylmethylene)(tricyclohexylphosphine) ruthenium
HCl hydrochloric acid
HOBT hydroxybenzotriazole
H$_2$SO$_4$ sulfuric acid
K$_2$CO$_3$ potassium carbonate
KCN potassium cyanide
KOAc potassium acetate
KOH potassium hydroxide
KO-t-Bu potassium tert-butoxide
LiOH or LiOH.H$_2$O lithium hydroxide or lithium hydroxide hydrate
LiCl lithium chloride
LiAlH$_4$ or LAH lithium aluminum hydride
mCPBA or m-CPBA meta-chloroperbenzoic acid
MgSO$_4$ magnesium sulfate
Ms methanesulfonate
MsCl methanesulfonyl chloride
MsOH or MSA methylsulfonic acid
NaCl sodium chloride
NaCN sodium cyanide
NaH sodium hydride
NaHCO$_3$ sodium bicarbonate NaI sodium iodide
NaN$_3$ sodium azide
NaOH sodium hydroxide
NaOEt NaOEt=sodium ethoxide
Na$_2$SO$_3$ sodium sulfite
Na$_2$S$_2$O$_3$ sodium thiosulphate
Na$_2$SO$_4$ sodium sulfate
NH$_3$ ammonia
NH$_4$OAc ammonium acetate
NH$_4$Cl ammonium chloride
NH$_4$OH ammonium hydroxide
NiCl$_2$.6H$_2$O nickel (II) chloride hexahydrate
Pd/C palladium on carbon
i-Pr$_2$NEt diisopropylethylamine
Ph$_3$P triphenylphosphine
PPTS pyridinium 4-toluenesulfonate
SiO$_2$ silica oxide/silica gel
TEA or Et$_3$N triethylamine
Tf trifluoromethanesulfonate
TFA trifluoroacetic acid
THF tetrahydrofuran
TMSCHN$_2$ (diazomethyl)trimethylsilane
p-TsOH p-toluenesulfonic acid
TsCl 4-toluenesulfonyl chloride
Ts 4-toluenesulfonate
Triton B benzyltrimethylammonium hydroxide
LG leaving group
PG protecting group The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. et al., *Protecting Groups in Organic Synthesis*, 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*, 6th Edition, Wiley & Sons, New York, N.Y. (2007); Katritzky, A. R. et al., eds., *Comprehensive Organic Functional Groups Transformations II*, Second Edition, Elsevier Science Inc., Tarrytown, N.Y. (2004); Larock, R. C., *Comprehensive Organic Transformations*, VCH Publishers, Inc., New York, N.Y. (1999), and references therein.

Representative compounds of this invention can be prepared as shown in Scheme 1. Palladium-catalyzed Suzuki-Miyaura coupling (e.g., *Chem. Soc. Rev.*, 43:412 (2014)) of aryl/heteroaryl halide 1 and a boronic acid or boronate-substituted aryl α,β-cyclopropyl ester 2, followed by ester deprotection, provides the desired biaryl α,β-cyclopropyl ester 5. Alternatively, Suzuki-Miyaura coupling of the corresponding aryl/heteroaryl boronate or boronic acid 3 and a halo-substituted aryl α,β-cyclopropyl ester 4, followed by ester deprotection, also provides the desired biaryl α,β-cyclopropyl acid 5.

In cases where suitably substituted boronic acids or boronates are not commercially available, a modification to this approach may be adopted wherein an aryl halide is subjected to a palladium mediated coupling with a diboron species such as bis(pinacolato) diboron or bis(neopentylglycolato)diboron to provide the corresponding 4,4,5,5-tetramethyl-[1,3,2]dioxaborolane or the 5,5-dimethyl-[1,3,2]dioxaborolane intermediates using the method of Ishiyama, T. et al. (*J. Org. Chem.*, 60(23):7508-7510 (1995)). Alternately, this same intermediate can be prepared by reaction of the intermediate halide with the corresponding dialkoxyhydroborane as described by Murata et al. (*J. Org. Chem.*, 62(19):6458-6459 (1997)). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., *Chem. Rev.*, 95:2457 (1995)).

It is also realized that the scope of intermediate synthesis can be further extended outside the use of Suzuki-Miyaura coupling methodology since the precursor aryl halides or triflates described above are also precursors for Stille, Negishi, Hiyama, and Kumada-type cross coupling methodologies (Tsuji, J., *Transition Metal Reagents and Catalysts: Innovations in Organic Synthesis*, John Wiley & Sons (2000); Tsuji, J., *Palladium Reagents and Catalysts: Innovations in Organic Synthesis*, John Wiley & Sons (1996)).

Scheme 1

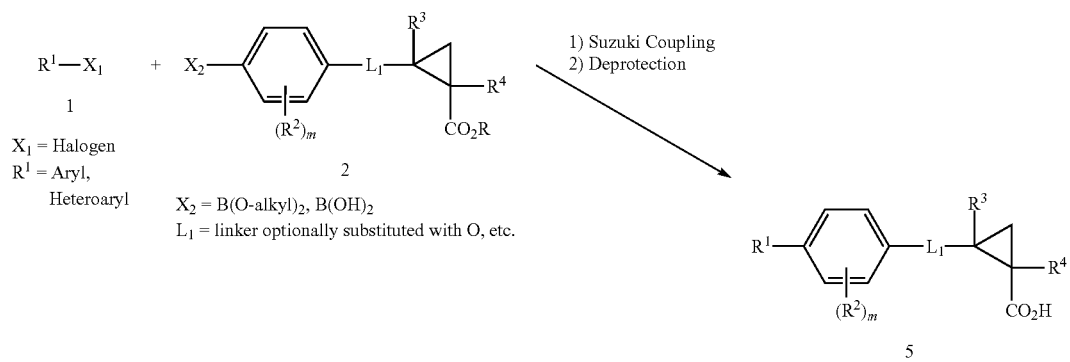

The synthesis of phenoxy α,β-cyclopropyl acids 10 is outlined in Scheme 2. Bromination of alcohol 6 (e.g., with PPh₃ and CBr₄) provides bromide 7. Nucleophilic displacement of bromide 7 with halo-substituted phenol 8 gives the α,β-cyclopropyl ester 9. Suzuki-Miyaura coupling of aryl halide 9 with an aryl/heteroaryl boronic acid/boronate 3 provides the desired biaryl ester, which is deprotected to give the desired phenoxy α,β-cyclopropyl acids 10.

Scheme 3 shows the synthesis of trans α,β-cyclopropyl acids 13. Nucleophilic displacement of epichlorohydrin with phenol 8 provides epoxide 11. Reaction of epoxide 11 with a phosphonate-ester reagent (e.g., methyl 2-(diethoxyphosphoryl) acetate) in the presence of base (e.g., *Org. Process Res. Dev.*, 6:618 (2002) and *Org. Biomol. Chem.*, 10:6987 (2012)) provides the trans α,β-cyclopropyl ester 12. Haloaryl cyclopropyl ester 12 then undergoes a Suzuki- Scheme 2

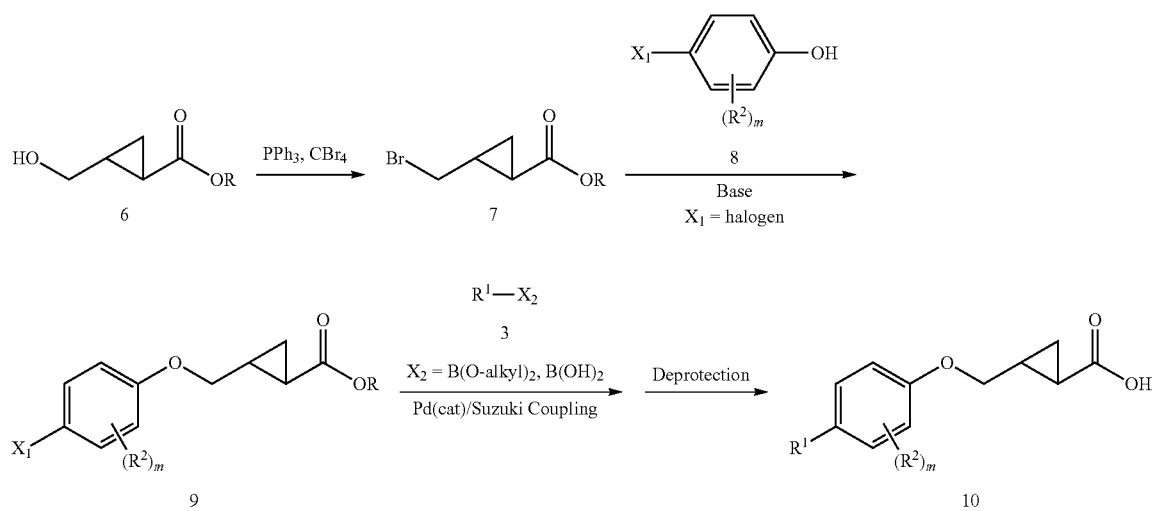

Miyaura reaction with an aryl/heteroaryl boronic acid derivative 3 according to Scheme 1, followed by deprotection to give the desired trans α,β-cyclopropyl acid 13. It should be noted that the synthetic route outlined in Scheme 3 can provide either enantiomer of α,β-cyclopropyl acid 13 through the use of the appropriate enantiomer of epichlorohydrin.

Scheme 3

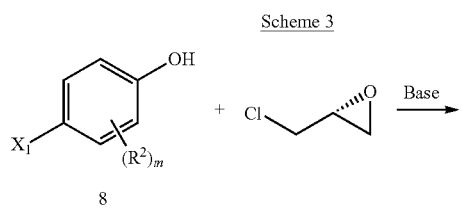

-continued

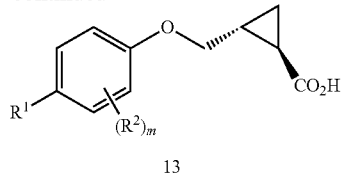

13

Scheme 4 shows the synthesis of 2-alkoxy α,β-cyclopropyl acids 18. Vinyl ether 15 can be obtained by reacting 4-halo-aryl alcohol 14 with ethyl vinyl ether in the presence of Hg(OAc)$_2$ (*J. Am. Chem. Soc.*, 115:3909-3917 (1993)). Rh$_2$(OAc)$_4$ catalyzed cyclopropanation of olefin 15 with diazo ester 16 (*Bioorg. Med. Chem. Lett.*, 14:3103-3107 (2004)) affords the 2-oxy α,β-cyclopropyl ester 17. Suzuki-Miyaura coupling of 17 with an appropriate aryl/heteroaryl boronic acid derivative 3 according to Scheme 1 followed by ester deprotection provides the desired 2-alkoxy α,β-cyclopropyl acids 18.

Scheme 4

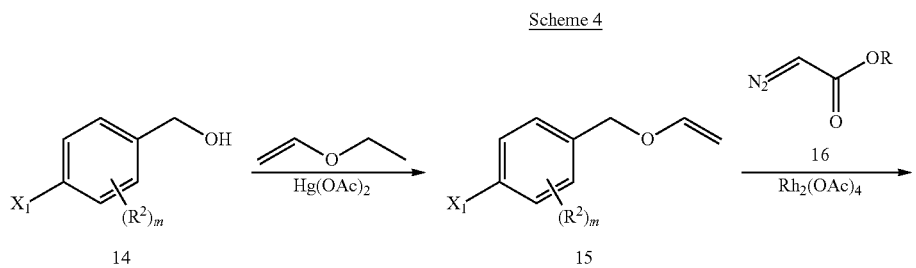

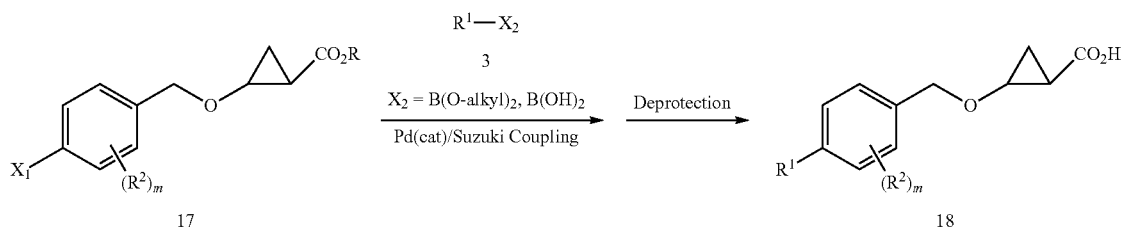

-continued

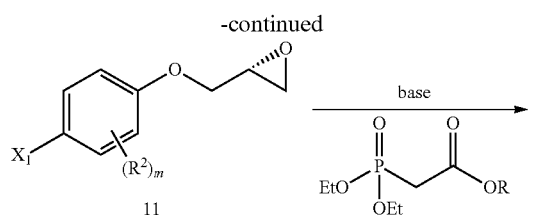

11

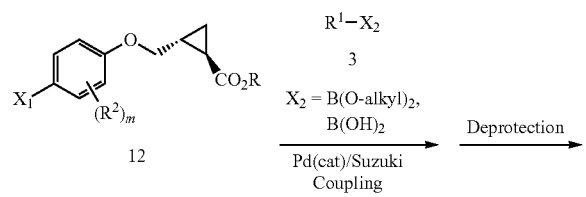

12

Scheme 5 shows the synthesis of β,γ-cyclopropyl acids 24. Palladium-mediated cyclopropanation (*Tetrahedron Lett.*, 1465-1466 (1972)) of the α,β-unsaturated ester 19 (obtained from Horner-Emmons reaction of the corresponding aryl acetaldehyde) affords the α,β-cyclopropyl ester 20. Reduction of ester 20 to the corresponding alcohol followed by mesylation gives the mesylate 21. Displacement of mesylate 21 with NaCN provides cyanide 22, which undergoes acid-mediated hydrolysis with an appropriate alcohol to give the α,β-cyclopropyl ester 23. Suzuki-Miyaura coupling of 23 with an appropriate aryl/heteroaryl boronic acid derivative 3 according to Scheme 1 followed by ester deprotection provides the desired β,γ-cyclopropyl acids 24.

Scheme 5

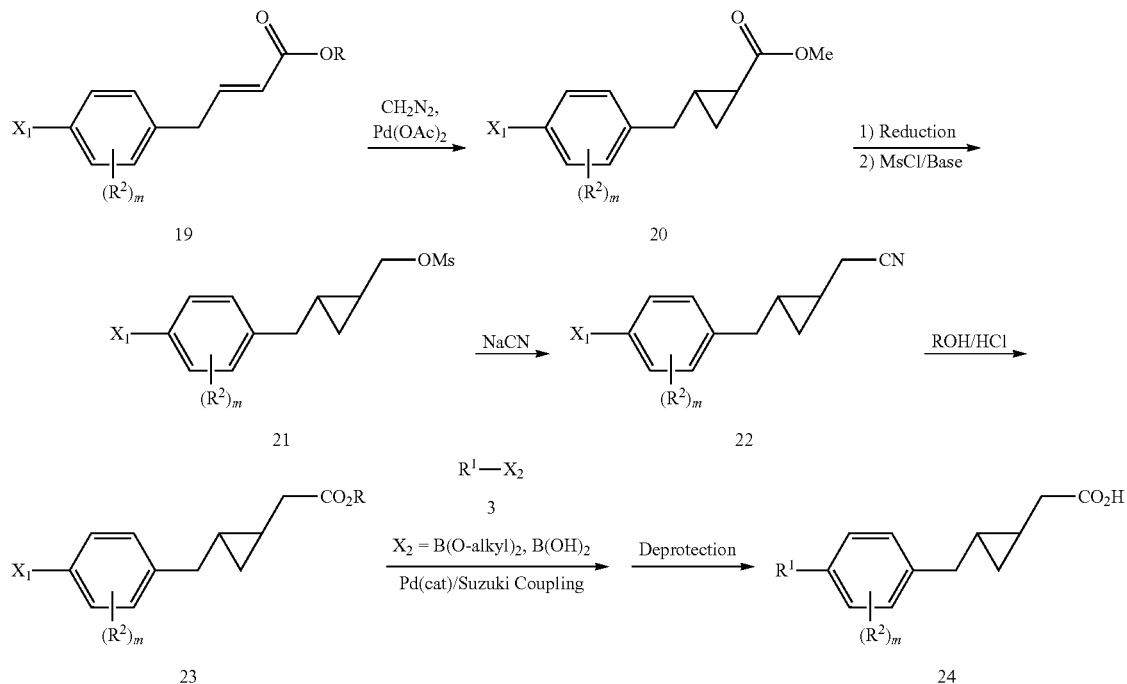

Scheme 6 shows the synthesis of cis-β,γ-cyclopropyl acids 30. Z-alkenyl esters 25 are synthesized from the corresponding 4-haloaryl acetaldehydes by reaction with $(CF_3CH_2O)_2POCH_2CO_2R$ (*Tetrahedron Lett.*, 24:4405 (1983)). Palladium-mediated cyclopropanation (*Tetrahedron Lett.*, 1465-1466 (1972)) of the Z-α,β-unsaturated ester 26 affords the cyclopropyl ester 26, which is deprotected to give the acid 27. Arndt-Eistert homologation (*Chem. Ber.*, 60:1364 (1927)) of acid 27 via the α-diazo-ketone 28 (through reaction of acid chloride of 27 with TMS-diazomethane) provides the β,γ-cyclopropyl ester 29. Suzuki-Miyaura coupling of 29 with an appropriate aryl/heteroaryl boronic acid derivative 3 according to Scheme 1 followed by ester deprotection provides the desired cis-β,γ-cyclopropyl acids 30.

Scheme 6

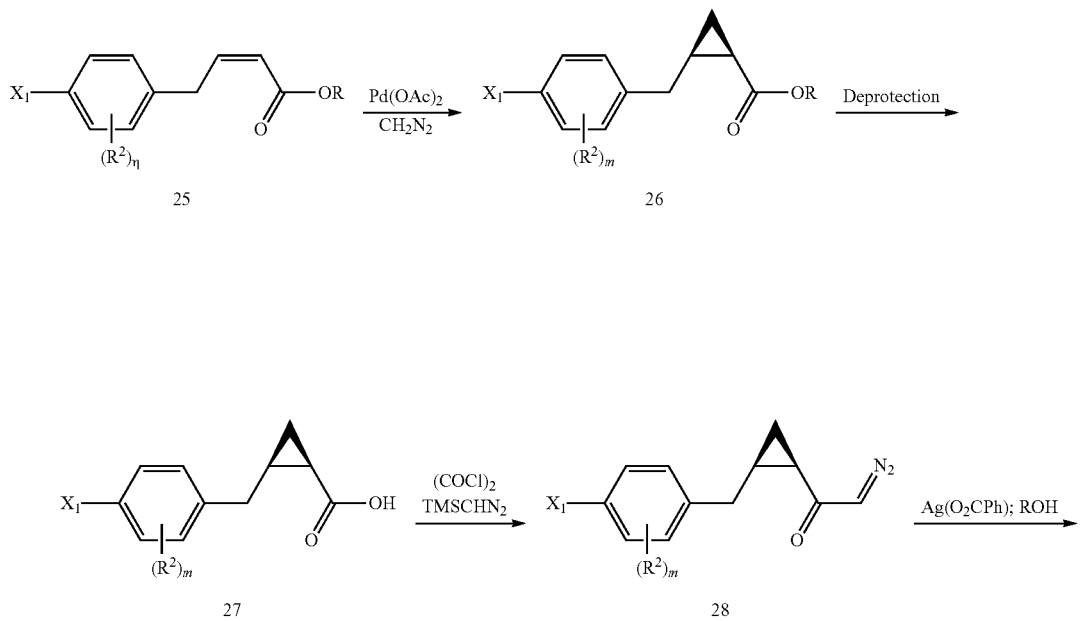

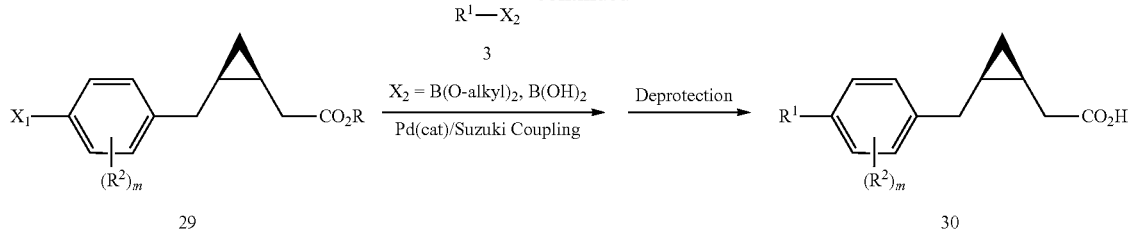

Scheme 7 shows the synthesis of phenylalkyl α,β-cyclopropyl acids 34. Horner-Wadsworth-Emmons reaction of 4-haloaryl propionaldehyde 31 provides the trans-α,β-unsaturated ester 32. Palladium-mediated cyclopropanation (*Tetrahedron Lett.*, 1465-1466 (1972)) of 32 gives the α,β-cyclopropyl ester 33. Suzuki-Miyaura coupling of 33 with an appropriate aryl/heteroaryl boronic acid derivative according to Scheme 1 followed by ester deprotection provides the desired α,β-cyclopropyl acids 34.

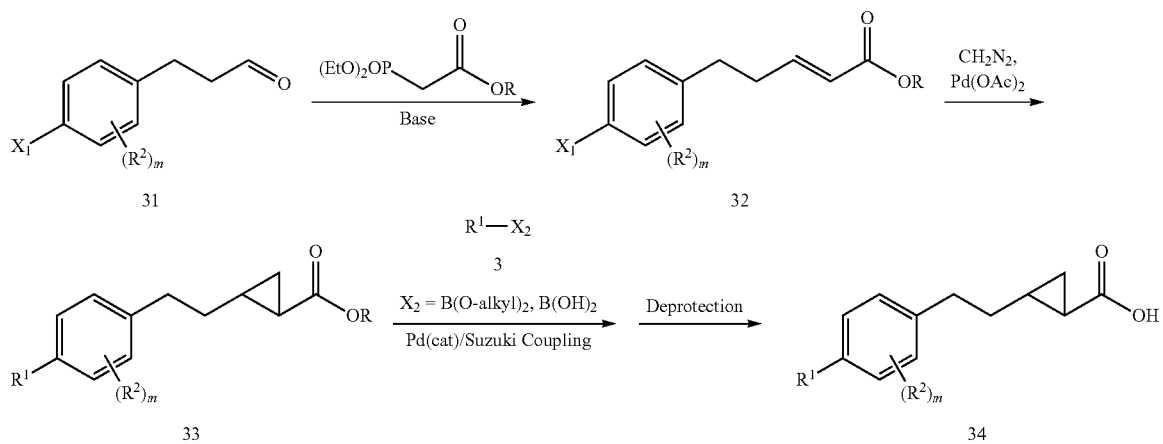

An alternative synthesis of α,β-cyclopropyl acids 34 is outlined in Scheme 8. Suzuki-Miyaura coupling of 33 with an appropriate aryl/heteroaryl boronic acid derivative 3 according to Scheme 1 gives biaryl ester 35. Palladium-mediated cyclopropanation (*Tetrahedron Lett.*, 1465-1466 (1972)) of α,β-unsaturated ester 35 gives α,β-cyclopropyl ester 33, followed by ester deprotection to afford α,β-cyclopropyl acids 34.

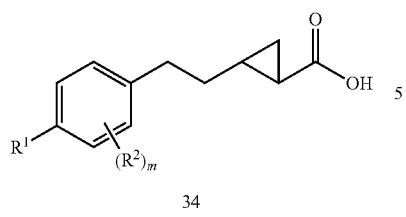

34

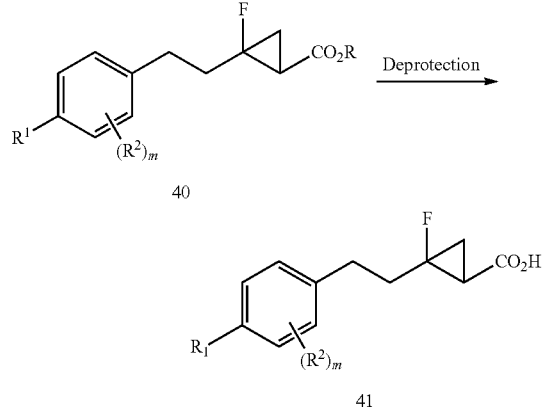

40

41

Scheme 9 shows the synthesis of 2-fluoro-cyclopropanecarboxylic acids 41 (e.g., *Synthesis*, 10:1479 (2000)). 4-halo-benzyl bromide is coupled with allyl magnesium chloride (e.g., WO 2008/001134, p. 73) to give the aryl butene 36. Bromofluorination (NBS and Et₃N.HF, e.g., *Synthesis*, 10:1479 (2000)) of aryl butene 36 provides the bromo-fluoride 37, which undergoes elimination to give the fluoro-olefin 38. Suzuki-Miyaura coupling of fluoro-olefin aryl halide 38 with an appropriate aryl/heteroaryl boronic acid derivative 3 according to Scheme 1 gives biaryl fluoro-olefin 39. Rhodium-mediated cyclopropanation of 39 with α-diazoester 16 gives the α,β-cyclopropyl ester 40. Deprotection of ester 45 affords the desired 2-fluoro-cyclopropanecarboxylic acids 41.

Scheme 10 shows the synthesis of a-methyl-α,β-cyclopropanecarboxylic acids 48. Suzuki-Miyaura coupling of 4-halo-aryl propanol 41 with an appropriate aryl/heteroaryl boronic acid derivative 3 according to Scheme 1 gives biaryl alcohol 42, which is converted to bromide 43 (e.g., PPh₃ and CBr₄). Formation of the Grignard reagent of bromide 43 with Mg followed by reaction with an oxalate ester 44 affords the α-keto-ester 45. Preferential addition of a Grignard reagent to the ketone of 45 followed by elimination of the resultant alcohol gives the α,β-unsaturated ester 46. Palladium-mediated cyclopropanation (*Tetrahedron Lett.*, 1465-1466 (1972)) of 46 gives the corresponding α,β-cyclopropyl ester 47. Deprotection of ester 54 affords α-methyl-α,β-cyclopropanecarboxylic acids 48.

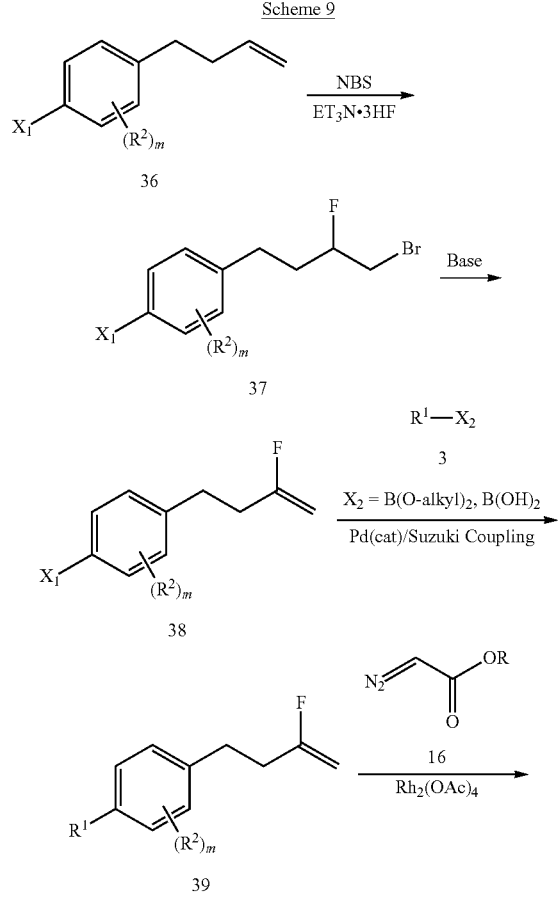

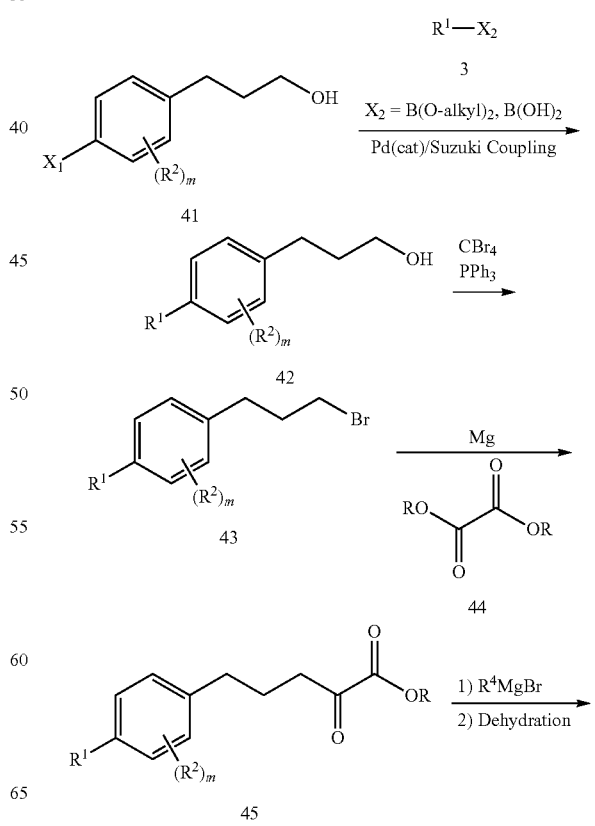

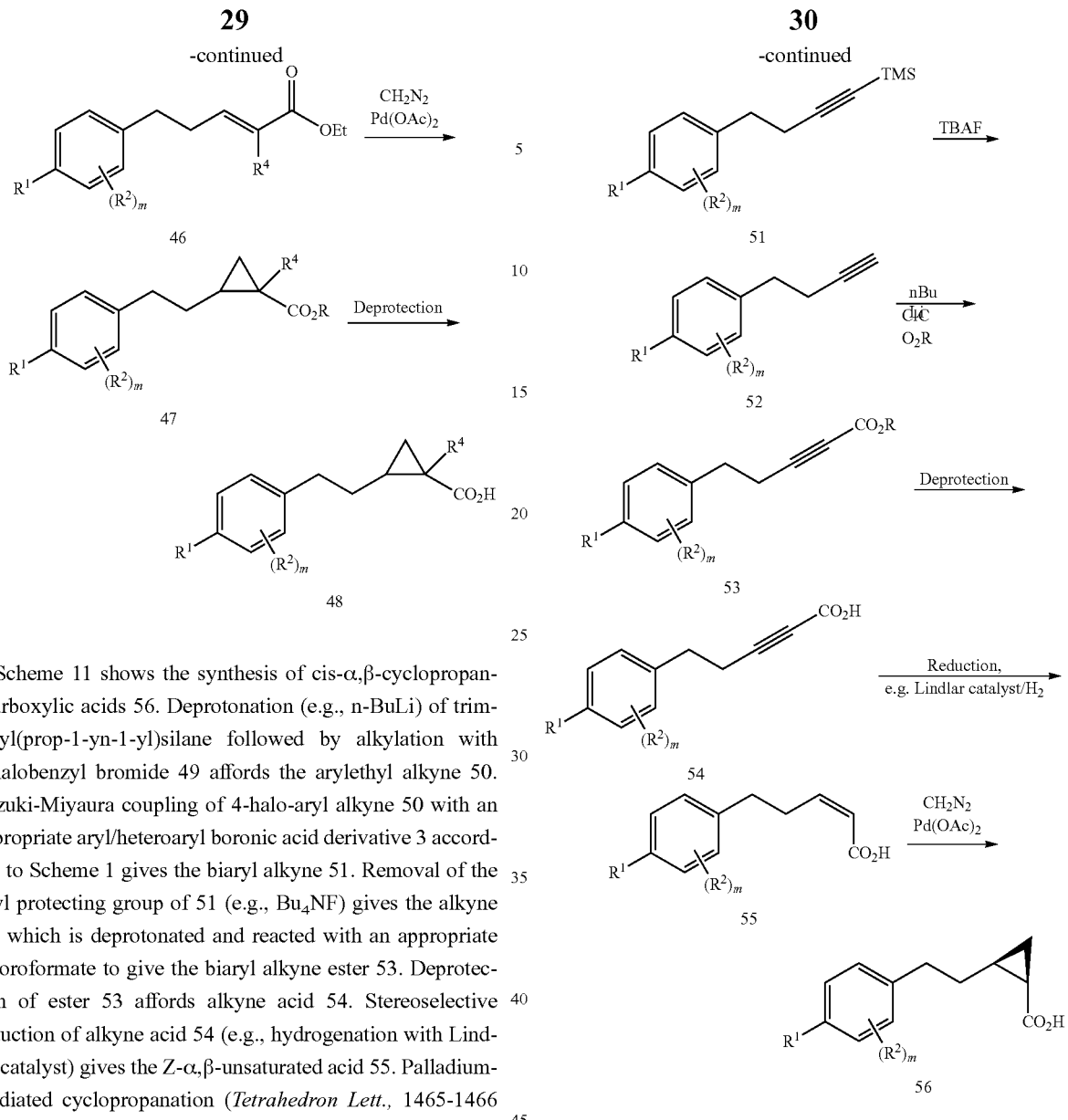

Scheme 11 shows the synthesis of cis-α,β-cyclopropanecarboxylic acids 56. Deprotonation (e.g., n-BuLi) of trimethyl(prop-1-yn-1-yl)silane followed by alkylation with 4-halobenzyl bromide 49 affords the arylethyl alkyne 50. Suzuki-Miyaura coupling of 4-halo-aryl alkyne 50 with an appropriate aryl/heteroaryl boronic acid derivative 3 according to Scheme 1 gives the biaryl alkyne 51. Removal of the silyl protecting group of 51 (e.g., Bu₄NF) gives the alkyne 52, which is deprotonated and reacted with an appropriate chloroformate to give the biaryl alkyne ester 53. Deprotection of ester 53 affords alkyne acid 54. Stereoselective reduction of alkyne acid 54 (e.g., hydrogenation with Lindlar catalyst) gives the Z-α,β-unsaturated acid 55. Palladium-mediated cyclopropanation (*Tetrahedron Lett.*, 1465-1466 (1972)) of Z-α,β-unsaturated acid 55 gives the desired cis-α,β-cyclopropyl acids 56.

Scheme 12 shows a stereoselective synthesis of trans α,β-cyclopropyl acids 59. Epoxidation of olefin 41 (e.g., mCPBA) gives the epoxide 57. Reaction of epoxide 57 with the appropriate phosphonate ester, e.g., ethyl 2-(diethoxyphosphoryl)acetate in the presence of base (e.g., *Org. Process Res. Dev.*, 6:618 (2002) and *Org. Biomol. Chem.*, 10:6987 (2012)) provides the cyclopropyl ester 58. Suzuki-Miyaura coupling of 4-halo-aryl cyclopropyl ester 58 with an appropriate aryl/heteroaryl boronic acid derivative 3 according to Scheme 1, followed by ester deprotection, gives the trans biaryl α,β-cyclopropyl acids 65.

Scheme 11

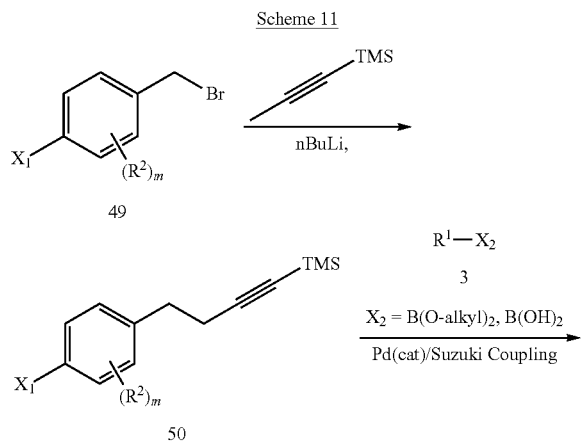

Scheme 12

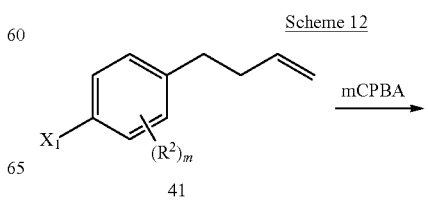

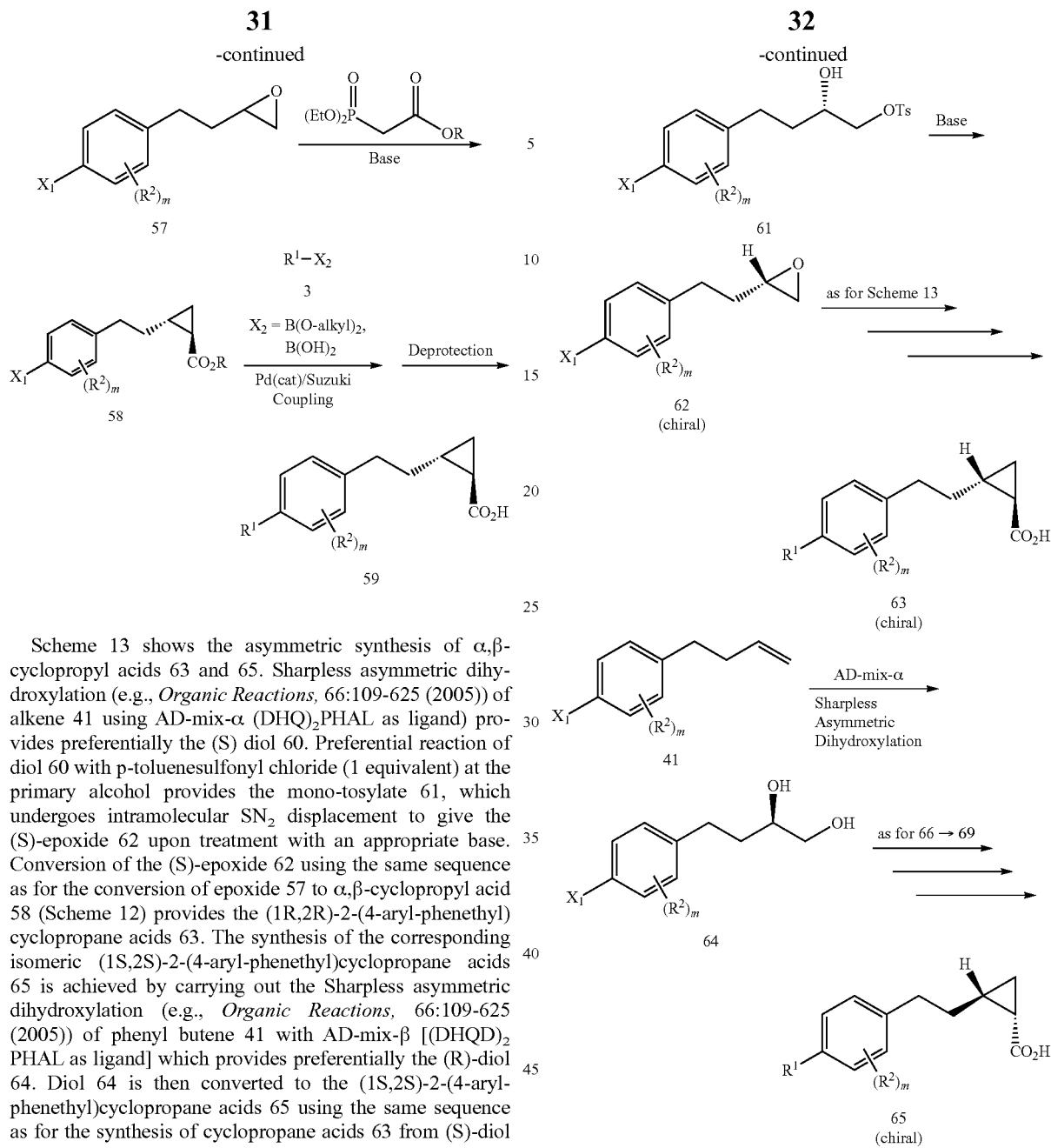

Scheme 13 shows the asymmetric synthesis of α,β-cyclopropyl acids 63 and 65. Sharpless asymmetric dihydroxylation (e.g., Organic Reactions, 66:109-625 (2005)) of alkene 41 using AD-mix-α (DHQ)₂PHAL as ligand) provides preferentially the (S) diol 60. Preferential reaction of diol 60 with p-toluenesulfonyl chloride (1 equivalent) at the primary alcohol provides the mono-tosylate 61, which undergoes intramolecular $SN_2$ displacement to give the (S)-epoxide 62 upon treatment with an appropriate base. Conversion of the (S)-epoxide 62 using the same sequence as for the conversion of epoxide 57 to α,β-cyclopropyl acid 58 (Scheme 12) provides the (1R,2R)-2-(4-aryl-phenethyl) cyclopropane acids 63. The synthesis of the corresponding isomeric (1S,2S)-2-(4-aryl-phenethyl)cyclopropane acids 65 is achieved by carrying out the Sharpless asymmetric dihydroxylation (e.g., Organic Reactions, 66:109-625 (2005)) of phenyl butene 41 with AD-mix-β [(DHQD)₂ PHAL as ligand] which provides preferentially the (R)-diol 64. Diol 64 is then converted to the (1S,2S)-2-(4-aryl-phenethyl)cyclopropane acids 65 using the same sequence as for the synthesis of cyclopropane acids 63 from (S)-diol 62.

Scheme 13

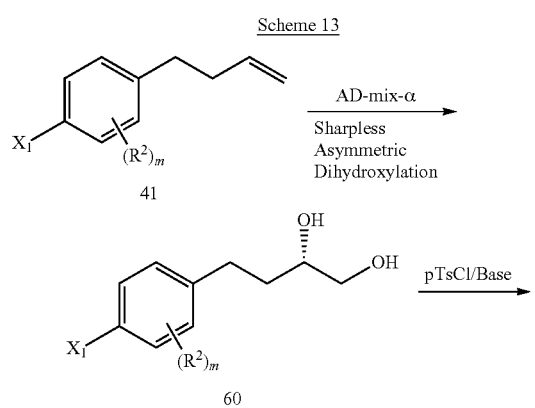

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Recently, five GPCRs (FFAR1 (GPR40), FFAR2 (GPR43), FFAR3 (GPR41), GPR84, and GPR120) were reported to recognize free fatty acids FFAR1, recognizes medium-long chainfatty acids like palmitic acid and linoleic acid FFAR2 and FFAR3 recognize short-chain fatty acids like acetate and butyrate whereas GPR84 recognizes medium-chain fatty acid like lauric acid. GPR120 recognizes long-chain fatty acids, especially EPA and DHA (Im, *Progress in Lipid Research*, 51:232-237 (2012)). GPR120 has been detected in macrophages, dendritic cells, adipocytes, clara cells in bronchiole epithelium, and enteroendocrine L cells in colon (Miyauchi et al., *Naunyn-Schmiedebergs Arch Pharmacol.*, 379:427-434 (2009)). The anti-inflammatory mechanism of omega-3 fatty acids using GPR120 knock-out mice was investigated (Oh et al., *Cell*, 142:687-698 (2010)). They suggested GPR120 activation by DHA interacts with TAB 1 via b-arrestin-2, and that this interaction interrupts TAK1 activation by LPS or TNF-alpha, suppressing inflammatory responses via NF-κB and JNK in macrophages and dendritic cells (Oh et al., *Cell*, 142:687-698 (2010)). Furthermore, GPR120 activation was shown to enhance insulin-induced glucose uptake in adipose tissues through Gq/11 proteins and PI 3-kinase.

Similarly, GPR120-deficient mice fed a high-fat diet develop obesity, glucose intolerance and fatty liver with decreased adipocyte differentiation and lipogenesis and enhanced hepatic lipogenesis (Ichimura et al., *Nature*, 483 (7389):350-354 (2012)). Insulin resistance in such mice was shown to be associated with reduced insulin signalling and enhanced inflammation in adipose tissue. In humans, GPR120 expression in adipose tissue was shown to be significantly higher in obese individuals than in lean controls. GPR120 gene sequencing in obese subjects revealed a deleterious non-synonymous mutation (p.R270H) that inhibits GPR120 signalling activity. Furthermore, the p.R270H variant was associated with increased risk of obesity in European populations.

Given the increase in the worldwide patient population afflicted by type 2 diabetes, there is a need for novel therapies which are effective with minimal adverse events. To decrease medical burden of type 2 diabetes through enhanced glycemic control, GPR120 modulator compounds of the present invention are being investigated here for their ability to increase glucose tolerance as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR120 modulator. Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR120 and/or to prevent or treat the disorders listed herein. When applied to a combination, the term refers to combined amounts of the active ingredients that result in the preventive or therapeutic effect, whether administered in combination, serially, or simultaneously.

GPR120 activity was monitored by measuring phosphorylation of ERK (pERK), since G protein receptors are known to activate the ERK signaling cascade either directly and/or through recruitment of arrestin that serves as a scaffold for downstream signaling events. Molecules that activated GPR120 with sufficient potency and efficacy in the pERK assay that also possessed desirable pharmacokinetic properties were evaluated in mice for glucose lowering by monitoring disposition of an oral glucose load by an oral glucose tolerance test (oGTT).

GPR120 pERK AlphaScreen SureFire Assay

The human and mouse GPR120-mediated intracellular phosphorylated ERK assays were established using CHOA12 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029), 500 μg/mL GENETICIN® (Life Technologies Cat. #10131-027) and 250 μg/mL Zeocin (Invitrogen Cat. #R250-01). Cells were cryo-preserved at a concentration of $2 \times 10^7$ cells/mL, in 90% Charcoal/Dextran FBS and 10% DMSO, and frozen in liquid nitrogen at a low passage number.

For the pERK assay, $2 \times 10^7$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.6 \times 10^6$ cells/mL. Cells were plated into 384-well clear bottom tissue culture plates (BD Cat. #353962) at 50 μL/well, for a density of 30,000 cells/well using a MULTIDROP® and incubated for 16-18 hours (overnight) at 37° C. with 5% $CO_2$. The next day, cells were serum starved in 30 μL of F-12 media without any serum or antibiotics for 2 hours at 37° C.

Test compounds were 3-fold, 11-point serially diluted in DMSO in a REMP assay plate (Matrix Cat. #4307) by Tecan and 5 μL was transferred into an ECHO source plate (Labcyte Cat. #LC-0200). Cells were then stimulated with 50 nL of compound dilutions using ECHO liquid handler for 7 min at 37° C. Compounds ranged from final assay concentrations of 33.33 μM to 0.56 nM.

The media was then dumped and cells lysed with 20 μL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 min after which 2 μL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 μL/well of this reagent mix was manually added to the proxiplate with a multichannel pipettor. Plates were spun down at 1000 rpm for 2 min, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100×(average sample-average blank)/(average total-average blank) where sample is the luminescence activity in the presence of test compound, blank is equal to the luminescence activity in the presence of DMSO control and the total is signal induced by 50 μM linolenic acid as reference compound. Activation data for the test compound over a range of concentrations was plotted as percentage activation of the test compound (100%=maximum response). After correcting for background, $EC_{50}$ values were determined. The $EC_{50}$ is defined as the concentration of test compound which produces 50% of the maximal response and was quantified using the 4 parameter logistic equation to fit the data.

The human and mouse GPR120-mediated intracellular phosphorylated ERK assays were also established using CHO-K1 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029) and 500 μg/mL GENETICIN® (Life Technologies Cat. #10131-027). Cells were cryo-preserved at a concentration of $3 \times 10^6$ cells/mL, in 70% F-12, 20% Charcoal/Dextran FBS and 10% DMSO, and frozen in liquid nitrogen at a low passage number.

For the pERK assay, $3 \times 10^6$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.5 \times 10^6$ cells/mL. Cells were plated into 384-well clear bottom tissue culture plates (BD Cat. #353962) at 50 μL/well, for a density of 25,000 cells/well using a MULTIDROP® and incubated for 16-18 hours (overnight) at 37° C. with 5% $CO_2$. The next day, cells were washed once with 50 μL of PBS without $Ca^{++}/Mg^{++}$ (Gibco Cat. #14190-036) and serum starved in 25 μL of F-12 media without any serum or antibiotics for 2 hours at 37° C.

Test compounds were 3-fold, 11-point serially diluted in DMSO in a REMP assay plate (Matrix Cat. #4307) by Tecan and 5 μL was transferred into an ECHO source plate (Labcyte Cat. #LC-0200). Cells were then stimulated with 40 nL of compound dilutions using ECHO liquid handler for 7 min at 37° C. Compounds ranged from final assay concentrations of 32 μM to 0.54 nM.

The media was then dumped and cells lysed with 20 μL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 min after which 2 μL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 μL/well of this reagent mix was manually added to the proxiplate with a multichannel pipettor. Plates were spun down at 1000 rpm for 2 min, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100×(average sample-average blank)/(average total-average blank) where sample is the luminescence activity in the presence of test compound, blank is equal to the luminescence activity in the presence of DMSO control and the total is signal induced by 50 μM linolenic acid as reference compound.

Activation data for the test compound over a range of concentrations was plotted as percentage activation of the test compound (100%=maximum response). After correcting for background, $EC_{50}$ values were determined. The $EC_{50}$ is defined as the concentration of test compound which produces 50% of the maximal response and was quantified using the 4 parameter logistic equation to fit the data.

The exemplified Examples disclosed below were tested in the GPR120 in vitro assays described above and were found having GPR120 agonist activity. Table 1 below lists the $EC_{50}$ values measured in the human GPR120 pERK assay for the following Examples.

| Example Number | EC$_{50}$ (μM) |
| --- | --- |
| 1 | 0.37 |
| 2 | 0.25 |
| 3 | 0.47 |
| 4 | 0.47 |
| 5 | 2.11 |
| 6 | 0.41 |
| 7 | 2.81 |
| 8 | 2.86 |
| 9 | 0.08 |
| 10 | 0.08 |
| 11 | 0.16 |
| 12 | 0.31 |
| 13 | 0.64 |
| 14 | 0.83 |
| 15 | 1.69 |
| 16 | 0.42 |
| 17 | 0.20 |
| 18 | 0.21 |
| 19 | Not active |
| 20 | 0.99 |
| 21 | Not active |
| 22 | 1.25 |
| 23 | 0.66 |
| 24 | 0.44 |
| 25 | 0.98 |
| 26 | 1.72 |
| 27 | 1.23 |
| 30 | 0.32 |
| 31 | 0.64 |
| 32 | 0.99 |
| 33 | 0.06 |
| 34 | 0.43 |
| 35 | 0.33 |
| 36 | 0.06 |
| 37 | 2.65 |
| 38 | 3.24 |
| 39 | 2.02 |
| 40 | 5.09 |
| 41 | 0.86 |
| 42 | 0.18 |
| 43 | 0.28 |
| 44 | 0.27 |
| 45 | 0.22 |
| 46 | 0.31 |
| 47 | 2.04 |
| 48 | 0.76 |
| 49 | 1.67 |
| 50 | 0.26 |
| 51 | 0.47 |
| 52 | 0.62 |
| 53 | 0.33 |
| 54 | 0.50 |
| 55 | 1.06 |
| 56 | 0.45 |
| 57 | 0.12 |
| 58 | 0.11 |
| 59 | 2.28 |
| 60 | 0.57 |
| 61 | 2.78 |
| 62 | 0.31 |
| 63 | 0.18 |
| 64 | 0.29 |
| 65 | 0.33 |
| 66 | 0.32 |
| 67 | 0.23 |
| 68 | 0.66 |
| 69 | 10.8 |
| 70 | 2.40 |
| 71 | 1.43 |
| 72 | 1.55 |
| 73 | 1.38 |
| 74 | 0.61 |
| 75 | 0.18 |
| 76 | 0.47 |
| 77 | 2.34 |
| 78 | 6.09 |
| 79 | 1.44 |
| 80 | 3.26 |
| 81 | 1.25 |
| 82 | 4.96 |
| 83 | 3.05 |
| 84 | 4.31 |
| 85 | 3.81 |
| 86 | 3.62 |
| 87 | 1.76 |
| 88 | 0.18 |
| 89 | 3.25 |
| 90 | 0.93 |
| 91 | 0.31 |
| 92 | 0.30 |
| 93 | 0.30 |
| 94 | 0.14 |
| 95 | 0.37 |
| 96 | 0.18 |
| 97 | 0.07 |
| 98 | 0.20 |
| 99 | 1.14 |
| 100 | 0.26 |
| 101 | 0.13 |
| 102 | 0.27 |
| 103 | 0.17 |
| 104 | 0.09 |
| 105 | 0.14 |
| 106 | 0.27 |
| 107 | 0.31 |
| 108 | 0.36 |
| 109 | 0.26 |
| 110 | 0.43 |
| 111 | 0.19 |
| 112 | 0.21 |
| 113 | 0.12 |
| 114 | 0.14 |
| 115 | 0.19 |
| 116 | 0.09 |
| 117 | 1.11 |
| 118 | 0.46 |
| 119 | 0.51 |
| 120 | 0.62 |
| 121 | 1.25 |
| 122 | 1.35 |
| 123 | 0.68 |
| 124 | 2.44 |
| 125 | 6.84 |
| 126 | 1.70 |
| 127 | 0.94 |
| 128 | 0.70 |
| 129 | 1.58 |
| 130 | 0.80 |
| 131 | 0.92 |
| 132 | 2.44 |
| 133 | 1.86 |

In Vivo GPR120 Assays

1) Acute Oral Glucose Tolerance Test

C57BL/6 mice were housed individually and fed a standard rodent chow diet. At approximately 11 weeks age, after a 5 h fast, these mice were orally treated with vehicle or test compounds 60 min before a glucose challenge (2 g/kg). Blood glucose levels were determined from tail bleeds taken at −60, 0, 15, 30, 60 and 120 min after the glucose challenge. The blood glucose excursion profile from t=0-120 min was used to calculate an area under the curve (AUC) for compound treatment. This AUC for compound treatment is compared to vehicle treatment. For instance, Example 105 (dosed at 30 mg/kg) reduced glucose AUC by 55% in this oral glucose tolerance test.

2) Acute Intraperitoneal Insulin Tolerance Test

C57BL/6 mice were housed individually and fed a standard rodent chow diet. At approximately 11 weeks age, after 5 h fast, these mice were orally treated with vehicle or test compounds 30 min before an insulin challenge (0.1μ/kg). Blood glucose levels were determined from tail bleeds taken at −30, 0, 15, 30, 60, 90 and 120 min after insulin injection. The blood glucose excursion profile from t=0-120 min was used to calculate a negative area under the curve (AUC) for compound treatment. This AUC for compound treatment is compared to vehicle treatment.

The compounds of the present invention possess activity as modulators of GPR120, and, therefore, may be used in the treatment of diseases associated with GPR120 activity. Via modulation of GPR120, the compounds of the present invention may preferably be employed to modulate the production/secretion of insulin and/or gut hormones, such as GLP-1, GIP, PYY, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, lipid disorders, lipodystrophy, liver diseases such as NASH (Non-Alcoholic SteatoHepatitis), NAFLD (Non-Alcoholic Fatty Liver Disease) and liver cirrhosis, and treatment of side-effects related to diabetes.

Metabolic Syndrome or "Syndrome X" is described in Ford et al., *J. Am. Med. Assoc.*, 287:356-359 (2002) and Arbeeny et al., Curr. *Med. Chem.—Imm., Endoc. & Metab. Agents*, 1:1-24 (2001).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/min during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR120 modulators or one or more other suitable therapeutic agents useful in the treatment of the aforementioned disorders including: antidiabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatitis agents, lipid lowering agents, anorectic agents, appetite suppressants, treatments for heart failure, treatments for peripheral arterial disease and anti-inflammatory agents.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin. alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, peliglitazar, tesaglitazar, aleglitazar), glucokinase activators (e.g., PF-04937319 and AMG-151, as well as other compounds described in Fyfe, M. C. T. et al., *Drugs of the Future*, 34(8):641-653 (2009) and incorporated herein by reference), GPR40 receptor modulators (e.g., TAK-875), GPR119 receptor modulators (e.g., MBX-2952, PSN821, APD597), other GPR120 receptor modulators (e.g., compound 43 from *J. Med. Chem.*, 55:4511-4515 (2012)), sodium-glucose transporter-2 (SGLT2) inhibitors (for example dapagliflozin, canagliflozin, remagliflozin), 11β-HSD-1 inhibitors (for example MK-0736, BI35585, BMS-823778, and LY2523199), amylin analogs such as pramlintide, and/or insulin. Reviews of current and emerging therapies for the treatment of diabetes can be found in: Mohler, M. L. et al., *Medicinal Research Reviews*, 29(1): 125-195 (2009), and Mizuno, C. S. et al., *Current Medicinal Chemistry*, 15:61-74 (2008).

The GPR120 receptor modulator of the present invention may also be optionally employed in combination with agents for treating complication of diabetes. These agents include PKC inhibitors and/or AGE inhibitors.

The GPR120 receptor modulator of the present invention way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 (monoacylglycerol transferase 2) inhibitors (for example, compounds from WO 2012/124744, or compound (S)-10 from *Bioorg. Med. Chem. Lett.* (2013), DOI: http://dx.doi.org/10.1016/j.bmcl.2013.02.084) and the like. The compound of structure I may also be employed in combination with an agonist of the glucagon-like peptide-1 receptor (GLP-1 R), such as exenatide, liraglutide, GLP-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery*, 5:369-370 (2006); Jones, D., *Nature Reviews: Drug Discovery*, 8:833-834 (2009); Obici, S., *Endocrinology*, 150(6):2512-2517 (2009); and Elangbam, C. S., *Vet. Pathol.*, 46(1):10-24 (2009).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR120 receptor. Such compounds may be provided in a commercial kit, for example, for use in pharmaceutical research involving GPR120 or anti-diabetic activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR120.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment and/or prophylaxis of multiple diseases or disorders associated with GPR120 (as defined previously). In another embodiment, the package insert states that the pharmaceutical composition can be used in combination (as defined previously) with a second therapeutic agent for the treatment and/or prophylaxis of multiple diseases or disorders associated with GPR120. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or Ar). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples NMR (nuclear magnetic resonance) spectra were typically obtained on Bruker or JEOL® 400 MHz and 500 MHz instruments in the indicated solvents. All chemical shifts are reported in ppm from tetramethylsilane with the solvent resonance as the internal standard. $^1$H NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography with one of following methods:

HPLC-1: SunFire C18 (4.6×150 mm) 3.5 m, gradient 10 to 100% B:A for 12 min, then 3 min hold at 100% B.

Mobile Phase A: 0.05% TFA in water: $CH_3CN$ (95:5)

Mobile Phase B: 0.05% TFA in $CH_3CN$: water (95:5)

TFA Buffer pH=2.5; Flow rate: 1 mL/min; Wavelength: 254 nm, 220 nm.

HPLC-2: XBridge Phenyl (4.6×150 mm) 3.5 m, gradient 10 to 100% B:A for 12 min, then 3 min hold at 100% B.

Mobile Phase A: 0.05% TFA in water: $CH_3CN$ (95:5)
Mobile Phase B: 0.05% TFA in $CH_3CN$: water (95:5)
TFA Buffer pH=2.5; Flow rate: 1 mL/min; Wavelength: 254 nm, 220 nm.
HPLC-3: CHIRALPAK® AD-H, 4.6×250 mm, 5 μm.
Mobile Phase: 30% EtOH-heptane (1:1)/70% $CO_2$
Flow rate=40 mL/min, 100 Bar, 35° C.; Wavelength: 220 nm
HPLC-4: Waters Acquity UPLC BEH C18, 2.1×50 mm, 1.7-μm particles;
Mobile Phase A: 5:95 MeCN:water with 10 mM $NH_4OAc$;
Mobile Phase B: 95:5 MeCN:water with 10 mM $NH_4OAc$;
Temperature: 50° C.; Gradient: 0-100% B over 3 min, then a 0.75-min hold at 100% B; Flow: 1.11 mL/min; Detection: UV at 220 nm.
HPLC-5: Waters Acquity UPLC BEH C18, 2.1×50 mm, 1.7-μm particles;
Mobile Phase A: 5:95 MeCN:water with 0.1% TFA;
Mobile Phase B: 95:5 MeCN:water with 0.1% TFA;
Temperature: 50° C.; Gradient: 0-100% B over 3 min, then a 0.75-min hold at 100% B; Flow: 1.11 mL/min; Detection: UV at 220 nm.

EXAMPLE 1

Trans-2-(((2'-fluoro-5'-isopropoxy-[1,1'-biphenyl]-4-yl)oxy)methyl) cyclopropanecarboxylic acid (racemate)

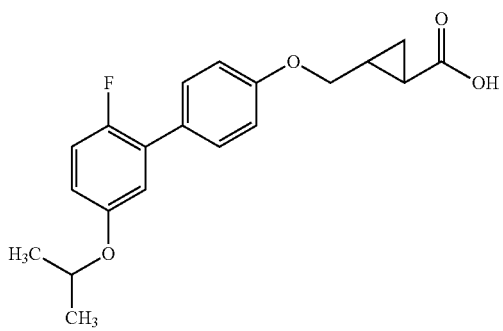

1A.
Trans-2-(methoxycarbonyl)cyclopropanecarboxylic acid (racemate)

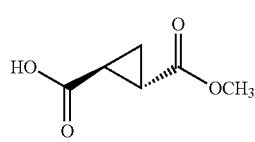

To a 250 mL round bottomed flask was added trans-diethyl cyclopropane-1,2-dicarboxylate (racemate, 21 g, 113 mmol), NaOH (4.51 g, 113 mmol), MeOH (160 mL) and water (16.00 mL). The reaction was stirred at rt for 27 h, then was acidified with 1 N aq. HCl (150 mL) and volatiles were removed in vacuo. The residue was extracted with EtOAc (2×100 mL). The combined organic extracts were washed with brine, dried over $Na_2SO_4$, filtered and concentrated in vacuo. This crude product was used for the next step without further purification. LCMS, [M−H]$^+$=143.0.

1B. Trans-methyl 2-(hydroxymethyl)cyclopropanecarboxylate

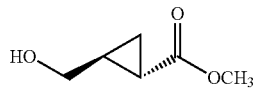

$BH_3$.THF (121 mL, 121 mmol) was added dropwise (gas evolution observed) to a cold (−15° C.) solution of 2-(methoxycarbonyl)cyclopropanecarboxylic acid (15.85 g, 110 mmol) in THF (200 mL) and the resulting solution was stirred at −15-0° C. for 2 h. The reaction was cooled to 0° C. and carefully quenched (gas evolution observed) with MeOH (~10 mL). Volatiles were removed in vacuo. The reaction mixture was then neutralized with 1N aq. HCl. The residue was diluted with 5% aq. $NaHCO_3$ and the mixture was extracted with EtOAc (3×100 mL). The combined organic extracts were washed with brine, dried ($MgSO_4$) and concentrated in vacuo. The residue was chromatographed ($SiO_2$; 220 g; continuous gradient from 0 to 40% Solvent B over 35 min, hold at 40% the title compound (9.38 g, 72.1 mmol, 65.5% yield) as a colorless oil. $^1$H NMR (500 MHz, $CDCl_3$) δ 3.61 (s, 3H), 3.57 (d, J=5.8 Hz, 1H), 3.41 (ddd, J=11.5, 6.4, 5.2 Hz, 1H), 1.75-1.62 (m, 1H), 1.54-1.46 (m, 2H), 1.24-1.09 (m, 1H), 0.81 (ddd, J=8.4, 6.2, 4.4 Hz, 1H).

1C. Trans-methyl 2-(bromomethyl)cyclopropanecarboxylate (racemate)

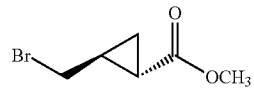

To a 0° C. solution of methyl 2-(hydroxymethyl)cyclopropanecarboxylate (6 g, 46.1 mmol) and $CBr_4$ (16.82 g, 50.7 mmol) in DCM (150 mL) was added $Ph_3P$ (13.30 g, 50.7 mmol) portionwise. The reaction was allowed to slowly warm to rt over 3 h (at this point TLC showed complete disappearance of the starting alcohol), then was concentrated in vacuo. The residue was chromatographed ($SiO_2$; 330 g cartridge; A=Hex, B=EtOAc; 40 min. gradient from 0% B to 20% B; flow rate=30 mL/min) to give the title compound (8.74 g, 45.3 mmol, 98% yield) as a colorless oil. LCMS, [M−H]$^+$=192.9.

1D. Methyl trans-2-((4-bromophenoxy)methyl)cyclopropanecarboxylate (racemate)

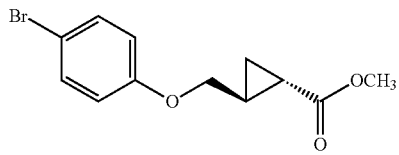 [SMILES: COC(=O)[C@H]1C[C@@H]1COc1ccc(Br)cc1]

A mixture of 4-bromophenol (300 mg, 1.73 mmol), trans-methyl 2-(bromomethyl)cyclopropanecarboxylate (335 mg, 1.74 mmol) and $K_2CO_3$ (479 mg, 3.47 mmol) in DMF (2 mL) was stirred overnight at rt. The mixture was filtered through a plug of CELITE®, washed with $CH_2Cl_2$ (4 mL); the combined filtrates were concentrated in vacuo. The residue was chromatographed ($SiO_2$; 40 g; continuous gradient from 0 to 40% Solvent B over 15 min, where Solvent A=hexanes and Solvent B=EtOAc) to afford the title compound (430 mg, 1.51 mmol, 87% yield) as a colorless oil. LCMS, $[M+Na]^+$=307. $^1$H NMR (500 MHz, $CDCl_3$) δ 7.36-7.32 (m, 2H), 6.75-6.72 (m, 2H), 3.91 (dd, J=5.9, 10.1 Hz, 1H), 3.79 (dd, J=6.6, 10.0 Hz, 1H), 3.68 (s, 3H), 1.90-1.83 (m, 1H), 1.69 (ddd, J=4.2, 4.8, 8.8 Hz, 1H), 1.30-1.26 (m, 1H), 0.97 (ddd, J=4.5, 6.3, 8.5 Hz, 1H).

EXAMPLE 1

A mixture of methyl trans-2-((4-bromophenoxy)methyl)cyclopropanecarboxylate (109 mg, 0.38 mmol), (2-fluoro-5-isopropoxyphenyl)boronic acid (98 mg, 0.50 mmol), $Pd(Ph_3P)_4$ (44 mg, 0.04 mmol) and $K_2CO_3$ (185 mg, 1.34 mmol) in THF (2 mL) and water (0.6 mL) was heated in a microwave reactor at 130° C. for 20 min under Ar, then was cooled to rt. A solution of LiOH (183 mg, 7.6 mmol) in water (1 mL) and MeOH (1 mL) was added. The reaction mixture was heated to 100° C. for 30 min in a microwave reactor, then was cooled to rt and concentrated in vacuo. The residue was acidified with 1N aq. HCl to pH=2-3. The mixture was extracted with EtOAc (3×5 mL), dried ($MgSO_4$) and concentrated in vacuo. The residue was purified by preparative HPLC (YMC reverse phase ODS-A-5μ 30×100 mm column; flow rate=40 mL/min, 0 to 100% Solvent B over 30 min, hold to 40 min, where Solvent A=90:10:0.1 $H_2O:CH_3CN$:TFA and Solvent B=90:10:0.1 $CH_3CN:H_2O$:TFA) to give the title compound (110 mg, 0.319 mmol, 84% yield) as a colorless oil. LCMS, $[M-H]^+$=343. $^1$H NMR (500 MHz, $CDCl_3$) δ 7.46-7.43 (m, 2H), 7.0 (dd, J=9.0, 10.1 Hz 1H), 6.94-6.91 (m, 2H), 6.89 (dd, J=3.1, 6.5 Hz, 1H), 6.77-6.74 (m, 1H), 4.48 (hept, J=6.1 Hz, 1H), 4.01 (dd, J=5.8, 10.1 Hz, 1H), 3.89 (dd, J=6.5, 10.1 Hz, 1H), 2.01-1.95 (m, 1H), 1.76-1.72 (m, 1H), 1.37 (dt, J=4.7, 9.2 Hz, 1H), 1.32 (d, J=6.1 Hz, 6H), 1.09 (ddd, J=4.6, 6.4, 8.4 Hz, 1H). HPLC-1: RT=11.3 min, purity=100%; HPLC-2: RT=10.0 min, purity=100%.

EXAMPLE 2 (METHOD A)

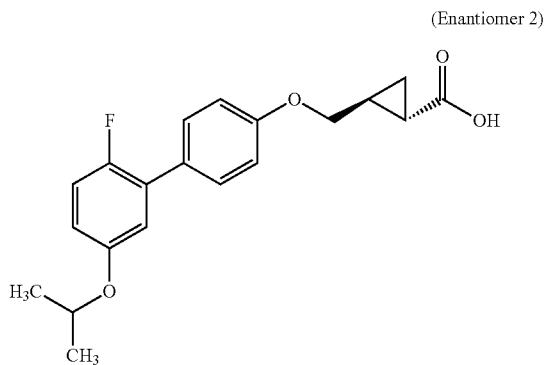 [SMILES: CC(C)Oc1ccc(F)c(-c2ccc(OC[C@H]3C[C@@H]3C(=O)O)cc2)c1]

(Enantiomer 2)

and

EXAMPLE 3 (METHOD A)

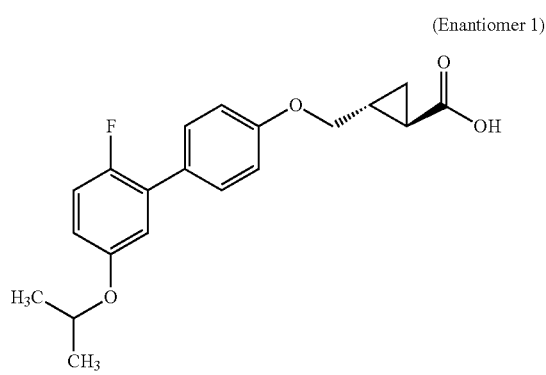 [SMILES: CC(C)Oc1ccc(F)c(-c2ccc(OC[C@@H]3C[C@H]3C(=O)O)cc2)c1]

(Enantiomer 1)

The two enantiomers of racemic trans-2-(((2'-fluoro-5'-isopropoxy-[1,1'-biphenyl]-4-yl)oxy)methyl)cyclopropanecarboxylic acid were separated by preparatory chiral SFC chromatography with a PIC 200 instrument using the following method: UV visualization at 220 nm; Column: CHIRALPAK® AD-H SFC, 250×30 mm ID, 5 am; Flow rate: 85.0 mL/min, 150 bar backpressure, 40° C. and Mobile Phase: 30% IPA/70% $CO_2$. Injection Details: 1.0 mL of 16 mg/mL in IPA-MeCN.

Analytical chiral SFC chromatography was performed on a Thar Analytical SFC chromatography instrument using the following method: UV visualization at 220 nm; Column: CHIRALPAK® AD-H, 250×4.6 mm ID, 5 μm; Flow rate: 2.0 mL/min, 100 bar backpressure, 35° C.; and Mobile Phase: 30% IPA/70% $CO_2$. Injection Details: 10 μL of 1 mg/mL in MeCN.

Example 2, later eluting enantiomer; LCMS, [M-H]+=343. $^1$H NMR (500 MHz, $CDCl_3$) δ 7.46-7.43 (m, 2H), 7.0 (dd, J=9.0, 10.1 Hz 1H), 6.94-6.91 (m, 2H), 6.89 (dd, J=3.1, 6.5 Hz, 1H), 6.77-6.74 (m, 1H), 4.48 (hept, J=6.1 Hz, 1H), 4.01 (dd, J=5.8, 10.1 Hz, 1H), 3.89 (dd, J=6.5, 10.1 Hz, 1H), 2.01-1.95 (m, 1H), 1.76-1.72 (m, 1H), 1.37 (dt, J=4.7, 9.2 Hz, 1H), 1.32 (d, J=6.1 Hz, 6H), 1.09 (ddd, J=4.6, 6.4, 8.4 Hz, 1H). HPLC-1: RT=11.2 min, purity=100%; HPLC-2: RT=10.0 min, purity=100%.

Example 3, early eluting enantiomer; LCMS, $[M-H]^+$=343. $^1$H NMR (500 MHz, $CDCl_3$) δ 7.46-7.43 (m, 2H), 7.0 (dd, J=9.0, 10.1 Hz 1H), 6.94-6.91 (m, 2H), 6.89 (dd, J=3.1, 6.5 Hz, 1H), 6.77-6.74 (m, 1H), 4.48 (hept, J=6.1 Hz, 1H), 4.01 (dd, J=5.8, 10.1 Hz, 1H), 3.89 (dd, J=6.5, 10.1 Hz, 1H), 2.01-1.95 (m, 1H), 1.76-1.72 (m, 1H), 1.37 (dt, J=4.7, 9.2 Hz, 1H), 1.32 (d, J=6.1 Hz, 6H), 1.09 (ddd, J=4.6, 6.4, 8.4 Hz, 1H). HPLC-1: HPLC-1: RT=11.2 min, purity=100%; HPLC-2: RT=10.0 min, purity=100%.

Alternative Method to Prepare Example 2 and Example 3

EXAMPLE 2 (METHOD B)

(1S,2S)-2-(((2'-Fluoro-5'-isopropoxy-[1,1'-biphenyl]-4-yl)oxy)methyl)-cyclopropanecarboxylic acid 2A. (R)-2-((4-Bromophenoxy)methyl)oxirane

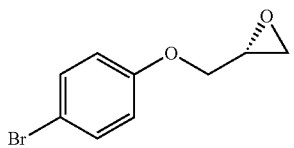 [SMILES: Brc1ccc(OC[C@H]2CO2)cc1]

To a 0° C. biphasic solution of (S)-2-(chloromethyl)oxirane (12.03 g, 130 mmol), N,N,N-trimethyl-1-phenylmethanaminium chloride (1.610 g, 8.67 mmol) in toluene (30 mL) and water (30 mL) was added 4-bromophenol (15 g, 87 mmol), followed by the dropwise addition of 6 N aq. NaOH (18.79 mL, 113 mmol) over 30 min. The reaction was then allowed to slowly warm to rt and stirred overnight at rt. The reaction was then diluted with EtOAc (150 mL), and washed with 1 N KOH (3×75 mL). The organic phase was washed with brine, dried ($Na_2SO_4$) and concentrated in vacuo. The residue was chromatographed ($SiO_2$; 120 g; A=Hex, B=EtOAc; 30 min gradient; 0% B to 20% B flow rate=80 mL/min) to afford the title compound (12.68 g, 55.4 mmol, 63.8% yield) as a colorless oil. $^1$H NMR (400 MHz, $CDCl_3$) δ 7.43-7.32 (m, 2H), 6.86-6.76 (m, 2H), 4.20 (dd, J=11.0, 3.1 Hz, 1H), 3.90 (dd, J=11.0, 5.7 Hz, 1H), 3.40-3.29 (m, 1H), 2.90 (dd, J=4.8, 4.2 Hz, 1H), 2.74 (dd, J=4.8, 2.6 Hz, 1H). $[\alpha]_D^{20}$=−9.2° (c=1 in MeOH).

2B. (1S,2S)-Ethyl 2-((4-bromophenoxy)methyl)cyclopropanecarboxylate

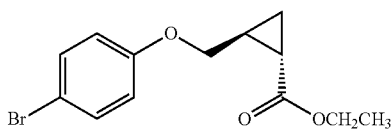 [SMILES: CCOC(=O)[C@H]1C[C@@H]1COc1ccc(Br)cc1]

To a 0° C. mixture of NaH (3.93 g, 98 mmol, 60% dispersion in mineral oil) in toluene (80 mL) was added freshly distilled ethyl 2-(diethoxyphosphoryl)acetate (26.2 mL, 131 mmol) dropwise over 50 min, then was stirred for 10 min at 0° C. A solution of (R)-2-((4-bromophenoxy)methyl)oxirane (7.50 g, 32.7 mmol; azeotroped with toluene) in toluene (20 mL) was added dropwise over 20 min; the reaction was then heated to 80° C. under Ar for 18 h, then was heated to reflux for 5 h. After cooling to rt, the mixture was diluted with EtOAc (150 mL) and washed successively with sat. aq. $NH_4Cl$ and brine, dried ($Na_2SO_4$) and concentrated in vacuo. The residue was chromatographed ($SiO_2$; 120 g; A=Hex, B=EtOAc; 30 min gradient, 0% B to 100% B; flow rate=80 mL/min) to afford the title compound (3.14 g, 10.50 mmol, 32.1% yield) as a colorless oil. $^1$H NMR (400 MHz, $CDCl_3$) δ 7.40-7.31 (m, 2H), 6.84-6.65 (m, 2H), 4.20-4.08 (m, 2H), 3.91 (dd, J=10.1, 5.9 Hz, 1H), 3.83 (dd, J=10.1, 6.6 Hz, 1H), 1.95-1.81 (m, 1H), 1.76-1.62 (m, 1H), 1.34-1.23 (m, 4H), 0.98 (ddd, J=8.5, 6.2, 4.4 Hz, 1H). $[\alpha]_D^{20}$=−63° (c=1 in MeOH).

EXAMPLE 2

A mixture of (1S,2S)-ethyl 2-((4-bromophenoxy)methyl)cyclopropanecarboxylate (50 mg, 0.167 mmol), (2-fluoro-5-isopropoxyphenyl)boronic acid (43.0 mg, 0.217 mmol) and $Cs_2CO_3$ (109 mg, 0.334 mmol) in water (0.5 mL) and THF (5 mL) was flushed with Ar, and charged with $Pd(Ph_3P)_4$ (19.3 mg, 0.017 mmol) and then flushed with Ar again. The reaction vial was then capped and heated at 65° C. for 18 h, then was cooled to rt. The mixture was then diluted with 10% aq. citric acid solution (10 mL) and extracted with EtOAc (2×5 mL). The combined organic extracts were washed with brine, dried ($Na_2SO_4$) and concentrated in vacuo. The residue was dissolved in 2 N methanolic KOH (2 mL), then was stirred overnight at rt. The mixture was diluted with 10% aq. citric acid solution (10 mL) and extracted with EtOAc (2×5 mL). The combined organic extracts were washed with brine, dried over $Na_2SO_4$, and concentrated in vacuo. The residue was purified by preparative HPLC (2 mL injection; Method: Grad. Solv. System: From 80% A: 20% B to 0% A: 100% B; (A=10% MeCN/90% $H_2O$+0.1% TFA); (B=90% MeCN/10% $H_2O$+0.1% TFA); Detection at 220 nm; 10 min grad; PHENOMENEX® Axia 5μ C18, 30×100 mm) to afford the title compound (24.8 mg, 0.070 mmol, 42.1% yield) as a pale yellow oil. $^1$H NMR (400 MHz, $CDCl_3$) δ 7.56-7.44 (m, 2H), 7.05 (dd, J=10.1, 8.8 Hz, 1H), 7.00-6.91 (m, 3H), 6.81 (dt, J=8.8, 3.5 Hz, 1H), 4.53 (dt, J=12.1, 6.1 Hz, 1H), 4.06 (dd, J=10.1, 5.7 Hz, 1H), 3.93 (dd, J=10.1, 6.4 Hz, 1H), 2.10-1.95 (m, 1H), 1.85-1.71 (m, 1H), 1.47-1.39 (m, 1H), 1.37 (d, J=5.9 Hz, 6H), 1.19-1.07 (m, 1H). $[\alpha]_D^{20}$=−56° (c=1 in MeOH).

EXAMPLE 3 (METHOD B)

(1R,2R)-2-(((2'-Fluoro-5'-isopropoxy-[1,1'-biphenyl]-4-yl)oxy)methyl) cyclopropanecarboxylic acid 3A. (S)-2-((4-Bromophenoxy)methyl)oxirane

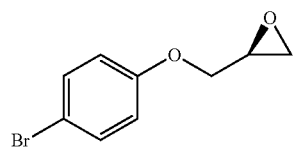

Example 3A was prepared by the same method as Example 1A. The title compound was obtained (4.21 g, 18.4 mmol, 68.1% yield) as a pale yellow oil. $^1$H NMR (400 MHz, $CDCl_3$) δ 7.44-7.36 (m, 2H), 6.87-6.78 (m, 2H), 4.23 (dd, J=11.0, 3.1 Hz, 1H), 3.92 (dd, J=11.2, 5.7 Hz, 1H), 3.40-3.31 (m, 1H), 2.92 (dd, J=4.8, 4.2 Hz, 1H), 2.77 (dd, J=4.8, 2.6 Hz, 1H). $[\alpha]_D^{20}$=+8.9° (c=1 in MeOH).

3B. (1R,2R)-Ethyl 2-((4-bromophenoxy)methyl)cyclopropanecarboxylate

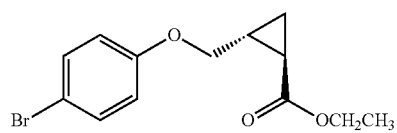 [SMILES: CCOC(=O)[C@@H]1C[C@H]1COc1ccc(Br)cc1]

Example 3B was prepared by the same method as Example 2B. The title compound was obtained (0.87 g, 2.91 mmol, 15.82% yield) as a colorless oil. $^1$H NMR (400 MHz, CDCl$_3$) δ 7.42-7.34 (m, 2H), 6.82-6.73 (m, 2H), 4.17 (qd, J=7.2, 0.8 Hz, 2H), 3.93 (dd, J=10.0, 6.1 Hz, 1H), 3.85 (dd, J=10.1, 6.4 Hz, 1H), 1.98-1.83 (m, 1H), 1.78-1.67 (m, 1H), 1.38-1.24 (m, 4H), 1.00 (ddd, J=8.4, 6.2, 4.5 Hz, 1H). $[\alpha]_D^{20}$=+63° (c=1 in MeOH).

EXAMPLE 3

Example 3 was prepared by the same method as Example 2 (Method B). The title compound was obtained (42 mg, 0.119 mmol, 71.3% yield) as a pale yellow oil. $^1$H NMR (400 MHz, CDCl$_3$) δ 7.44-7.33 (m, 2H), 6.94 (dd, J=10.0, 8.9 Hz, 1H), 6.90-6.79 (m, 3H), 6.70 (dt, J=8.9, 3.5 Hz, 1H), 4.42 (dt, J=12.1, 6.1 Hz, 1H), 3.95 (dd, J=10.1, 5.7 Hz, 1H), 3.82 (dd, J=10.1, 6.6 Hz, 1H), 2.00-1.85 (m, 1H), 1.75-1.58 (m, 1H), 1.37-1.28 (m, 1H), 1.26 (d, J=6.2 Hz, 6H), 1.09-0.97 (m, 1H). $[\alpha]_D^{20}$=+63° (c=1 in MeOH).

EXAMPLE 4

Cis-2-(((2'-fluoro-5'-phenoxy-[1,1'-biphenyl]-4-yl)oxy)methyl)cyclopropanecarboxylic acid (racemate)

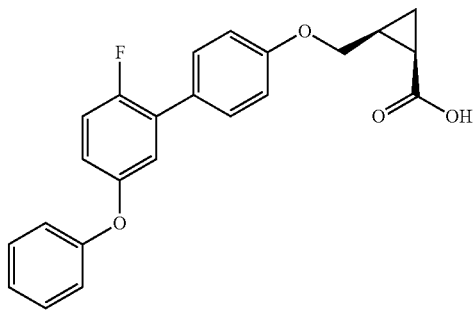 [SMILES: O=C(O)[C@@H]1C[C@@H]1COc1ccc(-c2cc(Oc3ccccc3)ccc2F)cc1]

4A. Cis-2-(methoxycarbonyl)cyclopropanecarboxylic acid

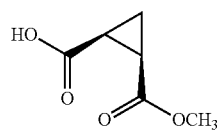

A solution of cis-(1R,2S)-dimethylcyclopropane-1,2-dicarboxylate (5.0 g, 31.6 mmol), NaOH (1.27 g, 31.6 mmol) in MeOH (120 mL) and water (10 mL) was stirred overnight at rt. The reaction was then acidified with 1 N aq. HCl (150 mL) and extracted with EtOAc (2×100 mL). The combined organic extracts were washed with brine, dried over Na$_2$SO$_4$ and concentrated in vacuo. This crude product was used in the next step without further purification. The title compound was obtained (4.24 g, 29.4 mmol, 93% yield) as a pale yellow oil. $^1$H NMR (400 MHz, CDCl$_3$) δ 3.69 (s, 3H), 2.22-2.05 (m, 2H), 1.77-1.59 (m, 1H), 1.31 (td, J=8.5, 5.1 Hz, 1H).

4B. Cis-methyl 2-(hydroxymethyl)cyclopropanecarboxylate (racemate)

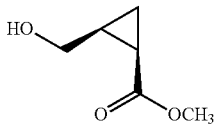

To a 0° C. solution of cis-2-(methoxycarbonyl)cyclopropanecarboxylic acid (4.24 g, 29.4 mmol) and THF (75 mL) was added dropwise BH$_3$·THF complex (29.4 mL of a 1 N solution in THF, 29.4 mmol). The reaction was allowed to slowly warm to rt overnight under Ar. The reaction was then quenched with AcOH (5 mL) and stirred for 15 min, then was neutralized with sat. aq. NaHCO$_3$ (50 mL) and extracted with EtOAc (50 mL). The organic phase was washed with brine, dried over Na$_2$SO$_4$, and concentrated in vacuo. The residue was chromatographed (SiO$_2$; 80 g; A=Hex, B=EtOAc; 20 min gradient; 0% B to 50% B flow rate=60 mL/min; KMnO$_4$ visualized, TLC R$_f$=0.5, 2:1 Hex:EtOAc) to afford the title compound (1.65 g, 12.68 mmol, 43.1% yield) as a pale yellow oil. $^1$H NMR (400 MHz, CDCl$_3$) δ 3.94 (dd, J=11.8, 5.2 Hz, 1H), 3.80-3.73 (m, 1H), 3.71 (s, 3H), 2.32 (br. s., 1H), 1.86-1.73 (m, 1H), 1.61 (td, J=7.9, 5.3 Hz, 1H), 1.21-1.07 (m, 2H).

4C. Cis-methyl 2-((4-bromophenoxy)methyl)cyclopropanecarboxylate (racemate)

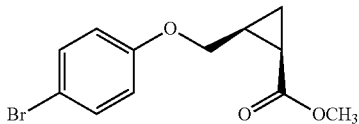 [SMILES: COC(=O)[C@@H]1C[C@@H]1COc1ccc(Br)cc1]

To a 0° C. mixture of cis-methyl 2-(hydroxymethyl)cyclopropanecarboxylate (1.65 g, 12.7 mmol), 4-bromophenol (4.39 g, 25.4 mmol) and Ph$_3$P (7.65 g, 29.2 mmol) in THF (16.9 mL) was added DIAD (5.67 ml, 29.2 mmol) dropwise. The reaction was allowed to slowly warm to rt overnight under Ar, then was heated to 65° C. and stirred overnight under Ar. The reaction was cooled to rt and concentrated in vacuo. The residue was chromatographed (SiO$_2$; 120 g; A=Hex, B=EtOAc; 30 min gradient; 0% B to 50% B flow rate=80 mL/min) to afford the title compound (2.76 g, 9.68 mmol, 76% yield) as a pink solid. $^1$H NMR (500 MHz, CDCl$_3$) δ 7.40-7.34 (m, 2H), 6.82-6.74 (m, 2H), 4.27 (dd, J=10.2, 6.1 Hz, 1H), 4.04 (dd, J=10.0, 8.7 Hz, 1H), 3.67 (s, 3H), 1.92 (td, J=8.3, 5.8 Hz, 1H), 1.79 (ddd, J=8.5, 7.2, 6.1 Hz, 1H), 1.25-1.16 (m, 2H).

4D. Cis-methyl 2-(((2'-fluoro-5'-phenoxy-[1,1'-biphenyl]-4-yl)oxy)methyl) cyclopropanecarboxylate (racemate)

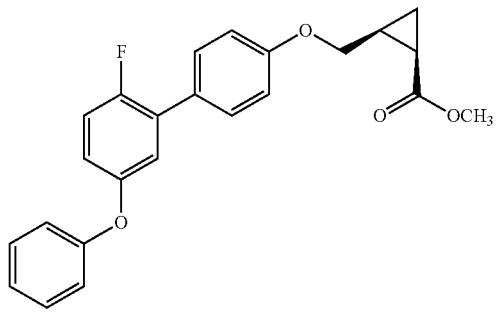 [SMILES: COC(=O)[C@@H]1C[C@@H]1COc1ccc(-c2cc(Oc3ccccc3)ccc2F)cc1]

A mixture of cis-methyl 2-((4-bromophenoxy)methyl) cyclopropanecarboxylate (40 mg, 0.140 mmol), (2-fluoro-5-phenoxyphenyl)boronic acid (39 mg, 0.168 mmol) and $Cs_2CO_3$ (91 mg, 0.281 mmol) in THF (2 mL) and water (0.20 mL) was degassed, then flushed with Ar, then charged with Pd(Ph$_3$P)$_4$ (8 mg, 7.0 μmol) and degassed again and filled with Ar. The reaction was heated at 65° C. for 18 h, then was cooled to rt and partitioned into brine (20 mL) and EtOAc (20 mL). The organic phase was washed with brine, dried over $Na_2SO_4$ and concentrated in vacuo. The residue was chromatographed (SiO$_2$; 12 g; A=Hex, B=EtOAc; 15 min gradient; 0% B to 50% B flow rate=12 mL/min) to afford the title compound (50 mg, 0.127 mmol, 91% yield) as a pale yellow oil. The product was taken onto the next step without further purification.

EXAMPLE 4

A solution of cis-methyl 2-(((2'-fluoro-5'-phenoxy-[1,1'-biphenyl]-4-yl)oxy) methyl)cyclopropanecarboxylate (50 mg, 0.127 mmol) and LiOH (30.5 mg, 1.274 mmol) in THF (5 mL) and water (5 mL) was stirred at rt for 18 h. The reaction was then acidified with 10% aq. citric acid (20 mL), and extracted with EtOAc (10 mL). The organic phase was washed with brine, dried over $Na_2SO_4$, and concentrated in vacuo. The residue was purified by preparative HPLC (2 mL injection; Method: Grad. Solv. System: From 60% A: 40% B to 0% A: 100% B; (A=10% MeOH/90% H$_2$O+0.1% TFA); (B=90% MeOH/10% H$_2$O+0.1% TFA); Detection at 220 nm; 10 min grad; PHENOMENEX® Axia 5μ C18, 30×100 mm) to afford the title compound (27.4 mg, 0.068 mmol, 53.4% yield) as a white solid. $^1$H NMR (500 MHz, CD$_2$Cl$_2$) δ 7.51-7.44 (m, 2H), 7.42-7.32 (m, 2H), 7.18-7.09 (m, 3H), 7.08-7.02 (m, 2H), 7.01-6.91 (m, 3H), 4.37 (td, J=6.1, 4.1 Hz, 1H), 4.21-4.05 (m, 1H), 1.97-1.84 (m, 2H), 1.35-1.16 (m, 2H).

EXAMPLE 5

(1S,2R)-2-(((2'-fluoro-5'-phenoxy-[1,1'-biphenyl]-4-yl)oxy)methyl) cyclopropanecarboxylic acid (Enantiomer 1; absolute stereochemistry drawn in an arbitrary manner)

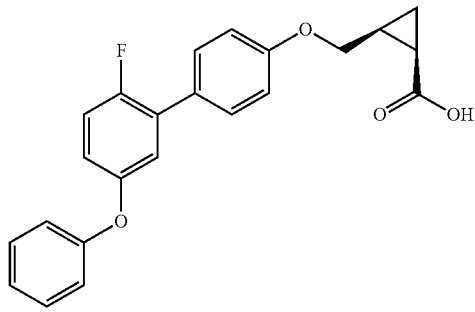 [SMILES: O=C(O)[C@@H]1C[C@@H]1COc1ccc(-c2cc(Oc3ccccc3)ccc2F)cc1]

and

EXAMPLE 6

(1R,2S)-Methyl 2-((4-bromophenoxy)methyl)cyclopropanecarboxylate (Enantiomer 2; absolute stereochemistry is drawn in an arbitrary manner)

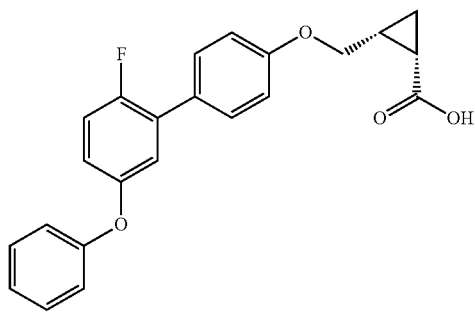 [SMILES: O=C(O)[C@H]1C[C@H]1COc1ccc(-c2cc(Oc3ccccc3)ccc2F)cc1]

5A. (1R,2S)-Methyl 2-((4-bromophenoxy)methyl)cyclopropanecarboxylate and 5B. (1S,2R)-Methyl 2-((4-bromophenoxy)methyl)cyclopropanecarboxylate

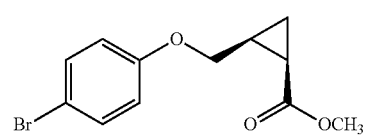

5A

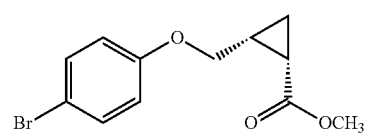

5B

The racemic mixture Example 4C was separated by chiral preparative HPLC (Instrument=Berger Multigram II SFC; Column: CHIRALPAK® AD-H, 30×250 mm, 5μ; Mobile Phase: 5% MeOH/95% CO$_2$; Flow Conditions: 65 mL/min, 100 Bar, 40° C.; Detector Wavelength: 220 nm; Injection Details: 0.75 mL of 20 mg/mL in MeOH) to afford the products: Example 5A (0.77 g, 2.70 mmol, 29.4% yield) as a pale yellow oil. ee>99%. $^1$H NMR (500 MHz, CDCl$_3$) δ 7.42-7.32 (m, 2H), 6.85-6.69 (m, 2H), 4.28 (dd, J=10.0, 5.9 Hz, 1H), 4.04 (dd, J=9.9, 8.5 Hz, 1H), 3.73-3.60 (m, 3H), 1.92 (td, J=8.1, 5.8 Hz, 1H), 1.86-1.73 (m, 1H), 1.28-1.12 (m, 2H).

Example 5B (0.807 g, 2.83 mmol, 30.8% yield) as a pale yellow oil. ee>99%. $^1$H NMR (500 MHz, CDCl$_3$) δ 7.41-7.32 (m, 2H), 6.83-6.74 (m, 2H), 4.27 (dd, J=10.2, 6.1 Hz, 1H), 4.04 (dd, J=10.0, 8.7 Hz, 1H), 3.67 (s, 3H), 1.97-1.87 (m, 1H), 1.79 (ddd, J=8.5, 7.2, 6.1 Hz, 1H), 1.25-1.17 (m, 2H).

EXAMPLE 5

Example 5 was synthesized from Example 5A using the same synthetic sequence as for the synthesis of Example 4. The title compound was obtained (12 mg, 0.031 mmol, 48.9% yield) as a white solid. $^1$H NMR (500 MHz, DMSO-d$_6$) δ 7.50-7.44 (m, J=8.3 Hz, 2H), 7.40 (t, J=7.7 Hz, 2H), 7.31 (t, J=9.6 Hz, 1H), 7.17-7.10 (m, 2H), 7.09-7.03 (m, J=8.3 Hz, 2H), 7.00 (d, J=8.5 Hz, 3H), 4.35-4.28 (m, 1H), 4.13-3.99 (m, 1H), 1.81-1.72 (m, 2H), 1.13 (td, J=8.1, 4.4 Hz, 1H), 1.01-0.91 (m, 1H). (single enantiomer; absolute stereochemistry shown is arbitrary).

EXAMPLE 6

Example 6 was synthesized from Example 5B using the same synthetic sequence as for the synthesis of Example 4. The title compound was obtained (29 mg, 0.076 mmol, 59.3% yield) as a white solid. $^1$H NMR (500 MHz, DMSO-d$_6$) δ 7.51-7.44 (m, J=8.0 Hz, 2H), 7.40 (t, J=7.8 Hz, 2H), 7.32 (t, J=9.6 Hz, 1H), 7.18-7.10 (m, 2H), 7.09-7.03 (m, J=8.5 Hz, 2H), 7.03-6.95 (m, 3H), 4.37-4.26 (m, 1H), 4.10-4.00 (m, 1H), 1.83-1.74 (m, 2H), 1.15 (td, J=8.0, 4.3 Hz, 1H), 1.03-0.92 (m, 1H). (single enantiomer; absolute stereochemistry shown is arbitrary).

EXAMPLE 7

(1R,2S)-2-(((2'-Fluoro-5'-isopropoxy-[1,1'-biphenyl]-4-yl)oxy)methyl) cyclopropanecarboxylic acid

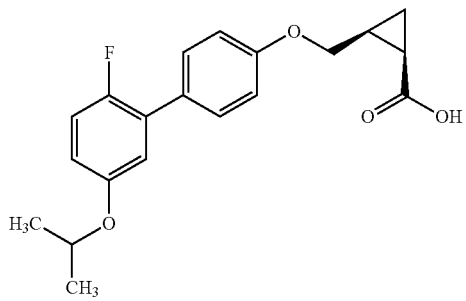 [SMILES: CC(C)Oc1ccc(F)c(-c2ccc(OC[C@H]3C[C@H]3C(=O)O)cc2)c1]

Example 7 was synthesized from Example 5A using the same synthetic sequence as for the synthesis of Example 4, except that (2-fluoro-5-isopropoxyphenyl) boronic acid was used instead of (2-fluoro-5-phenoxyphenyl)boronic acid. The title compound was obtained (47 mg, 0.136 mmol, 69.7%) as a pale yellow oil. $^1$H NMR (400 MHz, CD$_3$CN) δ 7.54-7.44 (m, 2H), 7.10 (dd, J=10.5, 8.9 Hz, 1H), 7.02-6.93 (m, 3H), 6.86 (dt, J=8.9, 3.5 Hz, 1H), 4.59 (dt, J=12.0, 6.1 Hz, 1H), 4.37 (dd, J=10.1, 5.5 Hz, 1H), 4.07 (dd, J=10.1, 8.8 Hz, 1H), 1.94-1.76 (m, 2H), 1.35-1.25 (m, 6H), 1.22 (dt, J=8.1, 4.1 Hz, 1H), 1.14-1.03 (m, 1H). (single enantiomer; absolute stereochemistry shown is arbitrary).

EXAMPLE 8

(1S,2R)-2-(((2'-Fluoro-5'-isopropoxy-[1,1'-biphenyl]-4-yl)oxy)methyl) cyclopropanecarboxylic acid

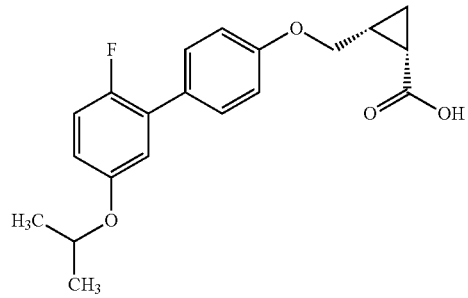 [SMILES: CC(C)Oc1ccc(F)c(-c2ccc(OC[C@@H]3C[C@@H]3C(=O)O)cc2)c1]

Example 8 was synthesized from Example 5B using the same synthetic sequence as for the synthesis of Example 4, except that (2-fluoro-5-isopropoxyphenyl) boronic acid was used instead of (2-fluoro-5-phenoxyphenyl)boronic acid. The title compound was obtained (101 mg, 0.293 mmol, 95% yield) as a pale yellow oil. $^1$H NMR (400 MHz, CD$_3$CN) δ 7.54-7.42 (m, 2H), 7.10 (dd, J=10.3, 9.0 Hz, 1H), 7.04-6.90 (m, 3H), 6.85 (dt, J=8.8, 3.5 Hz, 1H), 4.59 (dt, J=12.1, 6.1 Hz, 1H), 4.42-4.30 (m, 1H), 4.13-3.93 (m, 1H), 1.92-1.77 (m, 2H), 1.31 (d, J=5.9 Hz, 6H), 1.22 (td, J=8.2, 4.5 Hz, 1H), 1.15-1.04 (m, 1H). (single enantiomer; absolute stereochemistry shown is arbitrary).

EXAMPLE 9

(Trans)-(+/−)-2-(((2',3-difluoro-5'-phenoxy-[1,1'-biphenyl]-4-yl)oxy)methyl) cyclopropanecarboxylic acid

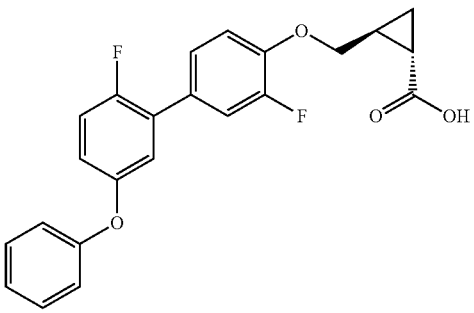 [SMILES: O=C(O)[C@H]1C[C@@H]1COc1ccc(-c2cc(Oc3ccccc3)ccc2F)cc1F]

Example 9 was synthesized using the same synthetic sequence as for the synthesis of Example 4, except that 4-bromo-2-fluorophenol was used instead of 4-bromophenol. The title compound was obtained (106 mg, 0.260 mmol, 75% yield) as a tan oil. ¹H NMR (500 MHz, CDCl₃) δ 9.9-9.5 (br, 1 H), 7.43-7.22 (m, 4H), 7.18-7.07 (m, 3H), 7.07-6.89 (m, 4H), 4.10 (dd, J=10.5, 6.1 Hz, 1H), 4.03 (dd, J=10.5, 6.3 Hz, 1H), 2.06-1.99 (m, 1H), 1.79 (dt, J=8.5, 4.4 Hz, 1H), 1.42 (dt, J=9.1, 4.6 Hz, 1H), 1.15 (ddd, J=8.4, 6.3, 4.5 Hz, 1H).

EXAMPLE 10

(1R,2R)-2-(((2',3-Difluoro-5'-phenoxy-[1,1'-biphenyl]-4-yl)oxy)methyl) cyclopropanecarboxylic acid (Enantiomer 1; absolute stereochemistry drawn in an arbitrary manner)

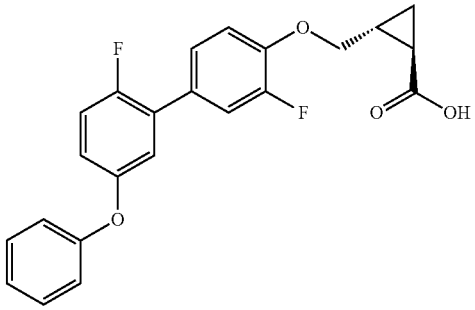 [SMILES: O=C(O)[C@@H]1C[C@H]1COc1ccc(-c2cc(Oc3ccccc3)ccc2F)cc1F]

and

EXAMPLE 11

(1S,2S)-2-(((2',3-Difluoro-5'-phenoxy-[1,1'-biphenyl]-4-yl)oxy)methyl) cyclopropanecarboxylic acid (Enantiomer 2; absolute stereochemistry drawn in an arbitrary manner)

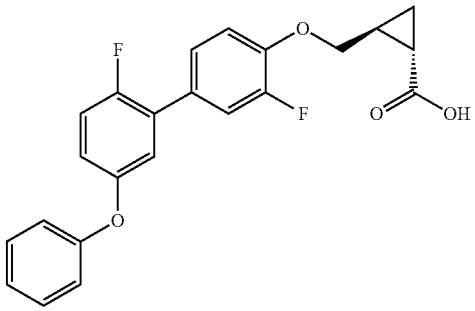 [SMILES: O=C(O)[C@H]1C[C@@H]1COc1ccc(-c2cc(Oc3ccccc3)ccc2F)cc1F]

The two enantiomers of Example 9 was separated by chiral preparative HPLC (Instrument=Berger Multigram II SFC; Column: CHIRALPAK® AD-H, 30×250 mm, 5μ; Mobile Phase: 17% EtOH/83% CO₂; Flow Conditions: 70 mL/min, 150 Bar, 40° C.; Detector Wavelength: 220 nm; Injection Details: 0.5 mL of 29 mg/mL in MeCN) to afford the title compounds:

Example 10, the first eluting isomer (23 mg, 0.058 mmol, 39.6% yield) as an off-white semisolid. ee=99%. ¹H NMR (400 MHz, CDCl₃) δ 7.32-7.10 (m, 4H), 7.09-6.97 (m, 3H), 6.97-6.79 (m, 4H), 4.08-3.85 (m, 2H), 1.94 (br. s., 1H), 1.71 (br. s., 1H), 1.37-1.25 (m, 1H), 1.04 (br. s., 1H).

Example 11, the second eluting isomer (22 mg, 0.056 mmol, 38.2% yield) as an off-white semisolid. ee=99%. ¹H NMR (400 MHz, CDCl₃) δ 7.34-7.11 (m, 4H), 7.10-6.98 (m, 3H), 6.98-6.80 (m, 4H), 4.03-3.87 (m, 2H), 1.93 (br. s., 1H), 1.68 (br. s., 1H), 1.39-1.24 (m, 1H), 1.09-0.98 (m, 1H).

EXAMPLE 12

Trans-2-(((3'-chloro-3-fluoro-5'-isopropoxy-[1,1'-biphenyl]-4-yl)oxy)methyl) cyclopropanecarboxylic acid (racemate)

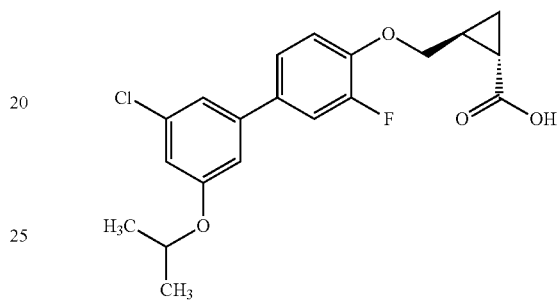

Example 12 was synthesized using the same synthetic sequence as for the synthesis of Example 9, except that (3-chloro-5-isopropoxyphenyl)boronic acid was used instead of (2-fluoro-5-phenoxyphenyl)boronic acid. The title compound was obtained (33 mg, 0.086 mmol, 85% yield) as a tan oil. ¹H NMR (500 MHz, CD₃CN) δ 7.44 (dd, J=12.9, 2.2 Hz, 1H), 7.38 (ddd, J=8.5, 2.2, 1.1 Hz, 1H), 7.19 (t, J=1.7 Hz, 1H), 7.11 (t, J=8.7 Hz, 1H), 7.06-7.01 (m, 1H), 6.92 (t, J=1.9 Hz, 1H), 4.69 (dt, J=12.1, 6.1 Hz, 1H), 4.10 (dd, J=10.5, 6.3 Hz, 1H), 3.95 (dd, J=10.3, 7.3 Hz, 1H), 1.92-1.80 (m, 1H), 1.75-1.63 (m, 1H), 1.33 (d, J=6.1 Hz, 6H), 1.24 (dt, J=8.9, 4.6 Hz, 1H), 1.05 (ddd, J=8.4, 6.2, 4.4 Hz, 1H).

EXAMPLE 13

(1R,2R)-2-(((3'-Chloro-3-fluoro-5'-isopropoxy-[1,1'-biphenyl]-4-yl)oxy)methyl) cyclopropanecarboxylic acid (Enantiomer 1; absolute stereochemistry drawn in an arbitrary manner)

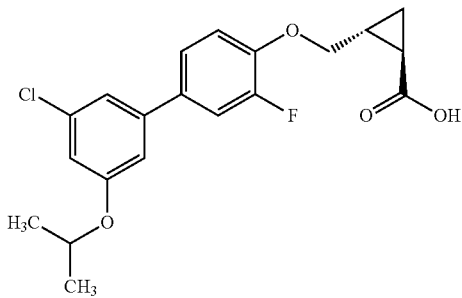 [SMILES: CC(C)Oc1cc(Cl)cc(-c2ccc(OC[C@@H]3C[C@H]3C(=O)O)c(F)c2)c1]

and

EXAMPLE 14

(1S,2S)-2-(((3'-Chloro-3-fluoro-5'-isopropoxy-[1,1'-biphenyl]-4-yl)oxy)methyl) cyclopropanecarboxylic acid (Enantiomer 2; absolute stereochemistry drawn in an arbitrary manner)

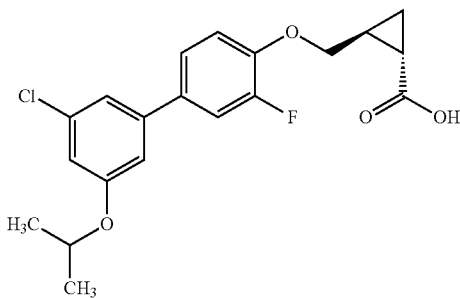 [SMILES: CC(C)Oc1cc(Cl)cc(-c2ccc(OC[C@H]3C[C@@H]3C(=O)O)c(F)c2)c1]

The racemic mixture Example 12 was separated by chiral preparative HPLC (Instrument=Berger Multigram II SFC; Column: CHIRALPAK® AD-H, 30×250 mm, 5μ; Mobile Phase: 7% EtOH/93% CO$_2$; Flow Conditions: 70 mL/min, 100 Bar, 35° C.; Detector Wavelength: 220 nm; Injection Details: 0.5 mL of 15 mg/mL in EtOH) to afford the title compounds.

Example 13, the first eluting isomer (9 mg, 0.023 mmol, 29.0% yield) as a pale yellow semisolid. ee=97%. $^1$H NMR (400 MHz, CDCl$_3$) δ 7.25-7.11 (m, 2H), 6.99 (t, J=1.7 Hz, 1H), 6.91 (t, J=8.5 Hz, 1H), 6.86-6.81 (m, 1H), 6.77 (t, J=2.0 Hz, 1H), 4.50 (dt, J=12.1, 6.1 Hz, 1H), 4.05-3.87 (m, 2H), 1.92 (br. s., 1H), 1.68 (br. s., 1H), 1.32-1.26 (m, 6H), 1.08-0.96 (m, 1H).

Example 14, the second eluting isomer (10 mg, 0.025 mmol, 32.1% yield) as a pale yellow semisolid. ee=97%. $^1$H NMR (400 MHz, CDCl$_3$) δ 7.23-7.11 (m, 2H), 6.99 (t, J=1.7 Hz, 1H), 6.91 (t, J=8.5 Hz, 1H), 6.86-6.81 (m, 1H), 6.77 (t, J=2.0 Hz, 1H), 4.50 (dt, J=12.1, 6.1 Hz, 1H), 4.07-3.87 (m, 2H), 1.92 (br. s., 1H), 1.68 (br. s., 1H), 1.32-1.25 (m, 6H), 1.09-0.94 (m, 1H).

EXAMPLE 15

(Cis)-(+/−)-2-(2-(2'-fluoro-5'-isopropoxy-[1,1'-biphenyl]-4-yl)ethyl) cyclopropanecarboxylic acid

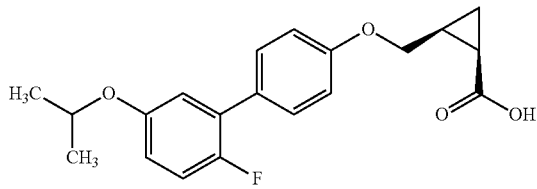 [SMILES: CC(C)Oc1ccc(F)c(-c2ccc(OC[C@H]3C[C@H]3C(=O)O)cc2)c1]

15A. (4-(4-Bromophenyl)but-1-yn-1-yl)trimethylsilane

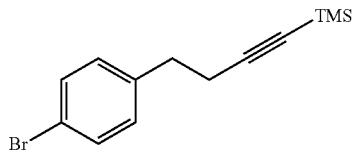 [SMILES: C[Si](C)(C)C#CCCc1ccc(Br)cc1]

To a −78° C. solution of trimethyl(prop-1-yn-1-yl)silane (4.48 mL, 30.0 mmol) in THF (20 mL) was added n-BuLi (12.80 mL of a 2.5 N solution in hexanes, 32.0 mmol) dropwise and the mixture was stirred for 30 min at −78° C., then was warmed to 0° C. and stirred for 30 min at 0° C. A solution of 1-bromo-4-(bromomethyl)benzene (5.0 g, 20.0 mmol) in THF (20 mL) was added dropwise at 0° C. over a period of 10 min, and the reaction was stirred for 2.5 h at rt. The mixture was quenched with sat. aq. NH$_4$Cl (100 mL) and extracted with Et$_2$O (2×50 mL). The combined organic extracts were washed with brine, and dried over Na$_2$SO$_4$ overnight, then was filtered and concentrated in vacuo. The residue was chromatographed (SiO$_2$; 80 g; A=Hex, B=EtOAc; 30 min gradient; 0% B to 0% B (isocratic) flow rate=60 mL/min) to afford the title compound (3.99 g, 11.63 mmol, 58.1% yield) as a pale yellow oil. $^1$H NMR (400 MHz, CD$_2$Cl$_2$) δ 7.37-7.24 (m, 2H), 7.05-6.95 (m, 2H), 2.64 (t, J=7.3 Hz, 2H), 2.35 (t, J=7.3 Hz, 2H), 0.04 (s, 9H).

15B. (4-(2'-Fluoro-5'-isopropoxy-[1,1'-biphenyl]-4-yl)but-1-yn-1-yl)trimethylsilane

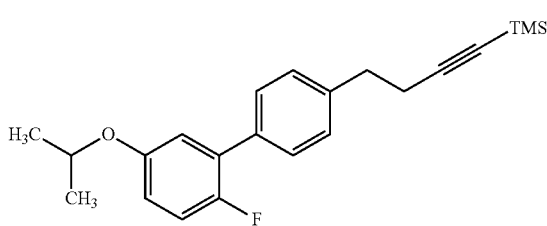 [SMILES: CC(C)Oc1ccc(F)c(-c2ccc(CCC#C[Si](C)(C)C)cc2)c1]

A mixture of (4-(4-bromophenyl)but-1-yn-1-yl)trimethylsilane (2.90 g, 8.45 mmol), (2-fluoro-5-isopropoxyphenyl)boronic acid (2.01 g, 10.2 mmol) and Cs$_2$CO$_3$ (5.51 g, 16.9 mmol) in THF (45 mL) and water (6 mL) was flushed with Ar and degassed (2×), after which Pd(Ph$_3$P)$_4$ (0.488 g, 0.423 mmol) was added and the mixture was flushed and degassed again. The reaction was heated at 65° C. under Ar overnight, then was cooled to rt and concentrated in vacuo. The residue was dissolved in EtOAc (30 mL) and washed successively with water (15 mL) and brine, and then dried over Na$_2$SO$_4$, and concentrated in vacuo. The residue was chromatographed (SiO$_2$; 80 g cartridge; A=Hex, B=EtOAc; 30 min grad.; 0% B to 10% B flow rate=60 mL/min) to afford the title compound (2.8 g, 7.90 mmol, 93% yield) as a pale yellow oil. The compound was taken onto the next step without further purification.

15C. 4'-(But-3-yn-1-yl)-2-fluoro-5-isopropoxy-1,1'-biphenyl

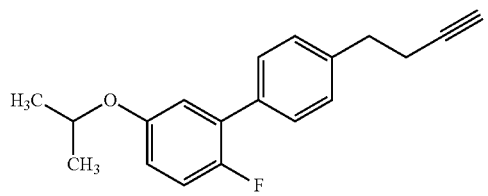 [SMILES: C#CCCc1ccc(-c2cc(OC(C)C)ccc2F)cc1]

To a 0° C. solution of (4-(2'-fluoro-5'-isopropoxy-[1,1'-biphenyl]-4-yl)but-1-yn-1-yl)trimethylsilane (2.8 g, 7.90 mmol) in THF (30 mL) was added TBAF (9.48 mL of a 1 N solution in THF, 9.48 mmol) dropwise over 10 min, and the reaction was stirred at 0° C. for 2.5 h. The reaction was diluted with water (50 mL) and extracted with EtOAc (2×25 mL). The combined organic phase, washed with brine, dried over Na$_2$SO$_4$, filtered and concentrated in vacuo. The residue was chromatographed (SiO$_2$; 40 g; A=Hex, B=EtOAc; 20 min grad.; 0% B to 10% B flow rate=40 mL/min) to afford the title compound (1.65 g, 5.84 mmol, 74.0% yield) as a pale yellow oil. $^1$H NMR (400 MHz, CD$_2$Cl$_2$) δ 7.35-7.25 (m, 2H), 7.20-7.09 (m, 2H), 6.87 (dd, J=10.2, 8.9 Hz, 1H), 6.76 (dd, J=6.5, 3.2 Hz, 1H), 6.69-6.55 (m, 1H), 4.33 (dt, J=12.1, 6.1 Hz, 1H), 2.71 (t, J=7.4 Hz, 2H), 2.36 (td, J=7.4, 2.6 Hz, 2H), 1.85 (t, J=2.6 Hz, 1H), 1.16-1.11 (m, 6H).

15D. Methyl 5-(2'-fluoro-5'-isopropoxy-[1,1'-biphenyl]-4-yl)pent-2-ynoate

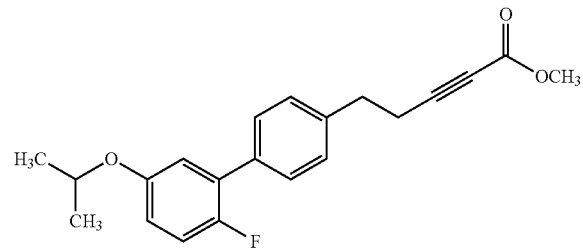 [SMILES: COC(=O)C#CCCc1ccc(-c2cc(OC(C)C)ccc2F)cc1]

To a −78° C. solution of 4'-(but-3-yn-1-yl)-2-fluoro-5-isopropoxy-1,1'-biphenyl (1.65 g, 5.84 mmol) in THF (30 ml) was added n-BuLi (2.81 mL of a 2 N solution in hexanes; 7.01 mmol) dropwise and the mixture was stirred for 45 min at −78° C. To this mixture was added methyl chloroformate (1.81 mL, 23.4 mmol) and the reaction was stirred at −78° C. for 2 h, then was warmed to rt over 1 h. An aliquot was then quenched with sat. aq. NaHCO$_3$, and TLC shows a new lower R$_f$ spot, in addition to apparent starting material (TLC R$_f$=0.5; 4:1 Hex:EtOAc). The reaction was quenched with sat. aq. NaHCO$_3$ (50 mL) and extracted with EtOAc (2×25 mL). The combined organic extracts were washed with brine, dried over Na$_2$SO$_4$, and concentrated in vacuo. The residue was chromatographed (SiO$_2$; 40 g; A=Hex, B=EtOAc; 25 min grad.; 0% to 10% B flow rate=40 mL/min) to afford the title compound (1.79 g, 5.26 mmol, 90% yield) as a pale yellow oil. The product was taken onto subsequent steps without further purification.

15E. 5-(2'-Fluoro-5'-isopropoxy-[1,1'-biphenyl]-4-yl)pent-2-ynoic acid

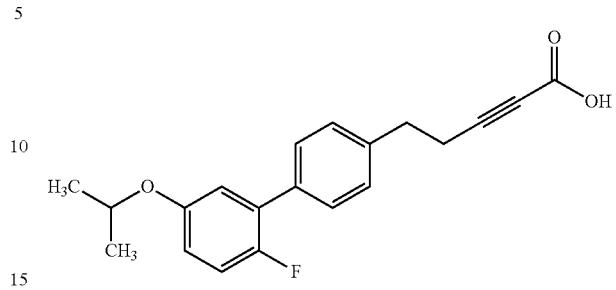

A solution of methyl 5-(2'-fluoro-5'-isopropoxy-[1,1'-biphenyl]-4-yl)pent-2-ynoate (1.79 g, 5.26 mmol) and LiOH (0.63 g, 26 mmol) in THF (10 mL) and water (10 mL) was stirred overnight at rt, then was acidified with 1N aq. HCl (60 mL) and extracted with EtOAc (2×30 mL). The combined organic extracts were washed with brine, dried over Na$_2$SO$_4$ and concentrated in vacuo. The residue was chromatographed (SiO$_2$; 80 g; A=Hex, B=EtOAc; 20 min gradient; 0% B to 100% B flow rate=60 mL/min) to afford the title compound (1.7 g, 5.21 mmol, 99% yield) as a pale yellow oil. $^1$H NMR (500 MHz, CD$_2$Cl$_2$) δ 7.42-7.33 (m, 2H), 7.26-7.17 (m, 2H), 6.93 (dd, J=10.2, 9.1 Hz, 1H), 6.82 (dd, J=6.5, 3.2 Hz, 1H), 6.75-6.66 (m, 1H), 4.39 (dt, J=12.1, 6.1 Hz, 1H), 2.84 (t, J=7.3 Hz, 2H), 2.59 (t, J=7.4 Hz, 2H), 1.25-1.16 (m, 6H).

15F. (Z)-5-(2'-Fluoro-5'-isopropoxy-[1,1'-biphenyl]-4-yl)pent-2-enoic acid

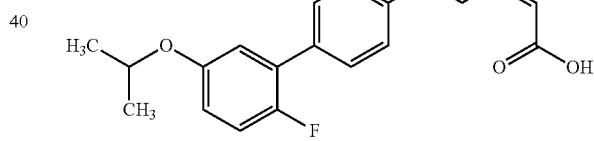

To a 25 mL round bottomed flask was added Lindlar catalyst (196 mg, 1.84 mmol), quinoline (0.22 mL, 1.84 mmol) and EtOH (10 mL). The mixture was stirred for 30 min, after which 5-(2'-fluoro-5'-isopropoxy-[1,1'-biphenyl]-4-yl)pent-2-ynoic acid (500 mg, 1.53 mmol) was added and the mixture was degassed with Ar, then was placed under an atmosphere of H$_2$ and the reaction was stirred overnight. The catalyst was filtered off and the filtrate was concentrated in vacuo. The residue was purified by preparative HPLC (3×2 mL injection; Method: Grad. Solv. System: From 40% A: 60% B to 0% A: 100% B; (A=10% MeOH/90% H$_2$O+0.1% TFA); (B=90% MeOH/10% H$_2$O+0.1% TFA); Detection at 220 nm; 10 min gradient; PHENOMENEX® Axia 5μ C18, 30×100 mm) to afford the title compound (290 mg, 0.883 mmol, 57.6% yield) as an off-white solid. $^1$H NMR (500 MHz, CD$_2$Cl$_2$) δ 7.56-7.45 (m, 2H), 7.34 (d, J=8.3 Hz, 2H), 7.08 (dd, J=10.2, 9.1 Hz, 1H), 6.97 (dd, J=6.3, 3.0 Hz, 1H), 6.84 (dt, J=8.9, 3.5 Hz, 1H), 6.47 (dt, J=11.3, 7.4 Hz, 1H), 5.88 (dt, J=11.5, 1.5 Hz, 1H), 4.55 (dt, J=12.1, 6.1 Hz, 1H), 3.06 (qd, J=7.6, 1.4 Hz, 2H), 2.96-2.79 (m, 2H), 1.40-1.31 (m, 6H).

EXAMPLE 15

Generation of diazomethane: To a 0° C. stirred solution of 50% aq. KOH (10 mL) and Et$_2$O (10 mL) at 0° C. was added portionwise N-methyl-N'-nitro-N-nitrosoguanidine (390 mg, 2.65 mmol). After 30 min, the aqueous phase was frozen by cooling the mixture to −78° C.; the ethereal diazomethane layer was decanted. To a 0° C. mixture of (Z)-5-(2'-fluoro-5'-isopropoxy-[1,1'-biphenyl]-4-yl)pent-2-enoic acid (290 mg, 0.883 mmol), Pd(OAc)$_2$ (20 mg, 0.088 mmol) in Et$_2$O (10 mL) was added the solution of diazomethane generated above. The mixture was allowed to slowly warm to rt overnight, after which AcOH (0.51 mL, 8.83 mmol) was added and the reaction was stirred for 30 min at rt, then was concentrated in vacuo. The residue was purified by preparative HPLC (2 mL injection; Method: Grad. Solv. System: From 40% A: 60% B to 0% A: 100% B; (A=10% MeOH/90% H$_2$O+0.1% TFA); (B=90% MeOH/10% H$_2$O+0.1% TFA); Detection at 220 nm; 10 min gradient; PHENOMENEX® Axia 5μ C18, 30×100 mm) to afford the title compound (165 mg, 0.467 mmol, 52.9% yield) as a pale yellow oil. $^1$H NMR (500 MHz, CDCl$_3$) δ 7.48 (dd, J=8.1, 1.5 Hz, 2H), 7.34-7.23 (m, 2H), 7.06 (dd, J=10.0, 8.9 Hz, 1H), 6.97 (dd, J=6.5, 3.2 Hz, 1H), 6.83 (dt, J=8.8, 3.6 Hz, 1H), 4.53 (dt, J=12.1, 6.1 Hz, 1H), 2.76 (t, J=7.6 Hz, 2H), 1.99 (dq, J=11.8, 7.3 Hz, 2H), 1.83-1.67 (m, 1H), 1.47-1.39 (m, 1H), 1.39-1.33 (m, 6H), 1.15 (td, J=8.2, 4.5 Hz, 1H), 1.05 (dt, J=7.4, 5.0 Hz, 1H).

EXAMPLE 16

(1R,2S)-2-(2-(2'-Fluoro-5'-isopropoxy-[1,1'-biphenyl]-4-yl)ethyl)cyclopropanecarboxylic acid (Enantiomer 1; absolute stereochemistry drawn in an arbitrary manner)

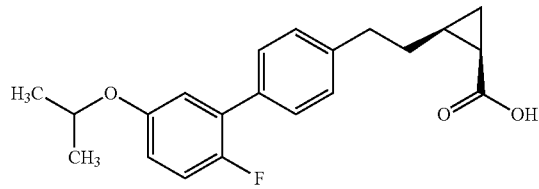 [SMILES: CC(C)Oc1ccc(F)c(-c2ccc(CC[C@H]3C[C@H]3C(=O)O)cc2)c1]

and

EXAMPLE 17

(1S,2R)-2-(2-(2'-Fluoro-5'-isopropoxy-[,1,1'-biphenyl]-4-yl)ethyl)cyclopropanecarboxylic acid (Enantiomer 2; absolute stereochemistry drawn in an arbitrary manner)

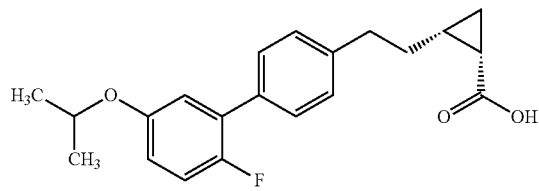 [SMILES: CC(C)Oc1ccc(F)c(-c2ccc(CC[C@@H]3C[C@@H]3C(=O)O)cc2)c1]

The two enantiomers of Example 15 was separated by chiral preparative HPLC (Instrument=Berger Multigram II SFC; Column: CHIRALPAK® AD-H, 30×250 mm, 5μ; Mobile Phase: 8% EtOH/92% CO$_2$; Flow Conditions: 85 mL/min, 100 Bar, 35° C.; Detector Wavelength: 220 nm; Injection Details: 0.5 mL of 30 mg/mL in EtOH) to afford the title compounds.

Example 16, the first eluting isomer (47 mg, 0.135 mmol, 30.8% yield) was obtained as a pale yellow oil. ee=>99.5%. $^1$H NMR (500 MHz, CD$_2$Cl$_2$) δ 7.53-7.43 (m, 2H), 7.32 (d, J=8.0 Hz, 2H), 7.15-7.04 (m, 1H), 6.99 (dd, J=6.3, 3.0 Hz, 1H), 6.85 (dt, J=9.0, 3.5 Hz, 1H), 4.56 (dt, J=12.1, 6.1 Hz, 1H), 2.88-2.67 (m, 2H), 1.99 (tt, J=14.5, 7.1 Hz, 2H), 1.84-1.68 (m, 1H), 1.53-1.41 (m, 1H), 1.41-1.29 (m, 6H), 1.18 (td, J=8.0, 4.5 Hz, 1H), 1.07 (dt, J=6.9, 5.1 Hz, 1H).

Example 17, the second eluting isomer (56 mg, 0.163 mmol, 37.2% yield) was obtained as a pale yellow oil. ee=96%. $^1$H NMR (500 MHz, CD$_2$Cl$_2$) δ 7.55-7.43 (m, J=7.7 Hz, 2H), 7.38-7.24 (m, J=7.4 Hz, 2H), 7.08 (t, J=9.6 Hz, 1H), 7.01-6.94 (m, 1H), 6.93-6.77 (m, 1H), 4.55 (dt, J=12.0, 5.9 Hz, 1H), 2.77 (br. s., 2H), 2.10-1.89 (m, 2H), 1.86-1.68 (m, 1H), 1.54-1.40 (m, 1H), 1.37 (d, J=6.1 Hz, 6H), 1.18 (d, J=4.1 Hz, 1H), 1.13-0.99 (m, 1H).

EXAMPLE 18

Trans-2-(((2'-chloro-3-fluoro-5'-isopropoxy-[1,1'-biphenyl]-4yl)oxy)methyl) cyclopropanecarboxylic acid (racemate)

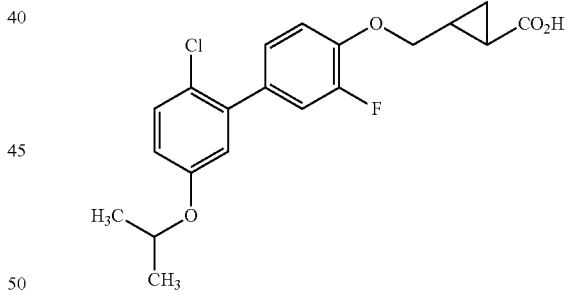

Example 18 was synthesized using the same synthetic sequence as for the synthesis of Example 9, except that (2-chloro-5-isopropoxyphenyl)boronic acid was used instead of (2-fluoro-5-phenoxyphenyl)boronic acid. The title compound was obtained (14 mg, 53%) as a white solid. LCMS, [M+Na]$^+$=401.1. $^1$H NMR (500 MHz, CDCl$_3$) δ 7.33 (d, J=8.8 Hz, 1H), 7.21 (dd, J=12.1, 2.2 Hz, 1H), 7.17-7.09 (m, 1H), 6.99 (t, J=8.5 Hz, 1H), 6.85-6.82 (m, 1H), 6.82-6.77 (m, 1H), 4.59-4.46 (m, 1H), 4.09 (d, J=5.8 Hz, 1H), 4.04 (d, J=6.6 Hz, 1H), 2.13-1.96 (m, 1H), 1.84-1.71 (m, 1H), 1.44-1.37 (m, 1H), 1.35 (d, J=6.1 Hz, 6H), 1.15 (ddd, J=8.5, 6.4, 4.7 Hz, 1H).

EXAMPLE 19

Trans-2-(((3'-fluoro-5'-((2-methylallyl)oxy)-[1,1'-biphenyl]-4-yl)oxy)methyl) cyclopropanecarboxylic acid (racemate)

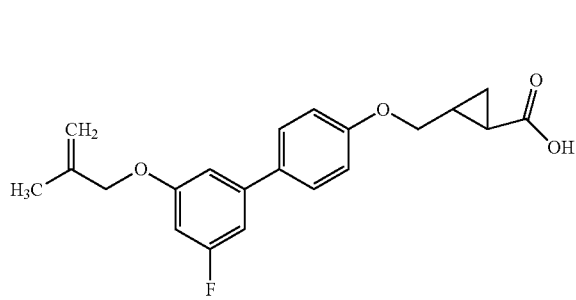 [SMILES: C=C(C)COc1cc(F)cc(-c2ccc(OCC3CC3C(=O)O)cc2)c1]

19A. Methyl trans-2-(((3'-fluoro-5'-hydroxy-[1,1'-biphenyl]-4-yl)oxy)methyl) cyclopropanecarboxylate (racemate)

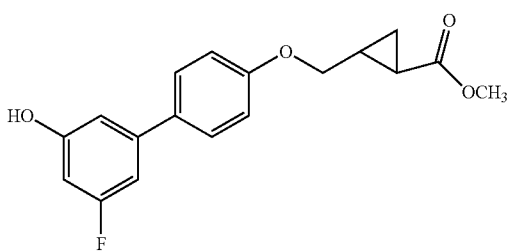 [SMILES: COC(=O)C1CC1COc1ccc(-c2cc(O)cc(F)c2)cc1]

A mixture of racemic methyl trans-2-((4-bromophenoxy)methyl) cyclopropanecarboxylate (112 mg, 0.39 mmol), 3-fluoro-5-(4,4,5,5-tetramethyl-1,3,2-dioxaborolan-2-yl)phenol (140 mg, 0.59 mmol), Pd(Ph$_3$P)$_4$ (45 mg, 0.039 mmol), and K$_2$CO$_3$ (217 mg, 1.57 mmol) in THF (1.5 mL) and water (0.5 mL) was heated in a microwave reactor at 130° C. for 20 min under Ar, then was cooled to rt. The mixture was acidified with 1N aq. HCl to pH=2-3, then was extracted with EtOAc (4×5 mL). The combined organic extracts were dried over MgSO$_4$ and concentrated in vacuo. The residue was chromatographed (SiO$_2$; 24 g; continuous gradient from 0 to 100% Solvent B over 20 min, hold at 100% Solvent B for 5 min, where Solvent A=hexanes and Solvent B=EtOAc) to afford the title compound (112 mg, 0.35 mmol, 90% yield) as a colorless oil. LCMS, [M–H]+=315. $^1$H NMR (500 MHz, CDCl$_3$) δ 7.44-7.41 (m, 2H), 6.91-6.88 (m, 2H), 6.81-6.74 (m, 2H), 6.50 (dt, J=2.3, 9.9 Hz, 1H), 3.97 (dd, J=5.9, 10.1 Hz, 1H), 3.84 (dd, J=6.6, 10.1 Hz, 1H), 3.7 (s, 3H), 1.96-1.89 (m, 1H), 1.73 (dt, J=4.5, 8.7 Hz, 1H), 1.32 (dt, J=4.7, 9.2 Hz, 1H), 1.02 (ddd, J=4.6, 6.3, 8.5 Hz, 1H).

19B. Methyl trans-2-(((3'-fluoro-5'-((2-methylallyl)oxy)-[1,1'-biphenyl]-4-yl)oxy)methyl) cyclopropanecarboxylate (racemate)

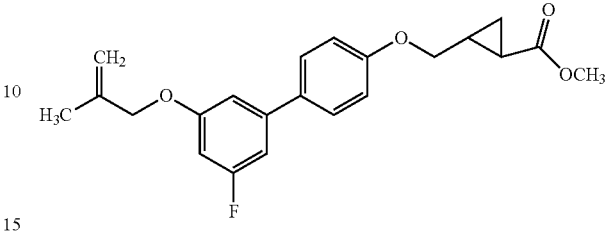

To a solution of methyl trans-2-(((3'-fluoro-5'-((2-methylallyl)oxy)-[1,1'-biphenyl]-4-yl)oxy)methyl)cyclopropanecarboxylate (68 mg, 0.22 mmol) in DMF (1 mL) were added K$_2$CO$_3$ (65 mg, 0.47 mmol) and KI (2 mg, 11 μmol) under N$_2$. The reaction mixture was heated to 65° C. and 3-chloro-2-methylprop-1-ene (39 mg, 0.43 mmol) was added. The reaction mixture was stirred at 65° C. for 16 h, then was cooled to rt, then was partitioned between water (3 mL) and EtOAc (10 mL). The organic layer was washed with and brine (3 mL), dried over MgSO$_4$ and concentrated in vacuo. The residue was chromatographed (SiO$_2$; 12 g; continuous gradient from 0 to 50% Solvent B over 20 min, hold at 50% Solvent B for 5 min, where Solvent A=hexanes and Solvent B=EtOAc) to afford the title compound (72 mg, 0.19 mmol, 90% yield) as a light yellow oil. LCMS, [M+Na]+=393. $^1$H NMR (500 MHz, CDCl$_3$) δ 7.47-7.44 (m, 2H), 6.93-6.90 (m, 2H), 6.88-6.86 (m, 1H), 6.84-6.80 (m, 1H), 6.55 (dt, J=2.3, 10.6 Hz, 1H), 5.09 (s, 1H), 5.0 (s, 1H), 4.44 (s, 2H), 3.98 (dd, J=5.9, 10.1 Hz, 1H), 3.87 (dd, J=6.6, 10.1 Hz, 1H), 3.7 (s, 3H), 1.96-1.88 (m, 1H), 1.82 (s, 3H), 1.74-1.70 (m, 1H), 1.31 (dt, J=4.7, 9.2 Hz, 1H), 1.01 (ddd, J=4.5, 6.2, 8.3 Hz, 1H).

EXAMPLE 19

To a solution of methyl trans-2-(((3'-fluoro-5'-((2-methylallyl)oxy)-[1,1'-biphenyl]-4-yl)oxy)methyl)cyclopropanecarboxylate (5 mg, 0.013 mmol) in THF (0.3 mL) was added LiOH.H$_2$O (11 mg, 0.27 mmol) in water (0.3 mL). The mixture was stirred at rt for 48 h, then was acidified with 1N aq. HCl to pH=2-3. The mixture was extracted with EtOAc (2×3 mL), dried over MgSO$_4$ and concentrated in vacuo. The residue was purified by preparative HPLC with the following conditions: Column: Waters XBridge C18, 19×200 mm, 5-μm particles; Mobile Phase A: 5:95 MeCN:water with 0.1% TFA; Mobile Phase B: 95:5 MeCN:water with 0.1% TFA; Gradient: 45-100% B over 15 min, then a 5-min hold at 100% B; Flow: 20 mL/min. Fractions containing the desired product were combined and dried via centrifugal evaporation to give the title compound (2.6 mg, 54% yield). LCMS, [M–H]+=357. $^1$H NMR (500 MHz, DMSO-d$_6$) δ 7.63-7.60 (m, 2H), 7.04-6.98 (m, 4H), 6.75 (dt, J=2.2, 10.9 Hz, 1H), 5.09 (s, 1H), 4.96 (s, 1H), 4.55 (s, 2H), 4.0 (dd, J=6.32, 10.5 Hz, 1H), 3.87 (dd, J=7.4, 10.5 Hz, 1H), 1.77 (s, 3H), 1.70-1.63 (m, 1H), 1.56 (dt, J=4.4, 8.6 Hz, 1H), 1.03 (dt, J=4.3, 8.7 Hz, 1H), 0.91-0.86 (m, 1H). HPLC-4: RT=1.84 min, purity=100%; HPLC-5: RT=2.2 min, purity=100%.

EXAMPLE 20

Trans-2-((4-(6-fluoro-2,2-dimethyl-2,3-dihydrobenzofuran-4-yl)phenoxy)methyl) cyclopropanecarboxylic acid (racemate)

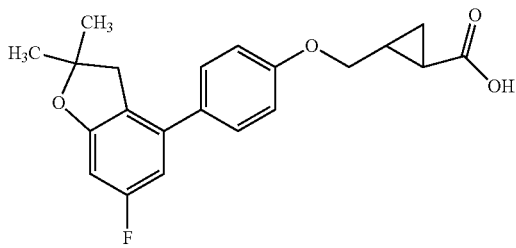 [SMILES: CC1(C)Cc2c(cc(F)cc2-c2ccc(OCC3CC3C(=O)O)cc2)O1]

and

EXAMPLE 21

Trans-2-((4-(4-fluoro-2,2-dimethyl-2,3-dihydrobenzofuran-6-yl)phenoxy)methyl) cyclopropanecarboxylic acid (racemate)

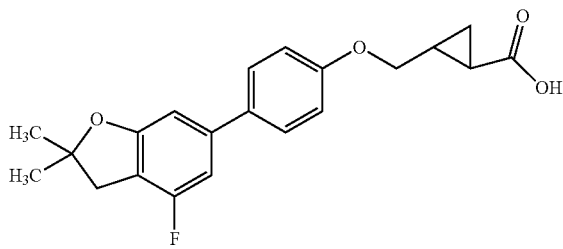 [SMILES: CC1(C)Cc2c(F)cc(-c3ccc(OCC4CC4C(=O)O)cc3)cc2O1]

20A. Methyl trans-2-((4-(6-fluoro-2,2-dimethyl-2,3-dihydrobenzofuran-4-yl)phenoxy) methyl)cyclopropanecarboxylate (racemate)

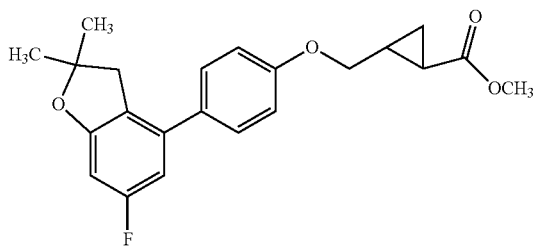 [SMILES: COC(=O)C1CC1COc1ccc(-c2cc(F)cc3c2CC(C)(C)O3)cc1]

and

21A. Methyl trans-2-((4-(4-fluoro-2,2-dimethyl-2,3-dihydrobenzofuran-6-yl) phenoxy)methyl)cyclopropanecarboxylate (racemate)

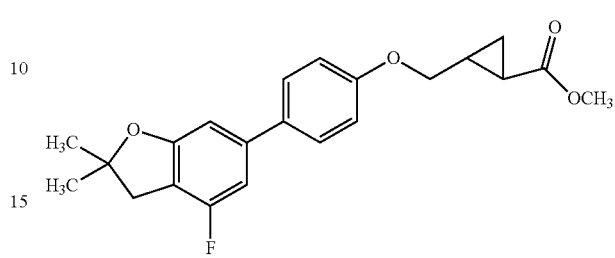

Methyl trans-2-(((3'-fluoro-5'-((2-methylallyl)oxy)-[1,1'-biphenyl]-4-yl)oxy) methyl)cyclopropanecarboxylate (67 mg, 0.18 mmol) was heated neat at 195° C. for 28 h, then was cooled to rt, dissolved in DMF and filtered. The filtrate was purified by preparative HPLC (YMC reverse phase ODS-A-5μ 30×100 mm column; flow rate=40 mL/min, 0 to 100% Solvent B over 30 min, hold to 40 min, where Solvent A=90:10:0.1 H$_2$O:MeCN:TFA and Solvent B=90:10:0.1 MeCN:H$_2$O:TFA) to give 20A (8 mg, 0.022 mmol, 12% yield) as a white solid. LCMS, [M+H]$^+$=371. $^1$H NMR (500 MHz, CDCl$_3$) δ 7.34-7.31 (m, 2H), 6.92-6.89 (m, 2H), 6.57 (dd, J=2.3, 10.4 Hz, 1H), 6.40 (dt, J=2.3, 9.2 Hz, 1H), 3.98 (dd, J=5.9, 10.1 Hz, 1H), 3.87 (dd, J=6.6, 10.1 Hz, 1H), 3.69 (s, 3H), 3.01 (d, J=1.1 Hz, 2H), 1.95-1.88 (m, 1H), 1.74-1.70 (m, 1H), 1.45 (s, 6H), 1.31 (dt, J=4.7, 9.2 Hz, 1H), 1.01 (ddd, J=4.5, 6.2, 8.4 Hz, 1H). Also obtained is 20B (4 mg, 10.8 μmol, 6% yield) as a white solid. LCMS, [M+H]$^+$=371. $^1$H NMR (500 MHz, CDCl$_3$) δ 7.44-7.41 (m, 2H), 6.91-6.88 (m, 2H), 6.72-6.68 (m, 2H), 3.97 (dd, J=5.9, 10.1 Hz, 1H), 3.86 (dd, J=6.6, 10.1 Hz, 1H), 3.69 (s, 3H), 3.03 (s, 2H), 1.94-1.88 (m, 1H), 1.73-1.70 (m, 1H), 1.50 (s, 6H), 1.30 (dt, J=4.7, 9.1 Hz, 1H), 1.0 (ddd, J=4.5, 6.2, 8.4 Hz, 1H).

The regiochemistry of these two compounds were determined by nOe experiments of the methylene protons of dihydrobenzofuran to the ortho-protons on the central phenyl ring.

EXAMPLE 20

A solution of 20A (8 mg, 0.02 mmol) and LiOH.H$_2$O (18 mg, 0.43 mmol) in THF (0.8 mL), water (0.8 mL) and MeOH (0.8 mL) was stirred at RT for 2 h, then was concentrated in vacuo to remove the MeOH. The mixture was acidified with 1N aq. HCl to pH=2-3 and extracted with EtOAc (3×5 mL). The combined organic extracts were dried over MgSO$_4$, and concentrated in vacuo. The residue was purified by preparative HPLC (YMC reverse phase ODS-A-5μ 30×100 mm column; flow rate=40 mL/min, 0 to 100% Solvent B over 30 min, hold to 40 min, where Solvent A=90:10:0.1 H$_2$O:MeCN:TFA and Solvent B=90:10:0.1 MeCN:H$_2$O:TFA) to Example 20 (6.9 mg, 0.019 mmol, 89% yield) as a white solid. LCMS, [M−H]$^+$=355. $^1$H NMR (500 MHz, CDCl$_3$) δ 7.33 (d, J=8.6 Hz, 2H), 6.91 (d, J=8.6 Hz, 2H), 6.57 (dd, J=2.1, 10.4 Hz, 1H), 6.40 (dt, J=2.0, 9.2 Hz, 1H), 4.02 (dd, J=5.7, 10.1 Hz, 1H), 3.88 (dd, J=6.6, 10.0 Hz, 1H), 3.02 (s, 2H), 2.0-1.94 (m, 1H), 1.75-1.72 (m, 1H), 1.45 (s, 6H), 1.37 (dt, J=4.6, 9.0 Hz, 1H), 1.12-1.08 (m, 1H). HPLC-1: RT=11.4 min, purity=100%; HPLC-2: RT=10.2 min, purity=100%.

EXAMPLE 21

Example 21 was prepared using a procedure analogous to that for the synthesis of Example 20 except that methyl trans-2-((4-(6-fluoro-2,2-dimethyl-2,3-dihydrobenzofuran-4-yl)phenoxy) methyl)cyclopropanecarboxylate was replaced with methyl trans-2-((4-(4-fluoro-2,2-dimethyl-2,3-dihydrobenzofuran-6-yl)phenoxy)methyl) cyclopropanecarboxylate. LCMS, [M−H]⁺=355. ¹H NMR (500 MHz, DMSO-$d_6$) δ 7.55 (d, J=8.5 Hz, 2H), 6.97 (d, J=8.6 Hz, 2H), 6.87 (d, J=10.2 Hz, 1H), 6.80 (s, 1H), 3.99 (dd, J=6.3, 10.4 Hz, 1H), 3.85 (dd, J=7.5, 10.3 Hz, 1H), 3.04 (s, 2H), 1.70-1.63 (m, 1H), 1.56 (dt, J=4.2, 8.4 Hz, 1H), 1.44 (s, 6H), 1.04 (dt, J=4.2, 8.6 Hz, 1H), 0.91-0.87 (m, 1H). HPLC-4: RT=1.64 min, purity=100%; HPLC-5: RT=2.07 min, purity=100%.

EXAMPLE 22

2-((4-(5-Fluoro-2,2-dimethyl-2,3-dihydrobenzofuran-4-yl)phenoxy)methyl) cyclopropanecarboxylic acid

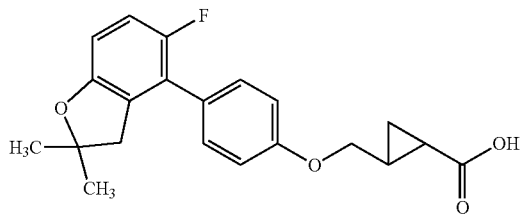 [SMILES: CC1(C)Cc2c(ccc(F)c2-c2ccc(OCC3CC3C(=O)O)cc2)O1]

22A. Methyl 2-(((2'-fluoro-5'-hydroxy-[1,1'-biphenyl]-4-yl)oxy)methyl) cyclopropanecarboxylate

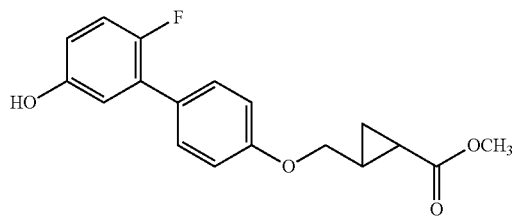 [SMILES: COC(=O)C1CC1COc1ccc(-c2cc(O)ccc2F)cc1]

A mixture of 1D (500 mg, 1.754 mmol), (5-((tert-butyldimethylsilyl)oxy)-2-fluorophenyl)boronic acid (569 mg, 2.104 mmol), Pd(PPh₃)₄(203 mg, 0.175 mmol) and K₂CO₃ (727 mg, 5.26 mmol) in THF (9 mL) and water (3 mL) was heated in a microwave reactor at 130° C. for 20 min under Ar, then was cooled to rt. The mixture was acidified with 1N aq. HCl to pH=2~3, and extracted with EtOAc (4×50 mL). The combined organic extracts were dried over MgSO₄, and concentrated in vacuo. The residue was chromatographed (SiO₂; 80 g; continuous gradient from 0 to 40% Solvent B over 30 min, hold at 40% Solvent B for 20 min, where Solvent A=hexanes and Solvent B=EtOAc) to give the title compound (283.5 mg, 0.896 mmol, 51% yield) as a clear oil. LCMS, [M+Na]⁺=339.1.

22B. Methyl 2-(((2'-fluoro-5'-((2-methylallyl)oxy)-[1,1'-biphenyl]-4-yl)oxy)methyl) cyclopropanecarboxylate

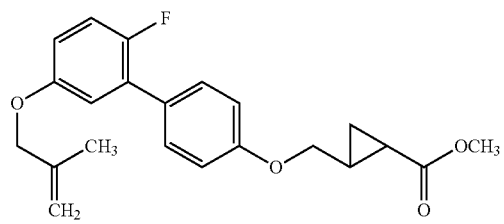 [SMILES: C=C(C)COc1ccc(F)c(-c2ccc(OCC3CC3C(=O)OC)cc2)c1]

To a solution of 22A (80 mg, 0.253 mmol) in DMF (3 mL) were added K₂CO₃ (77 mg, 0.556 mmol), KI (2 mg, 0.013 mmol) under N₂. The reaction mixture was heated to 65° C. and 3-chloro-2-methylprop-1-ene (0.050 mL, 0.506 mmol) was added. The reaction mixture was stirred at 65° C. for 16 h (LC/MS indicated the formation of the desired product), then was cooled to rt. Water (5 mL) and EtOAc (20 mL) were added. The organic layer was washed with H₂O (3 mL) and brine (5 mL), dried over MgSO₄, and evaporated in vacuo. The residue was chromatographed (SiO₂; 12 g; continuous gradient from 0 to 15% Solvent B over 20 min, hold at 15% Solvent B for 10 min, where Solvent A=hexanes and Solvent B=EtOAc) to give the title compound (84.4 mg, 0.228 mmol, 90% yield) as a colorless oil. LCMS, [M+Na]⁺=393.1.

22C. Methyl 2-((4-(5-fluoro-2,2-dimethyl-2,3-dihydrobenzofuran-4-yl)phenoxy)methyl) cyclopropanecarboxylate

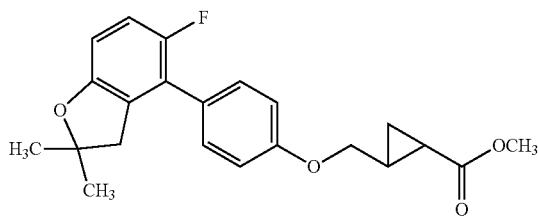 [SMILES: COC(=O)C1CC1COc1ccc(-c2c(F)ccc3c2CC(C)(C)O3)cc1]

22B (84 mg, 0.227 mmol) was azeotroped several times and heated in a heating block for 16 h at 195° C. The brown liquid was purified by preparative HPLC (PHENOMENEX® Synergi reverse phase ODS-A-5µ 21.2×250 mm column; flow rate=25 mL/min, 30 to 100% Solvent B over 30 min, hold to 37 min, where Solvent A=90:10:0.1 H₂O:ACN:TFA and Solvent B=90:10:0.1 ACN:H₂O:TFA) to give the title compound (14 mg, 0.038 mmol, 17% yield) as a white solid. LCMS, [M+Na]⁺=393.1. ¹H NMR (500 MHz, CDCl₃) δ 7.36-7.31 (m, 2H), 6.97-6.93 (m, 2H), 6.92-6.87 (m, 1H), 6.61 (dd, J=8.7, 3.7 Hz, 1H), 4.01 (dd, J=10.0, 5.9 Hz, 1H), 3.90 (dd, J=10.2, 6.6 Hz, 1H), 3.72 (s, 3H), 2.98 (s, 2H), 1.99-1.90 (m, 1H), 1.77-1.72 (m, 1H), 1.46 (s, 6H), 1.34 (dt, J=8.9, 4.6 Hz, 1H), 1.04 (ddd, J=8.5, 6.3, 4.5 Hz, 1H).

EXAMPLE 22

A mixture of LiOH.H₂O (6 mg, 0.140 mmol) and 22C (13 mg, 0.035 mmol) in THF (1 mL) and water (0.5 mL) was stirred at RT overnight, then was partitioned between EtOAc (5 mL) and H₂O (2 mL). The aqueous layer was washed with EtOAc (2×1 mL). The organic layer was extracted with H₂O (3×2 mL). The combined aqueous extracts were acidified with 1N aq. HCl to pH ~3 and extracted with EtOAc (3×5 mL). The combined organic extracts were washed with brine (2 mL), dried over MgSO₄, and evaporated in vacuo. The residue was purified by preparative LC/MS using the following conditions: Column: Waters XBridge C18, 19×200 mm, 5-μm particles; Guard Column: Waters XBridge C18, 19×10 mm, 5-μm particles; Mobile Phase A: 5:95 MeCN:water with 0.1% TFA; Mobile Phase B: 95:5 MeCN:water with 0.1% TFA; Gradient: 50-90% B over 20 min, then a 5-min hold at 100% B; Flow: 20 mL/min. Fractions containing the desired product were combined and dried via centrifugal evaporation to provide the title compound (12 mg, 0.035 mmol, 99% yield). LCMS, [M−H]⁺=355.1. ¹H NMR (500 MHz, DMSO-d₆) δ 7.36-7.34 (m, 2H), 7.04-6.94 (m, 3H), 6.64 (d, J=8.5 Hz, 1H), 4.06-3.99 (m, 1H), 3.88 (t, J=8.9 Hz, 1H), 2.97 (s, 2H), 1.73-1.71 (m, 1H), 1.63-1.61 (m, 1H), 1.38 (s, 6H), 1.10-1.08 (m, 1H), 0.98-0.96 (m, 1H). HPLC-4: RT=1.54 min, purity=100%; HPLC-5: RT=1.91 min, purity=100%.

EXAMPLE 23

Trans-2-(((3'-fluoro-5'-phenoxy-[1,1'-biphenyl]-4-yl)oxy)methyl)cyclopropanecarboxylic acid (racemate)

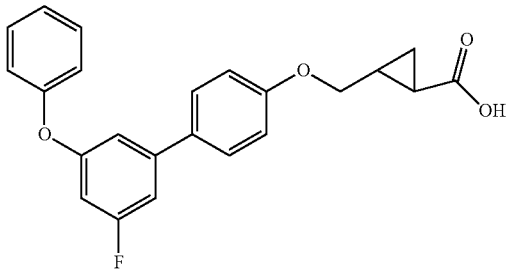 [SMILES: O=C(O)C1CC1COc1ccc(-c2cc(F)cc(Oc3ccccc3)c2)cc1]

23A. Methyl trans-2-(((3'-fluoro-5'-phenoxy-[1,1'-biphenyl]-4-yl)oxy)methyl) cyclopropanecarboxylate (racemate)

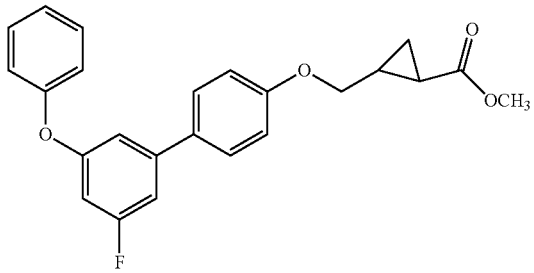 [SMILES: COC(=O)C1CC1COc1ccc(-c2cc(F)cc(Oc3ccccc3)c2)cc1]

To a mixture of 19A and phenylboronic acid (26 mg, 0.21 mmol), 4A molecular sieves (0.2 g), Et₃N (0.06 mL, 0.43 mmol), pyridine (0.04 mL, 0.43 mmol) in CH₂Cl₂(1 mL) was added Cu(OAc)₂ (39 mg, 0.21 mmol). The reaction was stirred at rt under an atmosphere of air for 72 h, then was taken up in CH₂Cl₂(5 mL) and filtered through a plug of CELITE®. The filtrate was concentrated in vacuo. The crude oil was chromatographed (SiO₂; 4 g; continuous gradient from 0 to 40% Solvent B over 12 min, where Solvent A=hexanes and Solvent B=EtOAc) to afford 23A (20 mg, 0.05 mmol, 72% yield) as a colorless oil. LCMS, [M+Na]⁺=415.1, ¹H NMR (500 MHz, CDCl₃) δ 7.45-7.41 (m, 2H), 7.38-7.33 (m, 2H), 7.16-7.12 (m, 1H), 7.07-7.04 (m, 2H), 6.97-6.94 (m, 2H), 6.92-6.88 (m, 2H), 6.6 (dt, J=2.2, 9.9 Hz, 1H), 3.98 (dd, J=5.9, 10.1 Hz, 1H), 3.86 (dd, J=6.6, 10.1 Hz, 1H), 3.69 (s, 3H), 1.94-1.87 (m, 1H), 1.73-1.69 (m, 1H), 1.30 (dt, J=4.7, 9.2 Hz, 1H), 1.0 (ddd, J=4.5, 6.2, 8.5 Hz, 1H).

EXAMPLE 23

The title compound was prepared using a procedure analogous to that for the synthesis of Example 22 from 23A. LCMS, [M+Na]⁺=401. ¹H NMR (500 MHz, DMSO-d₆) δ 7.60-7.56 (m, 2H), 7.45-7.40 (m, 2H), 7.26-7.22 (m, 1H), 7.21-7.18 (m, 1H), 7.13-7.09 (m, 2H), 7.07 (t, J=1.72 Hz, 1H), 7.0-6.97 (m, 2H), 6.74 (dt, J=2.2, 10.0 Hz, 1H), 4.0 (dd, J=6.3, 10.5 Hz, 1H), 3.86 (dd, J=7.4, 10.5 Hz, 1H), 1.94-1.87 (m, 1H), 1.60-1.56 (m, 1H), 1.06 (dt, J=4.3, 8.8 Hz, 1H), 0.93 (ddd, J=4.1, 6.1, 8.4 Hz, 1H). HPLC-4: RT=1.92 min, purity=100%; HPLC-5: RT=2.27 min, purity=100%.

EXAMPLE 24

Trans-2-(((2'-fluoro-5'-isopropoxy-[1,1'-biphenyl]-4-yl)methoxy)methyl) cyclopropanecarboxylic acid (racemate)

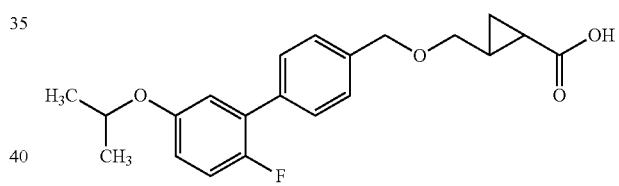

24A. Trans-2-(((4-bromobenzyl)oxy)methyl)cyclopropanecarboxylic acid (racemate)

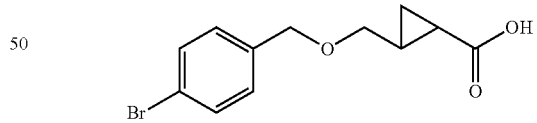

To a 0° C. solution of trans-2-(hydroxymethyl)cyclopropanecarboxylic acid (200 mg, 1.72 mmol) in DMF (5 mL) was added NaH (152 mg, 3.79 mmol, 60% in mineral oil). The reaction mixture was stirred at 0° C. for 30 min, after which 1-bromo-4-(bromomethyl)benzene (1.076 g, 4.31 mmol) was added. The mixture was stirred at 0° C. for 20 min, then at rt for 100 min. A solution of KOH (97 mg, 1.72 mmol) in water (3 mL) was added and the mixture was stirred at rt overnight, then was cooled to 0° C. and quenched with 1 N aq. HCl (5 mL). The mixture was extracted with EtOAc (3×10 mL). The combined organic extracts were dried over MgSO₄ and concentrated in vacuo. The residue was purified by preparative HPLC (YMC reverse phase ODS-A-5μ 30×100 mm column; flow rate=40 mL/min, 0 to 100% Solvent B over 30 min, hold to 40 min, where Solvent A=90:10:0.1 H$_2$O:MeCN:TFA and Solvent B=90:10:0.1 MeCN:H$_2$O:TFA) to ethyl trans-2-(((4-bromobenzyl)oxy) methyl)cyclopropanecarboxylate (180 mg, 0.63 mmol, 36.7% yield) as a slightly colored oil. LCMS, [M–H]$^+$=283. $^1$H NMR (500 MHz, CDCl$_3$) δ 7.47-7.43 (m, 2H), 7.19-7.16 (m, 2H), 4.45 (s, 2H), 3.46 (dd, J=5.8, 10.4 Hz, 1H), 3.32 (dd, J=6.6, 10.4 Hz, 1H), 1.80-1.73 (m, 1H), 1.57-1.53 (m, 1H), 1.26 (dt, J=4.6, 9.1 Hz, 1H), 0.92 (ddd, J=4.4, 6.4, 8.3 Hz, 1H).

EXAMPLE 24

A mixture of 24A (11 mg, 0.037 mmol), Pd(Ph$_3$P)4 (4 mg, 3.7 μmol) and (2-fluoro-5-isopropoxyphenyl)boronic acid (11 mg, 0.055 mmol) and K$_2$CO$_3$ (18 mg, 0.13 mmol) in THF (1 mL) and water (0.3 mL) was heated in a microwave reactor at 130° C. for 20 min under Ar, then was cooled to rt and acidified with 1N aq. HCl to pH=2-3. The mixture was extracted with EtOAc (3×5 mL), dried over MgSO$_4$ and concentrated in vacuo. The crude product was purified by preparative LC/MS (Column: Waters XBridge C18, 19×200 mm, 5-μm particles; Guard Column: Waters XBridge C18, 19×10 mm, 5-m particles; Mobile Phase A: 5:95 MeCN:water with 0.1% TFA; Mobile Phase B: 95:5 MeCN:water with 0.1% TFA; Gradient: 35-85% B over 20 min, then a 5-min hold at 100% B; Flow: 20 mL/min) to give the title compound (7.2 mg; 55% yield). LCMS, [M–H]$^+$=357, $^1$H NMR (500 MHz, DMSO-d$_6$) δ 7.53-7.50 (m, 2H), 7.40 (d, J=8.2 Hz, 2H), 7.19 (dd, J=9.0, 10.3 Hz, 1H), 6.97 (dd, J=3.1, 6.5 Hz, 1H), 6.92 (dt, J=3.6, 9.0 Hz, 1H), 4.65-4.58 (m, 1H), 4.51 (s, 2H), 3.48 (dd, J=5.9, 10.5 Hz, 1H), 3.34 (dd, J=6.6, 10.4 Hz, 1H), 1.56-1.5 (m, 1H), 1.46 (dt, J=4.4, 8.7 Hz, 1H), 1.26 (d, J=6.0 Hz, 6H), 0.99 (dt, J=4.2, 8.7 Hz, 1H), 0.86-0.80 (m, 1H). HPLC-4: RT=1.66 min, purity=97%; HPLC-5: RT=2.05 min, purity=97%.

EXAMPLE 25

Trans-2-(((2'-fluoro-5'-phenoxy-[1,1'-biphenyl]-4-yl) methoxy)methyl) cyclopropanecarboxylic acid (racemate)

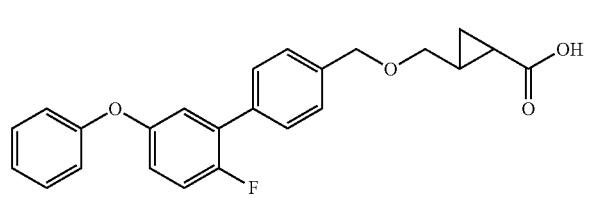 [SMILES: O=C(O)C1CC1COCc1ccc(-c2cc(Oc3ccccc3)ccc2F)cc1]

The title compound was prepared using a sequence analogous to that for the synthesis of Example 24. LCMS, [M–H]$^+$=391, $^1$H NMR (500 MHz, DMSO-d$_6$) δ 7.53-7.50 (m, 2H), 7.42-7.37 (m, 4H), 7.33 (dd, J=9.0, 10.3 Hz, 1H), 7.17-7.11 (m, 2H), 7.06-7.01 (m, 3H), 4.51 (s, 2H), 3.46 (dd, J=5.9, 10.5 Hz, 1H), 3.32 (dd, J=6.6, 10.4 Hz, 1H), 1.55-1.48 (m, 1H), 1.47-1.43 (dt, J=4.4, 8.7 Hz, 1H), 0.97 (dt, J=4.4, 8.7 Hz, 1H), 0.83-0.78 (m, 1H). HPLC-4: RT=1.82 min, purity=97%; HPLC-5: RT=2.19 min, purity=97%.

EXAMPLE 26

(1R,2R)-2-(4-(5-Chloro-2,2-dimethyl-2,3-dihydrobenzofuran-7-yl)phenethyl) cyclopropanecarboxylic acid (Enantiomer 1; absolute stereochemistry shown is arbitrary)

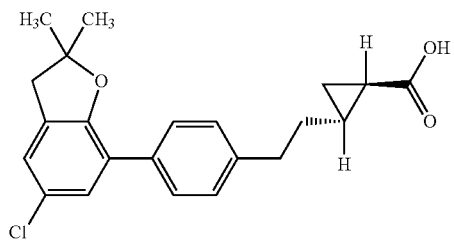 [SMILES: CC1(C)Cc2cc(Cl)cc(-c3ccc(CC[C@@H]4C[C@H]4C(=O)O)cc3)c2O1]

26A. 3-(4-Bromophenyl)propan-1-ol

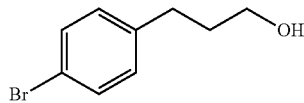 [SMILES: OCCCc1ccc(Br)cc1]

To a 0° C. solution of 3-(4-bromophenyl)propanoic acid (7.5 g, 32.7 mmol) and THF (100 mL) was added BH$_3$.THF (32.7 mL of a 1 M solution in THF, 32.7 mmol) dropwise. The reaction was slowly allowed to warm to rt, then was quenched with AcOH (5 mL) and stirred for 30 min, neutralized with sat. aq. NaHCO$_3$ (100 mL), and extracted with EtOAc (2×75 mL). The combined organic extracts were washed with brine, dried over Na$_2$SO$_4$, and concentrated in vacuo. The residue was chromatographed (SiO$_2$; 80 g; A=Hex, B=EtOAc; 30 min gradient from 0% B to 100% B; flow rate=60 mL/min) to afford the title compound (7.0 g, 32.5 mmol, 99% yield) as a pale yellow oil. $^1$H NMR (500 MHz, CDCl$_3$) δ 7.48-7.37 (m, 1H), 7.15-7.01 (m, 1H), 3.67 (t, J=6.3 Hz, 1H), 2.79-2.59 (m, 1H), 1.96-1.81 (m, 1H).

26B 3-(4-Bromophenyl)propanal

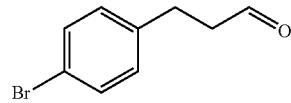 [SMILES: O=CCCc1ccc(Br)cc1]

To a 0° C. mixture of 26A (7 g, 32.5 mmol) and NaHCO$_3$ (3.28 g, 39.1 mmol) in DCM (200 mL) was added Dess-Martin periodinane (16.56 g, 39.1 mmol) and the reaction was allowed to slowly warm to rt overnight. The reaction was diluted with sat. aq. NaHCO$_3$ (150 mL) and extracted with DCM (50 mL). The combined organic extracts were washed with brine, dried over Na$_2$SO$_4$, and concentrated in vacuo. The residue was chromatographed (SiO$_2$; 80 g; A=Hex, B=EtOAc; 20 min gradient from 0% B to 40% B; flow rate=60 mL/min) to afford the title compound (4.06 g, 19.1 mmol, 58.5% yield) as a pale yellow oil. $^1$H NMR (500 MHz, CDCl$_3$) δ 9.82 (t, J=1.2 Hz, 1H), 7.48-7.37 (m, 2H), 7.19-6.97 (m, 2H), 3.02-2.88 (m, 2H), 2.83-2.70 (m, 2H).

26C (E)-Ethyl 5-(4-bromophenyl)pent-2-enoate

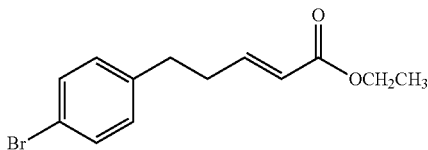 [SMILES: CCOC(=O)/C=C/CCc1ccc(Br)cc1]

To a 0° C. mixture of ethyl 2-(diethoxyphosphoryl)acetate (6.41 g, 28.6 mmol), LiCl (1.212 g, 28.6 mmol) in MeCN (47.6 ml) was added DBU (4.31 mL, 28.6 mmol) and the reaction was stirred for 30 min at 0° C. To this mixture was added 26B (4.06 g, 19.05 mmol) and the reaction was allowed to slowly warm to rt overnight. The reaction mixture was diluted with brine (100 mL) and extracted with EtOAc (2×50 mL). The combined organic extracts were dried over $Na_2SO_4$ and concentrated in vacuo. The residue was chromatographed ($SiO_2$; 80 g; A=Hex, B=EtOAc; 20 min gradient from 0% B to 40% B; flow rate=60 mL/min) to afford the title compound (4.5 g, 15.89 mmol, 83% yield) as a pale yellow oil. $^1$H NMR (400 MHz, $CDCl_3$) δ 7.50-7.39 (m, 2H), 7.16-7.04 (m, 2H), 6.98 (dt, J=15.6, 6.8 Hz, 1H), 5.85 (dt, J=15.6, 1.5 Hz, 1H), 4.20 (q, J=7.2 Hz, 2H), 2.83-2.68 (m, 2H), 2.59-2.41 (m, 2H), 1.44-1.21 (m, 3H).

26D. Ethyl 2-(4-bromophenethyl)cyclopropanecarboxylate (Enantiomer 1; absolute stereochemistry shown is arbitrary)

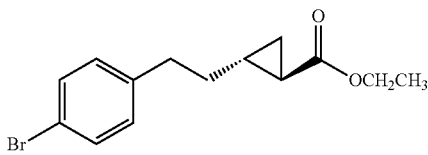 [SMILES: CCOC(=O)[C@@H]1C[C@H]1CCc1ccc(Br)cc1]

Generation of diazomethane: To a 0° C. stirred solution of 50% aq. KOH (100 mL) and $Et_2O$ (100 mL) at 0° C. was added portionwise N-methyl-N'-nitro-N-nitrosoguanidine (4.68 g, 31.8 mmol). After 30 min, the aqueous phase was frozen by cooling the mixture to −78° C.; the ethereal diazomethane layer was decanted. To a 0° C. mixture of (E)-ethyl 5-(4-bromophenyl)pent-2-enoate (4.50 g, 15.9 mmol) and $Pd(OAc)_2$ (0.357 g, 1.589 mmol) in $Et_2O$ (100 mL) was slowly decanted the above ethereal solution of diazomethane. The mixture was allowed to slowly warm to rt overnight, after which AcOH (9.10 mL, 159 mmol) was added. The reaction was stirred for 30 min at rt, then was basified with sat. aq. $NaHCO_3$. The organic phase was washed with brine, dried over $Na_2SO_4$, and concentrated in vacuo. The residue was chromatographed ($SiO_2$; 80 g; A=Hex, B=EtOAc; 30 min gradient from 0% B to 40% B; flow rate=60 mL/min) to afford the racemic trans-ethyl 2-(4-bromophenethyl)cyclopropanecarboxylate (4.29 g, 14.44 mmol, 91% yield) as a pale yellow oil. The 2 enantiomers of racemic trans-ethyl 2-(4-bromophenethyl) cyclopropanecarboxylate were separated by chiral SFC (CHIRALPAK® AD-H 25×5 cm, 5 cm, Mobile phase: $CO_2$/MEOH=88/12, Flow rate: 227 mL/min, Column Temp. 35° C. Detector Wavelength: 220 nm).

Example 26D is the early eluting enantiomer: $^1$H NMR (500 MHz, $CDCl_3$) δ 7.50-7.37 (m, 2H), 7.14-6.98 (m, 2H), 4.13 (q, J=7.1 Hz, 2H), 2.70 (t, J=7.6 Hz, 2H), 1.71-1.54 (m, 2H), 1.42-1.32 (m, 2H), 1.31-1.24 (m, 3H), 1.21-1.09 (m, 1H), 0.70 (ddd, J=8.3, 6.3, 4.1 Hz, 1H).

26E. Trans-ethyl 2-(2-(5'-chloro-2'-hydroxy-[1,1'-biphenyl]-4-yl)ethyl) cyclopropanecarboxylate (Enantiomer 1; absolute stereochemistry shown is arbitrary)

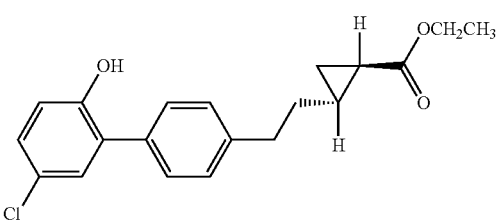 [SMILES: CCOC(=O)[C@@H]1C[C@H]1CCc1ccc(-c2cc(Cl)ccc2O)cc1]

A mixture of 26D (70 mg, 0.236 mmol), (5-chloro-2-hydroxyphenyl)boronic acid (49 mg, 0.283 mmol), $Pd(PPh_3)_4$ (27 mg, 0.024 mmol) and $K_2CO_3$ (98 mg, 0.707 mmol) in THF (3 mL) and water (1 mL) was heated in a microwave reactor at 80° C. for 20 min. under Ar, then was cooled to rt. The reaction was acidified with 1N aq. HCl to pH=2-3, and extracted with EtOAc (4×20 mL). The combined organic extracts were dried over $MgSO_4$, and concentrated in vacuo. The residue was chromatographed ($SiO_2$; 12 g; gradient of EtOAc/Hexane from 0% to 20% over 20 min) to give the title compound (60 mg, 0.174 mmol, 74% yield) as a colorless oil. LCMS, $[M-H]^+$=343.2.

26F. Trans-ethyl 2-(2-(5'-chloro-2'-((2-methylallyl)oxy)-[1,1'-biphenyl]-4-yl)ethyl) cyclopropanecarboxylate

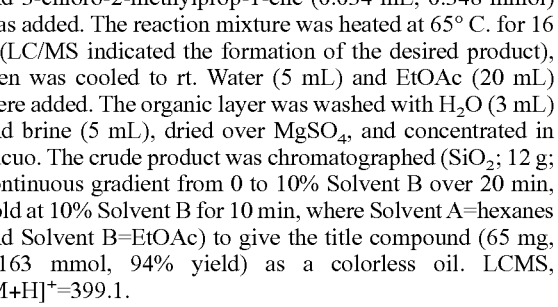

To a solution of 26E (60 mg, 0.174 mmol) in DMF (2 mL) was added $K_2CO_3$ (53 mg, 0.383 mmol) and KI (2 mg, 8.70 μmol) under $N_2$. The reaction mixture was heated to 65° C. and 3-chloro-2-methylprop-1-ene (0.034 mL, 0.348 mmol) was added. The reaction mixture was heated at 65° C. for 16 h (LC/MS indicated the formation of the desired product), then was cooled to rt. Water (5 mL) and EtOAc (20 mL) were added. The organic layer was washed with $H_2O$ (3 mL) and brine (5 mL), dried over $MgSO_4$, and concentrated in vacuo. The crude product was chromatographed ($SiO_2$; 12 g; continuous gradient from 0 to 10% Solvent B over 20 min, hold at 10% Solvent B for 10 min, where Solvent A=hexanes and Solvent B=EtOAc) to give the title compound (65 mg, 0.163 mmol, 94% yield) as a colorless oil. LCMS, $[M+H]^+$=399.1.

26G. Trans-ethyl 2-(2-(5'-chloro-2'-hydroxy-3'-(2-methylallyl)-[1,1'-biphenyl]-4-yl)ethyl)cyclopropanecarboxylate

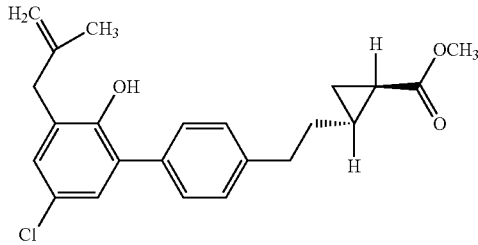 [SMILES: C=C(C)Cc1cc(Cl)cc(-c2ccc(CC[C@@H]3C[C@H]3C(=O)OC)cc2)c1O]

26F (60 mg, 0.150 mmol) was azeotroped several times from toluene and heated neat in a heating block for 16 h at 195° C. The resulting brown liquid was used in the next step without any further purification. LCMS, [M−H]⁺=397.2.

26H. Trans-ethyl 2-(4-(5-chloro-2,2-dimethyl-2,3-dihydrobenzofuran-7-yl)phenethyl) cyclopropanecarboxylate

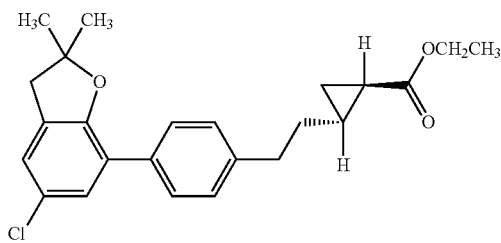 [SMILES: CCOC(=O)[C@@H]1C[C@H]1CCc1ccc(-c2cc(Cl)cc3c2OC(C)(C)C3)cc1]

A solution of 26G (60 mg, 0.150 mmol) in formic acid (1 mL) and water (0.1 mL) was heated at 110° C. for 30 h, then was cooled to rt. Volatiles were removed in vacuo and the residue was azeotroped from toluene to remove the remaining formic acid. The residue was triturated from toluene and directly used for the next step without further purification.

EXAMPLE 26

A mixture of LiOH.H₂O (25 mg, 0.60 mmol) and trans-ethyl 2-(4-(5-chloro-2,2-dimethyl-2,3-dihydrobenzofuran-7-yl)phenethyl) cyclopropanecarboxylate (60 mg, 0.150 mmol) in THF (1 mL), water (0.5 mL) and MeOH (1 mL) was stirred at rt overnight. The reaction was partitioned between EtOAc (10 mL) and H₂O (2 mL). The aqueous layer was washed with EtOAc (2×10 mL). The organic extracts were extracted with H₂O (3×5 mL). The combined aqueous layers were acidified with 1N aq. HCl to pH ~3 and extracted with EtOAc (3×10 mL). The combined organic extracts were washed with brine (10 mL), dried over MgSO₄, and concentrated in vacuo. The crude product was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 MeCN:water with 0.1% TFA; Mobile Phase B: 95:5 MeCN:water with 0.1% TFA; Gradient: 50-90% B over 20 min, then a 5-min hold at 100% B; Flow: 20 mL/min. Fractions containing the desired product were combined and dried via centrifugal evaporation to provide the title compound (26 mg, 0.070 mmol, 47% yield). LCMS, [M−H]⁺=369.0. ¹H NMR (500 MHz, DMSO-d₆) δ 7.59 (d, J=8.3 Hz, 2H), 7.29-7.24 (m, 3H), 7.20 (s, 1H), 3.06 (s, 2H), 2.69 (t, J=7.6 Hz, 2H), 1.63-1.55 (m, 2H), 1.35 (dt, J=8.1, 4.2 Hz, 1H), 1.27-1.18 (m, 1H), 0.97 (dt, J=8.7, 4.2 Hz, 1H), 0.77-0.71 (m, 1H). HPLC-4: RT=2.06 min, purity=100%; HPLC-5: RT=2.42 min, purity=98%.

EXAMPLE 27

Trans-2-(4-(2-methyl-4-phenylthiazol-5-yl)phenethyl)cyclopropanecarboxylic acid (Single Enantiomer; Absolute Stereochemistry Shown is Arbitrary)

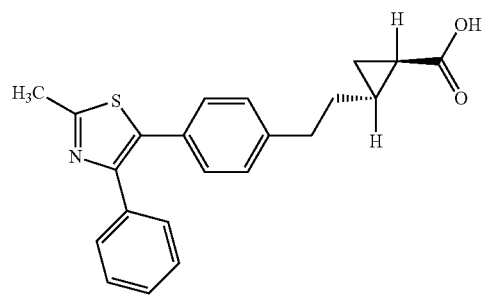 [SMILES: Cc1nc(-c2ccccc2)c(-c2ccc(CC[C@@H]3C[C@H]3C(=O)O)cc2)s1]

27A. Trans-ethyl 2-(4-(4,4,5,5-tetramethyl-1,3,2-dioxaborolan-2-yl)phenethyl) cyclopropanecarboxylate

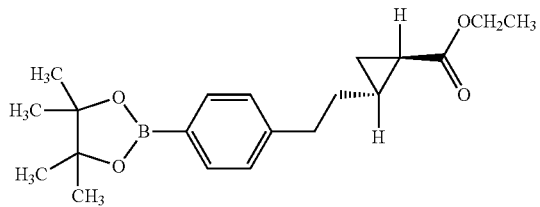

After a mixture of 26D (60 mg, 0.202 mmol), potassium acetate (59 mg, 0.606 mmol) and bis(pinacolato)diboron (62 mg, 0.242 mmol) in DMSO (1 mL) had been degassed with N₂ for 15 min, PdCl₂(dppf) (8 mg, 10.09 µmol) was added and the mixture was degassed again with N₂ for 15 min. The sealed reaction vessel was heated at 85° C. for 5 h, then was cooled to rt and filtered. The filter-cake was washed with EtOAc and the combined filtrates were concentrated in vacuo. The crude product was chromatographed (SiO₂; 12 g; continuous gradient from 0 to 10% Solvent B over 20 min, hold at 10% Solvent B for 10 min, where Solvent A=hexanes and Solvent B=EtOAc) to give the title compound (42 mg, 0.122 mmol, 60% yield) as a colorless oil. LCMS, [M+H]⁺=345.2.

27B. Trans-ethyl 2-(4-(2-methyl-4-phenylthiazol-5-yl)phenethyl) cyclopropanecarboxylate

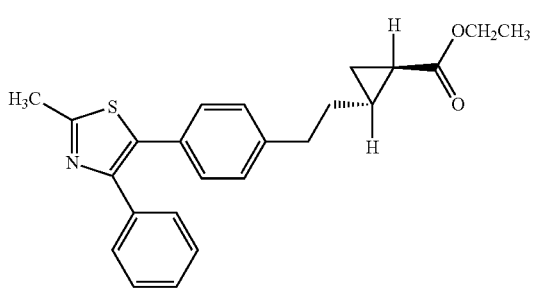 [SMILES: CCOC(=O)[C@@H]1C[C@H]1CCc1ccc(-c2sc(C)nc2-c2ccccc2)cc1]

A mixture of 27A (40 mg, 0.116 mmol), 5-bromo-2-methyl-4-phenylthiazole (59 mg, 0.232 mmol), Pd(PPh$_3$)$_4$ (13 mg, 0.012 mmol) and K$_2$CO$_3$ (48 mg, 0.349 mmol) in THF (3 mL) and water (1 mL) was heated in a microwave reactor at 130° C. for 20 min. under Ar, then was cooled to rt. The reaction was diluted with water (5 mL), and extracted with EtOAc (4×10 mL). The combined organic fractions were dried over MgSO$_4$, and concentrated in vacuo to give the crude title compound. This material was used directly for the next step without further purification. LCMS, [M+H]$^+$=392.1.

EXAMPLE 27

A solution of LiOH.H$_2$O (19 mg, 0.464 mmol) and 27B (45 mg, 0.116 mmol) in THF (1 mL), water (0.5 mL) and MeOH (1 mL) was stirred at rt overnight, then was partitioned between EtOAc (5 mL) and H$_2$O (15 mL). The aqueous layer was washed with EtOAc (2×10 mL). The combined organic layers were extracted with H$_2$O (3×10 mL). The combined aqueous extracts were acidified with 1N aq. HCl to pH ~3 and extracted with EtOAc (3×15 mL). The combined organic extracts were washed with brine (10 mL), dried over MgSO$_4$, and concentrated in vacuo. The crude product was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 MeCN:water with 0.1% TFA; Mobile Phase B: 95:5 MeCN:water with 0.1% TFA; Gradient: 50-90% B over 20 min, then a 5-min hold at 100% B; Flow: 20 mL/min. Fractions containing the desired product were combined and dried via centrifugal evaporation to provide the title compound (20 mg, 0.055 mmol, 48% yield) as a colorless oil. LCMS, [M−H]$^+$=362.0. $^1$H NMR (500 MHz, DMSO-d$_6$) δ 7.42 (dd, J=7.9, 1.5 Hz, 2H), 7.32-7.24 (m, 3H), 7.22-7.18 (m, 4H), 2.71-2.63 (m, 5H), 1.60-1.51 (m, 2H), 1.29 (dt, J=8.1, 4.1 Hz, 1H), 1.22-1.12 (m, 1H), 0.93-0.88 (m, 1H), 0.69-0.61 (m, 1H). HPLC-4: RT=1.66 min, purity=95%; HPLC-5: RT=1.89 min, purity=95%.

EXAMPLE 30

Trans-2-(2-(2'-fluoro-5'-isopropoxy-[1,1'-biphenyl]-4-yl)ethyl)cyclopropanecarboxylic acid (racemate)

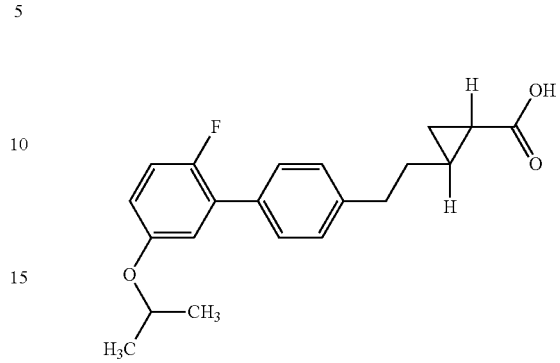

30A. (E)-Methyl 5-(4-bromophenyl)pent-2-enoate

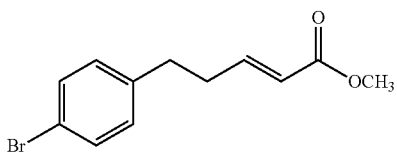 [SMILES: COC(=O)/C=C/CCc1ccc(Br)cc1]

Trimethyl phosphonoacetate (1 mL, 7.04 mmol) and DBU (1 mL, 7.04 mmol) was added to a suspension of LiCl (0.298 g, 7.04 mmol) in MeCN (10 mL) at 0° C. under N$_2$. The mixture was stirred at 0° C. for 30 min and 3-(4-bromophenyl)propanal (1.0 g, 4.69 mmol) was added. The reaction was warmed to rt and stirred for 2 h at rt, then was concentrated in vacuo. The residue was diluted with EtOAc, and the organic phase was washed in succession with 1N aq. HCl, sat. aq. NaHCO$_3$, and brine, dried over MgSO$_4$,and concentrated in vacuo. The crude oil was chromatographed (SiO$_2$; 80 g; gradient EtOAc/Hexanes from 0% to 15% over 30 min) to give the title compound (1.08 g, 4.01 mmol, 86% yield) as a white solid. LCMS, [M+H]$^+$=269.0. $^1$H NMR (500 MHz, CDCl$_3$) δ 7.44-7.39 (m, 2H), 7.08-7.04 (m, 2H), 6.97 (dt, J=15.4, 6.9 Hz, 1H), 5.84 (dt, J=15.7, 1.5 Hz, 1H), 3.73 (s, 3H), 2.74 (t, J=7.6 Hz, 2H), 2.54-2.48 (m, 2H).

30B. (E)-Methyl 5-(2'-fluoro-5'-isopropoxy-[1,1'-biphenyl]-4-yl)pent-2-enoate

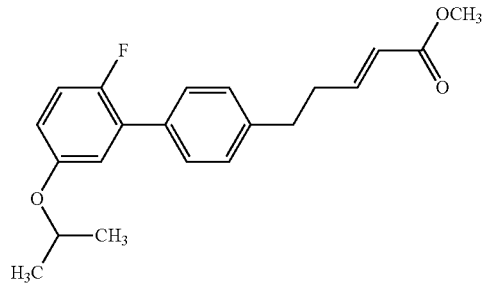 [SMILES: COC(=O)/C=C/CCc1ccc(-c2cc(OC(C)C)ccc2F)cc1]

A mixture of (E)-methyl 5-(4-bromophenyl)pent-2-enoate (100 mg, 0.372 mmol), (2-fluoro-5-isopropoxyphenyl)boronic acid (110 mg, 0.557 mmol), Pd(PPh₃)₄ (43 mg, 0.037 mmol) and K₂CO₃ (154 mg, 1.115 mmol) in THF (9 mL) and water (3 mL) was heated in a microwave reactor at 130° C. for 20 min. under Ar, then was cooled to rt. The reaction was diluted with water (5 mL), and extracted with EtOAc (4×20 mL). The combined organic extracts were dried over MgSO₄, and concentrated in vacuo. This crude product was chromatographed (SiO₂; 12 g; EtOAc/Hexanes gradient from 0 to 15% over 20 min) to afford the title compound (119 mg, 0.347 mmol, 93% yield) as a colorless oil. LCMS, [M+H]⁺=343.1.

30C. Trans-methyl 2-(2-(2'-fluoro-5'-isopropoxy-[1,1'-biphenyl]-4-yl)ethyl) cyclopropanecarboxylate

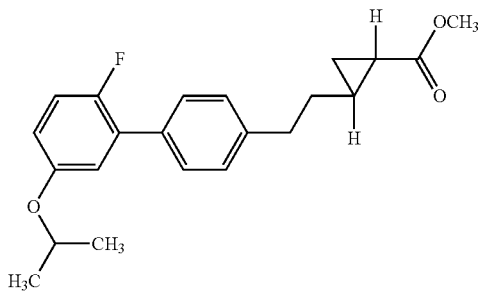 [SMILES: COC(=O)C1CC1CCc1ccc(-c2cc(OC(C)C)ccc2F)cc1]

30C was prepared using the same procedure as for the synthesis of Example 28C. The title compound was obtained (99 mg, 0.277 mmol, 99% yield) as a colorless oil. LCMS, [M+H]⁺=357.1. ¹H NMR (500 MHz, CDCl₃) δ 7.49-7.44 (m, 2H), 7.24 (d, J=8.3 Hz, 2H), 7.04 (dd, J=10.0, 8.9 Hz, 1H), 6.94 (dd, J=6.3, 3.0 Hz, 1H), 6.81 (dt, J=8.9, 3.5 Hz, 1H), 4.51 (dt, J=12.1, 6.1 Hz, 1H), 3.67 (s, 3H), 2.77 (t, J=7.6 Hz, 2H), 1.70-1.63 (m, 2H), 1.49-1.38 (m, 2H), 1.20 (dt, J=8.8, 4.4 Hz, 1H), 0.74 (ddd, J=8.1, 6.5, 4.4 Hz, 1H).

EXAMPLE 30

Example 30 was prepared using a procedure analogous to the synthesis of Example 28. The title compound was obtained (68 mg, 0.196 mmol, 71% yield) as a clear oil. LCMS, [M-H]⁺=341.1. ¹H NMR (500 MHz, CDCl₃) δ 7.49-7.45 (m, 2H), 7.25 (d, J=8.3 Hz, 2H), 7.04 (dd, J=10.0, 8.9 Hz, 1H), 6.96-6.92 (m, 1H), 6.81 (dt, J=8.9, 3.5 Hz, 1H), 4.51 (dt, J=12.1, 6.1 Hz, 1H), 2.78 (t, J=7.7 Hz, 2H), 1.71-1.65 (m, 2H), 1.56-1.48 (m, 1H), 1.42 (dt, J=8.2, 4.3 Hz, 1H), 1.27 (dt, J=8.8, 4.4 Hz, 1H), 0.83 (ddd, J=8.1, 6.5, 4.4 Hz, 1H). HPLC-1: RT=11.82 min, purity=99%; HPLC-2: RT=9.80 min, purity=96%.

EXAMPLE 31

(1R,2R)-2-(2-(2'-fluoro-5'-isopropoxy-[1,1'-biphenyl]-4-yl)ethyl)cyclopropane carboxylic acid

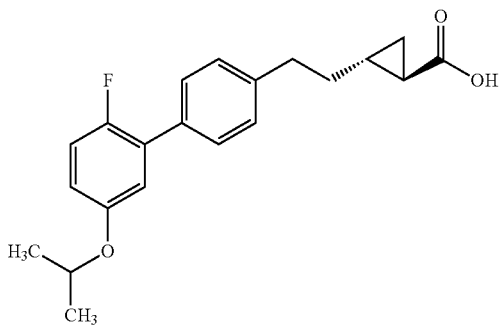 [SMILES: CC(C)Oc1ccc(F)c(-c2ccc(CC[C@@H]3C[C@H]3C(=O)O)cc2)c1]

(Enantiomer 1, absolute stereochemistry drawn in an arbitrary manner) and

EXAMPLE 32

(1S,2S)-2-(2-(2'-fluoro-5'-isopropoxy-[1,1'-biphenyl]-4-yl)ethyl)cyclopropane carboxylic acid

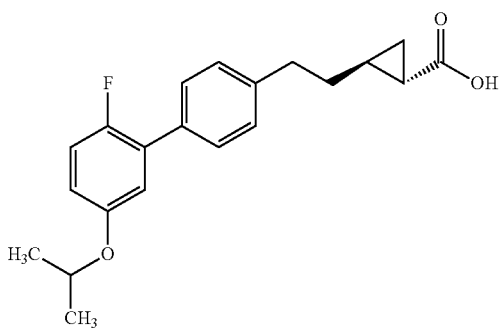 [SMILES: CC(C)Oc1ccc(F)c(-c2ccc(CC[C@H]3C[C@@H]3C(=O)O)cc2)c1]

(Enantiomer 2, absolute stereochemistry drawn in an arbitrary manner)

The two enantiomers of Example 30 were separated by chiral preparative HPLC (Instrument: Berger Multigram II SFC; Column: CHIRALPAK® AD-H, 21×250 mm, 5µ; Mobile Phase: 10% MeOH/90% CO₂; Flow Conditions: 45 mL/min, 100 Bar, 35° C.; Detector Wavelength: 246 nm; Injection Details: 0.5 mL of ~32 mg/mL in MeOH).

Example 31: Enantiomer 1: LCMS, [M-H]⁺=341.2. ¹H NMR (500 MHz, CDCl₃) δ 7.47 (dd, J=8.3, 1.4 Hz, 2H), 7.25 (d, J=8.0 Hz, 2H), 7.04 (dd, J=10.0, 8.9 Hz, 1H), 6.97-6.92 (m, 1H), 6.80 (dt, J=8.9, 3.5 Hz, 1H), 4.51 (dt, J=12.1, 6.1 Hz, 1H), 2.78 (t, J=7.6 Hz, 2H), 1.72-1.64 (m, 2H), 1.56-1.38 (m, 2H), 1.35 (d, J=6.1 Hz, 6H), 1.29-1.23 (m, 1H), 0.84-0.78 (m, 1H). HPLC-1: Rt=11.89 min, purity=98%; HPLC-2: RT=9.89 min, purity=96%.

Example 32: Enantiomer 2: LCMS, [M-H]⁺=341.2. ¹H NMR (500 MHz, CDCl₃) δ 7.46 (dd, J=8.0, 1.4 Hz, 2H), 7.25 (d, J=8.3 Hz, 2H), 7.04 (dd, J=9.9, 9.1 Hz, 1H), 6.94 (dd, J=6.3, 3.0 Hz, 1H), 6.80 (dt, J=8.9, 3.5 Hz, 1H), 4.51 (dt, J=12.1, 6.1 Hz, 1H), 2.78 (t, J=7.6 Hz, 2H), 1.72-1.64 (m, 2H), 1.55-1.38 (m, 2H), 1.35 (d, J=6.1 Hz, 6H), 1.30-

EXAMPLE 33

Trans-2-(2-((2'-fluoro-5'-isopropoxy-[1,1'-biphenyl]-4-yl)methyl)cyclopropyl)acetic acid (racemate)

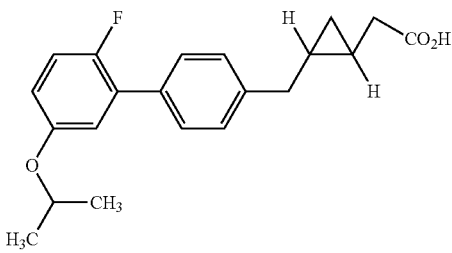 [SMILES: CC(C)Oc1ccc(F)c(-c2ccc(CC3CC3CC(=O)O)cc2)c1]

33A. Trans-methyl 4-(4-bromophenyl)but-2-enoate

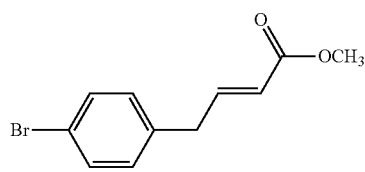 [SMILES: COC(=O)/C=C/Cc1ccc(Br)cc1]

A mixture of 1-allyl-4-bromobenzene (0.64 g, 3.25 mmol), methyl acrylate (0.877 mL, 9.74 mmol), Grubbs 2nd generation metathesis catalyst (0.138 g, 0.162 mmol), and CuI (0.031 g, 0.162 mmol) in THF (5 mL) was stirred at 40° C. under N₂ for 3 h, then was filtered. The filtrate was concentrated in vacuo and chromatographed (SiO₂; gradient from 0% to 30% EtOAc:hexanes) to give the title compound (0.677 g, 2.65 mmol, 82% yield) as clear oil. ¹H NMR (500 MHz, CDCl₃) δ 7.52-7.43 (m, 2H), 7.13-7.03 (m, 3H), 5.83 (dt, J=15.4, 1.7 Hz, 1H), 3.75 (s, 3H), 3.50 (dd, J=6.9, 1.4 Hz, 2H).

33B. Trans-methyl 2-(4-bromobenzyl)cyclopropanecarboxylate (racemate)

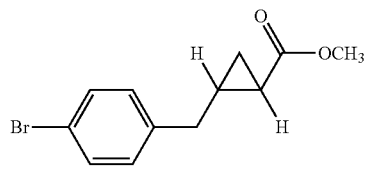 [SMILES: COC(=O)C1CC1Cc1ccc(Br)cc1]

To a vigorously stirred mixture of Et₂O (10 mL) and 40% KOH (10 mL) was added N-methyl-N'-nitro-N-nitrosoguanidine (0.781 g, 5.31 mmol) portionwise over 15 min at 0° C. Upon completion of the addition, stirring was stopped. The organic layer was separated and dried with KOH pellets. The 0° C. ethereal solution was poured into a 0° C. solution of trans-methyl 4-(4-bromophenyl)but-2-enoate (0.677 g, 2.65 mmol) in THF (5 mL). Pd(OAc)₂ (0.060 g, 0.265 mmol) was then added and the reaction was allowed to warm to rt and stirred at rt for 1 h. Volatiles were removed in vacuo and the residue was chromatographed (SiO₂; gradient from 0 to 30% EtOAc:hexanes) to give the title compound (0.70 g, 2.60 mmol, 98% yield) as a clear oil. ¹H NMR (50 OMHz, CDCl₃) δ 7.46-7.42 (m, 2H), 7.11 (d, J=8.3 Hz, 2H), 3.69 (s, 3H), 2.72-2.65 (m, 1H), 2.62-2.56 (m, 1H), 1.72-1.64 (m, 1H), 1.54 (dt, J=8.4, 4.3 Hz, 1H), 1.27 (dt, J=8.7, 4.6 Hz, 1H), 0.85 (ddd, J=8.3, 6.3, 4.4 Hz, 1H)

33C. Trans-(2-(4-bromobenzyl)cyclopropyl)methanol (racemate)

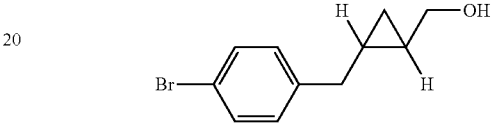

LiAlH₄ (197 mg, 5.20 mmol) was added portionwise to a solution of trans-methyl 2-(4-bromobenzyl)cyclopropanecarboxylate (0.70 g, 2.60 mmol) in THF (5 mL) at 0° C. The reaction was allowed to warm to rt and stirred at rt for 3 h. CELITE® (1 g) was added and the reaction was cooled to −78° C. and quenched with sat'd aq. NH₄Cl (1 mL), then was allowed to warm to rt and stirred at rt for 30 min, after which MgSO₄ (1 g) was added. The mixture was stirred at rt for 30 min and filtered. The filtrate was concentrated in vacuo and chromatographed (SiO₂; gradient from 0% to 30% EtOAc:hexanes) to afford the title compound (470 mg, 1.949 mmol, 74.9% yield) as a clear oil. ¹H NMR (400 MHz, CDCl₃) δ 7.45-7.36 (m, 2H), 7.12 (d, J=8.3 Hz, 2H), 3.54-3.38 (m, 2H), 2.59-2.51 (m, 2H), 1.40 (br. s., 1H), 1.07-0.95 (m, 1H), 0.95-0.83 (m, 1H), 0.56-0.43 (m, 2H).

33D. Trans-(2-(4-bromobenzyl)cyclopropyl)methyl-methanesulfonate (racemate)

MsCl (0.182 mL, 2.339 mmol) was added portionwise to a 0° C. solution of trans-(2-(4-bromobenzyl)cyclopropyl)methanol (470 mg, 1.949 mmol) and TEA (0.543 mL, 3.90 mmol) in DCM (5 mL). The reaction was allowed to warm to rt and stirred at rt for 18 h, then was concentrated in vacuo. The residue was dissolved in EtOAc (5 mL) and washed with 1N aq. HCl and water. The organic layer was dried over MgSO₄ and concentrated in vacuo to give the crude title compound (622 mg, 1.949 mmol, 100% yield) as a yellowish oil, which was used in the next step without further purification.

33E. Trans-2-(2-(4-bromobenzyl)cyclopropyl)acetonitrile (racemate)

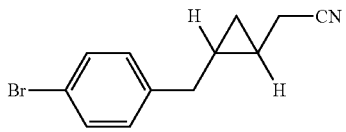 [SMILES: N#CCC1CC1Cc1ccc(Br)cc1]

A mixture of trans-(2-(4-bromobenzyl)cyclopropyl)methylmethanesulfonate (622 mg, 1.95 mmol) and NaCN (955 mg, 19.5 mmol) in DMSO (10 mL) was stirred at 100° C. for 18 h, then was cooled to rt and dissolved in EtOAc (5 mL). The solution was washed with water (2×), dried (MgSO$_4$) and concentrated in vacuo. The crude oil was chromatographed (SiO$_2$; continuous gradient from 0 to 20% EtOAc:hexanes) to give the title compound (130 mg, 0.520 mmol, 26.7% yield) as a clear oil. $^1$H NMR (500 MHz, CDCl$_3$) δ 7.46-7.42 (m, 2H), 7.14-7.09 (m, 2H), 2.67-2.51 (m, 2H), 2.43-2.39 (m, 2H), 1.07-0.93 (m, 2H), 0.66-0.57 (m, 2H).

33F. Trans-methyl 2-(2-(4-bromobenzyl)cyclopropyl)acetate (racemate)

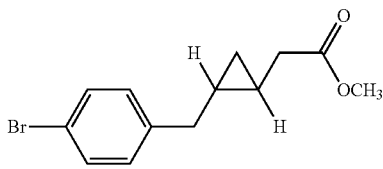 [SMILES: COC(=O)CC1CC1Cc1ccc(Br)cc1]

A mixture of acetyl chloride (0.370 mL, 5.20 mmol) and MeOH (2.103 mL, 52.0 mmol) was stirred at 0° C. for 30 min. Trans-2-(2-(4-bromobenzyl)cyclopropyl) acetonitrile (130 mg, 0.520 mmol) was then added. The reaction was stirred at rt for 18 h, then was concentrated in vacuo. The residue was dissolved in EtOAc (5 mL) and washed with water. The organic layer was dried (MgSO$_4$) and concentrated in vacuo. The residue was chromatographed on SiO$_2$ (gradient from 0% to 30% EtOAc:hexanes) to give the title compound (134 mg, 0.473 mmol, 91% yield) as a clear oil. $^1$H NMR (500 MHz, CDCl$_3$) δ 7.41-7.36 (m, 2H), 7.11-7.07 (m, 2H), 3.61 (s, 3H), 2.53 (d, J=6.9 Hz, 2H), 2.24 (qd, J=15.8, 7.2 Hz, 2H), 1.00-0.92 (m, 1H), 0.86-0.78 (m, 1H), 0.48 (dt, J=8.3, 5.1 Hz, 1H), 0.43 (dt, J=8.3, 5.0 Hz, 1H).

33G. Trans-methyl 2-(2-((2'-fluoro-5'-isopropoxy-[1,1'-biphenyl]-4-yl)methyl) cyclopropyl)acetate (racemate)

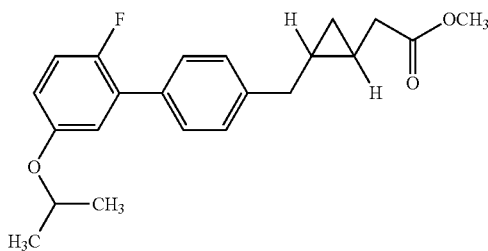 [SMILES: COC(=O)CC1CC1Cc1ccc(-c2cc(OC(C)C)ccc2F)cc1]

A mixture of trans-methyl 2-(2-(4-bromobenzyl)cyclopropyl)acetate (130 mg, 0.459 mmol), (2-fluoro-5-isopropoxyphenyl)boronic acid (109 mg, 0.551 mmol), and K$_2$CO$_3$ (317 mg, 2.30 mmol) in 1,4-dioxane (5 mL) and water (0.5 mL) was degassed with N$_2$ for 10 min and then Pd(Ph$_3$P)$_4$ (27 mg, 0.023 mmol) was added at rt. The reaction mixture was heated at 100° C. under N$_2$ for 2 h, then was cooled to rt and MgSO$_4$ was added. The mixture was filtered and the filtrate was concentrated in vacuo. The residue was chromatographed (SiO$_2$; gradient from 0 to 30% EtOAc:hexanes) to give the title compound (148 mg, 0.415 mmol, 90% yield) as a clear oil. LCMS [M+NH$_4$]+=374.3; $^1$H NMR (500 MHz, CDCl$_3$) δ 7.50 (dd, J=8.3, 1.7 Hz, 2H), 7.33 (d, J=8.5 Hz, 2H), 7.06 (dd, J=9.9, 9.1 Hz, 1H), 6.97 (dd, J=6.5, 3.2 Hz, 1H), 6.83 (dt, J=8.9, 3.5 Hz, 1H), 4.53 (dt, J=12.1, 6.1 Hz, 1H), 3.65 (s, 3H), 2.67 (d, J=6.9 Hz, 2H), 2.32-2.28 (m, 2H), 1.37 (d, J=6.1 Hz, 6H), 1.08-1.00 (m, 1H), 0.98-0.90 (m, 1H), 0.57 (dt, J=8.3, 5.1 Hz, 1H), 0.49 (dt, J=8.3, 5.0 Hz, 1H); $^{19}$F NMR (471 MHz, CDCl$_3$) δ −128.61 (s, 1F).

EXAMPLE 33

A mixture of trans-methyl 2-(2-((2'-fluoro-5'-isopropoxy-[1,1'-biphenyl]-4-yl)methyl)cyclopropyl)acetate (148 mg, 0.415 mmol) and 1N aq. NaOH (0.415 mL, 0.415 mmol) in THF (3 mL) was stirred at rt for 4 h and then concentrated in vacuo. The residue was diluted with EtOAc, washed successively with 1N aq. HCl and water, then was concentrated in vacuo. The residue was purified by preparative HPLC (PHENOMENEX® Axia 5μ C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to give the title compound (118 mg, 0.327 mmol, 79% yield) as a clear oil. LCMS [M−H]$^+$=341.1; $^1$H NMR (500 MHz, CDCl$_3$) δ 7.53-7.46 (m, 2H), 7.33 (d, J=8.3 Hz, 2H), 7.10-7.03 (m, 1H), 6.98 (dd, J=6.5, 3.2 Hz, 1H), 6.83 (dt, J=8.9, 3.4 Hz, 1H), 4.57-4.49 (m, 1H), 2.74 (dd, J=14.9, 6.6 Hz, 1H), 2.65-2.58 (m, 1H), 2.42-2.26 (m, 2H), 1.40-1.33 (m, 6H), 1.08-1.00 (m, 1H), 0.99-0.90 (m, 1H), 0.59 (dt, J=8.2, 5.0 Hz, 1H), 0.51 (dt, J=8.4, 4.9 Hz, 1H); $^{19}$F NMR (471 MHz, CDCl$_3$) δ −128.53 (s, 1F).

EXAMPLE 34

Cis-2-(2-((2'-fluoro-5'-isopropoxy-[1,1'-biphenyl]-4-yl)methyl)cyclopropyl)acetic acid (racemate)

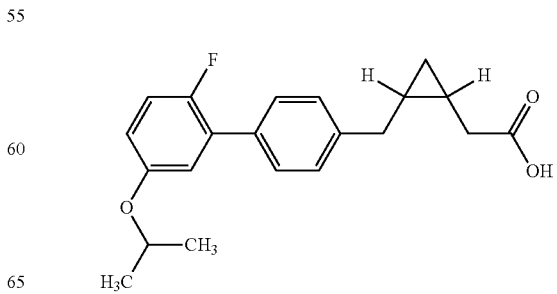

34A. 2-(4-Bromophenyl)acetaldehyde

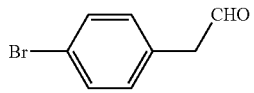

DIBAL-H (4.64 mL of a 1.0 M solution in DCM, 4.64 mmol) was added dropwise to a solution of 2-(4-bromophenyl)acetonitrile (0.70 g, 3.57 mmol) in DCM (50 mL) at rt under $N_2$. The reaction mixture was stirred at −78° C. for 2 h, after which 1 N aq. HCl (40 mL) was added. The aqueous phase was extracted with $CH_2Cl_2$(3×20 mL). The combined organic extracts were dried with $Na_2SO_4$ and concentrated in vacuo. The residue was chromatographed on $SiO_2$ (gradient from 0% to 50% EtOAc:hexanes) to afford the title compound (0.42 g, 2.110 mmol, 59.1% yield) as a clear yellowish oil. $^1$H NMR (500 MHz, $CDCl_3$) δ 9.76 (t, J=2.1 Hz, 1H), 7.51 (d, J=8.5 Hz, 2H), 7.11 (d, J=8.3 Hz, 2H), 3.68 (d, J=2.2 Hz, 2H).

34B. Cis-methyl 4-(4-bromophenyl)but-2-enoate

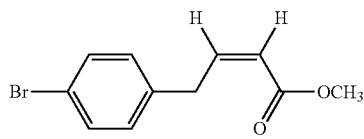 [SMILES: COC(=O)/C=C\Cc1ccc(Br)cc1]

To a −78° C. solution of bis(2,2,2-trifluoroethylmethoxycarbonylmethyl) phosphonate (0.536 mL, 2.53 mmol) and 18-Crown-6 (2.79 g, 10.55 mmol) in THF (10 mL) was added KHMDS (5.06 mL of a 0.5M solution in toluene, 2.53 mmol) dropwise. The reaction mixture was stirred at −78° C. for 15 min, after which a solution of 2-(4-bromophenyl)acetaldehyde (0.42 g, 2.11 mmol) in THF (4 mL) was added dropwise over 15 min. The reaction mixture was stirred at −78° C. for 30 min and then quenched with satd. aq. $NH_4Cl$ (10 mL). The mixture was allowed to warm to rt and extracted with EtOAc (3×). The combined organic extracts were dried over $MgSO_4$ and concentrated in vacuo. The residue was chromatographed ($SiO_2$; gradient from 0% to 20% EtOAc: hexanes) to afford the title compound (0.22 g, 0.862 mmol, 40.9% yield) as a light yellowish clear oil. $^1$H NMR (500 MHz, $CDCl_3$) δ 7.45-7.38 (m, 2H), 7.11 (d, J=8.5 Hz, 2H), 6.32 (dt, J=11.4, 7.5 Hz, 1H), 5.89 (dt, J=11.3, 1.8 Hz, 1H), 3.99 (dd, J=7.6, 1.5 Hz, 2H), 3.76 (s, 3H).

34C. Cis-methyl 2-(4-bromobenzyl)cyclopropanecarboxylate (racemate)

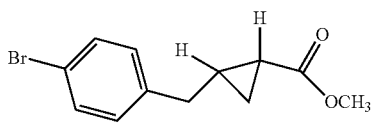 [SMILES: COC(=O)C1CC1Cc1ccc(Br)cc1]

To a vigorously stirred mixture of $Et_2O$ (5 mL) and 40% KOH (3 mL) was added a 50% solution of N-methyl-N'-nitro-N-nitrosoguanidine (1.015 g, 3.45 mmol) in water portionwise over 15 min at 0° C. Upon completion of addition, stirring was stopped. The organic layer was separated and dried over KOH pellets. The ethereal diazomethane solution was poured into a solution of cis-methyl 4-(4-bromophenyl)but-2-enoate (0.220 g, 0.862 mmol) in THF (5 mL). Pd(OAc)$_2$ (0.019 g, 0.086 mmol) was then added and the reaction was allowed to warm to rt and stirred for 1 h at rt. Volatiles were removed in vacuo and the residue was chromatographed on $SiO_2$ (0% to 20% EtOAc:hexanes) to give the title compound (0.129 g, 0.479 mmol, 55.6% yield) as a clear oil. $^1$H NMR (500 MHz, $CDCl_3$) δ 7.43-7.39 (m, 2H), 7.12-7.06 (m, 2H), 3.69 (s, 3H), 2.95-2.74 (m, 2H), 1.82 (ddd, J=8.7, 7.8, 5.8 Hz, 1H), 1.58-1.49 (m, 1H), 1.18-1.12 (m, 2H); $^{13}$C NMR (126 MHz, $CDCl_3$) δ 173.8, 140.3, 131.4, 130.0, 119.8, 51.8, 32.3, 22.5, 18.3, 13.9.

34D. Cis-2-(4-bromobenzyl)cyclopropanecarboxylic acid (racemate)

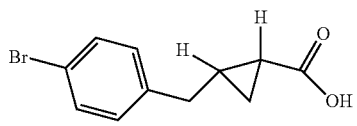 [SMILES: O=C(O)C1CC1Cc1ccc(Br)cc1]

A mixture of cis-methyl 2-(4-bromobenzyl)cyclopropanecarboxylate (0.129 g, 0.479 mmol) and conc. HCl (0.472 g, 4.79 mmol) in HOAc (1 mL) was stirred at 45° C. for 3 days, then was taken up in EtOAc (10 mL). The mixture was washed with water (5 mL×4), dried (MgSO$_4$) and concentrated in vacuo. The residue was chromatographed (SiO$_2$; gradient from 0 to 100% EtOAc:hexanes) to give the title compound (0.103 g, 0.404 mmol, 84% yield) as a light yellowish solid. $^1$H NMR (500 MHz, $CDCl_3$) δ 7.46-7.40 (d, J=8.2 Hz, 2H), 7.15-7.11 (d, J=8.2 Hz, 2H), 2.99-2.85 (h, J=7.6 Hz, 2H), 1.88-1.79 (m, 1H), 1.67-1.55 (m, 1H), 1.28-1.15 (m, 2H).

34E. Cis-1-(2-(4-bromobenzyl)cyclopropyl)-2-diazoethanone racemate)

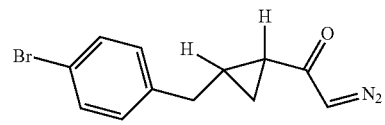

Oxalyl chloride (0.392 mL of a 2M solution in hexane, 0.784 mmol) was added to a solution of cis-2-(4-bromobenzyl)cyclopropanecarboxylic acid (0.1 g, 0.392 mmol) in DCM (1 mL) along with a catalytic amount of DMF at 0° C. The reaction was stirred at rt for 1 h and then concentrated in vacuo. The residue was dissolved in THF/MeCN (1:1, 1 mL) and Me$_3$SiCHN$_2$ (0.294 mL of a 2M solution in hexane, 0.588 mmol) was added at 0° C. The reaction was allowed to warm to rt and stirred at rt for 1 h, then was concentrated in vacuo to give the crude title compound (0.10 g, 0.358 mmol, 91% yield) as a yellowish oil, which was used in the next step without further purification.

34F. Cis-methyl 2-(2-(4-bromobenzyl)cyclopropyl)acetate (racemate)

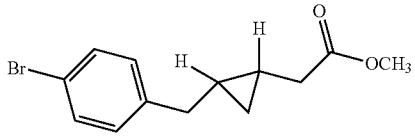 [SMILES: COC(=O)CC1CC1Cc1ccc(Br)cc1]

A solution of silver benzoate (0.164 g, 0.717 mmol) in TEA (0.250 mL, 1.79 mmol) was added dropwise to a solution of cis-1-(2-(4-bromobenzyl)cyclopropyl)-2-diazoethanone (0.1 g, 0.358 mmol) in MeOH (1 mL) at 0° C. under $N_2$. The reaction mixture was stirred at rt for 2 h, then was filtered. The filtrate was concentrated in vacuo. The residue was dissolved in EtOAc (5 mL) and washed with 1N aq. HCl, water, and concentrated in vacuo. The residue was purified on prep. HPLC (PHENOMENEX® Axia 5μ C18 30×100 mm column; detection at 220 nm; flow rate=40 mL/min; continuous gradient from 30% B to 100% B over 10 min+2 min hold time at 100% B, where A=90:10:0.1 $H_2O$:MeOH:TFA and B=90:10:0.1 MeOH:$H_2O$:TFA) to give the title compound (0.035 g, 0.124 mmol, 34.5% yield) as a light yellowish oil. $^1$H NMR (500 MHz, CDCl$_3$) δ 7.45-7.40 (d, J=8.4 Hz, 2H), 7.18-7.13 (d, J=8.4 Hz, 2H), 3.72-3.67 (s, 3H), 2.74-2.65 (dd, J=15.4, 6.6 Hz, 1H), 2.57-2.49 (dd, J=15.3, 8.0 Hz, 1H), 2.46-2.33 (m, 2H), 1.33-1.22 (m, 1H), 1.20-1.10 (m, 1H), 0.94-0.85 (td, J=8.5, 5.0 Hz, 1H), 0.14-0.07 (q, J=5.4 Hz, 1H); $^{13}$C NMR (126 MHz, CDCl$_3$) δ 173.93, 140.69, 131.35, 129.90, 119.62, 51.71, 33.99, 33.86, 15.95, 11.85, 11.21.

34G. Cis-2-(2-((2'-fluoro-5'-isopropoxy-[1,1'-biphenyl]-4-yl)methyl)cyclopropyl)acetic acid (racemate)

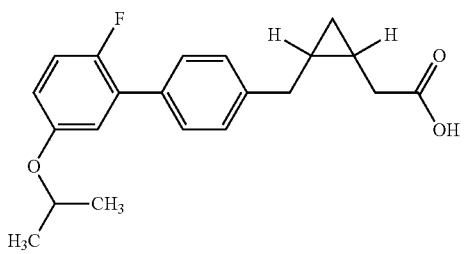 [SMILES: CC(C)Oc1ccc(F)c(-c2ccc(CC3CC3CC(=O)O)cc2)c1]

The title compound was prepared using the same sequence as for the synthesis of Example 33G and 33H from 34F. The title compound (40 mg, 0.111 mmol, 90% yield) was obtained as a light brownish oil. LCMS [M−H]$^+$=341.1; $^1$H NMR (CDCl$_3$) δ: 9.75-9.55 (s.b, 1H), 7.55-7.48 (dd, J=8.2, 1.7 Hz, 2H), 7.42-7.32 (m, 2H), 7.12-7.02 (dd, J=10.1, 8.9 Hz, 1H), 7.03-6.94 (dd, J=6.5, 3.1 Hz, 1H), 6.88-6.79 (dt, J=8.9, 3.4 Hz, 1H), 4.58-4.47 (p, J=6.0 Hz, 1H), 2.88-2.60 (m, 2H), 2.60-2.40 (m, 2H), 1.45-1.18 (m, 8H), 1.01-0.88 (td, J=8.4, 4.9 Hz, 1H), 0.24-0.12 (q, J=5.4 Hz, 1H); $^{19}$F NMR (CDCl$_3$) δ: −128.47 (s).

EXAMPLE 35

Trans-(2-((2'-fluoro-5'-isopropoxy-[1,1'-biphenyl]-4-yl)methyl)cyclopropyl)acetic acid (Enantiomer 1)

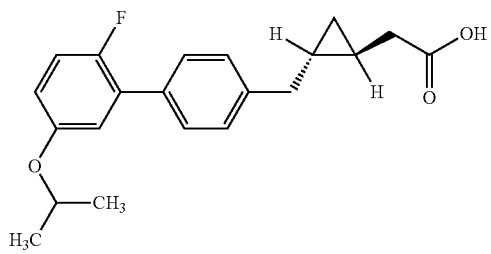 [SMILES: CC(C)Oc1ccc(F)c(-c2ccc(C[C@@H]3C[C@H]3CC(=O)O)cc2)c1]

and

EXAMPLE 36

Trans-(2-((2'-fluoro-5'-isopropoxy-[1,1'-biphenyl]-4-yl)methyl)cyclopropyl)acetic acid (Enantiomer 2)

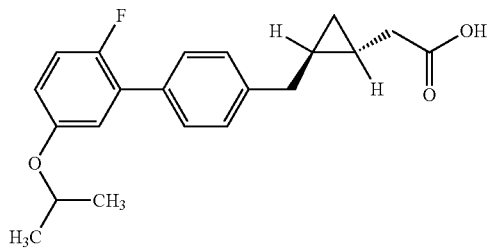 [SMILES: CC(C)Oc1ccc(F)c(-c2ccc(C[C@H]3C[C@@H]3CC(=O)O)cc2)c1]

The individual enantiomers Example 35 and Example 36 were separated from racemic Example 33 by chiral preparative HPLC (CHIRALPAK® AD-H, 20×250 mm, 5 μm column; detection at 254 nm; flow rate=45 mL/min, 100 Bar, 35° C.; Mobile Phase: 15% iPrOH/85% CO$_2$; Injection: 1 mL of 50 mg/mL iPrOH) to afford Example 35 as the faster eluting isomer on HPLC and Example 36 as the slower eluting isomer on HPLC.

Analysis for Example 35 (Enantiomer 1, clear oil): [M−H]$^+$=341.1; $^1$H NMR (CDCl$_3$) δ: 7.54-7.46 (m, 2H), 7.37-7.30 (d, J=7.7 Hz, 2H), 7.10-7.03 (dd, J=10.1, 8.9 Hz, 1H), 7.02-6.96 (dd, J=6.4, 3.1 Hz, 1H), 6.87-6.80 (dt, J=8.9, 3.5 Hz, 1H), 4.62-4.45 (hept, J=6.1 Hz, 1H), 2.81-2.57 (ddd, J=61.6, 14.8, 6.6 Hz, 2H), 2.54-2.20 (s, 2H), 1.42-1.33 (d, J=6.1 Hz, 6H), 1.10-0.88 (m, 2H), 0.66-0.45 (m, 2H); $^{19}$F NMR (CDCl$_3$) δ: −128.49 (s).

Analysis for Example 36 (Enantiomer 2, clear oil): [M−H]$^+$=341.1; $^1$H NMR (CDCl$_3$) δ: 7.54-7.46 (m, 2H), 7.37-7.30 (d, J=7.7 Hz, 2H), 7.10-7.03 (dd, J=10.1, 8.9 Hz, 1H), 7.02-6.96 (dd, J=6.4, 3.1 Hz, 1H), 6.87-6.80 (dt, J=8.9, 3.5 Hz, 1H), 4.62-4.45 (hept, J=6.1 Hz, 1H), 2.81-2.57 (ddd, J=61.6, 14.8, 6.6 Hz, 2H), 2.54-2.20 (s, 2H), 1.42-1.33 (d, J=6.1 Hz, 6H), 1.10-0.88 (m, 2H), 0.66-0.45 (m, 2H); $^{19}$F NMR (CDCl$_3$) δ: −128.49 (s); analytical chiral HPLC (Instrument: Berger; Column: AD-H, 4.6×250 mm, 5μ; Mobile Phase: 15% Isopropanol/85% CO$_2$; Flow Conditions: 2.0 mL/min, 100 Bar, 35° C.; Detector Wavelength: 254 nm; Injection Details: 10 μL of 1 mg/mL in isopropanol): RT=14.8 min for Example 35; RT=18.0 min for Example 36.

EXAMPLE 37

Trans-2-((2'-fluoro-5'-isopropoxy-[1,1'-biphenyl]-4-yl)methoxy)cyclopropanecarboxylic acid

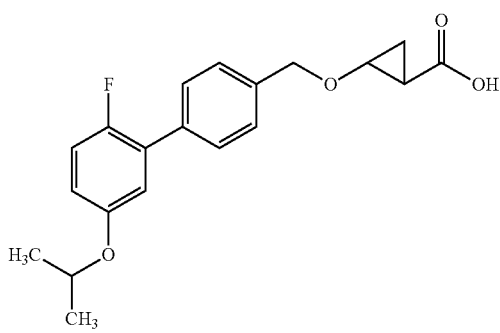 [SMILES: CC(C)Oc1ccc(F)c(-c2ccc(COC3CC3C(=O)O)cc2)c1]

37A. 1-Bromo-4-((vinyloxy)methyl)benzene

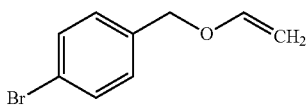

To a rt solution of (4-bromophenyl)methanol (1 g, 5.35 mmol) and ethoxyethene (6.43 ml, 64.2 mmol) added Hg(OAc)$_2$ (0.060 g, 0.188 mmol) and the reaction mixture was heated to 50° C. More Hg(OAc)$_2$ (20 mg) was added, and the reaction mixture was heated at 50° C. for 5.5 h, then was cooled to rt and partitioned between EtOAc and aq. K$_2$CO$_3$. The organic layer was washed with water and brine, dried (MgSO$_4$), and concentrated in vacuo. The residue was chromatographed on SiO$_2$ (gradient from 0% to 30% EtOAc:hexanes) to give the title compound as a colorless oil. (550 mg, 47.3% yield; 98% purity). $^1$H NMR (400 MHz, CDCl$_3$) δ 7.53-7.45 (m, 2H), 7.23 (d, J=8.6 Hz, 2H), 6.54 (dd, J=14.3, 6.8 Hz, 1H), 4.71 (s, 2H), 4.28 (dd, J=14.3, 2.2 Hz, 1H), 4.09 (dd, J=6.8, 2.2 Hz, 1H) Retention time=7.28 min (Agilent ZORBAX® S3.5 ODS 4.6×75 mm column; detection at 220 nm; flow rate=2.5 mL/min; continuous gradient from 0% B to 100% B over 8 min+2 min hold time at 100% B, where A=90:10:0.2 H$_2$O:MeOH:H$_3$PO$_4$ and B=90:10:0.2 MeOH:H$_2$O: H$_3$PO$_4$).

37B. Trans-ethyl 2-((4-bromobenzyl)oxy)cyclopropanecarboxylate

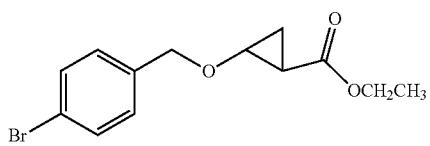 [SMILES: CCOC(=O)C1CC1OCc1ccc(Br)cc1]

To a 40° C. solution of 1-bromo-4-((vinyloxy)methyl) benzene (150 mg, 0.704 mmol) and Rh$_2$(OAc)$_4$ (31 mg, 0.070 mmol) in DCM (4 mL) was added ethyl diazoacetate (0.110 mL, 1.06 mmol) in DCM (4 mL) over 2 h. The reaction mixture was heated at 40° C. for 1 h, then was cooled to rt and stirred at rt overnight. The mixture was filtered through CELITE®; the filtrate was concentrated in vacuo and chromatographed on SiO$_2$ (gradient from 0% to 30% EtOAc:hexanes) to give the desired trans isomer (a later eluting fraction on HPLC; 80 mg, 19% yield) as a colorless oil. $^1$H NMR (400 MHz, CDCl$_3$) δ 7.47 (d, J=8.4 Hz, 2H), 7.19 (d, J=8.4 Hz, 2H), 4.53 (s, 2H), 4.16-4.06 (t, 2H), 3.65 (td, J=5.4, 2.1 Hz, 1H), 1.85-1.71 (m, 1H), 1.35-1.21 (m, 5H).

37C. Trans-ethyl 2-((2'-fluoro-5'-isopropoxy-[1,1'-biphenyl]-4-yl)methoxy) cyclopropanecarboxylate

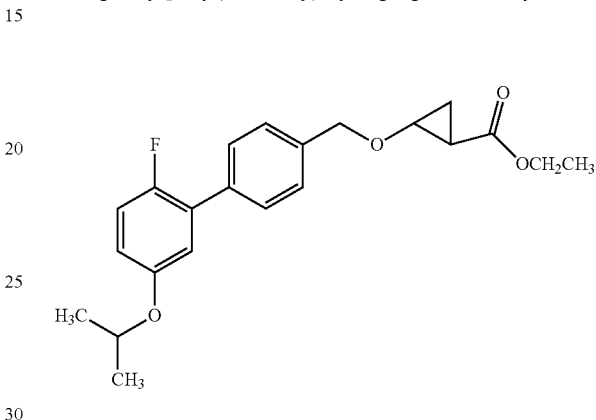

To a solution of trans-ethyl 2-((4-bromobenzyl)oxy)cyclopropanecarboxylate (40 mg, 0.134 mmol), (2-fluoro-5-isopropoxyphenyl)boronic acid (26.5 mg, 0.134 mmol) and Cs$_2$CO$_3$ (131 mg, 0.401 mmol) in (DMF/H$_2$O 10:1) was added Pd(Ph$_3$P)$_4$ (8 mg, 6.7 μmol). The reaction mixture was heated to 80° C. for 6 h, then was cooled to RT and diluted with EtOAc. The mixture was washed with water and brine, dried (MgSO$_4$), and concentrated in vacuo. The residue was chromatographed (SiO$_2$; gradient from 0% to 30% EtOAc: hexanes) to give the title compound (15 mg, 39% yield) as a colorless oil. [M+Na]$^+$=395.

EXAMPLE 37

To a solution of trans-ethyl 2-((2'-fluoro-5'-isopropoxy-[1,1'-biphenyl]-4-yl)methoxy)cyclopropanecarboxylate (15 mg, 0.024 mmol) in THF (1.5 mL)/MeOH (0.05 mL) was added NaOH (0.400 mL, 0.4 mmol). The reaction mixture was stirred at rt for 5 h, then was diluted with EtOAc. The reaction mixture was washed with water and brine, dried (MgSO$_4$), and concentrated in vacuo. The residue was purified by preparative HPLC (PHENOMENEX® Axia 5μ C18 30×100 mm column; detection at 220 nm; flow rate=40 mL/min; continuous gradient from 30% B to 100% B over 10 min+5 min hold time at 100% B, where A=90:10:0.1 H$_2$O:MeOH:TFA and B=90:10:0.1 MeOH:H$_2$O:TFA) to give the title compound (2 mg, 14% yield) as a colorless oil. [M−H]+=343.2. $^1$H NMR (400 MHz, CDCl$_3$) δ 7.53 (dd, J=8.3, 1.7 Hz, 2H), 7.39 (d, J=8.4 Hz, 2H), 7.04 (dd, J=9.9, 9.0 Hz, 1H), 6.93 (dd, J=6.5, 3.2 Hz, 1H), 6.81 (dt, J=9.0, 3.4 Hz, 1H), 4.64 (s, 2H), 4.50 (dt, J=12.1, 6.1 Hz, 1H), 3.84-3.72 (m, 1H), 1.85 (ddd, J=9.4, 6.1, 1.9 Hz, 1H), 1.44-1.36 (m, 1H), 1.34 (d, J=5.9 Hz, 6H) HPLC1:RT=11.0 min, purity=98%; HPLC-2: RT=9.29 min, purity=97%.

EXAMPLE 38

Trans-2-(2-(3'-(ethylthio)-[1,1'-biphenyl]-4-yl)ethyl) cyclopropanecarboxylic acid (racemate)

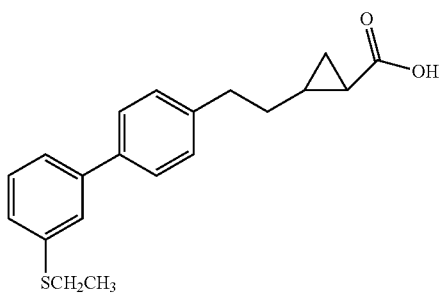

38A. Trans-methyl 2-(4-bromophenethyl)cyclopropanecarboxylate (racemate)

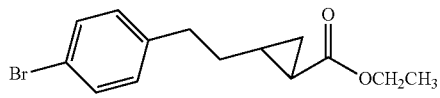 [SMILES: CCOC(=O)C1CC1CCc1ccc(Br)cc1]

To a solution of $Et_2O$ (5 mL) and aq. 40% KOH (2 mL) was added N-methyl-N'-nitro-n-nitrosoguanidine (1000 mg, 6.80 mmol) portionwise over 15 min at 0° C. The ether layer was dried with KOH pellets at 0° C., then was poured into a 0° C. solution of 30A (930 mg, 3.46 mmol) in THF (10 mL). $Pd(OAc)_2$ (78 mg, 0.35 mmol) was then added and the reaction was allowed to warm to rt and stirred for 1 h at rt, then was concentrated in vacuo. The crude oil was chromatographed (40 g $SiO_2$; 0% to 15% of EtOAc/hexanes in 40 min) to give the title compound (863 mg, 3.05 mmol, 88% yield), which was used in the next step without further purification. $^1$H NMR (500 MHz, $CDCl_3$) δ 7.32 (d, J=8.5 Hz, 2H), 6.96 (d, J=8.5 Hz, 2H), 3.59 (s, 3H), 2.70-2.53 (m, 1H), 1.57-1.48 (m, 4H), 1.34-1.24 (m, 1H), 1.13-0.98 (m, 1H), 0.62 (ddd, J=8.1, 6.5, 4.4 Hz, 1H).

38B. Trans-2-(4-bromophenethyl)cyclopropanecarboxylic acid (racemate)

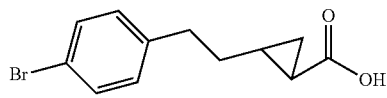 [SMILES: O=C(O)C1CC1CCc1ccc(Br)cc1]

LiOH.$H_2O$ (510 mg, 12.2 mmol) was added to a solution of 38A (860 mg, 3.04 mmol) in THF (10 mL) and water (5.00 mL) at rt. The reaction was stirred at rt overnight, then was partitioned between EtOAc (30 mL) and $H_2O$ (20 mL). The aqueous layer was washed with EtOAc (2×10 mL). The combined organic extracts were extracted with $H_2O$ (3×20 ML). The combined aqueous extracts were acidified with 1N aq. HCl to pH ~3 and extracted with EtOAc (3×50 mL). The combined organic extracts were washed with brine (10 mL), dried over $MgSO_4$, and evaporated in vacuo to afford the title compound (810.2 mg, 3.01 mmol, 99% yield) as a white solid. LCMS, $[M+H]^+=269.1$.

EXAMPLE 38

A mixture of 38B (25 mg, 0.093 mmol), (3-(ethylthio) phenyl)boronic acid (22 mg, 0.121 mmol), $Pd(Ph_3P)_4$ (10.73 mg, 9.29 μmol), and $Cs_2CO_3$ (45.4 mg, 0.139 mmol) in 5 mL of dioxane was degassed and charged with Ar. The mixture was stirred for 2 h at 90° C., then cooled to rt for 18 h and concentrated in vacuo. The residue was partitioned between EtOAc and 1 N aq. HCl. The organic layer was dried over $MgSO_4$ and concentrated in vacuo. The residue was purified by preparative HPLC (PHENOMENEX® Axia 5μ C18 30×100 mm column; detection at 220 nm; flow rate=40 mL/min; continuous gradient from 60% B to 100% B over 10 min, where A=90:10:0.1 $H_2O$:MeOH:TFA and B=90:10: 0.1 MeOH:$H_2O$:TFA) to give the title compound (26 mg, 0.078 mmol, 84% yield). LCMS, $[M-H]^+=325.2$. $^1$H NMR (500 MHz, $CDCl_3$) δ 7.56 (t, J=1.5 Hz, 1 H), 7.52 (d, J=8.2 Hz, 2 H), 7.41-7.30 (m, 3 H), 7.27 (d, J=8.2 Hz, 2 H), 3.02 (q, J=7.3 Hz, 2 H), 2.80 (t, J=7.5 Hz, 2 H), 1.73-1.67 (m, 2 H), 1.53 (ddd, J=8.8, 6.8, 4.1 Hz, 1 H), 1.43 (dt, J=8.12, 4.2 Hz, 1 H), 1.37 (t, J=7.4 Hz, 3 H), 1.31-1.24 (m, 1 H), 0.84 (ddd, J=8.0, 6.5, 4.4 Hz, 1 H). HPLC-1: RT=10.7 min, purity=95.8%; HPLC-2: RT=8.9 min, purity=96.5%.

EXAMPLE 39

Cis-2-fluoro-2-(2-(2'-fluoro-5'-isopropoxy-[1,1'-biphenyl]-4-yl)ethyl) cyclopropanecarboxylic acid (racemate)

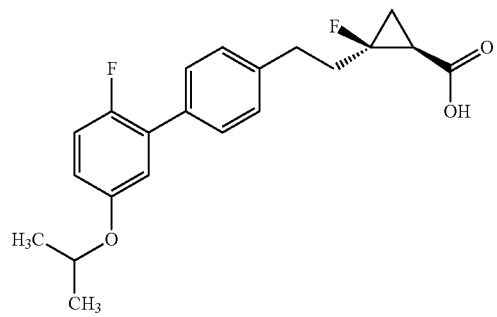 [SMILES: CC(C)Oc1ccc(F)c(-c2ccc(CC[C@]3(F)C[C@H]3C(=O)O)cc2)c1]

EXAMPLE 40

Trans-2-fluoro-2-(2-(2'-fluoro-5'-isopropoxy-[1,1'-biphenyl]-4-yl)ethyl) cyclopropanecarboxylic acid (racemate)

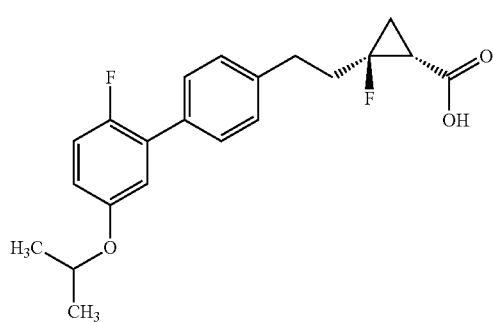 [SMILES: CC(C)Oc1ccc(F)c(-c2ccc(CC[C@]3(F)C[C@@H]3C(=O)O)cc2)c1]

39A. 1-Bromo-4-(but-3-en-1-yl)benzene

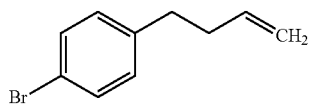

To a 0° C. solution of allylmagnesium chloride (15.0 mL, 30.0 mmol) was added 1-bromo-4-(bromomethyl)benzene (5.0 g, 20.0 mmol) portionwise over ~10 min. The reaction was stirred at 0° C. for 2 h and at rt for 18 h, then was cautiously quenched with water at 0° C. followed by addition of 1 N aq. HCl. The mixture was extracted with EtOAc (2×). The combined organic extracts were dried (MgSO$_4$) and concentrated in vacuo. The residue was chromatographed (40 g SiO$_2$; 10% EtOAc/hexanes; 30 min) to give the title compound (4.1 g, 18.84 mmol, 94% yield). $^1$H NMR (500 MHz, CDCl$_3$) δ ppm 7.44-7.38 (m, 2 H), 7.11-6.96 (m, 2 H), 5.85 (ddt, J=16.9, 10.2, 6.6, 6.6 Hz, 1 H), 5.09-4.96 (m, 2 H), 2.75-2.62 (m, 2 H), 2.44-2.29 (m, 2 H).

39B. 1-Bromo-4-(4-bromo-3-fluorobutyl)benzene

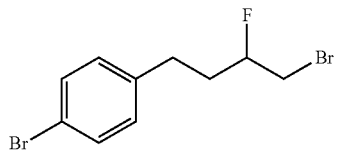 [SMILES: FC(CBr)CCc1ccc(Br)cc1]

To a solution of 1-bromo-4-(but-3-en-1-yl)benzene (1.0 g, 4.74 mmol) and triethylamine trihydrofluoride (1.17 g, 7.25 mmol) in DCM (5 mL) was added N-bromo succinimide (1.01 g, 5.68 mmol) at 0° C. The mixture was allowed to gradually warm to rt and stirred for 20 h at rt. The dark brown solution was poured into 10 mL of ice and aq. NH$_4$OH and extracted with DCM (2×). The combined organic extracts were washed with 1 N aq. HCl, dried over MgSO$_4$ and concentrated in vacuo. The residue was chromatographed (40 g SiO$_2$; 5% EtOAc/hexanes; 30 min) to give the title compound (1.25 g, 3.63 mmol, 77% yield). $^1$H NMR (500 MHz, CDCl$_3$) δ 7.46-7.41 (m, 2 H), 7.12-7.08 (m, 2 H), 4.74-4.53 (m, 1 H), 3.50 (dd, J=19.3, 5.2 Hz, 2 H), 2.87-2.65 (m, 2 H), 2.14-1.99 (m, 2 H).

39C. 1-Bromo-4-(3-fluorobut-3-en-1-yl)benzene

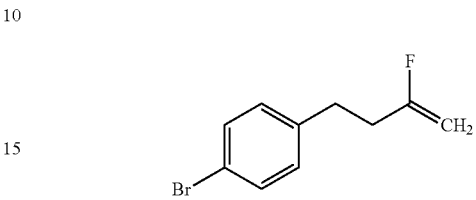

To a 0° C. solution of potassium tert-butoxide (6 ml, 6.00 mmol) in THF was added a solution of 1-bromo-4-(4-bromo-3-fluorobutyl)benzene (0.65 g, 2.097 mmol) in THF (2 mL). The reaction mixture was stirred for 1 h at rt; brine was then added. The mixture was extracted with EtOAc (2×). The combined organic extracts were dried over MgSO$_4$ and concentrated in vacuo. The residue was chromatographed (24 g SiO$_2$; 5% EtOAc/hexanes; 30 min) to give the title compound (0.35 g, 1.451 mmol, 69.2% yield). $^1$H NMR (500 MHz, CDCl$_3$) δ 7.44 (d, J=8.3 Hz, 2 H), 7.09 (d, J=8.5 Hz, 2 H), 4.55 (dd, J=17.5, 2.9 Hz, 1 H), 4.28-4.10 (m, 1 H), 2.81 (t, J=7.7 Hz, 2 H), 2.54-2.42 (m, 2 H).

39D. 2-Fluoro-4'-(3-fluorobut-3-en-1-yl)-5-isopropoxy-1,1'-biphenyl

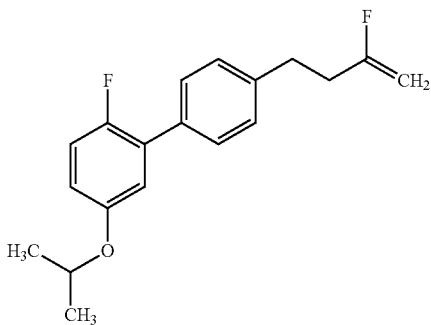 [SMILES: C=C(F)CCc1ccc(-c2cc(OC(C)C)ccc2F)cc1]

A mixture of 39C (0.30 g, 1.310 mmol), (2-fluoro-5-isopropoxyphenyl) boronic acid (0.285 g, 1.440 mmol), Pd(Ph$_3$P)$_4$ (0.151 g, 0.131 mmol), and Cs$_2$CO$_3$ (0.512 g, 1.571 mmol) in 10 mL of dioxane was degassed and flushed with Ar several times. The mixture was stirred for 7 h at 90° C. and for 2 days at rt, then was partitioned between brine and EtOAc. The aq. phase was extracted with EtOAc (2×). The combined organic extracts were dried over MgSO$_4$ and concentrated in vacuo. The residue was chromatographed (40 g SiO$_2$; 5% EtOAc/hexanes; 30 min) to give the title compound (0.31 g, 0.974 mmol, 74.4% yield). $^1$H NMR (500 MHz, CD$_2$Cl$_2$) δ 7.62-7.38 (m, 3H), 7.36-7.31 (m, 1H), 7.13-7.05 (m, 1H), 7.01-6.95 (m, 1H), 6.90-6.82 (m, 1H), 4.61-4.50 (m, 2H), 2.98-2.88 (m, 2H), 2.66-2.53 (m, 2H), 1.40-1.34 (m, 6H).

39E. Cis-ethyl 2-fluoro-2-(2-(2'-fluoro-5'-isopropoxy-[1,1'-biphenyl]-4-yl)ethyl) cyclopropanecarboxylate (racemate, stereochemistry arbitrarily assigned)

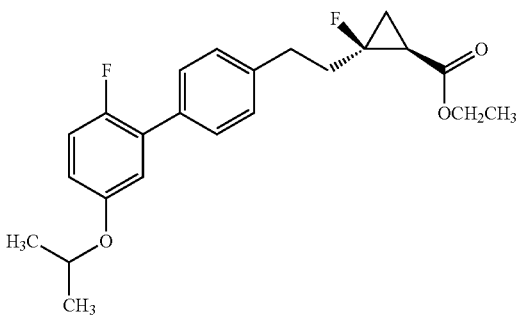 [SMILES: CCOC(=O)[C@@H]1C[C@@]1(F)CCc1ccc(-c2cc(OC(C)C)ccc2F)cc1]

39F. Trans-ethyl 2-fluoro-2-(2-(2'-fluoro-5'-isopropoxy-[1,1'-biphenyl]-4-yl)ethyl) cyclopropanecarboxylate (racemate, stereochemistry arbitrarily assigned)

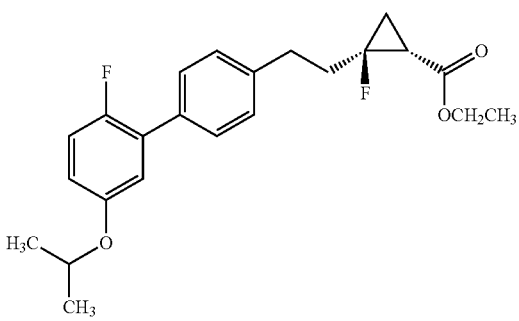 [SMILES: CCOC(=O)[C@H]1C[C@@]1(F)CCc1ccc(-c2cc(OC(C)C)ccc2F)cc1]

To a mixture of 2-fluoro-4'-(3-fluorobut-3-en-1-yl)-5-isopropoxy-1,1'-biphenyl (0.15 g, 0.496 mmol) and 2,4-pentanedione, Cu(acac)$_2$ (0.052 g, 0.198 mmol) in DCM (5 mL) was added a solution of ethyl diazoacetate (0.077 mL, 0.744 mmol) in DCM (4.5 mL) at 40° C. over 3 h. The reaction mixture was stirred for 1 h at 40° C. and at rt for 18 h. The mixture was chromatographed (24 g SiO$_2$; 10% of EtOAc/hexanes in 30 min) to give the two enantiomers 39E (56 mg, 0.144 mmol, 29.1% yield) and 39F (45 mg, 0.116 mmol, 23.4% yield). 39E: LCMS, [M+H]$^+$=389.2; 39F: LCMS, [M+H]$^+$=389.2.

EXAMPLE 39

To a solution of cis-ethyl 2-fluoro-2-(2-(2'-fluoro-5'-isopropoxy-[1,1'-biphenyl]-4-yl)ethyl)cyclopropanecarboxylate (40 mg, 0.103 mmol) in MeOH (2 mL) was added aq. NaOH (0.5 mL of a 1 M solution, 0.500 mmol). The mixture was stirred for 18 h at rt, then was acidified with 1 N aq. HCl and concentrated in vacuo. The mixture was extracted with EtOAc (2×). The combined organic extracts were dried over MgSO$_4$ and concentrated in vacuo. The residue was purified with Prep HPLC (PHENOMENEX® 30×100 mm Axia Luna column with 70-100% B over 10 min) to give the title compound (20 mg, 0.054 mmol, 52.8% yield) as a clear oil. LCMS, [M–H]$^+$=359.2. $^1$H NMR (500 MHz, CD$_2$Cl$_2$) δ 7.52 (dd, J=8.2, 1.6 Hz, 2 H), 7.34 (d, J=8.2 Hz, 2 H), 7.09 (dd, J=10.1, 9.0 Hz, 1 H), 6.98 (dd, J=6.6, 3.0 Hz, 1 H), 6.85 (dt, J=8.8, 3.4 Hz, 1 H), 4.55 (spt, J=6.0 Hz, 1 H), 3.00 (t, J=7.5 Hz, 2 H), 2.27-2.08 (m, 2 H), 1.96-1.87 (m, 1 H), 1.86-1.81 (m, 1 H), 1.36 (d, J=6.0 Hz, 6 H), 1.23-1.16 (m, 1 H). HPLC-1: RT=10.1 min, purity=99.9%; HPLC-2: RT=8.6 min, purity=99.7%.

EXAMPLE 40

To a solution of trans-ethyl 2-fluoro-2-(2-(2'-fluoro-5'-isopropoxy-[1,1'-biphenyl]-4-yl)ethyl) cyclopropanecarboxylate (50 mg, 0.129 mmol) in MeOH (2 mL) was added aq. NaOH (0.5 mL of a 1 M solution, 0.50 mmol). The mixture was stirred for 18 h at rt, then was acidified with 1 N aq. HCl and concentrated in vacuo. The mixture was extracted with EtOAc (2×). The combined organic extracts were dried over MgSO$_4$ and concentrated in vacuo. The residue was purified by Preparative HPLC (PHENOMENEX® 30×100 mm Axia Luna column with 70-100% B over 10 min) to give the title compound (29 mg, 0.079 mmol, 61.3% yield) as a clear oil. LCMS, [M–H]$^+$=359.2. $^1$H NMR (500 MHz, CD$_2$Cl$_2$) δ 7.48 (dd, J=8.2, 1.6 Hz, 2 H), 7.31 (d, J=8.5 Hz, 2 H), 7.07 (dd, J=10.1, 8.8 Hz, 1 H), 6.96 (dd, J=6.3, 3.0 Hz, 1 H), 6.81-6.87 (m, 1 H), 4.54 (dt, J=12.1, 6.0 Hz, 1 H), 2.81-3.04 (m, 2 H), 2.26-2.50 (m, 2 H), 2.20 (ddd, J=18.6, 10.6, 7.5 Hz, 1 H), 2.01 (s, 1 H). 1.63 (dddd, J=19.0, 10.3, 6.8, 1.1 Hz, 1 H), 1.36 (d, J=6.0 Hz, 6 H), 1.24-1.32 (m, 1 H). HPLC-1: RT=10.6 min, purity=99.9%; HPLC-2: RT=8.9 min, purity=99.9%.

EXAMPLE 41

Trans-2-(2-(2'-fluoro-5'-isopropoxy-[1,1'-biphenyl]-4-yl)ethyl)-1-methylcyclopropanecarboxylic acid (racemate)

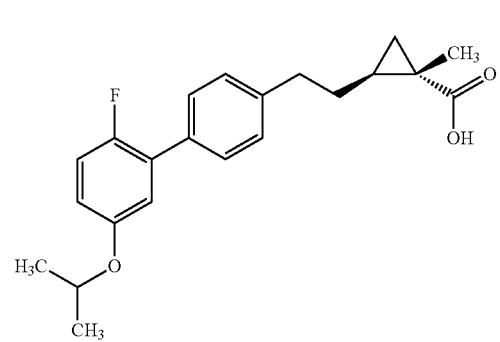 [SMILES: CC(C)Oc1ccc(F)c(-c2ccc(CC[C@H]3C[C@]3(C)C(=O)O)cc2)c1]

41A. 3-(2'-Fluoro-5'-isopropoxy-[1,1'-biphenyl]-4-yl)propan-1-ol

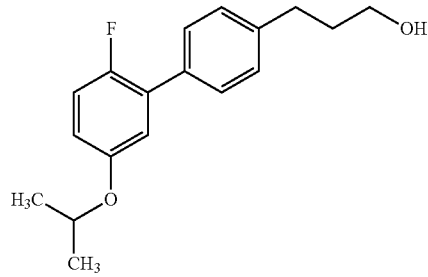 [SMILES: CC(C)Oc1ccc(F)c(-c2ccc(CCCO)cc2)c1]

To a solution of 3-(4-bromophenyl)propan-1-ol (1.5 g, 6.97 mmol) in dioxane (20 mL) was added (2-fluoro-5-isopropoxyphenyl)boronic acid (1.381 g, 6.97 mmol), Pd(Ph$_3$P)$_4$ (0.806 g, 0.697 mmol), and Cs$_2$CO$_3$ (2.95 g, 9.07 mmol). The mixture was degassed and charged with Ar. The mixture was stirred under Ar for 10 h at 100° C., then cooled to rt and stirred for 8 h at rt, after which sat'd aq. NaHCO$_3$ was added. The aqueous layer was extracted with EtOAc (2×). The combined organic extracts were dried over MgSO$_4$ and concentrated in vacuo. The residue was chromatographed (SiO$_2$; 40 g; EtOAc/Hexane=1/4) and then purified by preparative HPLC (PHENOMENEX® 30×100 mm Axia Luna column with 65-100% B over 10 min, A=90:10:0.1 H$_2$O:MeOH:TFA and B=90:10:0.1 MeOH:H$_2$O:TFA) to give the title compound (1.62 g, 5.34 mmol, 77% yield). $^1$H NMR (400 MHz, CDCl$_3$) δ 7.54-7.45 (m, 1H), 7.36-7.29 (m, 1H), 7.08 (dd, J=10.1, 9.0 Hz, 1H), 6.98 (dd, J=6.4, 3.1 Hz, 1H), 6.85 (dt, J=9.0, 3.5 Hz, 1H), 4.55 (dt, J=12.1, 6.1 Hz, 1H), 3.77 (t, J=6.5 Hz, 2H), 2.85-2.71 (m, 2H), 1.97 (dd, J=7.8, 6.7 Hz, 2H), 1.36 (d, J=5.9 Hz, 6H).

41B. 4'-(3-Bromopropyl)-2-fluoro-5-isopropoxy-1,1'-biphenyl

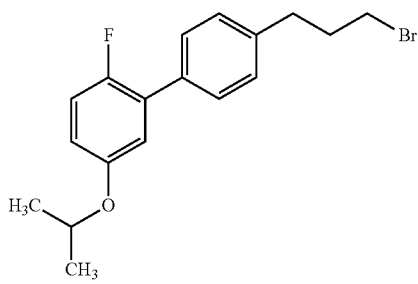

To a solution of 41A (1.5 g, 5.20 mmol) and CBr$_4$ (2.59 g, 7.80 mmol) in 20 mL of DCM was added Ph$_3$P (1.774 g, 6.76 mmol) at 0° C. The solution was warmed to rt and stirred for 1 h at rt, then was concentrated in vacuo. The residue was chromatographed (SiO$_2$; 40 g; EtOAc/Hexane=1/9) to give the title compound (1.51 g, 4.21 mmol, 81% yield). LCMS, [M+H]$^+$=353.2.

41C. Ethyl 5-(2'-fluoro-5'-isopropoxy-[1,1'-biphenyl]-4-yl)-2-oxopentanoate

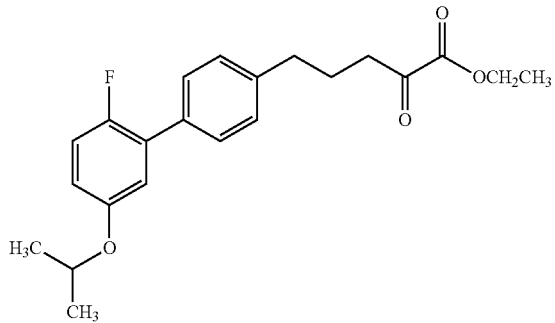 [SMILES: CCOC(=O)C(=O)CCCc1ccc(-c2cc(OC(C)C)ccc2F)cc1]

To a mixture of magnesium (0.235 g, 9.68 mmol) in THF (2 mL) was added 1,2-dibromoethane (0.535 g, 2.85 mmol). The mixture was sonicated to initiate the reaction; gas evolution occurred vigorously after ~2 min. After bubbling had slowed down, 1 crystal of iodine and 10 drops of the bromide 41B was added. The mixture was sonicated and stirred for 5 min, after which the remainder of the solution of 41B (2.0 g, 5.69 mmol) in 5 mL of THF was added dropwise. After half the bromide 41B had been added, the reaction had slowed down, and therefore was warmed to 65° C. and addition of bromide 41B was continued. The mixture was stirred for another 1 h at 65° C. after addition of the bromide had been completed, then was cooled to rt. After stirring at rt for 2 h, the mixture became a semi-solid and more THF (10 mL) was added. This Grignard reagent mixture was then added to a −78° C. solution of diethyl oxalate (0.832 g, 5.69 mmol) in 5 mL of THF. The reaction mixture was stirred for 2 h at −78° C. and for 14 h at −40° C. To the mixture at −40° C. was added 1 N aq. HCl and warmed to rt. The mixture was extracted with EtOAc. The combined organic extracts were dried over MgSO$_4$ and concentrated in vacuo. The residue was chromatographed (SiO$_2$; 40 g; EtOAc/Hexane=1/4) to give the title compound (1.33 g, 3.21 mmol, 56% yield). $^1$H NMR (500 MHz, CD$_2$Cl$_2$) δ 7.56-7.45 (m, 2H), 7.31 (d, J=8.5 Hz, 2H), 7.08 (dd, J=10.2, 8.8 Hz, 1H), 6.97 (dd, J=6.5, 3.2 Hz, 1H), 6.89-6.78 (m, 1H), 4.55 (dt, J=12.1, 6.1 Hz, 1H), 4.39-4.34 (m, 2H), 4.12 (q, J=7.2 Hz, 2H), 2.91 (t, J=7.3 Hz, 2H), 2.75 (t, J=7.7 Hz, 2H), 1.36 (d, J=6.1 Hz, 6H), 1.27 (t, J=7.2 Hz, 3H).

41D. Ethyl 5-(2'-fluoro-5'-isopropoxy-[1,1'-biphenyl]-4-yl)-2-hydroxy-2-methylpentanoate (racemate)

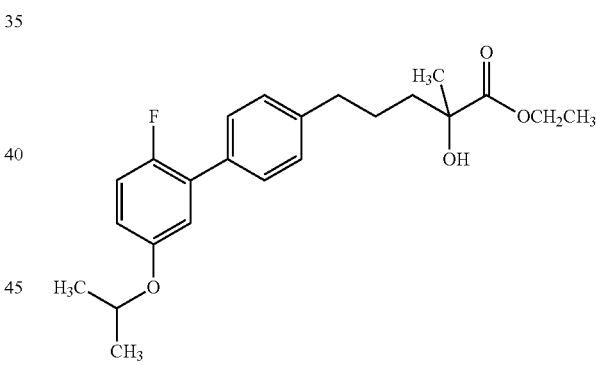

To a solution of 41C (0.2 g, 0.537 mmol) in 5 mL of THF was added CH$_3$MgBr (0.179 mL of a 3 M solution in THF, 0.537 mmol) at −78° C. The solution was stirred for 1 h at −78° C., after which 1 N aq. HCl was added. The mixture was warmed to rt and extracted with EtOAc (2×). The combined organic extracts were dried over MgSO$_4$ and concentrated in vacuo. The residue was chromatographed (SiO$_2$; 24 g; EtOAc/Hexane) to give the title compound (0.11 g, 0.27 mmol, 50.1% yield). $^1$H NMR (400 MHz, CD$_2$Cl$_2$) δ 7.49 (dd, J=8.2, 1.6 Hz, 2H), 7.29 (d, J=8.1 Hz, 2H), 7.08 (dd, J=10.2, 9.0 Hz, 1H), 6.98 (dd, J=6.3, 3.0 Hz, 1H), 6.85 (dt, J=8.9, 3.5 Hz, 1H), 4.55 (dt, J=12.1, 6.1 Hz, 1H), 4.31-4.16 (m, 2H), 3.16 (s, 1H), 2.77-2.61 (m, 2H), 1.92-1.68 (m, 2H), 1.62-1.47 (m, 1H), 1.41 (s, 3H), 1.36 (d, J=6.1 Hz, 6H), 1.30 (t, J=7.1 Hz, 3H).

41E. (E)-Ethyl 5-(2'-fluoro-5'-isopropoxy-[1,1'-biphenyl]-4-yl)-2-methylpent-2-enoate

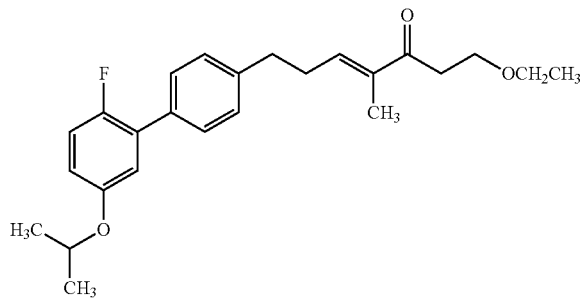 [SMILES: CCOCCC(=O)/C(C)=C/CCc1ccc(-c2cc(OC(C)C)ccc2F)cc1]

To a solution of 41D (75 mg, 0.193 mmol) in 5 mL of DCM was added DAST (0.031 mL, 0.232 mmol) at 0° C. The reaction was allowed to warm to rt and stirred for 30 min at rt and concentrated in vacuo. The residue was chromatographed (SiO$_2$; 12 g; EtOAc/Hexane=1/19) to give the title compound (40 mg, 0.103 mmol, 53.1% yield). $^1$H NMR (500 MHz, DMSO-d$_6$) δ 7.51-7.41 (m, 2H), 7.34 (d, J=8.3 Hz, 2H), 7.19 (dd, J=10.3, 8.9 Hz, 1H), 6.98 (dd, J=6.6, 3.3 Hz, 1H), 6.92 (dt, J=8.9, 3.5 Hz, 1H), 6.63 (br. s., 1H), 4.63 (dt, J=12.1, 6.1 Hz, 1H), 2.76 (t, J=7.6 Hz, 2H), 2.51-2.42 (m, 2H), 1.71 (s, 3H), 1.27 (d, J=6.1 Hz, 6H).

41F. Trans-ethyl 2-(2-(2'-fluoro-5'-isopropoxy-[1,1'-biphenyl]-4-yl)ethyl)-1-methylcyclopropanecarboxylate (racemate)

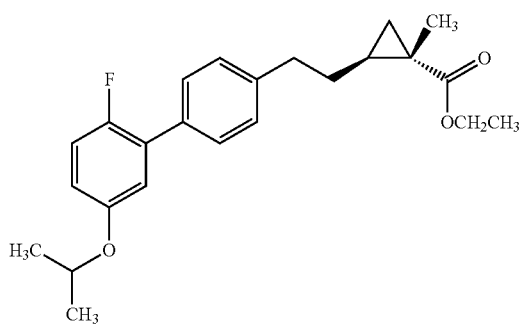 [SMILES: CCOC(=O)[C@@]1(C)C[C@@H]1CCc1ccc(-c2cc(OC(C)C)ccc2F)cc1]

To a vigorously stirred mixture of Et$_2$O (5 mL) and 40% aq. KOH (3 mL) was added a 50% solution of N-methyl-N'-nitro-N-nitrosoguanidine (159 mg, 0.54 mmol) in water portionwise over 15 min at 0° C. Upon completion of addition, stirring was stopped. The organic layer was separated and dried over KOH pellets. This ethereal diazomethane solution was added to a mixture of 41E (20 mg, 0.054 mmol) and Pd(OAc)$_2$ (12 mg, 0.054 mmol) in 5 mL of THF at 0° C. The mixture was warmed to rt and stirred for 18 h at rt. The mixture was concentrated in vacuo. The residue was chromatographed (SiO$_2$; 12 g; EtOAc/Hexane=1/9) to give the title compound (15 mg, 0.031 mmol, 57.8% yield). $^1$H NMR (500 MHz, CD$_2$Cl$_2$) δ 7.42-7.34 (m, 2H), 7.23-7.15 (m, 2H), 6.99-6.92 (m, 1H), 6.87-6.82 (m, 1H), 6.75-6.69 (m, 1H), 4.46-4.38 (m, 1H), 4.03-3.92 (m, 2H), 2.68 (t, J=7.7 Hz, 2H), 1.64 (dd, J=13.8, 7.4 Hz, 2H), 1.23 (d, J=6.1 Hz, 9H), 0.86-0.77 (m, 2H), 0.30 (dd, J=6.6, 3.9 Hz, 1H).

EXAMPLE 41

To a solution of 41F (12 mg, 0.031 mmol) in MeOH (2 mL) was added aq. NaOH (0.2 mL of a 1 M solution, 0.200 mmol). The mixture was stirred for 15 h at rt. The mixture was neutralized with 1 N aq. HCl and extracted with EtOAc. The combined organic layers were dried (MgSO$_4$) and concentrated in vacuo. The residue was purified by Prep HPLC (Column: Waters XBridge C18, 19×100 mm, 5 μm particles; Guard Column: Waters XBridge C18, 19×10 mm, 5-μm particles; Mobile Phase A: 5:95 MeCN:water with 10 mM aq. NH$_4$OAc; Mobile Phase B: 95:5 MeCN:water with 10 mM aq. NH$_4$OAc; Gradient: 35-75% B over 10 min, then a 5 min hold at 100% B; Flow: 20 mL/min.) to give Example 41. LCMS, [M−H]$^+$=355.2. $^1$H NMR (500 MHz, DMSO-d$_6$) δ 7.46 (dd, J=8.1, 1.5 Hz, 2H), 7.33-7.26 (m, 2H), 7.19 (dd, J=10.3, 8.9 Hz, 1H), 6.97 (dd, J=6.6, 3.3 Hz, 1H), 6.91 (dt, J=8.9, 3.5 Hz, 1H), 4.63 (dt, J=12.1, 6.1 Hz, 1H), 2.79-2.69 (m, 2H), 1.77-1.62 (m, 2H), 1.39-1.31 (m, 1H), 1.27 (d, J=5.8 Hz, 6H), 1.19 (s, 3H), 1.03 (d, J=2.8 Hz, 2H), 0.72-0.64 (m, 1H), 0.42 (dd, J=6.6, 3.6 Hz, 1H). HPLC-4: RT=2.2 min, purity=67.7%.

| Ex. No. | Structure and Name | Analytical Data | Method |
|---|---|---|---|
| 42 | ![structure] Trans-2-(((2'-fluoro-5'-(3-fluorophenoxy)-[1,1'-biphenyl]-4-yl)oxy)methyl)cyclopropanecarboxylic acid (racemate) | LCMS, [M − H]$^+$ = 395.0. $^1$H NMR (500 MHz, DMSO-d$_6$) δ 7.50-7.48 (m, 2H), 7.45-7.30 (m, 2H), 7.22-7.20 (m, 1H), 7.11-6.83 (m, 6H), 4.08-4.00 (m, 1H), 3.93-3.85 (m, 1H), 1.73-1.71 (m, 1H), 1.63-1.61 (m, 1H), 1.10-1.08 (m, 1H), 0.98-0.96 (m, 1H). | Ex. 1 |

| Ex. No. | Structure and Name | Analytical Data | Method |
|---|---|---|---|
| 43 | 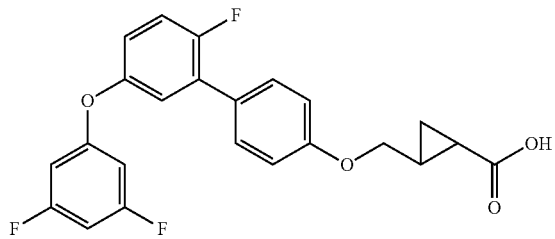 [SMILES: O=C(O)C1CC1COc1ccc(-c2cc(Oc3cc(F)cc(F)c3)ccc2F)cc1]<br>Trans-2-(((5'-(3,5-difluorophenoxy)-2'-fluoro-[1,1'-biphenyl]-4-yl)oxy)methyl)cyclopropanecarboxylic acid | LCMS, [M − H]$^+$ = 413.0. $^1$H NMR (500 MHz, DMSO-d$_6$) δ 7.51 (d, J = 8.0 Hz, 2H), 7.36 (t, J = 9.5 Hz, 1H), 7.30-7.25 (m, 1H), 7.13 (d, J = 6.6 Hz, 1H), 7.06-6.95 (m, 3H), 6.76 (d, J = 8.3 Hz, 2H), 4.06-4.00 (m, 1H), 3.89 (t, J = 8.8 Hz, 1H), 1.72-1.70 (m, 1H), 1.62 (d, J = 3.3 Hz, 1H), 1.09-1.07 (m, 1H), 0.98-0.96 (m, 1H). | Ex. 1 |
| 44 | 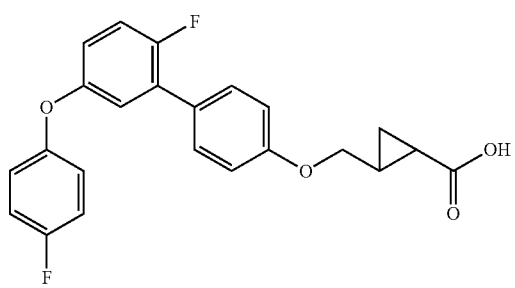<br>Trans-2-(((2'-fluoro-5'-(4-fluorophenoxy)-[1,1'-biphenyl]-4-yl)oxy)methyl)cyclopropanecarboxylic acid (racemate) | LCMS, [M − H]$^+$ = 395.0. $^1$H NMR (500 MHz, DMSO-d$_6$) δ 7.46 (d, J = 8.3 Hz, 2H), 7.30 (t, J = 9.6 Hz, 1H), 7.22 (t, J = 8.3 Hz, 2H), 7.14-7.08 (m, 3H), 7.02 (d, J = 7.7 Hz, 2H), 6.99-6.94 (m, 1H), 4.05-3.99 (m, 1H), 3.91-3.85 (m, 1H), 1.72-1.71 (m, 1H), 1.61 (d, J = 3.9 Hz, 1H), 1.11-1.05 (m, 1H), 0.97-0.95 (m, 1H). | Ex. 1 |
| 45 | 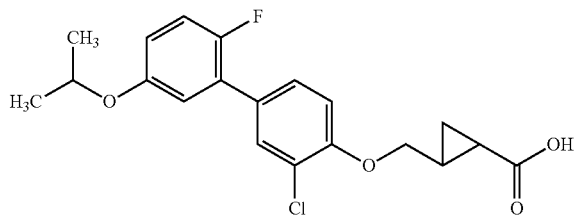 [SMILES: CC(C)Oc1ccc(F)c(-c2ccc(OCC3CC3C(=O)O)c(Cl)c2)c1]<br>Trans-2-(((3-chloro-2'-fluoro-5'-isopropoxy-[1,1'-biphenyl]-4-yl)oxy)methyl)cyclopropanecarboxylic acid (racemate) | LCMS, [M − H]$^+$ = 377.0. $^1$H NMR (500 MHz, DMSO-d$_6$) δ 7.61 (s, 1H), 7.48 (d, J = 8.5 Hz, 1H), 7.24-7.16 (m, 2H), 7.00 (dd, J = 6.3, 3.0 Hz, 1H), 6.93-6.88 (m, 1H), 4.64 (dt, J = 12.0, 5.9 Hz, 1H), 4.13 (dd, J = 10.5, 6.1 Hz, 1H), 4.03 (dd, J = 10.3, 7.0 Hz, 1H), 1.79-1.71 (m, 1H), 1.66 (dt, J = 8.4, 4.3 Hz, 1H), 1.26 (d, J = 6.1 Hz, 6H), 1.10 (dt, J = 8.6, 4.4 Hz, 1H), 1.04-0.98 (m, 1H). | Ex. 1 |
| 46 | 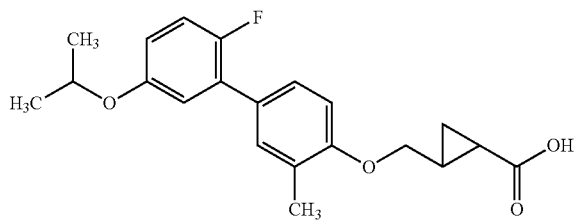<br>Trans-2-(((2'-fluoro-5'-isopropoxy-3-methyl-[1,1'-biphenyl]-4-yl)oxy)methyl)cyclopropanecarboxylic acid (racemate) | LCMS, [M − H]$^+$ = 357.0. $^1$H NMR (500 MHz, DMSO-d$_6$) δ 7.35-7.30 (m, 2H), 7.15 (t, J = 9.8 Hz, 1H), 6.98 (d, J = 8.3 Hz, 1H), 6.93 (dd, J = 6.5, 2.9 Hz, 1H), 6.89-6.84 (m, 1H), 4.61 (dt, J = 12.0, 5.9 Hz, 1H), 4.05 (dd, J = 10.5, 6.1 Hz, 1H), 3.93 (dd, J = 10.6, 7.0 Hz, 1H), 2.21 (s, 3H), 1.77-1.69 (m, 1H), 1.63 (dt, J = 8.3, 4.4 Hz, 1H), 1.26 (d, J = 5.8 Hz, 6H), 1.09 (dt, J = 8.8, 4.4 Hz, 1H), 1.02-0.96 (m, 1H). | Ex. 1 |

| Ex. No. | Structure and Name | Analytical Data | Method |
|---|---|---|---|
| 47 | 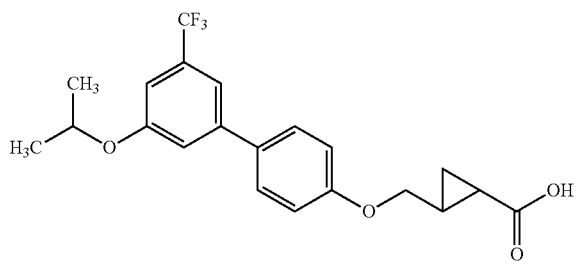 [SMILES: CC(C)Oc1cc(-c2ccc(OCC3CC3C(=O)O)cc2)cc(C(F)(F)F)c1]

Trans-2-(((3'-isopropoxy-5'-(trifluoromethyl)-[1,1'-biphenyl]-4-yl)oxy)methyl)cyclopropanecarboxylic acid (racemate) | LCMS, $[M - H]^+$ = 393.1. $^1$H NMR (500 MHz, DMSO-d$_6$) δ 7.68 (d, J = 8.0 Hz, 2H), 7.42 (d, J = 16.0 Hz, 2H), 7.13 (s, 1H), 7.03 (d, J = 8.0 Hz, 2H), 4.85 (dt, J = 11.8, 5.9 Hz, 1H), 4.08-4.01 (m, 1H), 3.90 (t, J = 8.9 Hz, 1H), 1.76-1.59 (m, 2H), 1.30 (d, J = 5.8 Hz, 6H), 1.12-1.06 (m, 1H), 1.01-0.94 (m, 1H). | Ex. 1 |
| 48 | 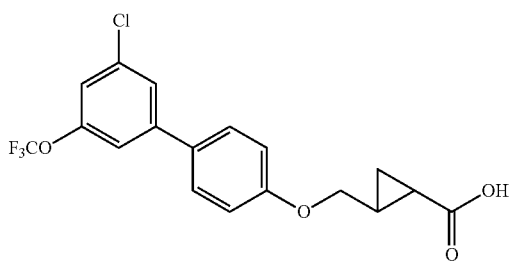 [SMILES: O=C(O)C1CC1COc1ccc(-c2cc(Cl)cc(OC(F)(F)F)c2)cc1]

Trans-2-(((3'-chloro-5'-(trifluoromethoxy)-[1,1'-biphenyl]-4-yl)oxy)methyl)cyclopropanecarboxylic acid (racemate) | LCMS, $[M - H]^+$ = 385.0. $^1$H NMR (500 MHz, DMSO-d$_6$) δ 7.78 (s, 1H), 7.71 (d, J = 8.8 Hz, 2H), 7.61 (s, 1H), 7.46 (s, 1H), 7.04 (d, J = 8.8 Hz, 2H), 4.05 (dd, J = 10.3, 6.2 Hz, 1H), 3.90 (dd, J = 10.5, 7.4 Hz, 1H), 1.76-1.68 (m, 1H), 1.62 (dt, J = 8.4, 4.3 Hz, 1H), 1.09 (dt, J = 8.8, 4.4 Hz, 1H), 1.00-0.94 (m, 1H). | Ex. 1 |
| 49 | 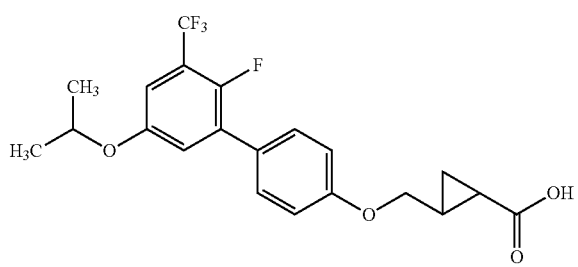 [SMILES: CC(C)Oc1cc(-c2ccc(OCC3CC3C(=O)O)cc2)c(F)c(C(F)(F)F)c1]

Trans-2-(((2'-fluoro-5'-isopropoxy-3'-(trifluoromethyl)-[1,1'-biphenyl]-4-yl)oxy)methyl)cyclopropanecarboxylic acid (racemate) | LCMS, $[M - H]^+$ = 411.1. $^1$H NMR (500 MHz, CDCl$_3$) δ 7.48-7.42 (m, 2H), 7.30 (d, J = 6.6 Hz, 2H), 6.99-6.94 (m, 2H), 4.64 (dt, J = 12.1, 6.1 Hz, 1H), 4.06 (dd, J = 10.2, 5.5 Hz, 1H), 3.91 (dd, J = 10.2, 6.6 Hz, 1H), 2.07-1.97 (m, 1H), 1.80-1.74 (m, 1H), 1.45-1.38 (m, 7H), 1.13 (ddd, J = 8.5, 6.4, 4.7 Hz, 1H). | Ex. 1 |
| 50 | 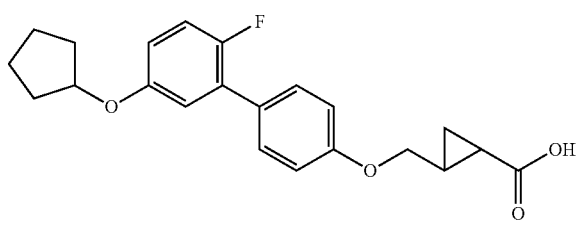 [SMILES: O=C(O)C1CC1COc1ccc(-c2cc(OC3CCCC3)ccc2F)cc1]

Trans-2-(((5'-cyclopentyloxy)-2'-fluoro-[1,1'-biphenyl]-4-yl)oxy)methyl)cyclopropanecarboxylic acid (racemate) | LCMS, $[M - H]^+$ = 369.2. $^1$H NMR (500 MHz, DMSO-d$_6$) δ 7.46 (d, J = 8.0 Hz, 2H), 7.16 (t, J = 9.6 Hz, 1H), 7.01 (d, J = 8.5 Hz, 2H), 6.92 (dd, J = 6.3, 3.0 Hz, 1H), 6.85 (dt, J = 8.7, 3.5 Hz, 1H), 4.84 (t, J = 5.6 Hz, 1H), 4.00 (dd, J = 10.5, 6.3 Hz, 1H), 3.88 (dd, J = 10.5, 7.4 Hz, 1H), 1.95-1.84 (m, 2H), 1.76-1.52 (m, 8H), 1.04 (dt, J = 8.7, 4.3 Hz, 1H), 0.93-0.85 (m, 1H). | Ex. 1 |

| Ex. No. | Structure and Name | Analytical Data | Method |
|---|---|---|---|
| 51 | 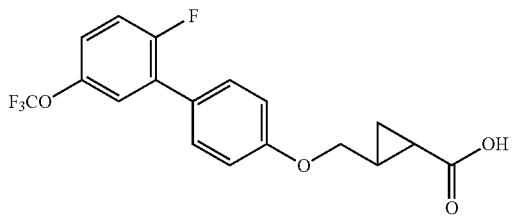<br>Trans-2-(((2'-fluoro-5'-(trifluoromethoxy)-[1,1'-biphenyl]-4-yl)oxy)methyl)cyclopropanecarboxylic acid (racemate) | LCMS, [M − H]+ = 369.0. 1H NMR (500 MHz, DMSO-d6) δ 7.52 (d, J = 8.0 Hz, 3H), 7.46-7.36 (m, 2H), 7.05 (d, J = 8.5 Hz, 2H), 4.04 (dd, J = 10.5, 6.3 Hz, 1H), 3.90 (dd, J = 10.2, 7.4 Hz, 1H), 1.75-1.67 (m, 1H), 1.61 (dt, J = 8.4, 4.3 Hz, 1H), 1.08 (dt, J = 8.8, 4.4 Hz, 1H), 0.98-0.91 (m, 1H). | Ex. 1 |
| 52 | 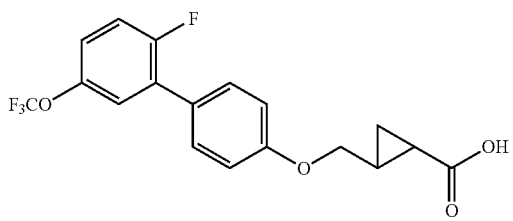 [SMILES: O=C(O)C1CC1COc1ccc(-c2cc(OC(F)(F)F)ccc2F)cc1]<br>Trans-2-(((2'-fluoro-5'-(trifluoromethoxy)-[1,1'-biphenyl]-4-yl)oxy)methyl)cyclopropanecarboxylic acid (chiral, Enantiomer 1) | LCMS, [M − H]+ = 369.0. 1H NMR (500 MHz, DMSO-d6) δ 7.54-7.49 (m, 3H), 7.47-7.36 (m, 2H), 7.05 (d, J = 8.0 Hz, 2H), 4.05 (dd, J = 10.0, 6.5 Hz, 1H), 3.93-3.86 (m, 1H), 1.76-1.58 (m, 2H), 1.12-1.06 (m, 1H), 1.01-0.94 (m, 1H). | Ex. 1 |
| 53 | 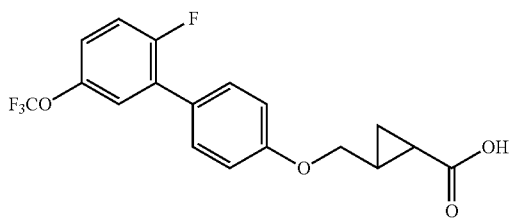<br>Trans-2-(((2'-fluoro-5'-(trifluoromethoxy)-[1,1'-biphenyl]-4-yl)oxy)methyl)cyclopropanecarboxylic acid (chiral, Enantiomer 2) | LCMS, [M − H]+ = 369.0. 1H NMR (500 MHz, DMSO-d6) δ 7.52 (d, J = 8.3 Hz, 3H), 7.47-7.36 (m, 2H), 7.05 (d, J = 8.3 Hz, 2H), 4.05 (dd, J = 10.2, 6.3 Hz, 1H), 3.94-3.87 (m, 1H), 1.77-1.59 (m, 2H), 1.12-1.06 (m, 1H), 1.00-0.94 (m, 1H). | Ex. 1 |
| 54 | 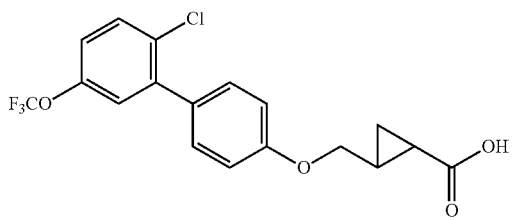 [SMILES: O=C(O)C1CC1COc1ccc(-c2cc(OC(F)(F)F)ccc2Cl)cc1]<br>Trans-2-(((2'-chloro-5'-(trifluoromethoxy)-[1,1'-biphenyl]-4-yl)oxy)methyl)cyclopropanecarboxylic acid (racemate) | LCMS, [M − H]+ = 385.0. 1H NMR (500 MHz, DMSO-d6) δ 7.69 (d, J = 8.3 Hz, 1H), 7.42-7.36 (m, 4H), 7.03 (d, J = 8.5 Hz, 2H), 4.02 (dd, J = 10.5, 6.3 Hz, 1H), 3.92-3.86 (m, 1H), 1.74-1.66 (m, 1H), 1.60 (dt, J = 8.4, 4.3 Hz, 1H), 1.06 (dt, J = 8.8, 4.4 Hz, 1H), 0.96-0.89 (m, 1H). | Ex. 1 |

| Ex. No. | Structure and Name | Analytical Data | Method |
|---|---|---|---|
| 55 | Trans-2-(((3'-fluoro-5'-isopropoxy-[1,1'-biphenyl]-4-yl)oxy)methyl)cyclopropanecarboxylic acid (racemate) | LCMS, [M − H]⁺ = 343.1. ¹H NMR (500 MHz, DMSO-$d_6$) δ 7.64-7.58 (m, 2H), 7.02-6.94 (m, 4H), 6.73 (dt, J = 1.0, 2.2 Hz, 1H), 4.72 (quin, J = 6.1 Hz, 1H), 4.02 (dd, J = 10.6, 6.2 Hz, 1H), 3.88 (dd, J = 10.5, 7.2 Hz, 1H), 1.74-1.66 (m, 1H), 1.60 (dt, J = 8.4, 4.3 Hz, 1H), 1.28 (d, J = 6.1 Hz, 6H), 1.07 (dt, J = 8.8, 4.4 Hz, 1H), 0.94 (ddd, J = 8.3, 5.8, 4.3 Hz, 1H). | Ex. 1 |
| 56 | Trans-2-(((2'-fluoro-5'-phenoxy-[1,1'-biphenyl]-4-yl)oxy)methyl)cyclopropanecarboxylic acid (racemate) | LCMS, [M − H]⁺ = 377. ¹H NMR (500 MHz, 1:1 CDCl₃:CD₃OD) δ 7.58 (s, 1H), 7.42 (dd, J = 1.5, 8.7 Hz, 2H), 7.33-7.29 (m, 2H), 7.11-7.05 (m, 2H), 7.03 (dd, J = 3.0, 6.5 Hz, 1H), 6.99-6.96 (m, 2H), 6.95-6.91 (m, 2H), 6.91-6.87 (m, 1H), 4.0 (dd, J = 5.9, 10.2 Hz, 1H), 3.86 (dd, J = 6.7, 10.2 Hz, 1H), 1.90-1.83 (m, 1H), 1.73-1.63 (m, 1H), 1.28-1.23 (m, 1H), 1.02-0.96 (m, 1H). | Ex. 1 |
| 57 | Trans-2-(((2'-fluoro-5'-phenoxy-[1,1'-biphenyl]-4-yl)oxy)methyl)cyclopropanecarboxylic acid (chiral, Enantiomer 1) | LCMS, [M − H]⁺ = 377. ¹H NMR (500 MHz, CDCl₃) δ 7.44 (d, J = 7.3 Hz, 2H), 7.34-7.29 (m, 2H), 7.10-7.04 (m, 3H), 6.99 (d, J = 7.9 Hz, 2H), 6.93-6.87 (m, 3H), 4.0 (dd, J = 5.8, 10.1 Hz, 1H), 3.88 (dd, J = 6.5, 10.1 Hz, 1H), 2.0-1.93 (m, 1H), 1.75-1.71 (m, 1H), 1.36 (dt, J = 4.7, 9.2 Hz, 1H), 1.11-1.05 (m, 1H). | Ex. 1 |
| 58 | Trans-2-(((2'-fluoro-5'-phenoxy-[1,1'-biphenyl]-4-yl)oxy)methyl)cyclopropanecarboxylic acid (chiral, Enantiomer 2) | LCMS, [M − H]⁺ = 377. ¹H NMR (500 MHz, CDCl₃) δ 7.44 (d, J = 7.3 Hz, 2H), 7.34-7.29 (m, 2H), 7.10-7.04 (m, 3H), 6.99 (d, J = 7.9 Hz, 2H), 6.93-6.87 (m, 3H), 4.0 (dd, J = 5.8, 10.1 Hz, 1H), 3.88 (dd, J = 6.5, 10.1 Hz, 1H), 2.0-1.93 (m, 1H), 1.75-1.71 (m, 1H), 1.36 (dt, J = 4.7, 9.2 Hz, 1H), 1.11-1.05 (m, 1H). | Ex. 1 |

| Ex. No. | Structure and Name | Analytical Data | Method |
|---|---|---|---|
| 59 | Trans-2-(((2'-fluoro-5'-methoxy-[1,1'-biphenyl]-4-yl)oxy)methyl)cyclopropanecarboxylic acid (racemate) | LCMS, [M − H]⁺ = 315. $^1$H NMR (500 MHz, 1:1 CDCl$_3$:CD$_3$OD) δ 7.43 (dd, J = 1.6, 8.8 Hz, 2H), 7.02 (dd, J = 9.0, 10.1 Hz, 1H), 6.96-6.92 (m, 2H), 6.89 (dd, J = 3.2, 6.4 Hz, 1H), 6.78 (dt, J = 3.5, 8.9 Hz, 1H), 4.02 (dd, J = 5.9, 10.2 Hz, 1H), 3.88 (dd, J = 6.8, 10.2 Hz, 1H), 3.79 (s, 3H), 1.91-1.84 (m, 1H), 1.69-1.64 (m, 1H), 1.29-1.23 (m, 1H), 1.01 (ddd, J = 4.5, 6.2, 8.4 Hz, 1H). | Ex. 1 |
| 60 | Trans-2-(((2,3'-difluoro-5'-isopropoxy-[1,1'-biphenyl]-4-yl)oxy)methyl)cyclopropanecarboxylic acid (racemate) | LCMS, [M − H]⁺ = 361. $^1$H NMR (500 MHz, DMSO-d$_6$) δ 7.47 (t, J = 8.9 Hz, 1H), 6.94 (d, J = 13.0 Hz, 1H), 6.93-6.82 (m, 3H), 6.80 (d, J = 11.0 Hz, 1H), 4.72-4.65 (m, 1H), 4.05-4.0 (m, 1H), 3.92-3.86 (m, 1H), 1.72-1.65 (m, 1H), 1.61-1.55 (m, 1H), 1.27 (d, J = 5.8 Hz, 6H), 1.08-1.03 (m, 1H), 0.95-0.89 (m, 1H). | Ex. 1 |
| 61 | Trans-2-(((2,2',3'-trifluoro-5'-isopropoxy-[1,1'-biphenyl]-4-yl)oxy)methyl)cyclopropanecarboxylic acid (racemate) | LCMS, [M − H]⁺ = 381. $^1$H NMR (500 MHz, DMSO-d$_6$) δ 7.38 (t, J = 8.1 Hz, 1H), 7.12-7.06 (m, 1H), 6.97 (d, J = 12.2 Hz, 1H), 6.89 (d, J = 8.2 Hz, 1H), 6.71 (br s, 1H), 4.67-4.59 (m, 1H), 4.08-4.02 (m, 1H), 3.90 (t, J = 8.5 Hz, 1H), 1.75-1.67 (m, 1H), 1.64-1.58 (m, 1H), 1.25 (br s, 6H), 1.11-1.05 (m, 1H), 0.99-0.93 (m, 1H). | Ex. 1 |
| 62 | Trans-2-(((2',3-difluoro-5'-isopropoxy-[1,1'-biphenyl]-4-yl)oxy)methyl)cyclopropanecarboxylic acid (racemate) | LCMS, [M − H]⁺ = 361. $^1$H NMR (500 MHz, DMSO-d$_6$) δ 7.43 (d, J = 12.6 Hz, 1H), 7.31 (d, J = 8.4 Hz, 1H), 7.24-7.15 (m, 2H), 7.01-6.97 (m, 1H), 6.96-6.87 (m, 1H), 4.66-4.60 (m, 1H), 4.12-4.06 (m, 1H), 3.99-3.93 (m, 1H), 1.76-1.69 (m, 1H), 1.65-1.60 (m, 1H), 1.25 (d, J = 5.6 Hz, 6H), 1.11-1.06 (m, 1H), 0.99-0.94 (m, 1H). | Ex. 1 |

| Ex. No. | Structure and Name | Analytical Data | Method |
|---|---|---|---|
| 63 | (1R,2R)-2-(((2',3-Difluoro-5'-isopropoxy-[1,1'-biphenyl]-4-yl)oxy)methyl)cyclopropanecarboxylic acid (chiral, Enantiomer 1) | LCMS, [M − H]$^+$ = 361. $^1$H NMR (500 MHz, DMSO-d$_6$) δ 7.43 (d, J = 12.6 Hz, 1H), 7.31 (d, J = 8.4 Hz, 1H), 7.24-7.15 (m, 2H), 7.01-6.97 (m, 1H), 6.96-6.87 (m, 1H), 4.66-4.60 (m, 1H), 4.12-4.06 (m, 1H), 3.99-3.93 (m, 1H), 1.76-1.69 (m, 1H), 1.65-1.60 (m, 1H), 1.25 (d, J = 5.6 Hz, 6H), 1.11-1.06 (m, 1H), 0.99-0.94 (m, 1H). | Ex. 1 |
| 64 | (1S,2S)-2-(((2',3-Difluoro-5'-isopropoxy-[1,1'-biphenyl]-4-yl)oxy)methyl)cyclopropanecarboxylic acid (chiral, Enantiomer 2) | LCMS, [M − H]$^+$ = 361. $^1$H NMR (500 MHz, DMSO-d$_6$) δ 7.43 (d, J = 12.6 Hz, 1H), 7.31 (d, J = 8.4 Hz, 1H), 7.24-7.15 (m, 2H), 7.01-6.97 (m, 1H), 6.96-6.87 (m, 1H), 4.66-4.60 (m, 1H), 4.12-4.06 (m, 1H), 3.99-3.93 (m, 1H), 1.76-1.69 (m, 1H), 1.65-1.60 (m, 1H), 1.25 (d, J = 5.6 Hz, 6H), 1.11-1.06 (m, 1H), 0.99-0.94 (m, 1H). | Ex. 1 |
| 65 | Trans-2-(((2',3,3'-trifluoro-5'-isopropoxy-[1,1'-biphenyl]-4-yl)oxy)methyl)cyclopropanecarboxylic acid (racemate) | LCMS, [M + Na]$^+$ = 403, $^1$H NMR (500 MHz, DMSO-d$_6$) δ 7.47 (d, J = 13 Hz, 1H), 7.34 (br d, J = 8.4 Hz, 1H), 7.23 (t, J = 8.4 Hz, 1H), 7.08-7.01 (m, 1H), 6.82 (br s, 1H), 4.70-4.63 (m, 1H), 4.13-4.07 (m, 1H), 4.0-3.95 (m, 1H), 1.76-1.69 (m, 1H), 1.65-1.60 (m, 1H), 1.25 (d, J = 2.6 Hz, 6H), 1.11-1.06 (m, 1H), 0.99-0.93 (m, 1H). | Ex. 1 |

| Ex. No. | Structure and Name | Analytical Data | Method |
|---|---|---|---|
| 66 | 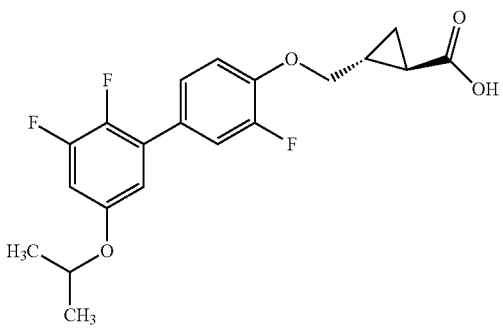 [SMILES: CC(C)Oc1cc(F)c(F)c(-c2ccc(OC[C@@H]3C[C@H]3C(=O)O)c(F)c2)c1]<br>(1R,2R)-2-(((2',3,3'-Trifluoro-5'-isopropoxy-[1,1'-biphenyl]-4-yl)oxy)methyl)cyclopropanecarboxylic acid (chiral, Enantiomer 1) | LCMS, $[M - H]^+$ = 379. $^1$H NMR (500 MHz, DMSO-$d_6$) δ 7.47 (d, J = 13 Hz, 1H), 7.34 (br d, J = 8.4 Hz, 1H), 7.23 (t, J = 8.4 Hz, 1H), 7.08-7.01 (m, 1H), 6.82 (br s, 1H), 4.70-4.63 (m, 1H), 4.13-4.07 (m, 1H), 4.0-3.95 (m, 1H), 1.76-1.69 (m, 1H), 1.65-1.60 (m, 1H), 1.25 (d, J = 2.6 Hz, 6H), 1.11-1.06 (m, 1H), 0.99-0.93 (m, 1H). | Ex. 1 |
| 67 | 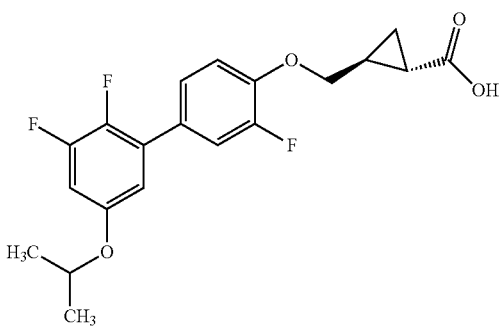 [SMILES: CC(C)Oc1cc(F)c(F)c(-c2ccc(OC[C@H]3C[C@@H]3C(=O)O)c(F)c2)c1]<br>(1S,2S)-2-(((2',3,3'-Trifluoro-5'-isopropoxy-[1,1'-biphenyl]-4-yl)oxy)methyl)cyclopropanecarboxylic acid (chiral, Enantioner 2) | LCMS, $[M - H]^+$ = 379. $^1$H NMR (500 MHz, DMSO-$d_6$) δ 7.47 (d, J = 13 Hz, 1H), 7.34 (br d, J = 8.4 Hz, 1H), 7.23 (t, J = 8.4 Hz, 1H), 7.08-7.01 (m, 1H), 6.82 (br s, 1H), 4.70-4.63 (m, 1H), 4.13-4.07 (m, 1H), 4.0-3.95 (m, 1H), 1.76-1.69 (m, 1H), 1.65-1.60 (m, 1H), 1.25 (d, J = 2.6 Hz, 6H), 1.11-1.06 (m, 1H), 0.99-0.93 (m, 1H). | Ex. 1 |
| 68 | 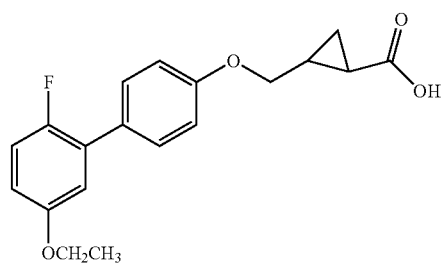 [SMILES: CCOc1ccc(F)c(-c2ccc(OCC3CC3C(=O)O)cc2)c1]<br>Trans-2-(((5'-ethoxy-2'-fluoro-[1,1'-biphenyl]-4-yl)oxy)methyl)cyclopropanecarboxylic acid (racemate) | LCMS, $[M + H]^+$ = 331.1. $^1$H NMR (500 MHz, DMSO-$d_6$) δ 7.49 (d, J = 7.3 Hz, 2H), 7.22-7.15 (m, 1H), 7.03 (d, J = 8.5 Hz, 2H), 6.97 (dd, J = 6.1, 3.1 Hz, 1H), 6.89 (dt, J = 8.9, 3.5 Hz, 1H), 4.14-3.99 (m, 3H), 3.89 (dd, J = 10.4, 7.3 Hz, 1H), 1.72 (br. s., 1H), 1.67-1.57 (m, 1H), 1.33 (t, J = 7.0 Hz, 3H), 1.16-1.06 (m, 1H), 0.99 (br. s., 1H). | Ex. 1 |

-continued

| Ex. No. | Structure and Name | Analytical Data | Method |
|---|---|---|---|
| 69 | 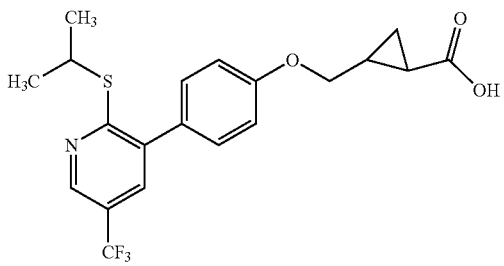 [SMILES: CC(C)Sc1ncc(C(F)(F)F)cc1-c1ccc(OCC2CC2C(=O)O)cc1]<br>Trans-2-((4-(2-(isopropylthio)-5-(trifluoromethyl)pyridin-3-yl)phenoxy)methyl)cyclopropanecarboxylic acid (racemate) | LCMS, [M + H]$^+$ = 412.2. $^1$H NMR (500 MHz, DMSO-d$_6$) δ 8.82 (s, 1H), 7.80 (s, 1H), 7.38 (d, J = 8.8 Hz, 2H), 7.05 (d, J = 8.8 Hz, 2H), 4.11-3.96 (m, 2H), 3.94-3.84 (m, 1H), 1.74 (br. s., 1H), 1.67-1.59 (m, 1H), 1.32 (d, J = 6.7 Hz, 6H), 1.10 (dt, J = 8.8, 4.4 Hz, 1H), 1.03-0.93 (m, 1H). | Ex. 1 |
| 70 | 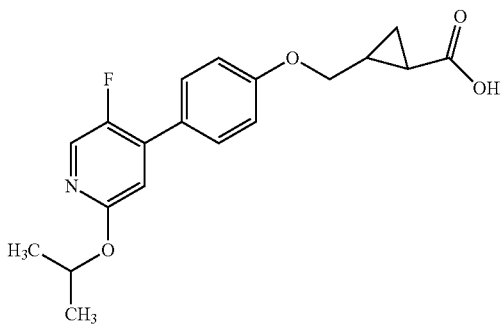 [SMILES: CC(C)Oc1cc(-c2ccc(OCC3CC3C(=O)O)cc2)c(F)cn1]<br>Trans-2-((4-(5-fluoro-2-isopropoxypyridin-4-yl)phenoxy)methyl)cyclopropanecarboxylic acid (racemate) | LCMS, [M + H]$^+$ = 346.1. $^1$H NMR (500 MHz, DMSO-d$_6$) δ 8.18 (d, J = 2.4 Hz, 1H), 7.60 (d, J = 7.4 Hz, 3H), 7.07 (d, J = 8.8 Hz, 3H), 6.88 (d, J = 5.1 Hz, 1H), 5.26-5.13 (m, 1H), 4.06 (dd, J = 10.6, 6.2 Hz, 1H), 3.91 (t, J = 9.1 Hz, 1H), 1.80-1.68 (m, 1H), 1.65-1.55 (m, 1H), 1.31 (d, J = 6.4 Hz, 6H), 1.14-1.06 (m, 1H), 0.97 (br. s., 1H). | Ex. 1 |
| 71 | 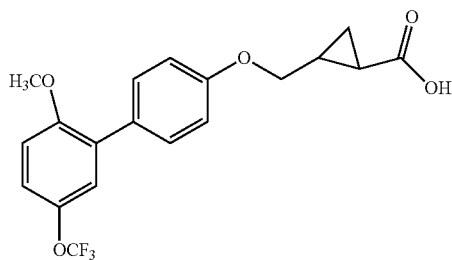 [SMILES: COc1ccc(OC(F)(F)F)cc1-c1ccc(OCC2CC2C(=O)O)cc1]<br>Trans-2-(((2'-methoxy-5'-(trifluoromethoxy)-[1,1'-biphenyl]-4-yl)oxy)methyl)cyclopropanecarboxylic acid (racemate) | LCMS, [M + H]$^+$ = 383.1. $^1$H NMR (500 MHz, DMSO-d$_6$) δ 7.43 (d, J = 8.5 Hz,2H), 7.31 (d, J = 9.2 Hz, 1H), 7.24 (d, J = 2.4 Hz, 1H), 7.18 (d, J = 9.2 Hz, 1H), 6.99 (d, J = 8.5 Hz, 2H), 4.03 (dd, J = 10.7, 6.4 Hz, 1H), 3.88 (dd, J = 10.4, 7.3 Hz, 1H), 3.79 (s, 3H), 1.79-1.69 (m, 1H), 1.63 (dt, J = 8.5, 4.3 Hz, 1H), 1.10 (dt, J = 8.5, 4.3 Hz, 1H), 1.02-0.93 (m, 1H). | Ex. 1 |

| Ex. No. | Structure and Name | Analytical Data | Method |
|---|---|---|---|
| 72 | Trans-2-(((3'-fluoro-5'-isobutoxy-[1,1'-biphenyl]-4-yl)oxy)methyl)cyclopropanecarboxylic acid (racemate) | LCMS, [M + H]$^+$ = 359.2. $^1$H NMR (500 MHz, DMSO-d$_6$) δ 7.64 (d, J = 8.8 Hz, 2H), 7.09-6.96 (m, 4H), 6.75 (d, J = 11.1 Hz, 1H), 4.04 (dd, J = 10.4, 6.1 Hz, 1H), 3.94-3.81 (m, 3H), 2.03 (dt, J = 13.0, 6.4 Hz, 1H), 1.72 (br. s., 1H), 1.65-1.57 (m, 1H), 1.14-1.06 (m, 1H), 1.00 (d, J = 6.7 Hz, 7H). | Ex. 1 |
| 73 | Trans-2-(((3'-isopropoxy-[1,1'-biphenyl]-4-yl)oxy)methyl)cyclopropanecarboxylic acid (racemate) | LCMS, [M + H]$^+$ = 327.2. $^1$H NMR (500 MHz, DMSO-d$_6$) δ 7.58 (d, J = 8.8 Hz, 2H), 7.32 (t, J = 7.9 Hz, 1H), 7.14 (d, J = 7.7 Hz, 1H), 7.09 (s, 1H), 7.01 (d, J = 8.8 Hz, 2H), 6.89-6.74 (m, 1H), 4.71 (dt, J = 12.1, 6.1 Hz, 1H), 4.03 (dd, J = 10.3, 6.2 Hz, 1H), 3.94-3.80 (m, 1H), 1.72 (br. s., 1H), 1.63 (dt, J = 8.2, 4.3 Hz, 1H), 1.29 (d, J = 6.1 Hz, 6H), 1.10 (dt, J = 8.8, 4.4 Hz, 1H), 1.02-0.92 (m, 1H). | Ex. 1 |
| 74 | Trans-2-(((3'-methoxy-5'-(trifluoromethoxy)-[1,1'-biphenyl]-4-yl)oxy)methyl)cyclopropanecarboxylic acid (racemate) | LCMS, [M − H]$^+$ = 381.1. $^1$H NMR (500 MHz, DMSO-d$_6$) δ 7.66 (d, J = 8.8 Hz, 2H), 7.21 (s, 1H), 7.15 (s, 1H), 7.03 (d, J = 8.8 Hz, 2H), 6.87 (br. s., 1H), 4.10-3.99 (m, 1H), 3.93-3.78 (m, 4H), 1.71 (br. s., 1H), 1.61 (br. s., 1H), 1.09 (d, J = 4.7 Hz, 1H), 0.97 (br. s., 1H). | Ex. 1 |
| 75 | Trans-2-(2-(3'-phenoxy-[1,1'-biphenyl]-4-yl)ethyl)cyclopropanecarboxylic acid (racemate) | LCMS, [M − H]$^+$ = 357.1. $^1$H NMR (500 MHz, CD$_3$OD) δ 7.47-7.43 (m, 2H), 7.39-7.29 (m, 4H), 7.24-7.18 (m, 3H), 7.12-7.07 (m, 1H), 7.05-6.99 (m, 2H), 6.94-6.89 (m, 1H), 2.74 (t, J = 7.7 Hz, 2H), 1.67-1.58 (m, 2H), 1.42-1.29 (m, 2H), 1.13 (dt, J = 8.8, 4.3 Hz, 1H), 0.72 (ddd, J = 8.2, 6.4, 4.2 Hz, 1H). | Ex. 30 |

| Ex. No. | Structure and Name | Analytical Data | Method |
|---|---|---|---|
| 76 | Trans-2-(2-(2'-fluoro-5'-phenoxy-[1,1'-biphenyl]-4-yl)ethyl)cyclopropanecarboxylic acid (racemate) | LCMS, [M − H]$^+$ = 375.1. $^1$H NMR (500 MHz, CD$_3$OD) δ 7.40 (dd, J = 8.1, 1.5 Hz, 2H), 7.34-7.28 (m, 2H), 7.22 (d, J = 8.3 Hz, 2H), 7.12-7.04 (m, 3H), 7.00-6.96 (m, 2H), 6.91 (dt, J = 8.8, 3.4 Hz, 1H), 2.74 (t, J = 7.7 Hz, 2H), 1.67-1.59 (m, 2H), 1.42-1.30 (m, 2H), 1.13 (dt, J = 8.8, 4.4 Hz, 1H), 0.72 (ddd, J = 8.0, 6.4, 4.3 Hz, 1H). | Ex. 30 |
| 77 | Trans-2-(2-(3'-chloro-5'-methoxy-[1,1'-biphenyl]-4-yl)ethyl)cyclopropanecarboxylic acid (racemate) | LCMS, [M − H]$^+$ = 329.1. $^1$H NMR (500 MHz, methanol-d$_4$) δ 7.46-7.41 (m, 2H), 7.23 (d, J = 8.3 Hz, 2H), 7.11 (t, J = 1.7 Hz, 1H), 6.97 (dd, J = 2.2, 1.7 Hz, 1H), 6.84 (d, J = 1.9 Hz, 1H), 3.83 (s, 3H), 2.77-2.71 (m, 2H), 1.65-1.58 (m, 2H), 1.37-1.27 (m, 2H), 1.08 (dt, J = 8.6, 4.4 Hz, 1H), 0.69-0.60 (m, 1H). | Ex. 30 |
| 78 | Trans-2-(4-(5-chloro-2-methoxypyridin-3-yl)phenethyl)cyclopropanecarboxylic acid (racemate) | LCMS, [M − H]$^+$ = 330.0. $^1$H NMR (500 MHz, methanol-d$_4$) δ 7.63-7.58 (m, 2H), 7.43 (d, J = 8.3 Hz, 2H), 7.23 (d, J = 8.0 Hz, 2H), 3.92 (s, 3H), 2.76 (t, J = 7.7 Hz, 2H), 1.70-1.58 (m, 2H), 1.42-1.31 (m, 2H), 1.14 (dt, J = 8.8, 4.4 Hz, 1H), 0.74 (ddd, J = 8.1, 6.3, 4.3 Hz, 1H). | Ex. 30 |
| 79 | Trans-2-(2-(2'-methoxy-5'-(trifluoromethoxy)-[1,1'-biphenyl]-4-yl)ethyl)cyclopropanecarboxylic acid (racemate) | LCMS, [M − H]$^+$ = 379.1. $^1$H NMR (500 MHz, methanol-d$_4$) δ 7.38 (d, J = 8.3 Hz, 2H), 7.21 (d, J = 8.0 Hz, 2H), 7.16-7.12 (m, 2H), 6.99 (d, J = 9.1 Hz, 1H), 3.79 (s, 3H), 2.75 (t, J = 7.6 Hz, 2H), 1.64 (qd, J = 7.3, 2.5 Hz, 2H), 1.43-1.31 (m, 2H), 1.13 (dt, J = 8.8, 4.4 Hz, 1H), 0.77-0.69 (m, 1H). | Ex. 30 |

| Ex. No. | Structure and Name | Analytical Data | Method |
|---|---|---|---|
| 80 | 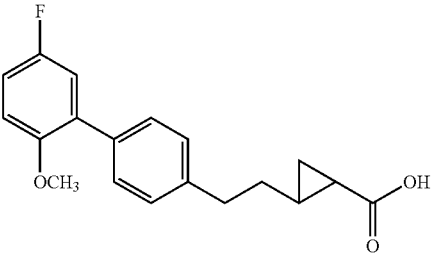 [SMILES: COc1ccc(F)cc1-c1ccc(CCC2CC2C(=O)O)cc1] Trans-2-(2-(2'-fluoro-5'-methoxy-[1,1'-biphenyl]-4-yl)ethyl) cyclopropanecarboxylic acid (racemate) | LCMS, [M − H]⁺ = 313.1. ¹H NMR (500 MHz, methanol-d₄) δ 7.45-7.40 (m, 2H), 7.23 (d, J = 8.0 Hz, 2H), 7.03 (t, J = 9.6 Hz, 1H), 6.91 (dd, J = 6.3, 3.3 Hz, 1H), 6.81 (dt, J = 8.8, 3.4 Hz, 1H), 3.80 (s, 3H), 2.76 (t, J = 7.6 Hz, 2H), 1.64 (q, J = 7.5 Hz, 2H), 1.41-1.31 (m, 2H), 1.13 (dt, J = 8.8, 4.4 Hz, 1H), 0.76-0.68 (m, 1H). | Ex. 30 |
| 81 | 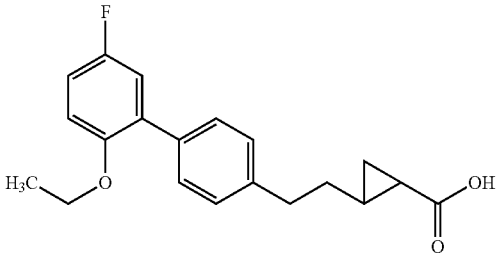 [SMILES: CCOc1ccc(F)cc1-c1ccc(CCC2CC2C(=O)O)cc1] Trans-2-(2-(5'-ethoxy-2'-fluoro-[1,1'-biphenyl]-4-yl)ethyl) cyclopropanecarboxylic acid (racemate) | LCMS, [M − H]⁺ = 327.1. ¹H NMR (500 MHz, methanol-d₄) δ 7.42 (dd, J = 8.1, 1.5 Hz, 2H), 7.23 (d, J = 8.3 Hz, 2H), 7.01 (dd, J = 10.0, 8.9 Hz, 1H), 6.91 (dd, J = 6.3, 3.0 Hz, 1H), 6.79 (dt, J = 8.9, 3.5 Hz, 1H), 4.02 (q, J = 7.0 Hz, 2H), 2.75 (t, J = 7.6 Hz, 2H), 1.64 (qd, J = 7.4, 2.3 Hz, 2H), 1.42-1.31 (m, 5H), 1.13 (dt, J = 8.7, 4.3 Hz, 1H), 0.73 (ddd, J = 8.0, 6.3, 4.1 Hz, 1H). | Ex. 30 |

EXAMPLE 82

Trans-2-((4-(1-(4-chlorophenyl)-3-methyl-1H-pyrazol-5-yl)phenoxy)methyl) cyclopropanecarboxylic acid (racemate)

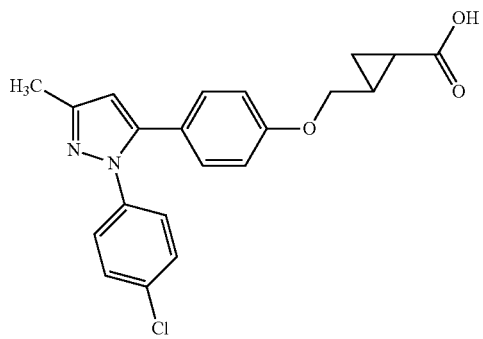 [SMILES: Cc1cc(-c2ccc(OCC3CC3C(=O)O)cc2)n(-c2ccc(Cl)cc2)n1]

82A. 1-(4-Chlorophenyl)-5-(4-iodophenyl)-3-methyl-1H-pyrazole

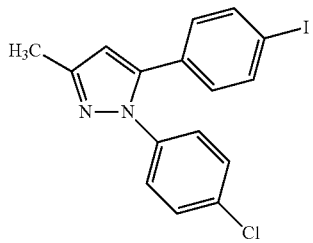 [SMILES: Cc1cc(-c2ccc(I)cc2)n(-c2ccc(Cl)cc2)n1]

1-(4-Iodophenyl)butane-1,3-dione (330 mg, 1.15 mmol) was added to a solution of (4-chlorophenyl)hydrazine hydrochloride (205 mg, 1.15 mmol) in EtOH (5 mL). The mixture was stirred at rt for 60 h, then was heated to reflux for 4 h and cooled to rt and concentrated in vacuo. The crude product was chromatographed (SiO₂; 40 g; continuous gradient from 0 to 25% Solvent B over 25 min, hold at 25% Solvent B for 10 min, where Solvent A=hexanes and Solvent B=EtOAc) to give the title compound (187 mg, 0.47 mmol, 41% yield) as a light yellow solid. LC-MS, [M+H]⁺=395.1.

$^1$H NMR (500 MHz, CDCl$_3$) δ 7.68-7.61 (m, 2H), 7.34-7.28 (m, 2H), 7.23-7.17 (m, 2H), 6.96-6.91 (m, 2H), 6.30 (s, 1H), 2.37 (s, 3H).

82B. Trans-methyl 2-((4-(1-(4-chlorophenyl)-3-methyl-1H-pyrazol-5-yl)phenoxy) methyl)cyclopropanecarboxylate

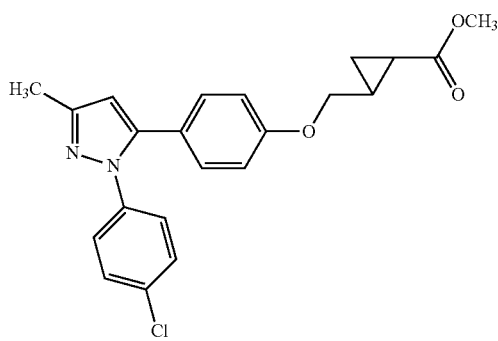 [SMILES: COC(=O)C1CC1COc1ccc(-c2cc(C)nn2-c2ccc(Cl)cc2)cc1]

A mixture of 1-(4-chlorophenyl)-5-(4-iodophenyl)-3-methyl-1H-pyrazole (50 mg, 0.13 mmol), trans-methyl 2-(hydroxymethyl)cyclopropanecarboxylate (27 mg, 0.19 mmol), Cs$_2$CO$_3$ (165 mg, 0.51 mmol), CuI (4.8 mg, 0.025 mmol), and 3,4,7,8-tetramethyl-1,10-phenanthroline (12 mg, 0.05 mmol) in toluene (0.3 mL) in a seal tube was heated under Ar for 16 h. The mixture was cooled to RT, filtered through CELITE® and washed with EtOAc. The combined filtrates were concentrated in vacuo to afford the crude title compound, which was used in the next step without further purification. LCMS, [M+H]$^+$=397.1.

EXAMPLE 82

A mixture of the crude trans-methyl 2-((4-(1-(4-chlorophenyl)-3-methyl-1H-pyrazol-5-yl)phenoxy)methyl)cyclopropanecarboxylate (52 mg, 0.13 mmol), LiOH.H$_2$O (107 mg, 2.5 mmol) in THF (2 mL), and water (2 mL) was stirred for 18 h at rt, then was acidified with 1N aq. HCl to pH=2-3. The mixture was extracted with EtOAc (3×5 mL); the combined organic extracts were dried over MgSO$_4$ and concentrated in vacuo. The crude product was purified via preparative LC/MS with the following conditions: Column: Waters XBridge C18, 19×100 mm, 5-µm particles; Guard Column: Waters XBridge C18, 19×10 mm, 5-µm particles; Mobile Phase A: 5:95 MeCN:water with 10-mM NH$_4$OAc; Mobile Phase B: 95:5 MeCN:water with 10-mM NH$_4$OAc; Gradient: 30-70% B over 10 min, then a 5-min hold at 100% B; Flow: 20 mL/min. Fractions containing the desired product were combined and dried via centrifugal evaporation to afford the title compound (20 mg, 41% yield). LCMS, [M+H]$^+$=383.1. $^1$H NMR (500 MHz, DMSO-d$_6$) δ 7.44 (d, J=8.6 Hz, 2H), 7.27-7.20 (m, 2H), 7.12 (d, J=8.7 Hz, 2H), 6.92 (d, J=8.6 Hz, 2H), 6.37 (s, 1H), 3.98 (dd, J=10.4, 6.3 Hz, 1H), 3.83 (dd, J=10.5, 7.4 Hz, 1H), 2.25 (s, 3H), 1.73-1.63 (m, 1H), 1.59 (dt, J=8.7, 4.4 Hz, 1H), 1.06 (dt, J=8.8, 4.4 Hz, 1H), 0.93 (ddd, J=9.5, 6.1, 3.9 Hz, 1H). HPLC-4: RT=1.48 min, purity=100%; HPLC-5: RT=1.83 min, purity=100%.

EXAMPLE 83

Trans-2-((4-(1-benzyl-1H-pyrazol-4-yl)phenoxy)methyl)cyclopropanecarboxylic acid (racemate)

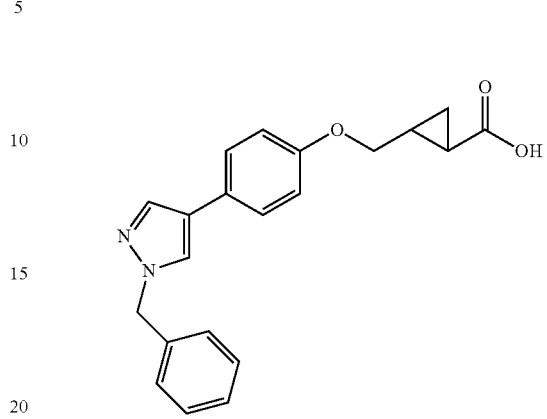

83A. Trans-methyl 2-((4-(1-benzyl-1H-pyrazol-4-yl)phenoxy)methyl) cyclopropanecarboxylate

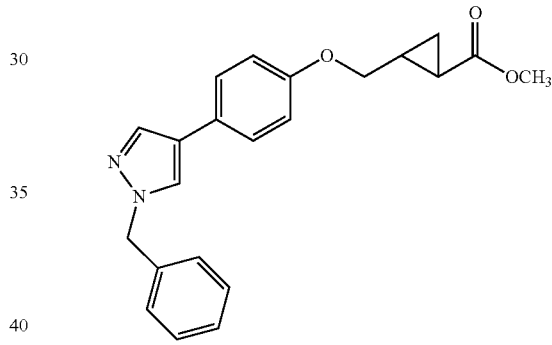

A mixture of trans-methyl 2-((4-bromophenoxy)methyl) cyclopropanecarboxylate (15 mg, 0.053 mmol), 1-benzyl-4-(4,4,5,5-tetramethyl-1,3,2-dioxaborolan-2-yl)-1H-pyrazole (22 mg, 0.08 mmol), K$_2$CO$_3$ (22 mg, 0.16 mmol), and Pd(Ph$_3$P)$_4$ (6 mg, 5.3 µmol) in THF (1.5 mL) and water (0.5 mL) was heated in a microwave reactor at 130° C. for 20 min. The mixture was cooled to RT and was used in the next reaction without further workup. LCMS, [M+H]$^+$=363.2.

EXAMPLE 83

To the above crude product mixture was added MeOH (0.5 mL), water (0.5 mL) and KOH (60 mg, 1.06 mmol). The mixture was heated to 100° C. for 30 min in a microwave reactor, then was cooled to rt and concentrated in vacuo. The residue was acidified with 1N aq. HCl to pH=2-3, then was extracted with EtOAc (3×5 mL). The combined organic extracts were dried over MgSO$_4$ and concentrated in vacuo. The crude product was purified via preparative LC/MS with the following conditions: Column: Waters XBridge C18, 19×100 mm, 5-µm particles; Guard Column: Waters XBridge C18, 19×10 mm, 5-am particles; Mobile Phase A: 5:95 MeCN:water with 0.1% TFA; Mobile Phase B: 95:5 MeCN:water with 0.1% TFA; Gradient: 25-65% B over 20 min, then a 5-min hold at 100% B; Flow: 20 mL/min.

Fractions containing the desired product were combined and dried via centrifugal evaporation to afford the title compound (14 mg, 72% yield). LCMS, [M+H]⁺=349.2. ¹H NMR (500 MHz, DMSO-d₆) δ 8.17 (s, 1H), 7.82 (s, 1H), 7.47 (d, J=8.0 Hz, 2H), 7.34 (t, J=7.4 Hz, 2H), 7.29 (d, J=7.1 Hz, 1H), 7.25 (d, J=7.7 Hz, 2H), 6.91 (d, J=8.2 Hz, 2H), 5.32 (s, 2H), 3.98 (dd, J=10.9, 5.5 Hz, 1H), 3.87-3.76 (m, 1H), 1.69 (s, 1H), 1.60 (s, 1H), 1.07 (s, 1H), 0.95 (s, 1H). HPLC-4: RT=1.33 min, purity=96%; HPLC-5: RT=1.67 min, purity=96%.

EXAMPLE 84

Trans-2-((4-(1-benzyl-3-methyl-1H-pyrazol-4-yl)phenoxy)methyl) cyclopropanecarboxylic acid (racemate)

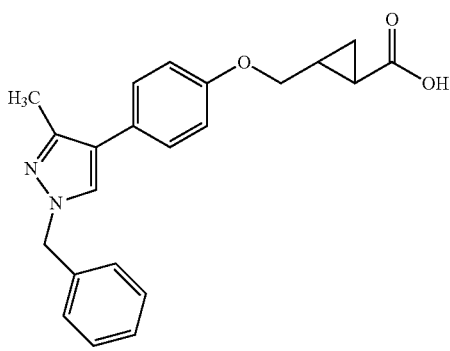 [SMILES: Cc1nn(Cc2ccccc2)cc1-c1ccc(OCC2CC2C(=O)O)cc1]

84A. Trans-methyl 2-((4-(3-methyl-1H-pyrazol-4-yl)phenoxy)methyl) cyclopropanecarboxylate

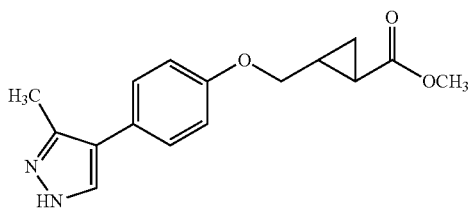 [SMILES: COC(=O)C1CC1COc1ccc(-c2c[nH]nc2C)cc1]

A mixture of methyl 2-((4-bromophenoxy)methyl)cyclopropanecarboxylate (88 mg, 0.31 mmol), 3-methyl-4-(4,4,5,5-tetramethyl-1,3,2-dioxaborolan-2-yl)-1H-pyrazole (96 mg, 0.463 mmol), K₂CO₃ (171 mg, 1.23 mmol), and Pd(Ph₃P)₄ (36 mg, 0.031 mmol) in THF (1.5 mL) and water (0.5 mL) was heated in a microwave reactor at 130° C. for 20 min, then was cooled to rt. The mixture was extracted with EtOAc (3×3 mL). The combined organic extracts were dried over MgSO₄, and concentrated in vacuo. This crude product was purified by preparative HPLC (YMC reverse phase ODS-A-5 30×100 mm column; flow rate=40 mL/min, 0 to 100% Solvent B over 30 min, hold to 40 min, where Solvent A=90:10:0.1 H₂O:MeCN:TFA and Solvent B=90:10:0.1 CH₃CN:H₂O:TFA) to give trans-methyl 2-((4-(3-methyl-1H-pyrazol-4-yl)phenoxy) methyl)cyclopropanecarboxylate (40 mg, 45% yield) as a white solid. LCMS, [M+H]⁺=287.1. ¹H NMR (500 MHz, CDCl₃) δ 11.50 (s, 2H), 7.74 (s, 1H), 7.32-7.27 (m, 2H), 7.00-6.88 (m, 2H), 4.00 (dd, J=10.1, 5.9 Hz, 1H), 3.88 (dd, J=10.1, 6.6 Hz, 1H), 3.71 (s, 3H), 2.50 (s, 3H), 1.93 (dqd, J=12.6, 6.3, 4.0 Hz, 1H), 1.74 (dt, J=8.8, 4.6 Hz, 1H), 1.33 (dt, J=9.2, 4.7 Hz, 1H), 1.02 (ddd, J=8.4, 6.2, 4.5 Hz, 1H).

84B. Trans-methyl 2-((4-(1-benzyl-3-methyl-1H-pyrazol-4-yl)phenoxy)methyl) cyclopropanecarboxylate

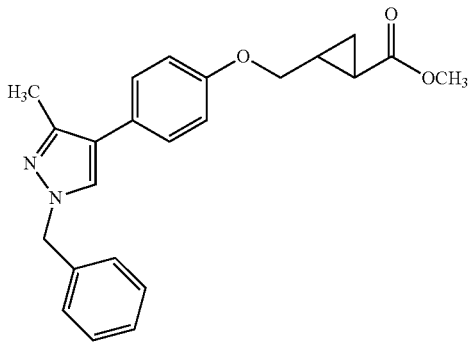 [SMILES: COC(=O)C1CC1COc1ccc(-c2cn(Cc3ccccc3)nc2C)cc1]

A solution of trans-methyl 2-((4-(3-methyl-1H-pyrazol-4-yl)phenoxy)methyl) cyclopropanecarboxylate (10 mg, 0.035 mmol), (bromomethyl)benzene (12 mg, 0.07 mmol) and K₂CO₃ (17 mg, 0.12 mmol) in DMF (1 mL) was heated to 130° C. for 30 min. The mixture was cooled to RT and was used in the next step without further workup. LCMS, [M+H]⁺=377.2.

EXAMPLE 84

To the above crude reaction mixture was added MeOH (0.5 mL), water (0.5 mL) and LiOH.H₂O (17 mg, 0.7 mmol). The mixture was heated to 100° C. for 30 min in a microwave reactor, then was cooled to rt and concentrated in vacuo. The residue was acidified with 1N aq. HCl to pH=2-3, then was extracted with EtOAc (3×5 mL). The combined organic extracts were dried over MgSO₄ and concentrated in vacuo. The crude product was purified via preparative LC/MS with the following conditions: Column: Waters XBridge C18, 19×100 mm, 5-μm particles; Guard Column: Waters XBridge C18, 19×10 mm, 5-am particles; Mobile Phase A: 5:95 MeCN:water with 0.1% TFA; Mobile Phase B: 95:5 MeCN:water with 0.1% TFA; Gradient: 20-60% B over 30 min, then a 5-min hold at 100% B; Flow: 20 mL/min. Fractions containing the desired product were combined and dried via centrifugal evaporation to afford the title compound (8 mg, 62% yield). LCMS, [M+H]⁺=363.2. ¹H NMR (500 MHz, DMSO-d₆) δ 7.93 (d, J=3.2 Hz, 1H), 7.37-7.25 (m, 7H), 6.94 (d, J=8.1 Hz, 2H), 5.22 (s, 2H), 3.99 (dt, J=9.8, 4.1 Hz, 1H), 3.88-3.77 (m, 1H), 2.25 (d, J=3.0 Hz, 3H), 1.70 (s, 1H), 1.60 (h, J=4.0 Hz, 1H), 1.08 (dq, J=8.3, 4.1 Hz, 1H), 0.96 (dt, J=8.7, 4.5 Hz, 1H). HPLC-4: RT=1.32 min, purity=99%; HPLC-5: RT=1.61 min, purity=99%.

EXAMPLE 85

Trans-2-((4-(1-(4-chlorobenzyl)-3-methyl-1H-pyrazol-4-yl)phenoxy)methyl) cyclopropanecarboxylic acid (racemate)

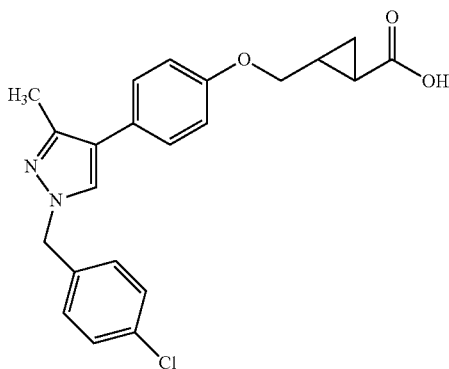 [SMILES: Cc1nn(Cc2ccc(Cl)cc2)cc1-c1ccc(OCC2CC2C(=O)O)cc1]

The title compound was synthesized via the same route as for the synthesis of Example 84 from trans-methyl 2-((4-(3-methyl-1H-pyrazol-4-yl)phenoxy)methyl) cyclopropanecarboxylate and 1-(bromomethyl)-4-chlorobenzene. LCMS, [M+H]$^+$=397.2. $^1$H NMR (500 MHz, DMSO-d$_6$) δ 7.94 (d, J=2.8 Hz, 1H), 7.41 (dd, J=8.3, 2.8 Hz, 2H), 7.30 (dt, J=9.8, 5.4 Hz, 4H), 6.94 (dd, J=8.6, 2.9 Hz, 2H), 5.23 (s, 2H), 3.99 (s, 1H), 3.87-3.79 (m, 1H), 2.25 (d, J=2.9 Hz, 3H), 1.70 (s, 1H), 1.60 (dq, J=8.3, 4.0 Hz, 1H), 1.08 (dt, J=8.8, 4.3 Hz, 1H), 0.96 (h, J=3.6 Hz, 1H). HPLC-4: RT=1.45 min, purity=94%; HPLC-5: RT=1.8 min, purity=94%.

EXAMPLE 86

Trans-2-(((3'-isopropoxy-5'-(methoxymethyl)-[1,1'-biphenyl]-4-yl)oxy)methyl) cyclopropanecarboxylic acid (racemate)

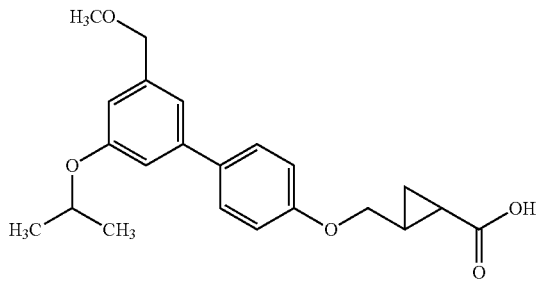 [SMILES: COCc1cc(OC(C)C)cc(-c2ccc(OCC3CC3C(=O)O)cc2)c1]

86A. Trans-methyl 2-(((3'-formyl-5'-isopropoxy-[1,1'-biphenyl]-4-yl)oxy)methyl) cyclopropanecarboxylate (racemate)

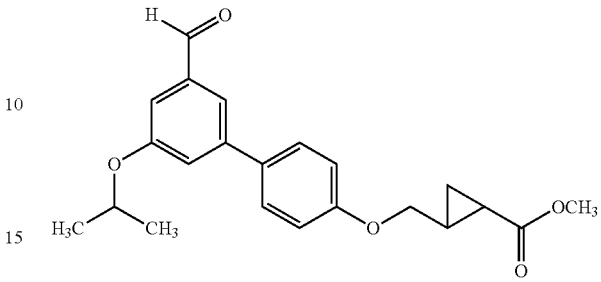

A mixture of trans-methyl 2-((4-bromophenoxy)methyl) cyclopropanecarboxylate (1.37 g, 4.81 mmol), 3-formyl-5-isopropoxyphenyl)boronic acid (1 g, 4.81 mmol), Pd(Ph$_3$P)$_4$ (0.56 g, 0.48 mmol) and K$_2$CO$_3$ (1.99 g, 14.42 mmol) in THF (10 mL) and water (3 mL) was heated in a microwave reactor at 130° C. for 20 min under Ar, then was cooled to rt. The mixture was acidified with 1N aq. HCl to pH=2-3, and extracted with EtOAc (4×50 mL). The combined organic extracts were dried over MgSO$_4$, and concentrated in vacuo. The crude product was chromatographed (SiO$_2$; 220 g; continuous gradient from 0 to 30% Solvent B over 40 min, hold at 30% Solvent B for 20 min, where Solvent A=hexanes and Solvent B=EtOAc) to give the title compound (760 mg, 2.06 mmol, 43% yield) as a clear oil. LCMS, [M+Na]$^+$=391.1.

86B. Trans-methyl 2-(((3'-(hydroxymethyl)-5'-isopropoxy-[1,1'-biphenyl]-4-yl)oxy) methyl)cyclopropanecarboxylate

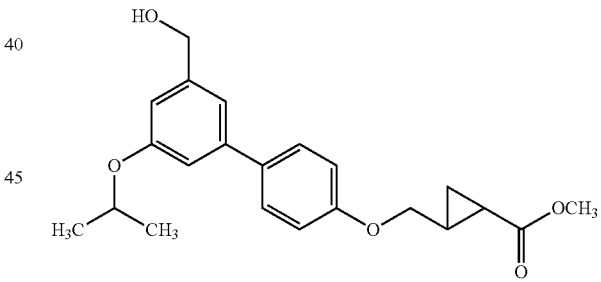

To a solution of trans-methyl 2-(((3'-formyl-5'-isopropoxy-[1,1'-biphenyl]-4-yl)oxy)methyl)cyclopropanecarboxylate (50 mg, 0.14 mmol) in MeOH (1 mL) was added NaBH$_4$ (10 mg, 0.27 mmol). The resulting reaction mixture was stirred at rt overnight, then was acidified with 1N aq. HCl to pH=2-3, and extracted with EtOAc (4×15 mL). The combined organic fractions were dried over MgSO$_4$ and concentrated in vacuo. The crude product was chromatographed (SiO$_2$; 8 g; continuous gradient from 0 to 50% Solvent B over 15 min, hold at 50% Solvent B for 10 min, where Solvent A=hexanes and Solvent B=EtOAc) to give the title compound (49 mg, 0.13 mmol, 97% yield) as a colorless oil. LCMS, [M+Na]$^+$=393.1.

EXAMPLE 86

To a 0° C. suspension of trans-methyl 2-(((3'-(hydroxymethyl)-5'-isopropoxy-[1,1'-biphenyl]-4-yl)oxy)methyl)cyclopropanecarboxylate (15 mg, 0.04 mmol), 2,6-di-tert-butylpyridine (0.03 mL, 0.14 mmol), and AgOTf (31 mg, 0.12 mmol) in CH₂Cl₂ (1.0 mL) was added MeI (18 mg, 0.13 mmol); a yellow precipitate formed within a few minutes. After stirred at rt overnight, the reaction was diluted with CH₂Cl₂ and filtered through a plug of CELITE®. The filtrate was concentrated in vacuo to give the desired crude methylation product. LiOH.H₂O (8 mg, 0.200 mmol) was added to a solution of the above crude methylation product in THF (1 mL), water (0.5 mL) and MeOH (1 mL) at rt; the reaction was stirred at rt overnight. The reaction mixture was acidified with 1N aq. HCl to pH ~3 and extracted with EtOAc (3×5 mL). The combined organic layers were washed with brine (5 mL), dried over MgSO₄, and evaporated in vacuo. The crude product was purified via preparative LC/MS with the following conditions: Column: Waters XBridge C18, 19×100 mm, 5-am particles; Guard Column: Waters XBridge C18, 19×10 mm, 5-µm particles; Mobile Phase A: 5:95 MeCN:water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation to give the title compound (8 mg, 0.02 mmol, 52% yield). LCMS, [M−H]⁺=369.1. ¹H NMR (500 MHz, DMSO-d₆) δ 7.57 (d, J=8.8 Hz, 2H), 7.08 (s, 1H), 6.99 (d, J=8.8 Hz, 3H), 6.79 (s, 1H), 4.69 (spt, J=6.0 Hz, 1H), 4.41 (s, 2H), 4.02 (dd, J=10.5, 6.3 Hz, 1H), 3.87 (dd, J=10.2, 7.4 Hz, 1H), 3.30 (s, 3H), 1.75-1.67 (m, 1H), 1.61 (dt, J=8.3, 4.4 Hz, 1H), 1.28 (d, J=6.1 Hz, 6H), 1.08 (dt, J=8.8, 4.4 Hz, 1H), 0.99-0.93 (m, 1H). HPLC-4: RT=1.59 min, purity=100%; HPLC-5: RT=1.97 min, purity=100%.

EXAMPLE 87

Trans-2-(((2'-fluoro-3-formyl-5'-isopropoxy-[1,1'-biphenyl]-4-yl)oxy)methyl) cyclopropanecarboxylic acid (racemate)

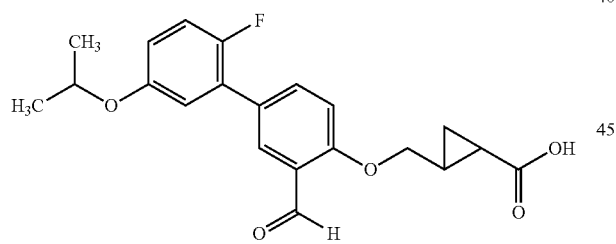

87A. Trans-methyl 2-((4-bromo-2-formylphenoxy)methyl)cyclopropanecarboxylate (racemate)

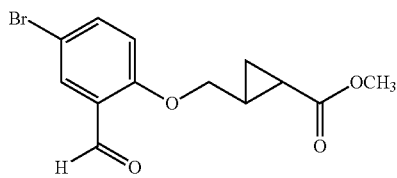 [SMILES: COC(=O)C1CC1COc1ccc(Br)cc1C=O]

A mixture of 5-bromo-2-hydroxybenzaldehyde (219 mg, 1.09 mmol), trans-methyl 2-(bromomethyl)cyclopropanecarboxylate (200 mg, 1.04 mmol) and K₂CO₃ (286 mg, 2.07 mmol) in DMF (1.5 mL) was stirred overnight at rt, then was partitioned between EtOAc and water. The aqueous layer was extracted with EtOAc (2×). The combined organic layers were washed with brine (10 mL), dried over MgSO₄, and evaporated in vacuo. The crude product was chromatographed (SiO₂; 12 g; continuous gradient from 0 to 30% Solvent B over 25 min, hold at 30% Solvent B for 10 min, where Solvent A=hexanes and Solvent B=EtOAc) to give the title compound (326 mg, 1.04 mmol, 100% yield) as a colorless oil. LCMS, [M+Na]⁺=336.9.

87B. Trans-methyl 2-(((2'-fluoro-3-formyl-5'-isopropoxy-[1,1'-biphenyl]-4-yl)oxy) methyl)cyclopropanecarboxylate

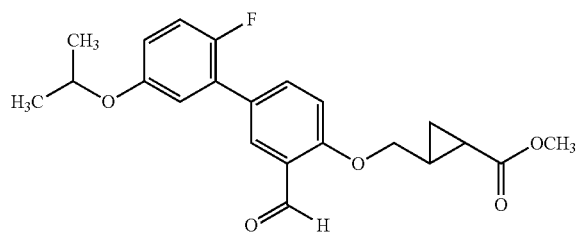 [SMILES: COC(=O)C1CC1COc1ccc(-c2cc(OC(C)C)ccc2F)cc1C=O]

A mixture of trans-methyl 2-((4-bromo-2-formylphenoxy)methyl) cyclopropanecarboxylate (120 mg, 0.38 mmol), (2-fluoro-5-isopropoxyphenyl)boronic acid (114 mg, 0.58 mmol), Pd(Ph₃P)₄ (44 mg, 0.04 mmol) and K₂CO₃ (159 mg, 1.15 mmol) in THF (1.8 mL) and water (0.6 mL) was heated in a microwave reactor at 130° C. for 20 min under Ar, then was cooled to rt. The reaction was acidified with 1N aq. HCl to pH=2-3, and extracted with EtOAc (4×15 mL). The combined organic extracts were dried over MgSO₄ and concentrated in vacuo. The crude product was chromatographed (SiO₂; 12 g; continuous gradient from 0 to 30% Solvent B over 20 min, hold at 30% Solvent B for 10 min, where Solvent A=hexanes and Solvent B=EtOAc) to give the title compound (146 mg, 0.38 mmol, 98% yield) as a colorless oil. LCMS, [M+Na]⁺=409.1.

EXAMPLE 87

LiOH.H₂O (5 mg, 0.13 mmol) was added to trans-methyl 2-(((2'-fluoro-3-formyl-5'-isopropoxy-[1,1'-biphenyl]-4-yl)oxy)methyl)cyclopropanecarboxylate (10 mg, 0.03 mmol) in THF (1 mL) and water (0.5 mL) at rt; the reaction was then stirred at rt overnight. The reaction was acidified with 1N aq. HCl to pH ~3 and extracted with EtOAc (3×5 mL). The combined organic extracts were washed with brine (5 mL), dried over MgSO₄, and concentrated in vacuo. The crude product was purified via preparative LC/MS with the following conditions: Column: Waters XBridge C18, 19×100 mm, 5-µm particles; Guard Column: Waters XBridge C18, 19×10 mm, 5-µm particles; Mobile Phase A: 5:95 MeCN:water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation to give the title compound (5 mg, 0.01 mmol, 46% yield). LCMS, [M−H]⁺=371.0. ¹H NMR (500 MHz, DMSO-d₆) δ 10.41 (s, 1H), 7.86-7.82 (m, 2H), 7.35-7.30 (m, 1H), 7.21 (dd, J=10.3, 9.2 Hz, 1H), 7.01 (dd, J=6.6, 3.3 Hz, 1H), 6.93 (dt, J=9.0, 3.5 Hz, 1H), 4.68-4.59 (m, 1H), 4.23 (dd, J=10.5, 6.3 Hz, 1H), 4.11 (dd, J=10.5, 7.2 Hz, 1H), 1.83-1.75 (m, 1H), 1.69 (dt, J=8.3, 4.4 Hz, 1H), 1.26 (d, J=6.1 Hz, 6H), 1.11 (dt, J=8.7, 4.3 Hz, 1H), 1.07-1.00 (m, 1H). HPLC-4: RT=1.59 min, purity=96%; HPLC-5: RT=1.97 min, purity=96%.

EXAMPLE 88

Trans-2-(((2'-fluoro-5'-isopropoxy-3-(trifluoromethyl)-[1,1'-biphenyl]-4-yl)oxy)methyl) cyclopropanecarboxylic acid (racemate)

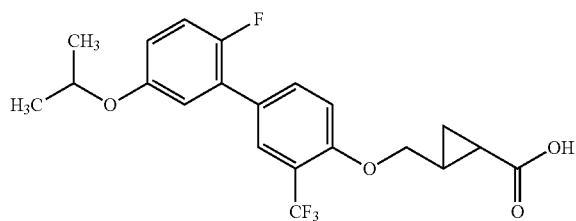 [SMILES: CC(C)Oc1ccc(F)c(-c2ccc(OCC3CC3C(=O)O)c(C(F)(F)F)c2)c1]

The title compound was synthesized using the same synthetic sequence as for the synthesis of Example 87, except that 4-bromo-2-(trifluoromethyl)phenol was used instead of 5-bromo-2-hydroxybenzaldehyde. The title compound was obtained (24 mg, 0.06 mmol, 100% yield) as a pale yellow oil. LCMS, [M−H]⁺=411.0. $^1$H NMR (500 MHz, DMSO-$d_6$) δ 7.79 (d, J=8.3 Hz, 1H), 7.73 (br. s., 1H), 7.34 (d, J=8.3 Hz, 1H), 7.21 (t, J=9.4 Hz, 1H), 7.04 (d, J=3.0 Hz, 1H), 6.93 (d, J=5.5 Hz, 1H), 4.69-4.61 (m, 1H), 4.26-4.20 (m, 1H), 4.14-4.07 (m, 1H), 1.77-1.69 (m, 1H), 1.67-1.61 (m, J=3.9 Hz, 1H), 1.26 (d, J=1.0 Hz, 6H), 1.12-1.06 (m, J=4.4 Hz, 1H), 1.03-0.96 (m, 1H). HPLC-4: RT=1.91 min, purity=100%; HPLC-5: RT=2.23 min, purity=100%.

EXAMPLE 89

Trans-2-(((2'-fluoro-5'-isopropoxy-3-(2-methoxyethyl)-[1,1'-biphenyl]-4-yl)oxy)methyl) cyclopropanecarboxylic acid (racemate)

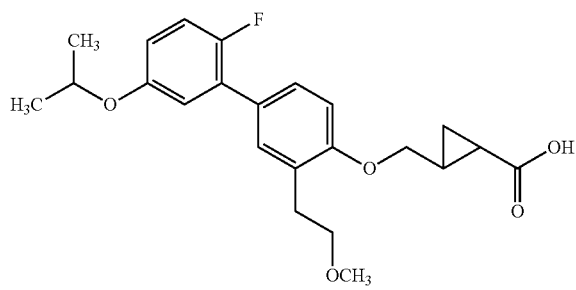 [SMILES: COCCc1cc(-c2cc(OC(C)C)ccc2F)ccc1OCC1CC1C(=O)O]

89A. 4-Bromo-2-(2-hydroxyethyl)phenol

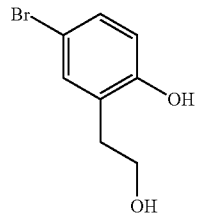 [SMILES: OCCc1cc(Br)ccc1O]

Conc. $H_2SO_4$ (11 μL, 0.20 mmol) and N-bromo succinimide (779 mg, 4.38 mmol) were added to a solution of 2-(2-hydroxyethyl)phenol (550 mg, 3.98 mmol) in THF (7 mL) at −25° C. The mixture was allowed to warm to rt and stirred overnight. Aq. sodium thiosulfite (10% aq. solution, 10 mL) and water (5 mL) were added and the resulting mixture was extracted with EtOAc (2×50 mL). The combined organic layers were washed with brine (10 mL), dried over $MgSO_4$, and concentrated in vacuo. The crude product was chromatographed ($SiO_2$; 40 g; continuous gradient from 0 to 40% Solvent B over 35 min, hold at 40% Solvent B for 10 min, where Solvent A=hexanes and Solvent B=EtOAc) to give the title compound (558 mg, 2.57 mmol, 65% yield) as a beige solid. 1H NMR (500 MHz, $CDCl_3$ d) δ 7.91 (s, 1H), 7.27-7.23 (m, 1H), 7.19 (d, J=2.5 Hz, 1H), 6.81 (d, J=8.5 Hz, 1H), 4.01 (td, J=5.2, 3.4 Hz, 2H), 2.89-2.85 (m, 2H), 2.28 (t, J=3.2 Hz, 1H).

89B. Trans-methyl 2-((4-bromo-2-(2-hydroxyethyl)phenoxy)methyl) cyclopropanecarboxylate

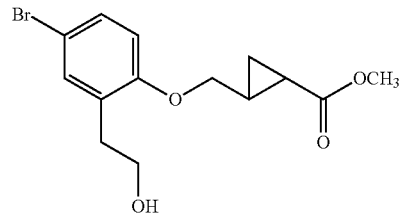 [SMILES: COC(=O)C1CC1COc1ccc(Br)cc1CCO]

A mixture of 4-bromo-2-(2-hydroxyethyl)phenol (118 mg, 0.54 mmol), trans-methyl 2-(bromomethyl)cyclopropanecarboxylate (100 mg, 0.52 mmol) and $K_2CO_3$ (143 mg, 1.04 mmol) in DMF (0.8 mL) was stirred overnight at rt. The mixture was partitioned between EtOAc and water. The aqueous layer was extracted with EtOAc (2×). The combined organic layers were washed with brine (10 mL), dried over $MgSO_4$, and evaporated in vacuo. The crude product was chromatographed ($SiO_2$; 12 g; continuous gradient from 0 to 40% Solvent B over 25 min, hold at 40% Solvent B for 10 min, where Solvent A=hexanes and Solvent B=EtOAc) to give the title compound (113 mg, 0.34 mmol, 66% yield) as a colorless oil. $^1$H NMR (500 MHz, $CDCl_3$) δ 7.32-7.27 (m, 2H), 6.68 (d, J=8.5 Hz, 1H), 3.97 (dd, J=10.2, 5.8 Hz, 1H), 3.89-3.81 (m, 3H), 3.71 (s, 3H), 2.87 (t, J=6.5 Hz, 2H), 1.94-1.86 (m, 1H), 1.76-1.69 (m, 1H), 1.33 (dt, J=9.0, 4.7 Hz, 1H), 1.01 (ddd, J=8.5, 6.3, 4.5 Hz, 1H).

89C. Trans-methyl 2-(((2'-fluoro-3-(2-hydroxyethyl)-5'-isopropoxy-[1,1'-biphenyl]-4-yl)oxy)methyl)cyclopropanecarboxylate

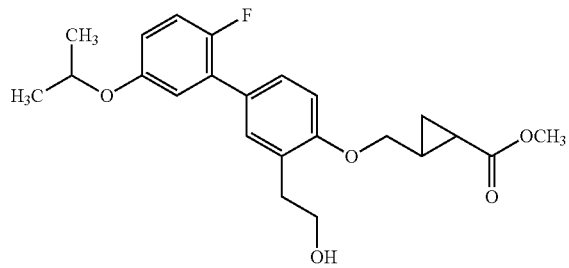 [SMILES: COC(=O)C1CC1COc1ccc(-c2cc(OC(C)C)ccc2F)cc1CCO]

A mixture of trans-methyl 2-((4-bromo-2-(2-hydroxyethyl)phenoxy)methyl) cyclopropanecarboxylate (113 mg, 0.34 mmol), (2-fluoro-5-isopropoxyphenyl)boronic acid (102 mg, 0.52 mmol), Pd(Ph$_3$P)$_4$ (40 mg, 0.03 mmol) and K$_2$CO$_3$ (142 mg, 1.03 mmol) in THF (1.5 mL) and water (0.5 mL) was heated in a microwave reactor at 130° C. for 20 min under Ar, then was cooled to rt. The reaction was acidified with 1N aq. HCl to pH=2-3, and extracted with EtOAc (4×10 mL). The combined organic extracts were dried over MgSO$_4$, and concentrated in vacuo to afford the crude product, which was used in the next step without further purification.

89D. Trans-2-(((2'-fluoro-3-(2-hydroxyethyl)-5'-isopropoxy-[1,1'-biphenyl]-4-yl)oxy)methyl)cyclopropanecarboxylic acid

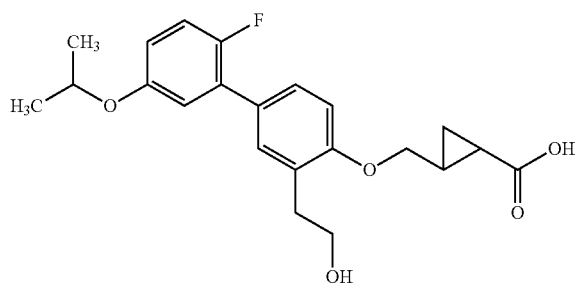 [SMILES: CC(C)Oc1ccc(F)c(-c2ccc(OCC3CC3C(=O)O)c(CCO)c2)c1]

To a solution of crude trans-methyl 2-(((2'-fluoro-3-(2-hydroxyethyl)-5'-isopropoxy-[1,1'-biphenyl]-4-yl)oxy)methyl)cyclopropanecarboxylate (138 mg, 0.34 mmol) in THF (1 mL) and water (0.5 mL) was added KOH (577 mg, 10.3 mmol). The mixture was heated to 80° C. in a microwave vial for 30 min, then was cooled to rt. The mixture was acidified with 1N aq. HCl to pH=2-3 then was extracted with EtOAc (3×10 mL). The combined organic extracts were dried over MgSO$_4$ and concentrated in vacuo to afford the crude title compound (109 mg, 0.28 mmol, 80% yield), which was used in the next step without further purification. LCMS, [M+Na]$^+$=412.1.

89E. Trans-methyl 2-(((2'-fluoro-5'-isopropoxy-3-(2-methoxyethyl)-[1,1'-biphenyl]-4-yl)oxy)methyl)cyclopropanecarboxylate

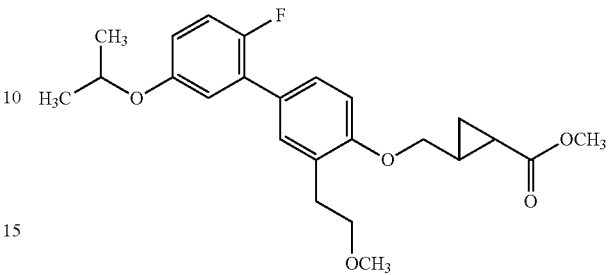

A suspension of trans-2-(((2'-fluoro-3-(2-hydroxyethyl)-5'-isopropoxy-[1,1'-biphenyl]-4-yl)oxy)methyl)cyclopropanecarboxylic acid (15 mg, 0.04 mmol), 2,6-di-tert-butylpyridine (0.03 mL, 0.14 mmol), and AgOTf (30 mg, 0.12 mmol) in CH$_2$Cl$_2$ (0.8 mL) was cooled to 0° C. MeI (18 mg, 0.12 mmol) was added and a yellow precipitate was formed within a few minutes. After stirring at RT overnight, the reaction was diluted with CH$_2$Cl$_2$ and filtered through a plug of CELITE®. The filtrate was concentrated in vacuo to give the crude title compound, which was used directly for the next step without further purification.

EXAMPLE 89

LiOH.H$_2$O (8 mg, 0.20 mmol) was added to a solution of trans-methyl 2-(((2'-fluoro-5'-isopropoxy-3-(2-methoxyethyl)-[1,1'-biphenyl]-4-yl)oxy)methyl) cyclopropanecarboxylate (16 mg, 0.04 mmol) in THF (1 mL), water (0.5 mL) and MeOH (1 mL) at rt; the reaction was then stirred at rt overnight. The solution was acidified with 1N aq. HCl to pH ~3 and extracted with EtOAc (3×5 mL). The combined organic layers were washed with brine (5 mL), dried over MgSO$_4$, and evaporated in vacuo. The crude product was purified via preparative LC/MS with the following conditions: Column: Waters XBridge C18, 19×100 mm, 5-μm particles; Guard Column: Waters XBridge C18, 19×10 mm, 5-jm particles; Mobile Phase A: 5:95 MeCN:water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation to give the title compound (6 mg, 0.02 mmol, 38% yield). LCMS, [M+Na]$^+$=401.0. $^1$H NMR (DMSO-d$_6$, 500 MHz): δ 7.35 (br. s., 2H), 7.16 (t, J=9.5 Hz, 1H), 7.01 (d, J=7.4 Hz, 1H), 6.94 (d, J=2.8 Hz, 1H), 6.87 (d, J=6.3 Hz, 1H), 4.57-4.66 (m, 1H), 4.06-4.13 (m, 1H), 3.87-3.94 (m, 1H), 3.51-3.57 (m, 2H), 3.25 (br. s., 3H), 2.82-2.88 (m, 2H), 1.70-1.78 (m, 1H), 1.61-1.67 (m, 1H), 1.26 (br. d, J=1.0 Hz, 6H), 1.07-1.12 (m, 1H), 0.96-1.03 ppm (m, 1H). HPLC-4: RT=1.76 min, purity=100%; HPLC-5: RT=2.10 min, purity=100%.

EXAMPLE 90

Trans-2-(((2'-fluoro-5'-isopropoxy-3-(2-oxoethyl)-[1,1'-biphenyl]-4-yl)oxy)methyl) cyclopropanecarboxylic acid (racemate)

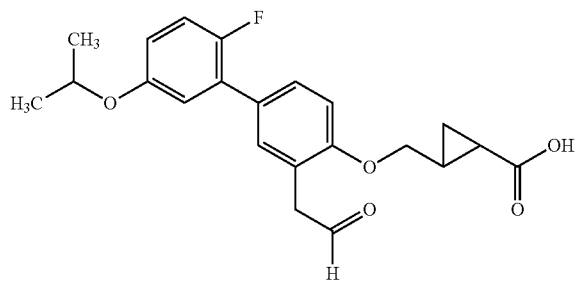 [SMILES: CC(C)Oc1ccc(F)c(-c2ccc(OCC3CC3C(=O)O)c(CC=O)c2)c1]

90A. Trans-methyl 2-(((2'-fluoro-5'-isopropoxy-3-(2-oxoethyl)-[1,1'-biphenyl]-4-yl)oxy) methyl)cyclopropanecarboxylate

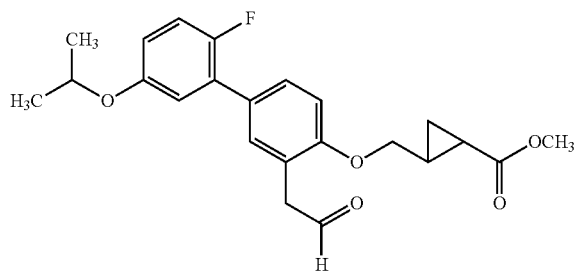 [SMILES: COC(=O)C1CC1COc1ccc(-c2cc(OC(C)C)ccc2F)cc1CC=O]

To a solution of trans-methyl 2-(((2'-fluoro-3-(2-hydroxyethyl)-5'-isopropoxy-[1,1'-biphenyl]-4-yl)oxy)methyl)cyclopropanecarboxylate (310 mg, 0.77 mmol) in CH$_2$Cl$_2$(4 mL) was added Dess-Martin periodinane (392 mg, 0.92 mmol) and the reaction was stirred at rt for 1 h. TLC (hexanes/EtOAc=3/1) showed the disappearance of the starting material and appearance of a new spot (product). The white solid was filtered off using CELITE® and the filter cake was rinsed with EtOAc. The combined filtrates were washed with sat'd aq. NaHCO$_3$, water and brine, dried, and concentrated in vacuo. The residue was chromatographed (SiO$_2$; gradient of 0% EtOAc/hexanes to 30% EtOAc/hexanes over 35 min) to afford the title compound (245 mg, 0.61 mmol, 79% yield) as a colorless oil. $^1$H NMR (500 MHz, CDCl$_3$) δ 9.75 (t, J=2.1 Hz, 1H), 7.46 (dt, J=8.5, 1.9 Hz, 1H), 7.36-7.34 (m, 1H), 7.03 (dd, J=10.0, 8.9 Hz, 1H), 6.94-6.89 (m, 2H), 6.79 (dt, J=8.8, 3.4 Hz, 1H), 4.51 (spt, J=6.1 Hz, 1H), 4.05 (dd, J=10.2, 5.8 Hz, 1H), 3.99-3.94 (m, 1H), 3.72 (s, 3H), 2.05 (s, 2H), 1.96-1.86 (m, 1H), 1.75-1.69 (m, 1H), 1.38-1.30 (m, 7H), 1.01 (ddd, J=8.4, 6.2, 4.7 Hz, 1H).

EXAMPLE 90

A solution of LiOH.H$_2$O (8 mg, 0.19 mmol) and trans-methyl 2-(((2'-fluoro-5'-isopropoxy-3-(2-oxoethyl)-[1,1'-biphenyl]-4-yl)oxy)methyl)cyclopropanecarboxylate (15 mg, 0.04 mmol) in THF (1 mL) and water (0.5 mL) was stirred at rt overnight. The reaction was acidified with 1N aq. HCl to pH ~3 and extracted with EtOAc (3×5 mL). The combined organic layers were washed with brine (5 mL), dried over MgSO$_4$ and evaporated in vacuo. The crude product was purified via preparative LC/MS with the following conditions: Column: Waters XBridge C18, 19×100 mm, 5-μm particles; Guard Column: Waters XBridge C18, 19×10 mm, 5-μm particles; Mobile Phase A: 5:95 MeCN:water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation to give the title compound (4 mg, 2.59 μmol, 28% yield). LCMS, [M+Na]$^+$=385.0. $^1$H NMR (DMSO-d$_6$, 500 MHz): δ 10.41 (s, 1H), 7.83 (d, J=1.9 Hz, 2H), 7.30-7.34 (m, 1H), 7.17-7.24 (m, 1H), 7.01 (dd, J=6.6, 3.0 Hz, 1H), 6.90-6.95 (m, 1H), 4.64 (spt, J=6.1 Hz, 1H), 4.23 (dd, J=10.5, 6.3 Hz, 1H), 4.12 (dd, J=10.3, 7.0 Hz, 1H), 3.30-3.35 (s, 2H), 1.75-1.83 (m, 1H), 1.70 (dt, J=8.3, 4.4 Hz, 1H), 1.26 (d, J=6.1 Hz, 6H), 1.09-1.15 (m, 1H), 1.01-1.07 ppm (m, 1H). HPLC-4: RT=1.91 min, purity=100%; HPLC-5: RT=2.00 min, purity=98%.

EXAMPLE 91

Trans-2-(((5'-(3,4-difluorophenoxy)-2'-fluoro-[1,1'-biphenyl]-4-yl)oxy)methyl) cyclopropanecarboxylic acid (racemate)

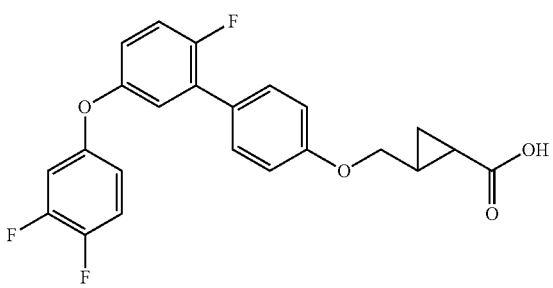 [SMILES: O=C(O)C1CC1COc1ccc(-c2cc(Oc3ccc(F)c(F)c3)ccc2F)cc1]

91A. Trans-methyl 2-(((5'-(3,4-difluorophenoxy)-2'-fluoro-[1,1'-biphenyl]-4-yl)oxy) methyl)cyclopropanecarboxylate (racemate)

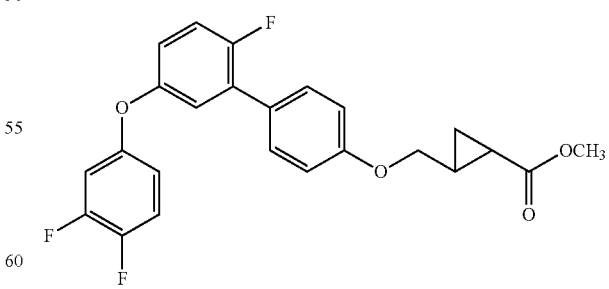

To a mixture of 22A (15 mg, 0.05 mmol), (3,4-difluorophenyl)boronic acid (15 mg, 0.10 mmol), molecular sieves (4A°, 0.1 g), TEA (0.03 mL, 0.24 mmol) and pyridine (0.02 mL, 0.24 mmol) in DCM (0.5 mL) was added Cu(OAc)$_2$ (17 mg, 0.10 mmol). The reaction was stirred at rt under an atmosphere of air overnight. LC-MS showed that the reaction was complete at this point. The reaction was filtered, concentrated in vacuo. The crude product was used for the next step without further purification. LCMS, [M+Na]⁺=451.1.

EXAMPLE 91

To a solution of crude trans-methyl 2-(((5'-(3,4-difluorophenoxy)-2'-fluoro-[1,1'-biphenyl]-4-yl)oxy)methyl)cyclopropanecarboxylate (20 mg, 0.05 mmol) in THF (1 mL) and water (0.5 mL) was added KOH (79 mg, 1.41 mmol). The mixture was heated to 80° C. in a microwave vial for 30 min, then was cooled to rt. The mixture was acidified with 1N aq. HCl to pH=2-3, extracted with EtOAc (3×10 mL), dried over MgSO₄ and concentrated in vacuo. This crude product was dissolved in DMF (2 mL) and purified via preparative LC/MS with the following conditions: Column: Waters XBridge C18, 19×100 mm, 5-μm particles; Guard Column: Waters XBridge C18, 19×10 mm, 5-μm particles; Mobile Phase A: 5:95 MeCN:water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation to provide the title compound (13 mg, 0.03 mmol, 67% yield). LCMS, [M–H]⁺=413.1. ¹H NMR (DMSO-d₆, 500 MHz): δ 7.41-7.51 (m, 3H), 7.33 (t, J=9.6 Hz, 1H), 7.21-7.27 (m, 1H), 7.18 (dd, J=6.6, 3.0 Hz, 1H), 7.00-7.06 (m, 3H), 6.86-6.91 (m, 1H), 4.03 (dd, J=10.5, 6.3 Hz, 1H), 3.88 (dd, J=10.3, 7.6 Hz, 1H), 1.67-1.76 (m, 1H), 1.61 (dt, J=8.3, 4.2 Hz, 1H), 1.08 (dt, J=8.7, 4.3 Hz, 1H), 0.93-1.00 ppm (m, 1H) HPLC-4: RT=1.91 min, purity=100%; HPLC-5: RT=2.28 min, purity=100%.

EXAMPLE 92

Trans-2-(((5'-(4-Chlorophenoxy)-2'-fluoro-[1,1'-biphenyl]-4-yl)oxy)methyl) cyclopropanecarboxylic acid (racemate)

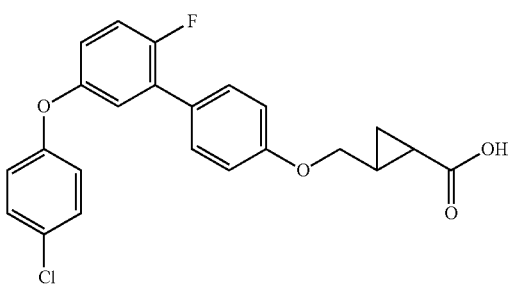 [SMILES: O=C(O)C1CC1COc1ccc(-c2cc(Oc3ccc(Cl)cc3)ccc2F)cc1]

The title compound was synthesized using the same synthetic sequence as for the synthesis of Example 91, except that (4-chlorophenyl)boronic acid was used instead of (3,4-difluorophenyl)boronic acid. The title compound was obtained (14 mg, 0.03 mmol, 100% yield) as a pale yellow oil. LCMS, [M–H]⁺=411.1. ¹H NMR (DMSO-d₆, 500 MHz): δ 7.47 (d, J=7.7 Hz, 2H), 7.40-7.44 (m, 2H), 7.29-7.35 (m, 1H), 7.16 (dd, J=6.6, 3.0 Hz, 1H), 7.00-7.08 (m, 5H), 4.03 (dd, J=10.5, 6.3 Hz, 1H), 3.87 (dd, J=10.5, 7.4 Hz, 1H), 1.67-1.75 (m, 1H), 1.61 (dt, J=8.4, 4.3 Hz, 1H), 1.08 (dt, J=8.8, 4.4 Hz, 1H), 0.93-1.00 ppm (m, 1H). HPLC-4: RT=1.92 min, purity=100%; HPLC-5: RT=2.30 min, purity=100%.

EXAMPLE 93

Trans-2-(((5'-((R)-sec-butoxy)-2'-fluoro-[1,1'-biphenyl]-4-yl)oxy)methyl) cyclopropanecarboxylic acid

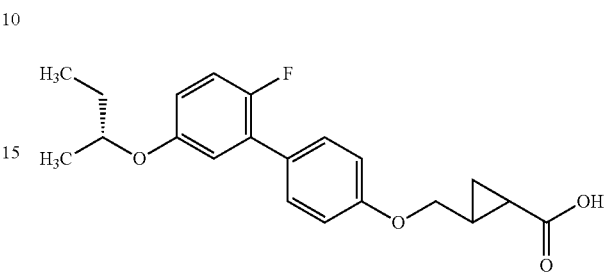

93A. Trans-methyl 2-(((5'-((R)-sec-butoxy)-2'-fluoro-[1,1'-biphenyl]-4-yl)oxy)methyl) cyclopropanecarboxylate

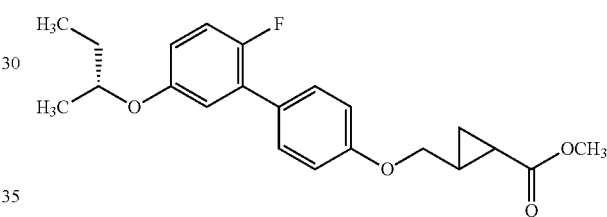

To a 0° C. solution of trans-methyl 2-(((2'-fluoro-5'-hydroxy-[1,1'-biphenyl]-4-yl) oxy)methyl)cyclopropanecarboxylate (15 mg, 0.05 mmol), (S)-butan-2-ol (9 μl, 0.10 mmol) and Ph₃P (19 mg, 0.07 mmol) in THF (0.5 mL) was added DIAD (0.014 mL, 0.07 mmol) dropwise. The reaction was allowed to warm to rt and stirred overnight at rt under Ar. LC-MS showed that the starting material had been converted to the desired product. Solids were filtered off and the filtrate was evaporated in vacuo. The residue was partitioned between EtOAc (10 mL) and H₂O (2 mL). The aqueous layer was extracted with EtOAc (3×10 mL). The combined organic layers were washed with 1N aq. NaOH (5 mL) and brine (5 mL), dried over MgSO₄, and evaporated in vacuo to afford the crude product, which was used in the next step without further purification. LCMS, [M+Na]⁺=395.1.

EXAMPLE 93

A mixture of LiOH.H₂O (8 mg, 0.19 mmol) and trans-methyl 2-(((5'-((R)-sec-butoxy)-2'-fluoro-[1,1'-biphenyl]-4-yl)oxy)methyl)cyclopropanecarboxylate (18 mg, 0.05 mmol) in THF (1 mL), water (0.5 mL) and MeOH (1 mL) was heated in a microwave at 80° C. for 30 min, then was cooled to rt. The reaction was partitioned between EtOAc (5 mL) and H₂O (5 mL). The aqueous layer was washed with EtOAc (2×1 mL). The combined organic layers were washed with H₂O (3×2 mL). The combined aqueous layers were acidified with 1N aq. HCl to pH ~3 and extracted with EtOAc (3×5 mL). The combined organic extracts were washed with brine (2 mL), dried over MgSO$_4$, and evaporated in vacuo. The crude product was purified by preparative LC/MS with the following conditions: Column: Waters XBridge C18, 19×100 mm, 5-μm particles; Guard Column: Waters XBridge C18, 19×10 mm, 5-μm particles; Mobile Phase A: 5:95 MeCN:water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation to give the title compound (12.5 mg, 0.04 mmol, 74% yield). LCMS, [M−H]$^+$=357.1. $^1$H NMR (DMSO-d$_6$, 500 MHz): δ 7.47 (d, J=7.2 Hz, 2H), 7.16 (t, J=9.5 Hz, 1H), 7.02 (d, J=7.4 Hz, 2H), 6.94 (d, J=2.8 Hz, 1H), 6.88 (d, J=5.2 Hz, 1H), 4.34-4.43 (m, 1H), 4.00-4.07 (m, 1H), 3.85-3.92 (m, 1H), 1.51-1.77 (m, 4H), 1.20-1.25 (m, 3H), 1.09 (d, J=3.9 Hz, 1H), 0.88-1.01 ppm (m, 4H). HPLC-4: RT=1.81 min, purity=100%; HPLC-5: RT=2.19 min, purity=100%.

The following Examples were synthesized using a sequence similar to that use for the preparation of Example 93.

| Ex. No. | Structure and Name | Analytical Data |
|---|---|---|
| 94 | Trans-2-(((5'-cyclobutoxy-2'-fluoro-[1,1'-biphenyl]-4-yl)oxy)methyl)cyclopropanecarboxylic acid (racemate) | LCMS, [M − H]$^+$ = 355.0. $^1$H NMR (DMSO-d$_6$, 500 MHz): δ 7.46 (d, J = 7.2 Hz, 2H), 7.16 (t, J = 9.2 Hz, 1H), 7.02 (d, J = 7.4 Hz, 2H), 6.86 (d, J = 2.8 Hz, 1H), 6.80 (d, J = 6.3 Hz, 1H), 4.67-4.76 (m, 1H), 4.00-4.07 (m, 1H), 3.85-3.92 (m, 1H), 2.37-2.46 (m, 2H), 2.03 (t, J = 8.8 Hz, 2H), 1.59-1.83 (m, 4H), 1.05-1.13 (m, 1H), 0.94-1.01 ppm (m, 1H). HPLC-4: RT = 1.76 min, purity = 100%; HPLC-5: RT = 2.14 min, purity = 100%. |
| 95 | Trans-2-(((5'-(cyclopropylmethoxy)-2'-fluoro-[1,1'-biphenyl]-4-yl)oxy)methyl)cyclopropanecarboxylic acid (racemate) | LCMS, [M − H]$^+$ = 355.0. $^1$H NMR (DMSO-d$_6$, 500 MHz): δ 7.48 (d, J = 6.9 Hz, 2H), 7.17 (t, J = 9.4 Hz, 1H), 7.02 (d, J = 7.4 Hz, 2H), 6.94-6.98 (m, 1H), 6.88 (d, J = 4.4 Hz, 1H), 4.00-4.06 (m, J = 5.0 Hz,1H), 3.81-3.92 (m, 3H), 1.67-1.75 (m, 1H), 1.58-1.64 (m, 1H), 1.16-1.26 (m, 1H), 1.04-1.11 (m, 1H), 0.92-0.99 (m, 1H), 0.53-0.60 (m, 2H), 0.28-0.35 ppm (m, 2H). HPLC-4: RT = 1.69 min, purity = 100%; HPLC-5: RT = 2.04 min, purity = 100%. |

EXAMPLE 96

Trans-2-(((2',3-difluoro-5'-(3-fluorophenoxy)-[1,1'-biphenyl]-4-yl)oxy)methyl) cyclopropanecarboxylic acid

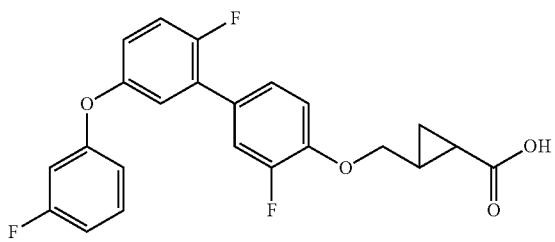 [SMILES: O=C(O)C1CC1COc1ccc(-c2cc(Oc3cccc(F)c3)ccc2F)cc1F]

96A. Trans-ethyl 2-(((5'-((tert-butyldimethylsilyl)oxy)-2',3-difluoro-[1,1'-biphenyl]-4-yl) oxy)methyl) cyclopropanecarboxylate (racemate)

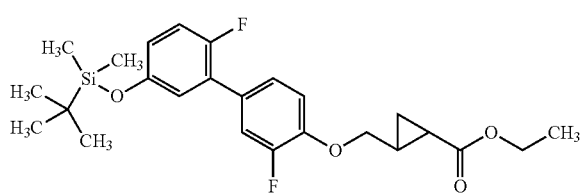 [SMILES: CCOC(=O)C1CC1COc1ccc(-c2cc(O[Si](C)(C)C(C)(C)C)ccc2F)cc1F]

A mixture of trans-ethyl 2-((4-bromo-2-fluorophenoxy)methyl) cyclopropanecarboxylate (150 mg, 0.47 mmol), Pd(Ph$_3$P)$_4$ (55 mg, 0.05 mmol) and K$_2$CO$_3$ (196 mg, 1.42 mmol) in THF (2 mL) and water (0.7 mL) was heated in a microwave reactor at 130° C. for 20 min under Ar, then was cooled to rt. The reaction was acidified with 1N aq. HCl to pH=2-3, and extracted with EtOAc (4×10 mL). The combined organic fractions were dried over MgSO$_4$, and concentrated in vacuo. The crude product was chromatographed (SiO$_2$; 40 g; continuous gradient from 0 to 20% Solvent B over 30 min, hold at 20% Solvent B for 20 min, where Solvent A=hexanes and Solvent B=EtOAc) to give the title compound (137 mg, 0.30 mmol, 63% yield) as a light yellow oil. LCMS, [M+Na]$^+$=485.2.

96B. Trans-ethyl 2-(((2',3-difluoro-5'-hydroxy-[1,1'-biphenyl]-4-yl)oxy)methyl) cyclopropanecarboxylate (racemate)

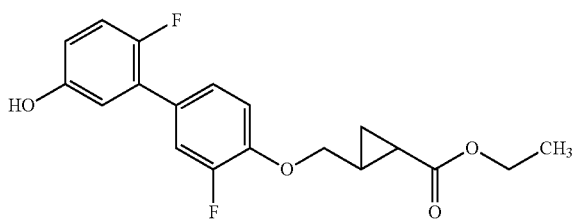 [SMILES: CCOC(=O)C1CC1COc1ccc(-c2cc(O)ccc2F)cc1F]

To a solution of trans-ethyl 2-(((5'-((tert-butyldimethylsilyl)oxy)-2',3-difluoro-[1,1'-biphenyl]-4-yl)oxy)methyl)cyclopropanecarboxylate (135 mg, 0.29 mmol) in THF (2.5 mL) was added TBAF (0.58 mL, 0.58 mmol) dropwise. The reaction was stirred at rt for 1 h. The reaction was quenched with 1N aq. HCl (10 mL), extracted with EtOAc (3×10 mL). The combined organic layers were dried over MgSO$_4$, filtered and concentrated in vacuo. The crude product was chromatographed (SiO$_2$; 12 g; continuous gradient from 0 to 40% Solvent B over 20 min, hold at 40% Solvent B for 10 min, where Solvent A=hexanes and Solvent B=EtOAc) to afford the title compound (102 mg, 0.29 mmol, 100% yield) as a colorless oil. LCMS, [M+Na]$^+$=371.0.

EXAMPLE 96

To a solution of trans-methyl 2-(((2',3-difluoro-5'-hydroxy-[1,1'-biphenyl]-4-yl)oxy)methyl)cyclopropanecarboxylate (30 mg, 0.09 mmol) and (3-fluorophenyl)boronic acid (25 mg, 0.18 mmol) in DCM (1 mL) were added molecular sieves (4A, 0.1 g), TEA (0.06 mL, 0.45 mmol) and pyridine (0.04 mL, 0.45 mmol), followed by Cu(OAc)$_2$ (33 mg, 0.18 mmol). The reaction was stirred at rt under an atmosphere of air overnight. LC-MS showed the reaction was complete. The reaction was filtered and concentrated in vacuo. The crude aryl ether product was used in the next step without further purification. To a solution of the above crude aryl ether product in THF (1 mL) and water (0.5 mL) was added KOH (151 mg, 2.70 mmol). The mixture was heated to 80° C. in a microwave vial for 30 min, then was cooled to rt. The mixture was acidified with 1N aq. HCl to pH=2-3. The mixture was extracted with EtOAc (3×10 mL), dried over MgSO$_4$ and concentrated in vacuo. The crude product was dissolved in DMF (2 mL) and purified via preparative LC/MS with the following conditions: Column: Waters XBridge C18, 19×100 mm, 5-µm particles; Guard Column: Waters XBridge C18, 19×10 mm, 5-µm particles; Mobile Phase A: 5:95 MeCN:water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation to give the title compound (22 mg, 0.05 mmol, 58% yield). LCMS, [M-H]$^-$=413.0. $^1$H NMR (DMSO-d$_6$, 500 MHz): δ 7.32-7.50 (m, 4H), 7.28 (dd, J=6.6, 2.8 Hz, 1H), 7.21-7.26 (m, 1H), 7.07-7.12 (m, 1H), 6.94-6.99 (m, 1H), 6.90 (d, J=10.5 Hz, 1H), 6.85 (d, J=8.3 Hz, 1H), 4.10 (dd, J=10.5, 6.3 Hz, 1H), 3.97 (dd, J=10.3, 7.6 Hz, 1H), 1.68-1.77 (m, 1H), 1.63 (dt, J=8.4, 4.3 Hz, 1H), 1.09 (dt, J=8.7, 4.3 Hz, 1H), 0.94-1.00 ppm (m, 1H). HPLC-4: RT=1.90 min, purity=100%; HPLC-5: RT=2.27 min, purity=100%. The two enantiomers of Example 96 were separated by chiral preparative HPLC (Instrument: Berger Multigram II SFC; Column: CHIRALPAK® AD-H, 30×250 mm, 5 µm; Mobile Phase: 15% MeOH/85% CO$_2$; Flow Conditions: 85 mL/min, 150 Bar, 40° C.; Detector Wavelength: 220 nm; Injection Details: 0.75 mL of 7 mg/mL in MeCN).

EXAMPLE 97

Enantiomer 1: The first eluting peak. LCMS, [M-H]$^+$=413.1. $^1$H NMR (DMSO-d$_6$, 500 MHz): δ 7.31-7.49 (m, 4H), 7.19-7.30 (m, 2H), 7.09 (d, J=5.0 Hz, 1H), 6.82-6.99 (m, 3H), 4.06-4.14 (m, 1H), 3.94-4.02 (m, 1H), 1.55-1.77 (m, 2H), 1.03-1.11 (m, 1H), 0.88-0.97 ppm (m, 1H). HPLC-4: Rt=1.84 min, purity=100%; HPLC-5: Rt=2.22 min, purity=100%.

EXAMPLE 98

Enantiomer 2: The second eluting peak. LCMS, [M-H]$^+$=413.0. $^1$H NMR (DMSO-d$_6$, 500 MHz): δ 7.31-

7.49 (m, 4H), 7.19-7.30 (m, 2H), 7.09 (d, J=5.0 Hz, 1H), 6.82-6.99 (m, 3H), 4.06-4.14 (m, 1H), 3.93-4.01 (m, 1H), 1.55-1.77 (m, 2H), 1.03-1.12 (m, 1H), 0.88-0.98 ppm (m, 1H). HPLC-4: Rt=1.90 min, purity=100%; HPLC-5: Rt=2.33 min, purity=100%.

EXAMPLE 99

Trans-2-(((2'-fluoro-5'-(3-fluorophenoxy)-3-methoxy-[1,1'-biphenyl]-4-yl)oxy)methyl) cyclopropanecarboxylic acid

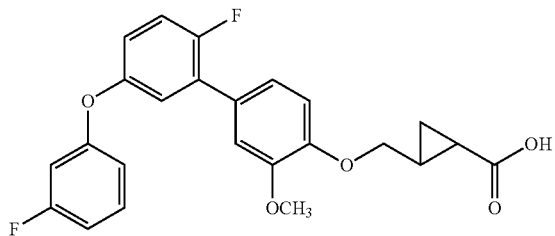 [SMILES: COc1cc(-c2cc(Oc3cccc(F)c3)ccc2F)ccc1OCC1CC1C(=O)O]

99A. Trans-methyl 2-((4-bromo-2-methoxyphenoxy)methyl)cyclopropanecarboxylate (racemate)

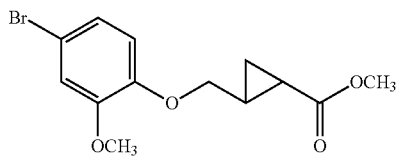 [SMILES: COC(=O)C1CC1COc1ccc(Br)cc1OC]

A mixture of 4-bromo-2-methoxyphenol (110 mg, 0.54 mmol), trans-methyl 2-(bromomethyl)cyclopropanecarboxylate (100 mg, 0.52 mmol) and $K_2CO_3$ (143 mg, 1.04 mmol) in DMF (2.5 mL) was stirred overnight at rt. The mixture was partitioned between EtOAc and water. The layers were separated and the aqueous layer was extracted with EtOAc. The combined organic layers were washed with brine (10 mL), dried over $MgSO_4$, and concentrated in vacuo, The crude product was chromatographed ($SiO_2$; 12 g; continuous gradient from 0 to 30% Solvent B over 20 min, hold at 30% Solvent B for 10 min, where Solvent A=hexanes and Solvent B=EtOAc) to give the title compound (116 mg, 0.37 mmol, 71% yield) as a colorless oil. LCMS, $[M+Na]^+=337.0$.

EXAMPLE 99

The title compound was synthesized using the same synthetic sequence as used for the synthesis of Example 96, except that trans-methyl 2-((4-bromo-2-methoxyphenoxy)methyl)cyclopropanecarboxylate was used instead of trans-ethyl 2-((4-bromo-2-fluorophenoxy)methyl)cyclopropanecarboxylate. The title compound was obtained (8 mg, 0.02 mmol, 42% yield). LCMS, $[M-H]^+=425.1$. $^1H$ NMR (DMSO-$d_6$, 500 MHz): δ 7.38-7.43 (m, 1H), 7.33 (dd, J=10.2, 9.1 Hz, 1H), 7.26-7.30 (m, 1H), 7.13 (s, 1H), 7.04-7.10 (m, 2H), 7.00-7.03 (m, 1H), 6.95 (td, J=8.4, 2.2 Hz, 1H), 6.89 (dt, J=10.6, 2.3 Hz, 1H), 6.84 (dd, J=8.3, 2.2 Hz, 1H), 3.99 (dd, J=10.6, 6.2 Hz, 1H), 3.86 (dd, J=10.5, 7.4 Hz, 1H), 3.81 (s, 3H), 1.65-1.74 (m, 1H), 1.59 (dt, J=8.4, 4.3 Hz, 1H), 1.06 (dt, J=8.8, 4.4 Hz, 1H), 0.89-0.96 ppm (m, 1H). HPLC-4: RT=1.72 min, purity=99%; HPLC-5: RT=2.20 min, purity=96%.

The following Examples were synthesized using a sequence similar to that use for the preparation of Example 99.

| Ex. No. | Structure and Name | Analytical Data |
|---|---|---|
| 100 | Trans-2-(((2',3-difluoro-5'-(3-fluoro-4-methylphenoxy)-[1,1'-biphenyl]-4-yl)oxy)methyl)cyclopropanecarboxylic acid (racemate) | LCMS, $[M - H]^+ = 427.0$. $^1H$ NMR (DMSO-$d_6$, 500 MHz): δ 7.44 (d, J = 12.7 Hz, 1H), 7.19-7.36 (m, 5H), 7.04 (dt, J = 8.8, 3.4 Hz, 1H), 6.87 (dd, J = 11.0, 2.5 Hz, 1H), 6.78 (dd, J = 8.3, 2.5 Hz, 1H), 4.11 (dd, J = 10.5, 6.3 Hz, 1H), 3.97 (dd, J = 10.6, 7.6 Hz, 1H), 2.19 (s, 3H), 1.69-1.77 (m, 1H), 1.63 (dt, J = 8.5, 4.4 Hz, 1H), 1.09 (dt, J = 8.9, 4.5 Hz, 1H), 0.94-1.02 ppm (m, 1H). HPLC-4: RT = 1.95 min, purity = 100%; HPLC-5: RT = 2.35 min, purity = 96%. |

| Ex. No. | Structure and Name | Analytical Data |
|---|---|---|
| 101 | 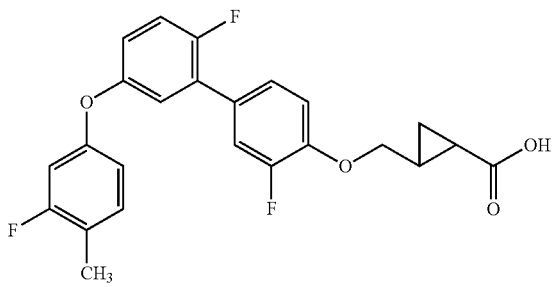 [SMILES: Cc1ccc(Oc2ccc(F)c(-c3ccc(OCC4CC4C(=O)O)c(F)c3)c2)cc1F]<br>Enantiomer 1<br>Trans-2-(((2',3-difluoro-5'-(3-fluoro-4-methylphenoxy)-[1,1'-biphenyl]-4-yl)oxy)methyl)cyclopropanecarboxylic acid | LCMS, [M − H]$^+$ = 427.3. $^1$H NMR (CDCl$_3$, 500 MHz): δ 7.30 (dd, J = 12.1, 1.7 Hz, 1H), 7.23 (d, J = 8.5 Hz, 1H), 7.10-7.16 (m, 2H), 7.06 (dd, J = 6.3, 3.0 Hz, 1H), 7.00 (t, J = 8.7 Hz, 1H), 6.95 (td, J = 4.5, 3.2 Hz, 1H), 6.67-6.73 (m, 2H), 4.07-4.12 (m, 1H), 3.99-4.05 (m, 1H), 2.25 (d, J = 1.7 Hz, 3H), 1.96-2.08 (m, 1H), 1.73-1.85 (m, 1H), 1.36-1.44 (m, 1H), 1.08-1.17 ppm (m, 1H). HPLC-1: RT =12.53 min, purity = 100%; HPLC-2: RT = 10.95 min, purity = 100%. |
| 102 | 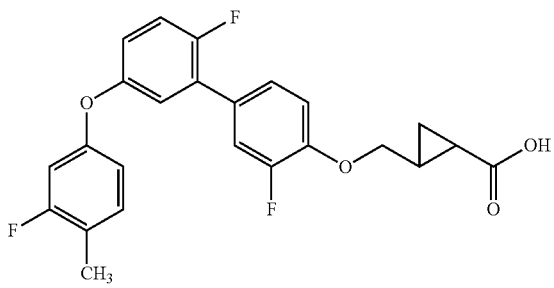 [SMILES: Cc1ccc(Oc2ccc(F)c(-c3ccc(OCC4CC4C(=O)O)c(F)c3)c2)cc1F]<br>Enantiomer 2<br>Trans-2-(((2',3-difluoro-5'-(3-fluoro-4-methylphenoxy)-[1,1'-biphenyl]-4-yl)oxy)methyl)cyclopropanecarboxylic acid | LCMS, [M − H]$^+$ = 427.3. $^1$H NMR (CDCl$_3$, 500 MHz): δ 7.30 (d, J = 12.4 Hz, 1H), 7.23 (d, J = 8.3 Hz, 1H), 7.09-7.17 (m, 2H), 7.06 (dd, J = 6.1, 2.8 Hz, 1H), 6.92-7.03 (m, 2H), 6.66-6.75 (m, 2H), 3.98-4.13 (m, 2H), 2.25 (s, 3H), 1.96-2.08 (m, 1H), 1.74-1.86 (m, 1H), 1.35-1.45 (m, 1H), 1.07-1.18 ppm (m, 1H). HPLC-1: RT =12.55 min, purity = 100%; HPLC-2: RT = 10.97 min, purity = 100%. |
| 103 | 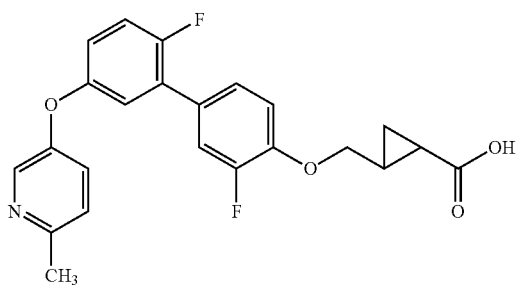 [SMILES: Cc1ccc(Oc2ccc(F)c(-c3ccc(OCC4CC4C(=O)O)c(F)c3)c2)cn1]<br>Trans-2-(((2',3-difluoro-5'-((6-methylpyridin-3-yl)oxy)-[1,1'-biphenyl]-4-yl)oxy)methyl)cyclopropanecarboxylic acid (racemate) | LCMS, [M − H]$^+$ = 410.0. $^1$H NMR (DMSO-d$_6$, 500 MHz): δ 8.28 (d, J = 3.0 Hz, 1H), 7.45 (d, J = 12.7 Hz, 1H), 7.39 (dd, J = 8.4, 2.9 Hz, 1H), 7.30-7.36 (m, 2H), 7.21-7.29 (m, 3H), 7.04 (dt, J = 8.9, 3.5 Hz, 1H), 4.11 (dd, J = 10.7, 6.3 Hz, 1H), 3.98 (dd, J = 10.7, 7.4 Hz, 1H), 2.45 (s, 3H), 1.69-1.78 (m, 1H), 1.63 (dt, J = 8.4, 4.3 Hz, 1H), 1.09 (dt, J = 8.8, 4.4 Hz, 1H), 0.98 ppm (ddd, J = 8.3, 6.1, 4.1 Hz, 1H). HPLC-4: RT = 1.53 min, purity = 95%; HPLC-5: RT = 1.36 min, purity = 99%. |

| Ex. No. | Structure and Name | Analytical Data |
|---|---|---|
| 104 | 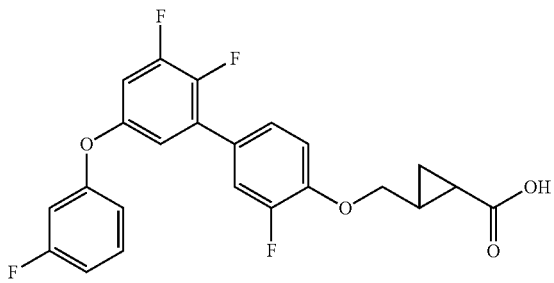 [SMILES: O=C(O)C1CC1COc1ccc(-c2cc(Oc3cccc(F)c3)cc(F)c2F)cc1F]<br>Trans-2-(((2',3,3'-trifluoro-5'-(3-fluorophenoxy)-[1,1'-biphenyl]-4-yl)oxy)methyl)cyclopropanecarboxylic acid (racemate) | LCMS, [M − H]⁺ = 431.0. ¹H NMR (DMSO-d₆, 500 MHz): δ 7.40-7.52 (m, 2H), 7.36 (d, J = 8.3 Hz, 1H), 7.22-7.29 (m, 2H), 7.10 (br. s., 1H), 6.88-7.03 (m, 3H), 4.08-4.15 (m, 1H), 3.94-4.03 (m, 1H), 1.69-1.78 (m, 1H), 1.58-1.67 (m, J = 3.9 Hz, 1H), 1.06-1.13 (m, J = 4.1 Hz, 1H), 0.93-1.02 ppm (m, 1H). HPLC-4: RT = 1.93 min, purity = 100%; HPLC-5: RT = 2.27 min, purity = 95%. |
| 105 | 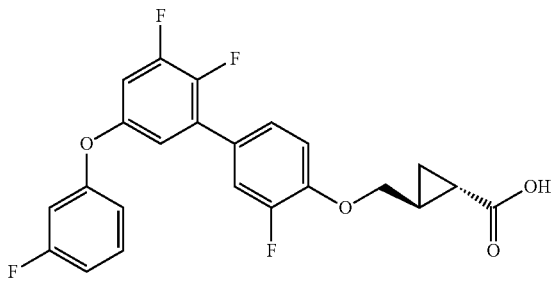 [SMILES: O=C(O)[C@H]1C[C@@H]1COc1ccc(-c2cc(Oc3cccc(F)c3)cc(F)c2F)cc1F]<br>Enantiomer 1<br>(1S,2S)-2-(((2',3,3'-Trifluoro-5'-(3-fluorophenoxy)-[1,1'-biphenyl]-4-yl)oxy)methyl)cyclopropanecarboxylic acid | LCMS, [M − H]⁺ = 431.0. ¹H NMR (DMSO-d₆, 500 MHz): δ 7.39-7.51 (m, 2H), 7.35 (d, J = 8.5 Hz, 1H), 7.25 (t, J = 8.5 Hz, 2H), 7.08 (br. s., 1H), 6.87-7.03 (m, 3H), 4.12 (dd, J = 10.2, 6.3 Hz, 1H), 3.93-4.00 (m, 1H), 1.69-1.78 (m, 1H), 1.58-1.67 (m, 1H), 1.05-1.13 (m, 1H), 0.94-1.02 ppm (m, 1H). HPLC-4: RT = 1.79 min, purity = 100%; HPLC-5: RT = 2.30 min, purity = 99%. |
| 106 | 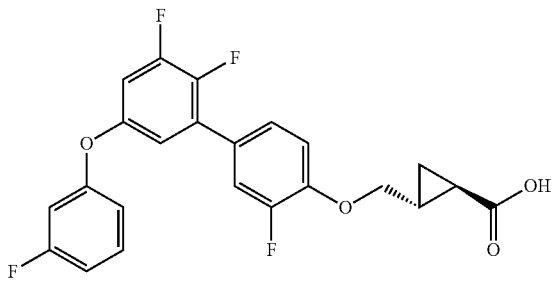 [SMILES: O=C(O)[C@@H]1C[C@H]1COc1ccc(-c2cc(Oc3cccc(F)c3)cc(F)c2F)cc1F]<br>Enantiomer 2<br>(1R,2R)-2-(((2',3,3'-Trifluoro-5'-(3-fluorophenoxy)-[1,1'-biphenyl]-4-yl)oxy)methyl)cyclopropanecarboxylic acid | LCMS, [M − H]⁺ = 431.0. ¹H NMR (500 MHz, DMSO-d₆) δ 7.51-7.39 (m, 2H), 7.35 (d, J = 8.2 Hz, 1H), 7.25 (t, J = 8.2 Hz, 2H), 7.08 (br. s., 1H), 7.03-6.88 (m, 3H), 4.12 (dd, J = 10.1, 6.4 Hz, 1H), 4.00-3.93 (m, 1H), 1.78-1.68 (m, 1H), 1.67-1.59 (m, 1H), 1.12-1.06 (m, 1H), 1.02-0.93 (m, 1H). HPLC-4: RT = 1.79 min, purity = 99%; HPLC-5: RT = 2.30 min, purity = 95%. |

| Ex. No. | Structure and Name | Analytical Data |
|---|---|---|
| 107 | 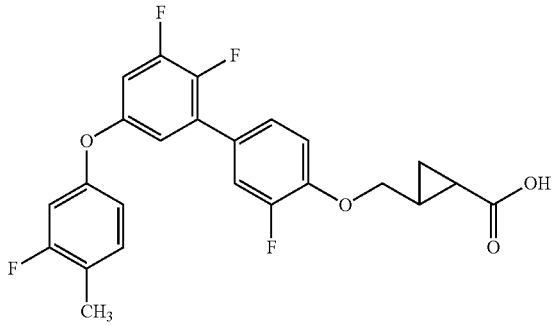 [SMILES: Cc1ccc(Oc2cc(F)c(F)c(-c3ccc(OCC4CC4C(=O)O)c(F)c3)c2)cc1F]<br>Trans-2-(((2',3,3'-Trifluoro-5'-(3-fluorophenoxy)-[1,1'-biphenyl]-4-yl)oxy)methyl)cyclopropanecarboxylic acid (racemate) | LCMS, [M − H]⁺ = 445.1. ¹H NMR (500 MHz, DMSO-$d_6$) δ 7.48 (d, J = 12.4 Hz, 1H), 7.37-7.16 (m, 4H), 7.04 (br. s., 1H), 6.95 (d, J = 10.7 Hz, 1H), 6.84 (d, J = 8.3 Hz, 1H), 4.11 (dd, J = 10.6, 6.5 Hz, 1H), 4.02-3.95 (m, 1H), 2.20 (s, 3H), 1.77-1.70 (m, 1H), 1.63 (dt, J = 8.3, 4.1 Hz, 1H), 1.09 (dt, J = 8.6, 4.1 Hz, 1H), 1.01-0.94 (m, 1H). HPLC-4: RT = 2.02 min, purity = 95%; HPLC-5: RT = 2.37 min, purity = 95%. |
| 108 | 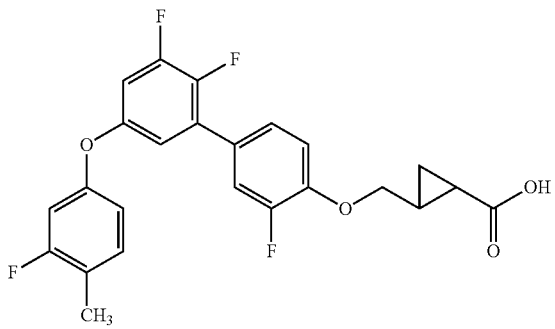 [SMILES: Cc1ccc(Oc2cc(F)c(F)c(-c3ccc(OCC4CC4C(=O)O)c(F)c3)c2)cc1F]<br>Enantiomer 1<br>Trans-2-(((2',3,3'-trifluoro-5'-(3-fluorophenoxy)-[1,1'-biphenyl]-4-yl)oxy)methyl)cyclopropanecarboxylic acid | LCMS, [M − H]⁺ = 445.1. ¹H NMR (500 MHz, DMSO-$d_6$) δ 7.47 (d, J = 12.9 Hz, 1H), 7.36-7.22 (m, 3H), 7.19 (ddd, J = 11.3, 6.3, 3.0 Hz, 1H), 7.05-7.01 (m, 1H), 6.95 (dd, J = 11.0, 2.5 Hz, 1H), 6.84 (dd, J = 8.4, 2.3 Hz, 1H), 4.10 (dd, J = 10.6, 6.5 Hz, 1H), 3.98 (dd, J = 10.5, 7.4 Hz, 1H), 2.20 (s, 3H), 1.77-1.68 (m, 1H), 1.62 (dt, J = 8.3, 4.2 Hz, 1H), 1.08 (dt, J = 8.8, 4.4 Hz, 1H), 0.99-0.93 (m, 1H). HPLC-4: RT = 2.43 min, purity = 100%; HPLC-5: RT = 2.43 min, purity = 100%. |
| 109 | 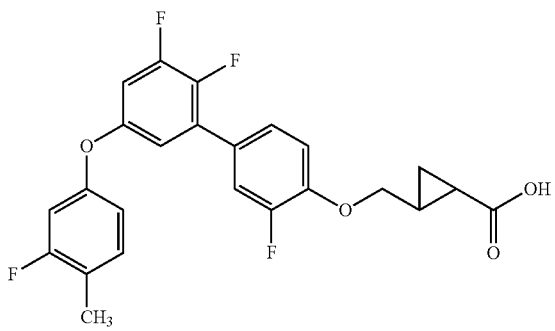<br>Enantiomer 2<br>Trans-2-(((2',3,3'-trifluoro-5'-(3-fluorophenoxy)-[1,1'-biphenyl]-4-yl)oxy)methyl)cyclopropanecarboxylic acid | LCMS, [M − H]⁺ = 445.1. ¹H NMR (500 MHz, DMSO-$d_6$) δ 7.47 (d, J = 12.9 Hz, 1H), 7.36-7.22 (m, 3H), 7.18 (ddd, J = 11.3, 6.3, 3.0 Hz, 1H), 7.03 (dt, J = 5.2, 2.5 Hz, 1H), 6.95 (dd, J = 11.0, 2.5 Hz, 1H), 6.84 (dd, J = 8.4, 2.3 Hz, 1H), 4.10 (dd, J = 10.7, 6.3 Hz, 1H), 3.98 (dd, J = 10.7, 7.4 Hz, 1H), 2.20 (s, 3H), 1.76-1.69 (m, 1H), 1.62 (dt, J = 8.4, 4.3 Hz, 1H), 1.08 (dt, J = 8.8, 4.4 Hz, 1H), 0.99-0.93 (m, 1H). HPLC-4: RT= 1.99 min, purity = 100%; HPLC-5: RT = 2.44 min, purity = 100%. |

EXAMPLE 110

Trans-2-((4-(2-chloro-5-phenoxypyridin-3-yl)phenoxy)methyl)cyclopropanecarboxylic acid (racemate)

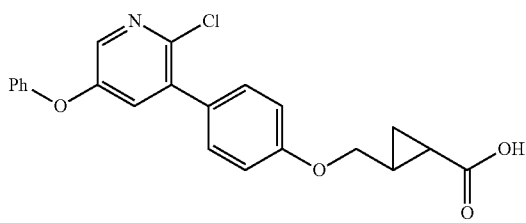 [SMILES: O=C(O)C1CC1COc1ccc(-c2cc(Oc3ccccc3)cnc2Cl)cc1]

110A. Trans-methyl 2-((4-(4,4,5,5-tetramethyl-1,3,2-dioxaborolan-2-yl)phenoxy)methyl) cyclopropanecarboxylate (racemate)

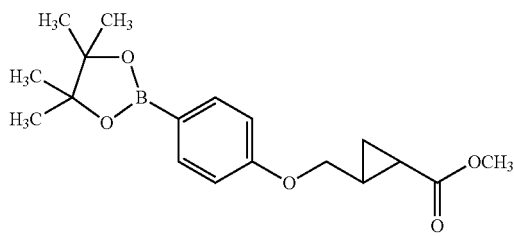 [SMILES: COC(=O)C1CC1COc1ccc(B2OC(C)(C)C(C)(C)O2)cc1]

A mixture of trans-methyl 2-((4-bromophenoxy)methyl)cyclopropanecarboxylate (400 mg, 1.40 mmol), KOAc (413 mg, 4.21 mmol) and bis(pinacolato)diboron (427 mg, 1.68 mmol) in DMSO (1.6 mL) was degassed with $N_2$ for 15 min; PdCl2(dppf) (103 mg, 0.14 mmol) was then added and the reaction mixture was degassed again with $N_2$ for 15 min. The reaction vessel was sealed and heated at 85° C. for 5 h, then was cooled to rt and filtered. The filter-cake was washed with EtOAc and the combined filtrates were concentrated in vacuo. The residue was chromatographed ($SiO_2$: 80 g; A=Hex, B=EtOAc; 30 min gradient; 0% B to 20% B; flow rate=60 mL/min) to give the title compound (385 mg, 1.16 mmol, 83% yield) as a colorless oil. LCMS, [M+Na]$^+$=355.1.

110B. Trans-methyl 2-((4-(2-chloro-5-phenoxypyridin-3-yl)phenoxy)methyl) cyclopropanecarboxylate

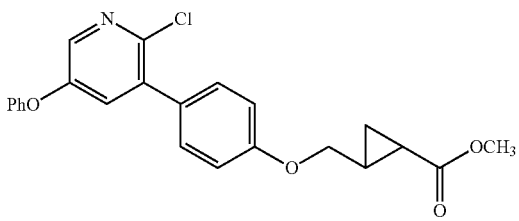 [SMILES: COC(=O)C1CC1COc1ccc(-c2cc(Oc3ccccc3)cnc2Cl)cc1]

A mixture of trans-methyl 2-((4-(4,4,5,5-tetramethyl-1,3,2-dioxaborolan-2-yl)phenoxy)methyl)cyclopropanecarboxylate (21 mg, 0.06 mmol), 3-bromo-2-chloro-5-phenoxypyridine (15 mg, 0.05 mmol), Pd(Ph$_3$P)$_4$ (6 mg, 5.27 µmol) and K$_2$CO$_3$ (22 mg, 0.16 mmol) in THF (2 mL) and water (0.7 mL) was heated in a microwave reactor at 130° C. for 20 min under Ar, then was cooled to rt. The reaction was diluted with water (5 mL), and extracted with EtOAc (4×10 mL). The combined organic extracts were dried over MgSO$_4$, and concentrated in vacuo to give the crude product, which was used in the next step without further purification.

EXAMPLE 110

To the above crude product in THF (1 mL) and water (0.5 mL) was added KOH (89 mg, 1.59 mmol). The mixture was heated to 80° C. in a microwave vial for 30 min, then was cooled to rt. The mixture was acidified with 1N aq. HCl to pH=2-3, then was extracted with EtOAc (3×10 mL), dried over MgSO$_4$, and concentrated in vacuo. The crude product was dissolved in DMF (2 mL) and purified via preparative LC/MS with the following conditions: Column: Waters XBridge C18, 19×100 mm, 5-µm particles; Guard Column: Waters XBridge C18, 19×10 mm, 5-µm particles; Mobile Phase A: 5:95 MeCN:water with 0.1% TFA; Mobile Phase B: 95:5 MeCN:water with 0.1% TFA; Gradient: 45-85% B over 10 min, then a 5-min hold at 100% B; Flow: 20 mL/min. Fractions containing the desired product were combined and dried via centrifugal evaporation to give the title compound (2 mg, 4.6 µmol, 9% yield). LCMS, [M+H]$^+$=396.1. $^1$H NMR (500 MHz, DMSO-d$_6$) δ 8.17 (d, J=2.8 Hz, 1H), 7.47-7.40 (m, 5H), 7.23-7.14 (m, 3H), 7.02 (d, J=8.5 Hz, 2H), 4.03 (dd, J=10.3, 6.2 Hz, 1H), 3.89 (dd, J=10.2, 7.4 Hz, 1H), 1.76-1.68 (m, 1H), 1.62 (dt, J=8.4, 4.3 Hz, 1H), 1.09 (dt, J=8.8, 4.4 Hz, 1H), 1.00-0.94 (m, 1H). HPLC-4: RT=1.64 min, purity=86%; HPLC-5: RT=2.04 min, purity=83%.

EXAMPLE 111

Trans-2-((4-(2-chloro-5-(3-fluorophenoxy)pyridin-3-yl)phenoxy)methyl) cyclopropanecarboxylic acid (racemate)

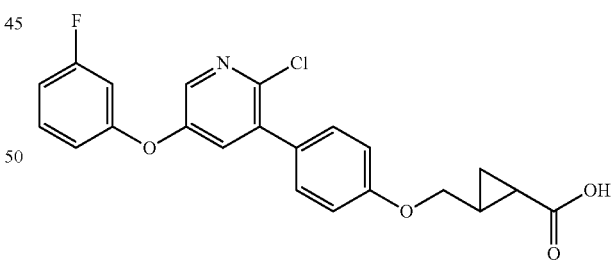

The title compound was synthesized using the same synthetic sequence as used for the synthesis of Example 110, except that 3-bromo-2-chloro-5-(3-fluoro-phenoxy)pyridine was used instead of 3-bromo-2-chloro-5-phenoxypyridine. The title compound was obtained (25 mg, 0.06 mmol, 45% yield). LCMS, [M-H]$^+$=412.1. $^1$H NMR (500 MHz, DMSO-d$_6$) δ 8.21 (br. s., 1H), 7.53 (br. s., 1H), 7.48-7.38 (m, 3H), 7.09-6.94 (m, 5H), 4.07-4.00 (m, 1H), 3.86 (t, J=8.7 Hz, 1H), 1.75-1.66 (m, 1H), 1.65-1.58 (m, 1H), 1.11-1.05 (m, 1H), 1.01-0.94 (m, 1H). HPLC-4: RT=1.60 min, purity=100%; HPLC-5: RT=2.03 min, purity=100%. The two enantiomers of Example 111 were separated by chiral preparative HPLC (Instrument: Berger Multigram II SFC; Column: CHIRALPAK® OJ-H, 21×250 mm, 5 μm; Mobile Phase: 18% EtOH-0.1% TFA/82% $CO_2$; Flow Conditions: 45 mL/min, 150 Bar, 40° C.; Detector Wavelength: 220 nm; Injection Details: 1 mL of 6.6 mg/mL in EtOH).

EXAMPLE 112

Enantiomer 1: The first eluting peak. LCMS, [M−H]+=412.1. $^1$H NMR (500 MHz, DMSO-$d_6$) δ 8.21 (d, J=2.4 Hz, 1H), 7.53 (s, 1H), 7.47-7.39 (m, 3H), 7.08-6.94 (m, 5H), 4.03 (dd, J=10.7, 6.1 Hz, 1H), 3.89-3.83 (m, 1H), 1.75-1.66 (m, 1H), 1.64-1.57 (m, 1H), 1.11-1.05 (m, 1H), 1.01-0.94 (m, 1H). HPLC-4: Rt=1.64 min, purity=100%; HPLC-5: RT=2.05 min, purity=95%.

EXAMPLE 113

Enantiomer 2: The second eluting peak. LCMS, [M−H]+=412.1. $^1$H NMR (500 MHz, DMSO-$d_6$) δ 8.20 (br. s., 1H), 7.53 (br. s., 1H), 7.48-7.38 (m, 3H), 7.08-6.94 (m, 5H), 4.06-4.00 (m, 1H), 3.89-3.82 (m, 1H), 1.75-1.66 (m, 1H), 1.64-1.57 (m, 1H), 1.11-1.04 (m, 1H), 1.01-0.94 (m, 1H). HPLC-4: Rt=1.65 min, purity=100%; HPLC-5: RT=2.05 min, purity=100%.

EXAMPLE 114

Trans-2-(((2'-fluoro-5'-((6-methylpyridin-3-yl)oxy)-[1,1'-biphenyl]-4-yl)oxy)methyl) cyclopropanecarboxylic acid (racemate)

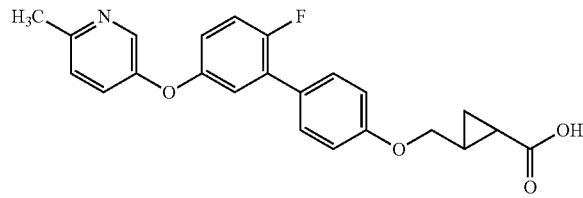 [SMILES: Cc1ccc(Oc2ccc(F)c(-c3ccc(OCC4CC4C(=O)O)cc3)c2)cn1]

114A.
5-(3-Bromo-4-fluorophenoxy)-2-methylpyridine

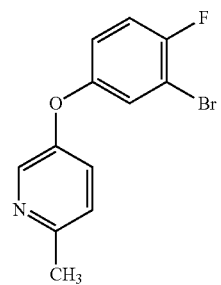 [SMILES: Cc1ccc(Oc2ccc(F)c(Br)c2)cn1]

To a solution of 6-methylpyridin-3-ol (299 mg, 2.74 mmol) and (3-bromo-4-fluorophenyl)boronic acid (500 mg, 2.29 mmol) in DCM (10 mL) were added molecular sieves (4A, 0.1 g), TEA (1.59 mL, 11.4 mmol) and pyridine (0.92 mL, 11.4 mmol), followed by $Cu(OAc)_2$ (830 mg, 4.57 mmol). The reaction was stirred at rt under an atmosphere of air overnight. LC-MS showed the reaction was complete at this point. The reaction was filtered, concentrated in vacuo and the crude product was chromatographed ($SiO_2$; 80 g; continuous gradient from 0 to 80% Solvent B over 30 min, hold at 80% Solvent B for 10 min, where Solvent A=hexanes and Solvent B=EtOAc) to give the title compound (261 mg, 0.92 mmol, 40% yield) as a brown oil. LCMS, [M+H]+=283.9.

EXAMPLE 114

The title compound was synthesized using the same synthetic sequence as used for the synthesis of Example 110, except that 5-(3-bromo-4-fluorophenoxy)-2-methylpyridine was used instead of 3-bromo-2-chloro-5-phenoxypyridine. The title compound was obtained (32 mg, 0.08 mmol, 100% yield). LCMS, [M−H]+=392.1. $^1$H NMR (500 MHz, DMSO-$d_6$) δ 8.23 (d, J=2.7 Hz, 1H), 7.45 (d, J=7.9 Hz, 2H), 7.39 (dd, J=8.4, 2.9 Hz, 1H), 7.32-7.26 (m, 2H), 7.11 (dd, J=6.6, 2.9 Hz, 1H), 7.03-6.97 (m, 3H), 4.03 (dd, J=10.7, 6.1 Hz, 1H), 3.83 (dd, J=10.4, 7.3 Hz, 1H), 2.43 (s, 3H), 1.75-1.66 (m, 1H), 1.60 (dt, J=8.4, 4.3 Hz, 1H), 1.07 (dt, J=8.9, 4.4 Hz, 1H), 1.00-0.94 (m, J=9.3, 9.3 Hz, 1H). HPLC-4: RT=1.51 min, purity=99%; HPLC-5: RT=1.33 min, purity=100%. The two enantiomers of Example 114 were separated by chiral preparative HPLC (Instrument: Berger Multigram II SFC; Column: CHIRALPAK OJ-H, 21×250 mm, 5; Mobile Phase: 15% EtOH-0.1% FA/85% $CO_2$; Flow Conditions: 45 mL/min, 150 Bar, 40° C.; Detector Wavelength: 220 nm; Injection Details: 2 mL of 1.4 mg/mL in EtOH-5% DMF).

EXAMPLE 115

The first eluting peak (Enantiomer 1) was isolated as Example 115. LCMS, [M−H]+=392.1. $^1$H NMR (500 MHz, DMSO-$d_6$) δ 8.27 (br. s., 1H), 7.48-7.40 (m, 3H), 7.34-7.27 (m, 2H), 7.13 (dd, J=6.6, 2.9 Hz, 1H), 7.01 (d, J=8.5 Hz, 3H), 4.03 (dd, J=10.7, 6.1 Hz, 1H), 3.84 (dd, J=10.5, 7.5 Hz, 1H), 2.45 (s, 3H), 1.75-1.66 (m, 1H), 1.61 (dt, J=8.2, 4.4 Hz, 1H), 1.11-1.05 (m, 1H), 1.01-0.93 (m, 1H). HPLC-4: Rt=1.50 min, purity=98%; HPLC-5: Rt=1.34 min, purity=100%.

EXAMPLE 116

The second (slower) eluting peak (Enantiomer 2) was isolated as Example 116. LCMS, [M−H]+=392.1. $^1$H NMR (500 MHz, DMSO-$d_6$) δ 8.25 (br. s., 1H), 7.45 (d, J=7.6 Hz, 2H), 7.39 (dd, J=8.5, 2.7 Hz, 1H), 7.33-7.24 (m, 2H), 7.14-7.09 (m, 1H), 7.04-6.96 (m, 3H), 4.03 (dd, J=10.4, 6.1 Hz, 1H), 3.84 (dd, J=10.4, 7.6 Hz, 1H), 2.44 (s, 3H), 1.75-1.66 (m, 1H), 1.61 (dt, J=8.4, 4.3 Hz, 1H), 1.08 (dt, J=8.9, 4.4 Hz, 1H), 1.00-0.94 (m, J=9.3, 9.3 Hz, 1H). HPLC-4: Rt=1.48 min, purity=100%; HPLC-5: Rt=1.34 min, purity=100%.

The following Examples were synthesized using an analogous sequence to the one used for the preparation of Example 1 or Example 38.

| Ex. No. | Structure and Name | Analytical Data | Method |
|---|---|---|---|
| 117 | Trans-2-(((3'-isopropoxy-5'-methoxy-[1,1'-biphenyl]-4-yl)oxy)methyl)cyclopropanecarboxylic acid (racemate) | LCMS, [M + H]$^+$ = 357.2. $^1$H NMR (500 MHz, DMSO-d$_6$) δ 7.57 (d, J = 8.5 Hz, 2H), 6.98 (d, J = 8.4 Hz, 2H), 6.68 (s, 2H), 6.40 (s, 1H), 4.68 (p, J = 6.0 Hz, 1H), 4.02 (dd, J = 10.4, 6.2 Hz, 1H), 3.91-3.81 (m, 1H), 3.77 (s, 3H), 1.70 (q, J = 8.2, 6.7 Hz, 1H), 1.61 (dt, J = 8.7, 4.4 Hz, 1H), 1.27 (d, J = 6.0 Hz, 6H), 1.08 (dt, J = 8.9, 4.5 Hz, 1H), 0.97 (dt, J = 9.6, 4.9 Hz, 1H). | Ex. 1 |
| 118 | Trans-2-(((3'-benzoyl-[1,1'-biphenyl]-4-yl)oxy)methyl)cyclopropanecarboxylic acid (racemate) | LCMS, [M + H]$^+$ = 373.2. $^1$H NMR (500 MHz, DMSO-d$_6$) δ 8.01-7.85 (m, 2H), 7.78 (d, J = 7.7 Hz, 2H), 7.69 (t, J = 7.4 Hz, 1H), 7.67-7.53 (m, 6H), 7.04 (d, J = 8.5 Hz, 2H), 4.03 (dd, J = 10.4, 6.2 Hz, 1H), 3.92-3.84 (m, 1H), 1.72 (q, J = 7.3, 6.3 Hz, 1H), 1.62 (dt, J = 9.3, 4.4 Hz, 1H), 1.09 (dt, J = 8.9, 4.2 Hz, 1H), 0.97 (q, J = 6.1 Hz, 1H). | Ex. 1 |
| 119 | Trans-2-(((2'-chloro-5'-isopropoxy-[1,1'-biphenyl]-4-yl)oxy)methyl)cyclopropanecarboxylic acid (racemate) | LCMS, [M + H]$^+$ = 361.1. $^1$H NMR (500 MHz, CDCl$_3$) δ 7.44-7.35 (m, 2H), 7.33 (d, J = 8.8 Hz, 1H), 6.97-6.89 (m, 2H), 6.86 (d, J = 3.0 Hz, 1H), 6.80 (dd, J = 8.7, 2.9 Hz, 1H), 4.53 (dt, J = 12.1, 6.1 Hz, 1H), 4.05 (dd, J = 10.2, 5.8 Hz, 1H), 3.92 (dd, J = 10.0, 6.5 Hz, 1H), 2.09-1.95 (m, 1H), 1.76 (dt, J = 8.4, 4.3 Hz, 1H), 1.40 (dt, J = 9.1, 4.6 Hz, 1H), 1.35 (d, J = 6.1 Hz, 6H), 1.13 (ddd, J = 8.4, 6.5, 4.7 Hz, 1H). | Ex. 1 |
| 120 | Trans-2-(((3'-chloro-5'-isopropoxy-[1,1'-biphenyl]-4-yl)oxy)methyl)cyclopropanecarboxylic acid (racemate) | LCMS, [M + H]$^+$ = 361.1. $^1$H NMR (500 MHz, CDCl$_3$) δ 7.45 (d, J = 8.5 Hz, 2H), 7.08 (s, 1H), 6.95-6.89 (m, 3H), 6.82 (s, 1H), 4.61-4.47 (m, 1H), 4.04-3.95 (m, 1H), 3.91-3.82 (m, 1H), 1.97 (d, J = 2.8 Hz, 1H), 1.77-1.66 (m, 1H), 1.39-1.27 (m, 8H), 1.07 (d, J = 2.8 Hz, 1H). | Ex. 1 |

| Ex. No. | Structure and Name | Analytical Data | Method |
|---|---|---|---|
| 121 | 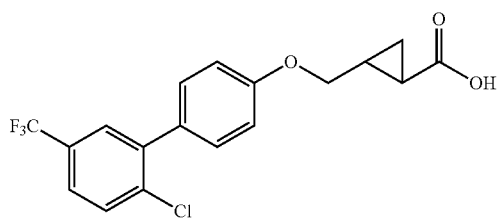 [SMILES: O=C(O)C1CC1COc1ccc(-c2cc(C(F)(F)F)ccc2Cl)cc1]<br>Trans-2-(((2'-chloro-5'-(trifluoromethyl)-[1,1'-biphenyl]-4-yl)oxy)methyl)cyclopropanecarboxylic acid (racemate) | LCMS, [M − H]⁺ = 369.1. ¹H NMR (500 MHz, CDCl₃) δ 7.61-7.57 (m, 2H), 7.53-7.49 (m, 1H), 7.40-7.36 (m, 2H), 7.00-6.95 (m, 2H), 4.04 (dd, J = 10.0, 5.9 Hz, 1H), 3.92 (dd, J = 9.9, 6.6 Hz, 1H), 2.00-1.92 (m, 1H), 1.79-1.74 (m, 1H), 1.35 (dt, J = 9.0, 4.7 Hz, 1H), 1.05 (ddd, J = 8.5, 6.3, 4.5 Hz, 1H). HPLC-1: RT = 11.47 min, purity = 100%; HPLC-2: RT = 9.67 min, purity = 100%. | Ex. 1 |
| 122 | 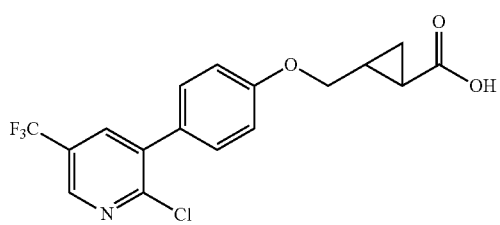 [SMILES: O=C(O)C1CC1COc1ccc(-c2cc(C(F)(F)F)cnc2Cl)cc1]<br>Trans-2-((4-(2-chloro-5-(trifluoromethyl)pyridin-3-yl)phenoxy)methyl)cyclopropanecarboxylic acid (racemate) | LCMS, [M − H]⁺ = 370.2. ¹H NMR (500 MHz, CDCl₃) δ 8.64 (dd, J = 2.2, 0.8 Hz, 1H), 7.88 (d, J = 2.5 Hz, 1H), 7.44-7.38 (m, 2H), 7.02-6.97 (m, 2H), 4.08 (dd, J = 10.2, 5.8 Hz, 1H), 3.93 (dd, J = 10.0, 6.7 Hz, 1H), 2.06-1.99 (m, 1H), 1.81-1.74 (m, 1H), 1.42 (dt, J = 9.1, 4.6 Hz, 1H), 1.14 (ddd, J = 8.4, 6.5, 4.7 Hz, 1H). HPLC-1: RT = 9.95 min, purity = 97%; HPLC-2: RT = 8.39 min, purity = 97%. | Ex. 1 |
| 123 | 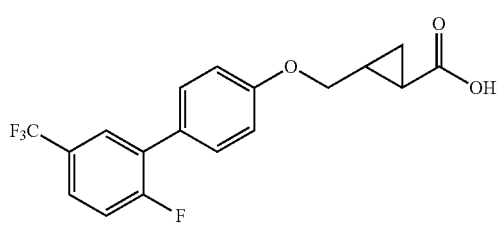 [SMILES: O=C(O)C1CC1COc1ccc(-c2cc(C(F)(F)F)ccc2F)cc1]<br>Trans-2-(((2'-fluoro-5'-(trifluoromethyl)-[1,1'-biphenyl]-4-yl)oxy)methyl)cyclopropanecarboxylic acid (racemate) | LCMS, [M − H]⁺ = 353.1 ¹H NMR (500 MHz, CDCl₃) δ 7.69 (d, J = 5.2 Hz, 1H), 7.59-7.54 (m, 1H), 7.50 (d, J = 7.4 Hz, 2H), 7.26-7.21 (m, 1H), 6.99 (d, J = 8.8 Hz, 2H), 4.06 (dd, J = 10.2, 5.8 Hz, 1H), 3.92 (dd, J = 9.9, 6.6 Hz, 1H), 2.07-1.97 (m, 1H), 1.77 (dt, J = 8.3, 4.1 Hz, 1H), 1.41 (dt, J = 8.9, 4.6 Hz, 1H), 1.17-1.09 (m, 1H). HPLC-1: RT = 10.99 min, purity = 100%; HPLC-2: RT = 9.29 min, purity = 100%. | Ex. 1 |
| 124 | 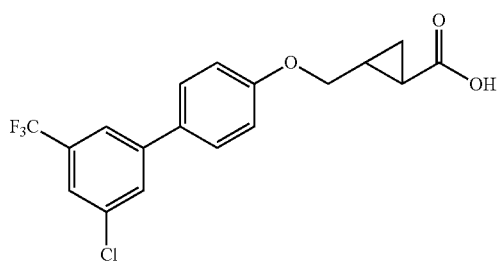 [SMILES: O=C(O)C1CC1COc1ccc(-c2cc(Cl)cc(C(F)(F)F)c2)cc1]<br>Trans-2-(((3'-chloro-5'-(trifluoromethyl)-[1,1'-biphenyl]-4-yl)oxy)methyl)cyclopropanecarboxylic acid (racemate) | LCMS, [M − H]⁺ = 369.1 ¹H NMR (500 MHz, CDCl₃) δ 7.69 (d, J = 17.1 Hz, 2H), 7.58-7.48 (m, 3H), 6.98 (d, J = 8.8 Hz, 2H), 4.07 (dd, J = 9.9, 5.8 Hz, 1H), 3.91 (dd, J = 10.2, 6.6 Hz, 1H), 2.07-1.96 (m, 1H), 1.81-1.74 (m, 1H), 1.41 (dt, J = 8.9, 4.5 Hz, 1H), 1.17-1.10 (m, 1H). HPLC-1: RT = 12.20 min, purity = 95%; HPLC-2: RT = 9.99 min, purity = 95%. | Ex. 1 |

| Ex. No. | Structure and Name | Analytical Data | Method |
|---|---|---|---|
| 125 | Trans-2-((([1,1':2,1''-terphenyl]-4-yloxy)methyl)cyclopropanecarboxylic acid (racemate) | $^1$H NMR (500 MHz, DMSO-$d_6$) δ 7.47-7.36 (m, 4H), 7.27 (br. s., 3H), 7.12 (d, J = 6.3 Hz, 2H), 7.01 (d, J = 7.7 Hz, 2H), 6.80 (d, J = 7.7 Hz, 2H), 3.98-3.91 (m, 1H), 3.84-3.77 (m, 1H), 1.73-1.64 (m, 1H), 1.63-1.56 (m, 1H), 1.11-1.04 (m, 1H), 0.98-0.91 (m, 1H) | Ex. 1 |
| 126 | Trans-2-((([1,1':3,1''-terphenyl]-4-yloxy)methyl)cyclopropanecarboxylic acid (racemate) | $^1$H NMR (500 MHz, DMSO-$d_6$) δ 7.88-7.83 (m, 1H), 7.76 (br. s., 2H), 7.73-7.69 (m, 2H), 7.65-7.59 (m, 2H), 7.58-7.48 (m, 3H), 7.44-7.38 (m, 1H), 7.10-7.02 (m, 2H), 4.10-4.03 (m, 1H), 3.95-3.87 (m, 1H), 1.79-1.71 (m, 1H), 1.68-1.62 (m, 1H), 1.15-1.08 (m, 1H), 1.04-0.96 (m, 1H) | Ex. 1 |
| 127 | Trans-2-(((2',6'-difluoro-3'-isopropoxy-[1,1'-biphenyl]-4-yl)oxy)methyl)cyclopropanecarboxylic acid | $^1$H NMR (500 MHz, DMSO-$d_6$) δ 7.36 (d, J = 7.4 Hz, 2H), 7.18 (d, J = 3.9 Hz, 1H), 7.13-7.02 (m, 3H), 4.59 (d, J = 5.2 Hz, 1H), 4.03 (d, J = 5.0 Hz, 1H), 3.91 (t, J = 7.6 Hz, 1H), 1.72 (br. s., 1H), 1.61 (d, J = 3.0 Hz, 1H), 1.30 (br. s., 6H), 1.09 (d, J = 4.1 Hz, 1H), 0.95 (br. s., 1H) | Ex. 1 |
| 128 | Trans-2-(2-(3'-(1H-pyrazol-1-yl)-[1,1'-biphenyl]-4-yl)ethyl)cyclopropanecarboxylic acid (racemate) | LCMS, [M + H]$^+$ = 333.2; $^1$H NMR (500 MHz, DMSO-$d_6$) δ 8.65 (s, 1H), 8.09 (br. s., 1H), 7.96 (s, 1H), 7.88-7.75 (m, 2H), 7.68 (d, J = 8.1 Hz, 2H), 7.63-7.51 (m, 2H), 7.34 (d, J = 8.1 Hz, 2H), 6.65-6.50 (m, 1H), 2.76-2.69 (m, 2H), 1.70-1.54 (m, 2H), 1.43-1.31 (m, 1H), 1.23 (br. s., 1H), 0.97 (d, J = 3.7 Hz, 1H), 0.74 (br. s., 1H) | Ex. 38 |

-continued

| Ex. No. | Structure and Name | Analytical Data | Method |
|---|---|---|---|
| 129 | 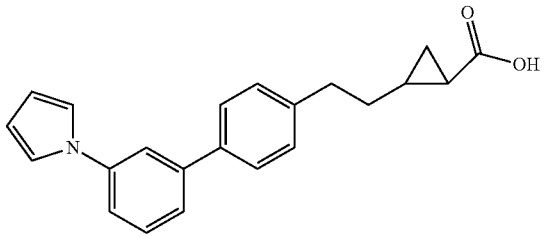 [SMILES: O=C(O)C1CC1CCc1ccc(-c2cccc(-n3cccc3)c2)cc1]<br>Trans-2-(2-(3'-(1H-pyrrol-1-yl)-[1,1'-biphenyl]-4-yl)ethyl) cyclopropanecarboxylic acid (racemate) | LCMS, [M − H]$^+$ = 330.2; $^1$H NMR (500 MHz, DMSO-d$_6$) δ 7.79 (s, 1H), 7.70 (d, J = 7.7 Hz, 2H), 7.51 (d, J = 18.3 Hz, 5H), 7.33 (d, J = 7.7 Hz, 2H), 6.29 (s, 2H), 2.77-2.68 (m, 2H), 1.62 (q, J = 7.2 Hz, 2H), 1.41-1.29 (m, 1H), 1.24 (br. s., 1H), 1.02-0.92 (m, 1H), 0.75 (t, J = 9.2 Hz, 1H). | Ex. 38 |
| 130 | 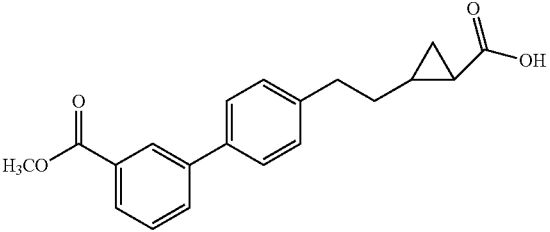 [SMILES: COC(=O)c1cccc(-c2ccc(CCC3CC3C(=O)O)cc2)c1]<br>Trans-2-(2-(3'-(methoxycarbonyl)-[1,1'-biphenyl]-4-yl)ethyl) cyclopropanecarboxylic acid (racemate) | LCMS, [M − H]$^+$ = 323.2 | Ex. 38 |
| 131 | 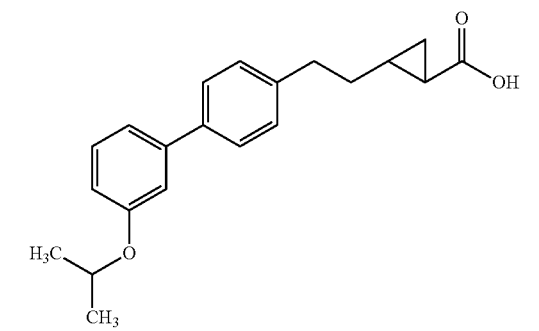 [SMILES: CC(C)Oc1cccc(-c2ccc(CCC3CC3C(=O)O)cc2)c1]<br>Trans-2-(2-(3'-isopropoxy-[1,1'-biphenyl]-4-yl)ethyl) cyclopropanecarboxylic acid (racemate) | LCMS, [M + H]$^+$ = 325.2; $^1$H NMR (500 MHz, DMSO-d$_6$) δ 7.54 (d, J = 7.9 Hz, 2H), 7.37-7.30 (m, 1H), 7.27 (d, J = 7.9 Hz, 2H), 7.16 (d, J = 7.6 Hz, 1H), 7.11 (s, 1H), 6.91-6.84 (m, 1H), 4.69 (dt, J = 12.0, 6.1 Hz, 1H), 2.69 (t, J = 7.5 Hz, 2H), 1.59 (q, J = 7.1 Hz, 2H), 1.37-1.17 (m, 8H), 0.95 (dt, J = 8.5, 4.2 Hz, 1H), 0.77-0.68 (m, 1H) | Ex. 38 |
| 132 | 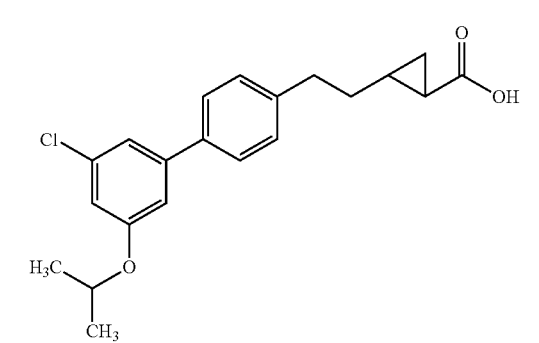 [SMILES: CC(C)Oc1cc(Cl)cc(-c2ccc(CCC3CC3C(=O)O)cc2)c1]<br>Trans-2-(2-(3'-chloro-5'-isopropoxy-[1,1'-biphenyl]-4-yl)ethyl) cyclopropanecarboxylic acid | LCMS, [M + H]$^+$ = 359.1; $^1$H NMR (500 MHz, CDCl$_3$) δ 7.48 (d, J = 8.3 Hz, 1H), 7.26 (d, J = 8.0 Hz, 1H), 7.15 (t, J = 1.5 Hz, 1H), 7.02-6.98 (m, 1H), 6.89-6.86 (m, 1H), 4.61 (spt, J = 6.0 Hz, 1H), 2.79 (t, J = 7.6 Hz, 2H), 1.74-1.65 (m, 2H), 1.56-1.48 (m, 1H), 1.46-1.34 (m, 7H), 1.31-1.24 (m, 1H), 0.83 (ddd, J = 7.9, 6.5, 4.3 Hz, 1H) | Ex. 38 |

| Ex. No. | Structure and Name | Analytical Data | Method |
|---|---|---|---|
| 133 | 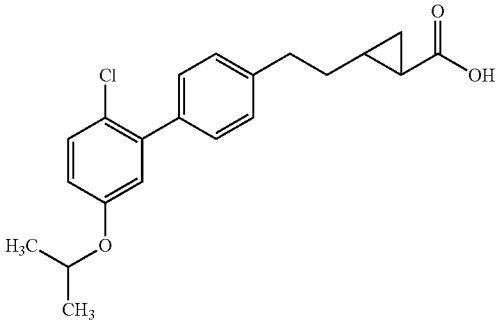<br>Trans-2-(2-(2'-chloro-5'-isopropoxy-[1,1'-biphenyl]-4-yl)ethyl)cyclopropanecarboxylic acid | LCMS, $[M + H]^+$ = 359.1; $^1$H NMR (500 MHz, CDCl$_3$) δ 7.42-7.33 (m, 3H), 7.26 (d, J = 8.0 Hz, 2H), 6.89 (d, J = 3.0 Hz, 1H), 6.83 (dd, J = 8.5, 3.0 Hz, 1H), 4.55 (spt, J = 6.1 Hz, 1H), 2.81 (t, J = 7.7 Hz, 2H), 1.74-1.68 (m, 2H), 1.59-1.50 (m, 1H), 1.43 (dt, J = 8.2, 4.3 Hz, 1H), 1.36 (d, J = 6.1 Hz, 6H), 1.29 (dt, J = 8.8, 4.4 Hz, 1H), 0.84 (ddd, J = 8.0, 6.5, 4.4 Hz, 1H) | Ex. 38 |

What is claimed is:

1. A compound of Formula (IIa), (IIb), (IIc), (IId) or (IIe):

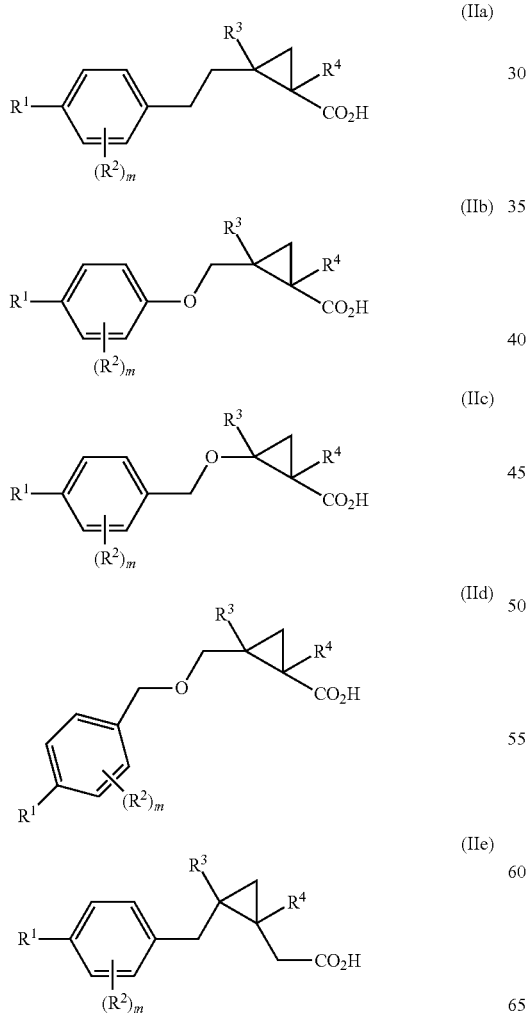

or a stereoisomer, a tautomer, a pharmaceutically acceptable salt, a polymorph, or a solvate thereof, wherein:

$R^1$ is independently selected from: phenyl and a 5- to 6-membered heteroaryl comprising carbon atoms and 1-4 heteroatoms selected from N, $NR^b$, O, and $S(O)_p$; wherein said phenyl and heteroaryl are substituted with 0-4 $R^5$;

$R^2$, at each occurrence, is independently selected from: halogen, $C_{1-6}$ alkyl substituted with 0-1 $R^a$, $C_{1-4}$ alkoxy, $C_{1-4}$ alkylthio, $C_{1-4}$ haloalkyl, and $C_{1-4}$ haloalkoxy;

$R^3$ and $R^4$, at each occurrence, are independently selected from the group consisting of H, halogen, $C_{1-4}$ alkyl, $C_{1-4}$ alkoxy, and $C_{1-4}$ haloalkyl;

$R^5$ at each occurrence, is independently selected from: halogen, $C_{1-6}$ alkyl, $C_{1-6}$ alkoxy, $C_{1-6}$ alkylthio, $C_{1-6}$ haloalkyl, $C_{1-6}$ haloalkoxy, —O—$C_{2-6}$ alkenyl, $SO_2$ ($C_{1-4}$ alkyl), and —$(O)_{0-1}$—$(CH_2)_{0-2}$—$R^6$;

alternatively, two $R^5$ groups, when they are attached to two adjacent carbon atoms and together with the carbon atoms to which they are attached, combine to form a 5- to 6-membered carbocyclic or heterocyclic ring comprising carbon atoms and 0-3 heteroatoms selected from N, $NR^b$, O, and $S(O)_p$; wherein said heterocycle is substituted with 0-2 $R^c$;

$R^6$ is independently selected from: $C_{3-6}$ carbocycle and a 5- to 6-membered heterocycle comprising carbon atoms and 1-4 heteroatoms selected from N, $NR^b$, O, and S; wherein said carbocycle and heterocycle are substituted with 0-3 $R^c$;

$R^a$, at each occurrence, is independently selected from: $C_{1-4}$ alkoxy and C(=O)H;

$R^b$, at each occurrence, is independently selected from: H, $C_{1-4}$ alkyl, and —$(CH_2)_{0-2}$-phenyl;

$R^c$, at each occurrence, is independently selected from: halogen, $C_{1-6}$ alkyl, $C_{1-4}$ alkoxy, $C_{1-4}$ alkylthio, $C_{1-4}$ haloalkyl, $C_{1-4}$ haloalkoxy, $CO_2(C_{1-4}$ alkyl), and COPh;

m is independently 0, 1, or 2; and p is, independently at each occurrence, selected from 0, 1, and 2.

2. A compound according to claim 1 or a stereoisomer, a tautomer, a pharmaceutically acceptable salt, a polymorph, or a solvate thereof, wherein:

$R^2$ is independently selected from: halogen and $C_{1-4}$ alkyl;

$R^3$ is independently H or halogen;

$R^4$ is independently H or $C_{1-4}$ alkyl; and m is independently 0 or 1.

3. A compound according to claim 2 or a stereoisomer, a tautomer, a pharmaceutically acceptable salt, a polymorph, or a solvate thereof, wherein:

$R^1$ is independently selected from: phenyl substituted with 0-3 $R^5$, pyridyl substituted with 0-2 $R^5$, thiazolyl substituted with 0-2 $R^5$,

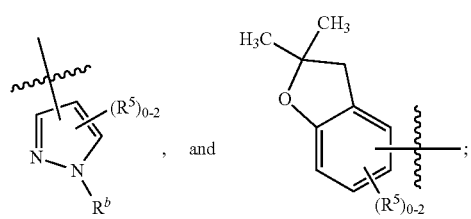

and $R^5$ at each occurrence, is independently selected from: halogen, $C_{1-6}$ alkyl, $C_{1-6}$ alkoxy, $C_{1-4}$ alkylthio, $C_{1-4}$ haloalkyl, $C_{1-4}$ haloalkoxy, —O—$C_{2-6}$ alkenyl, —O($C_{3-6}$ cycloalkyl), —OCH$_2$($C_{3-6}$ cycloalkyl), —(O)$_{0-1}$-(phenyl substituted with 0-2 $R^c$), and —(O)$_{0-1}$-(pyridyl substituted with 0-2 $R^c$).

4. A compound according to claim 3 or a stereoisomer, a tautomer, a pharmaceutically acceptable salt, a polymorph, or a solvate thereof, wherein:

$R^3$ is independently H or F; and $R^4$ is independently H or Me.

5. A compound according to claim 4 or a stereoisomer, a tautomer, a pharmaceutically acceptable salt, or a solvate thereof, wherein:

$R^3$ and $R^4$ are H.

6. A pharmaceutical composition, comprising a pharmaceutically acceptable carrier and a compound of claim 1, or a stereoisomer, a tautomer, or a pharmaceutically acceptable salt thereof.

7. The pharmaceutical composition according to claim 6, further comprising one or more other suitable therapeutic agents selected from: a dipeptidyl peptidase-IV inhibitor, a sodium-glucose transporter-2 inhibitor and a 11b-HSD-1 inhibitor.

8. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 1.

9. A compound selected from:

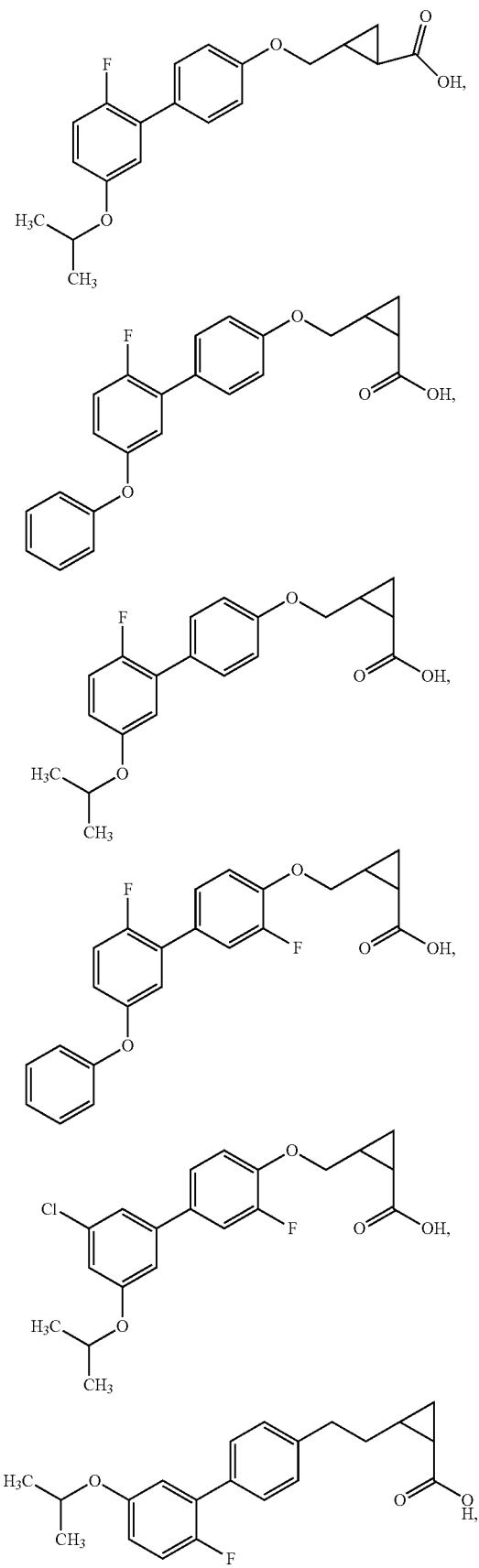

169
-continued
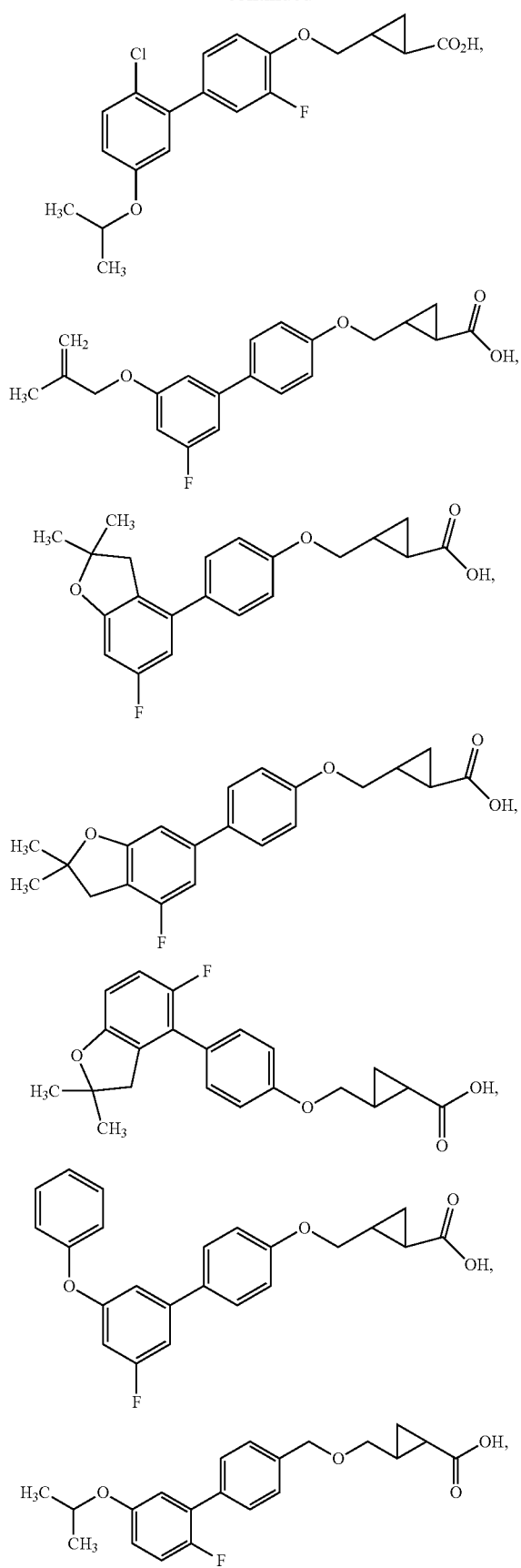
170
-continued
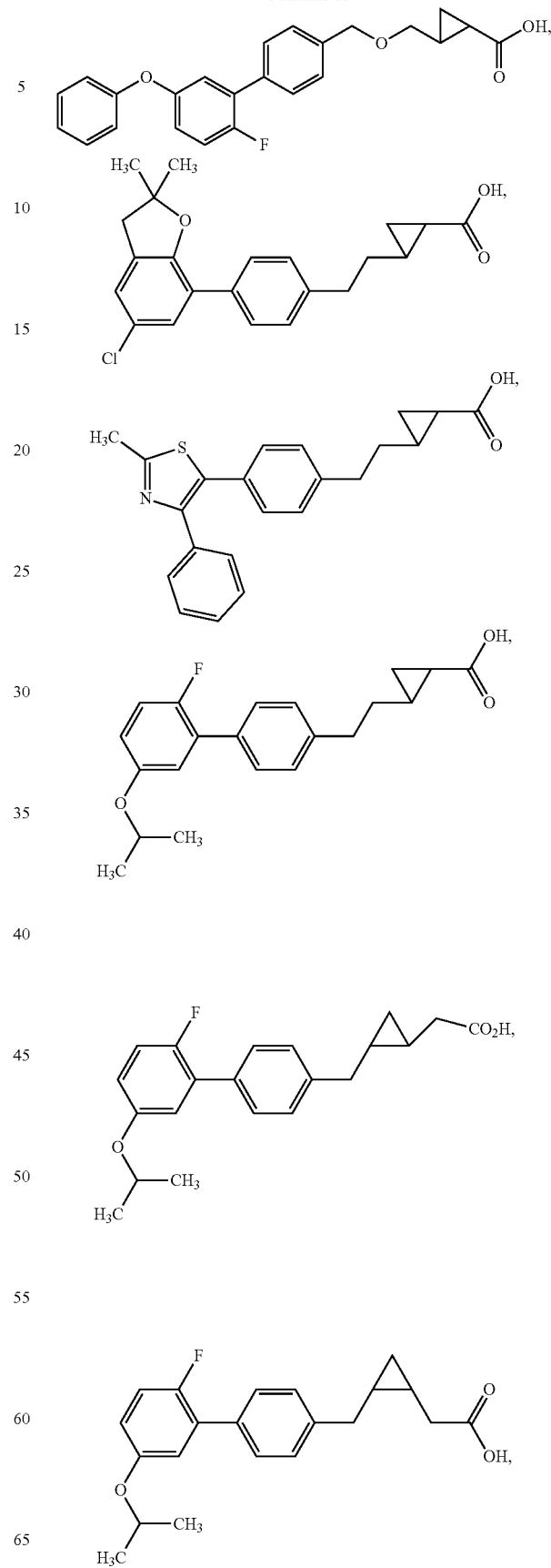

-continued
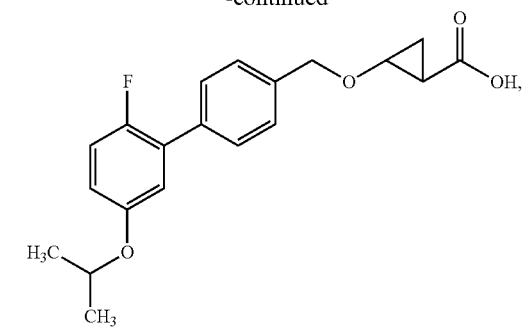
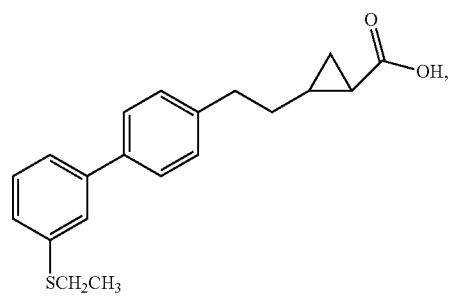
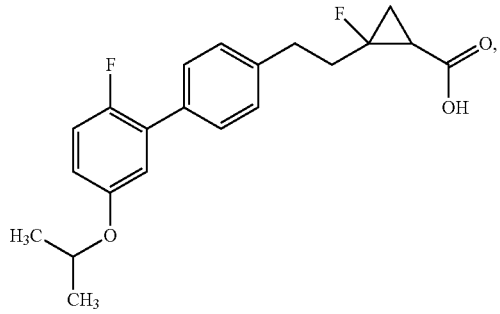
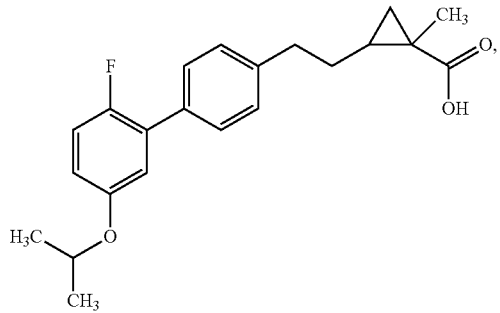
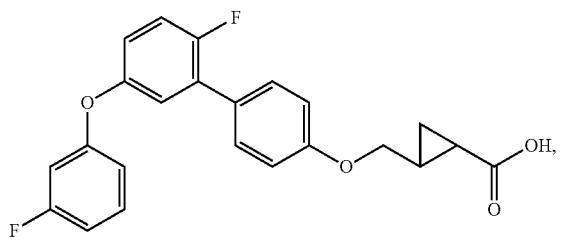
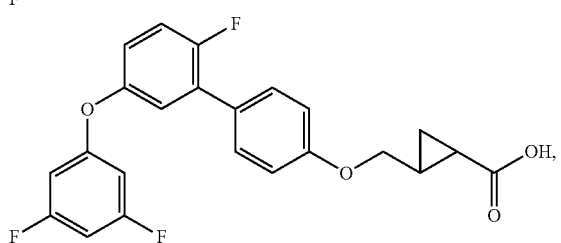
-continued
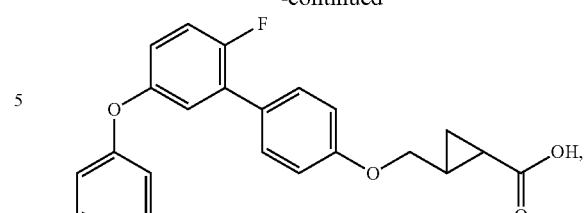
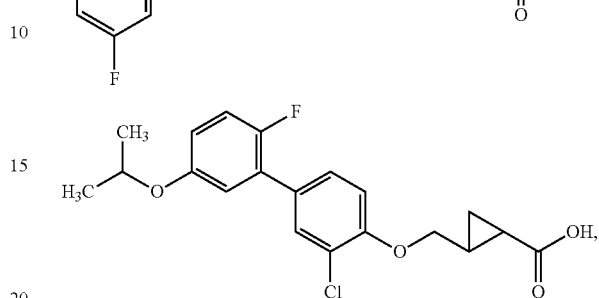
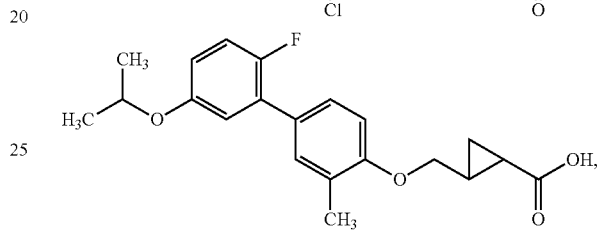
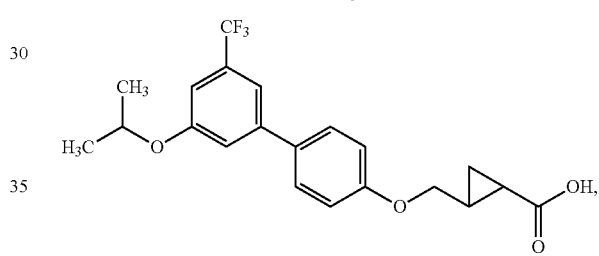
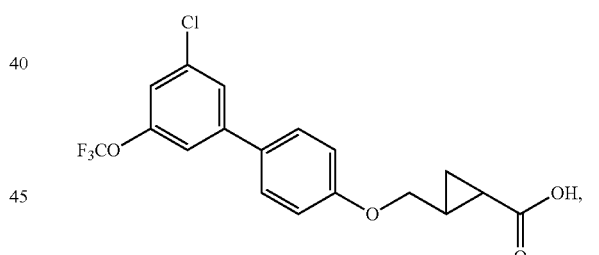
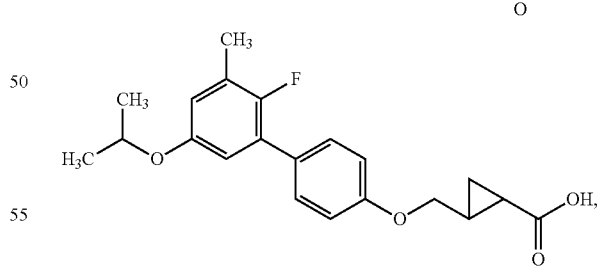
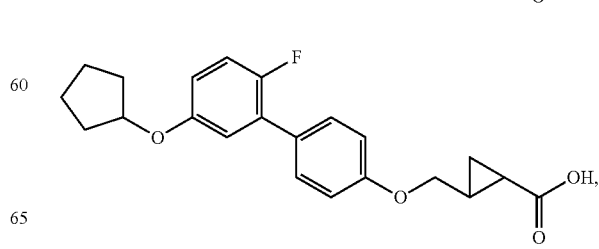

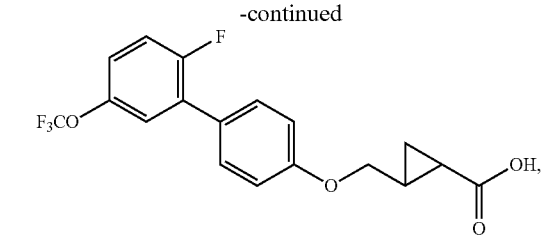
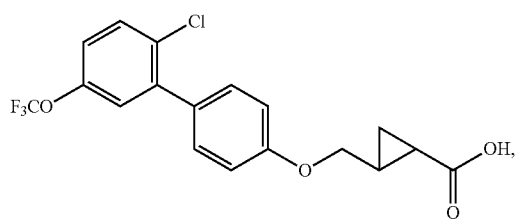
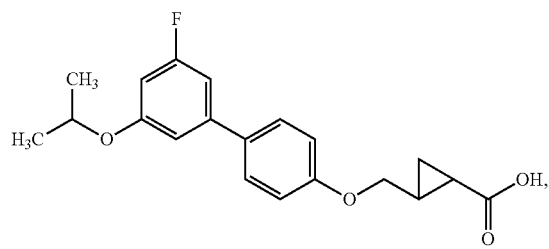
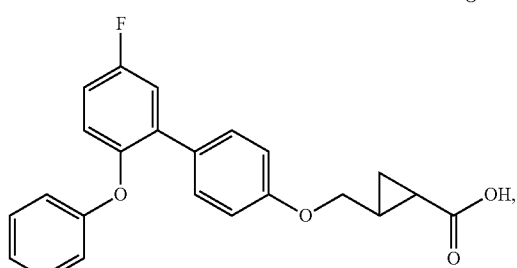
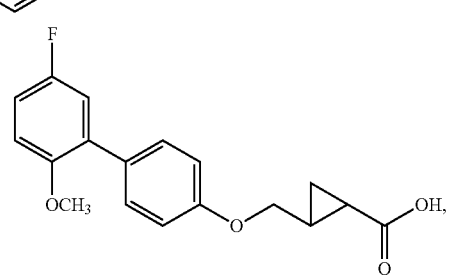
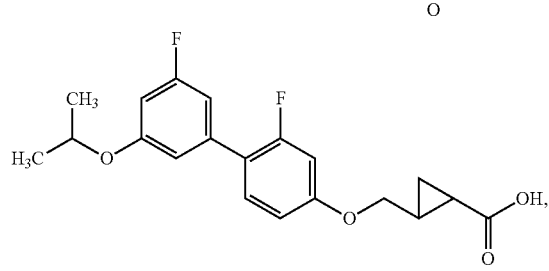
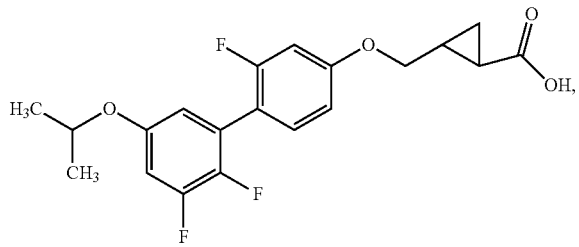
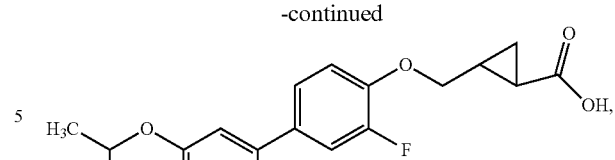
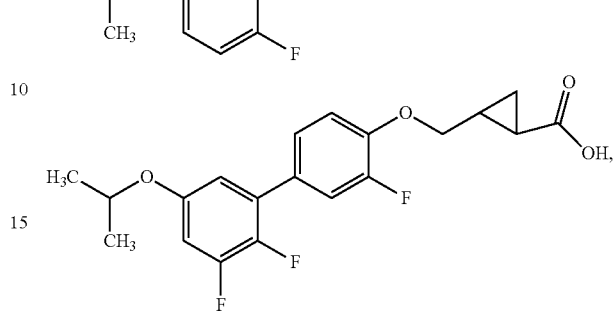
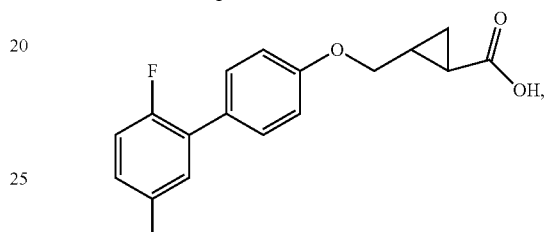
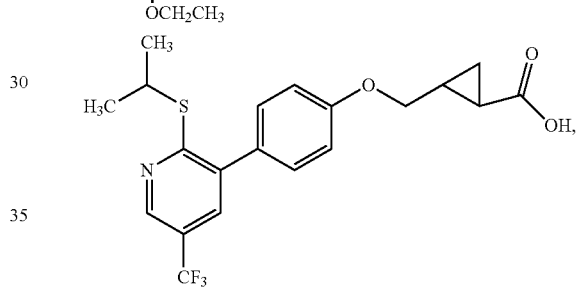
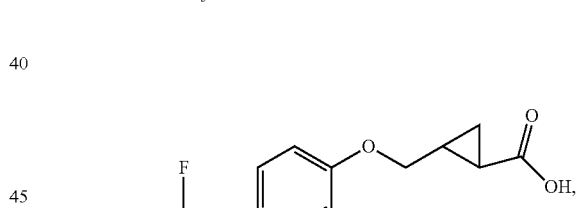
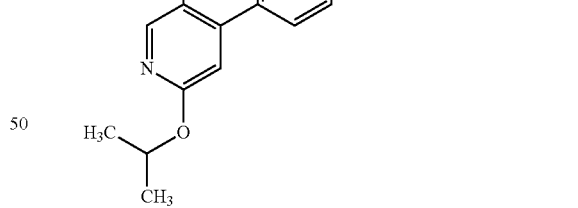
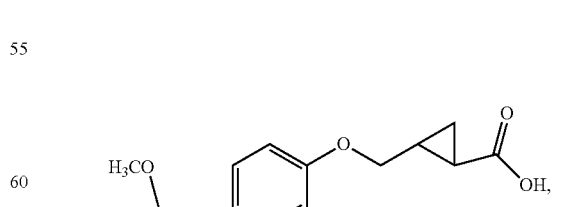
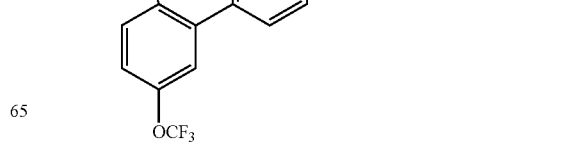

-continued
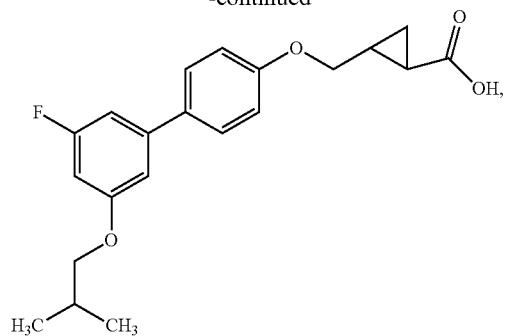
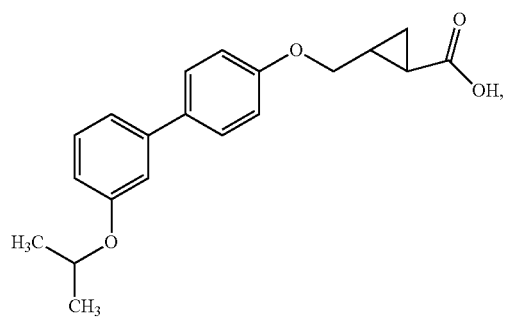
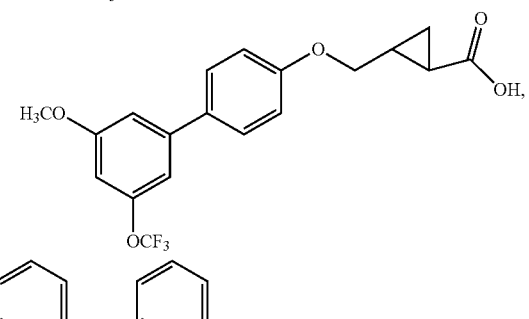
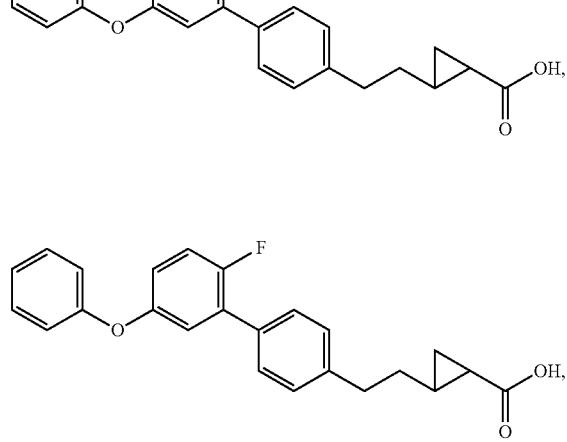
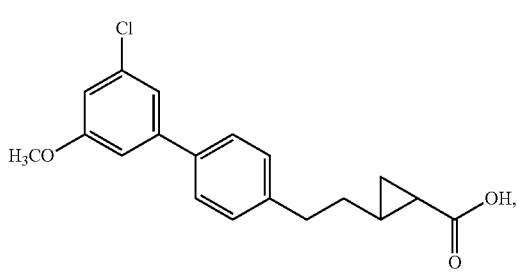
-continued
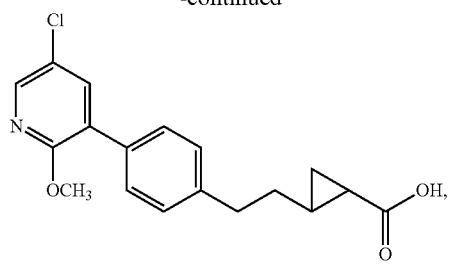
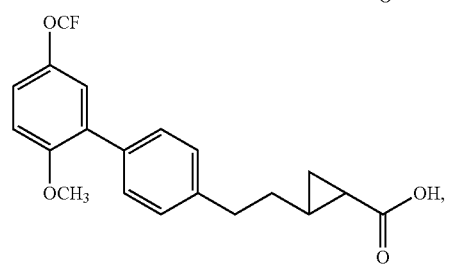
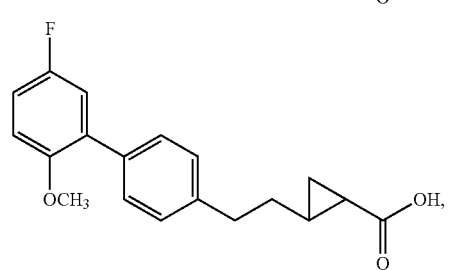
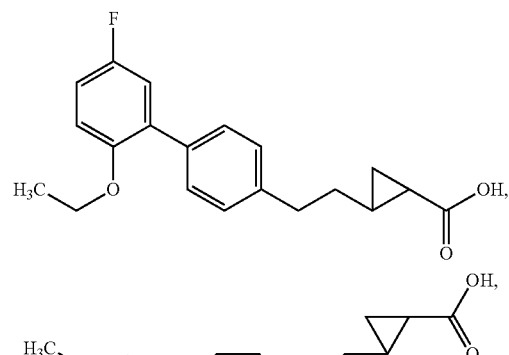
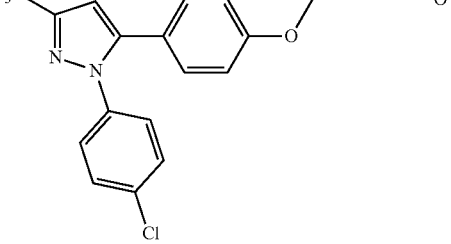
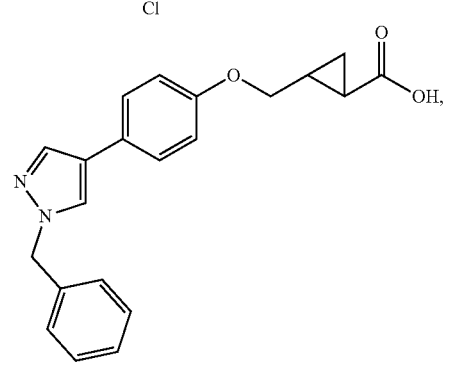

177
-continued
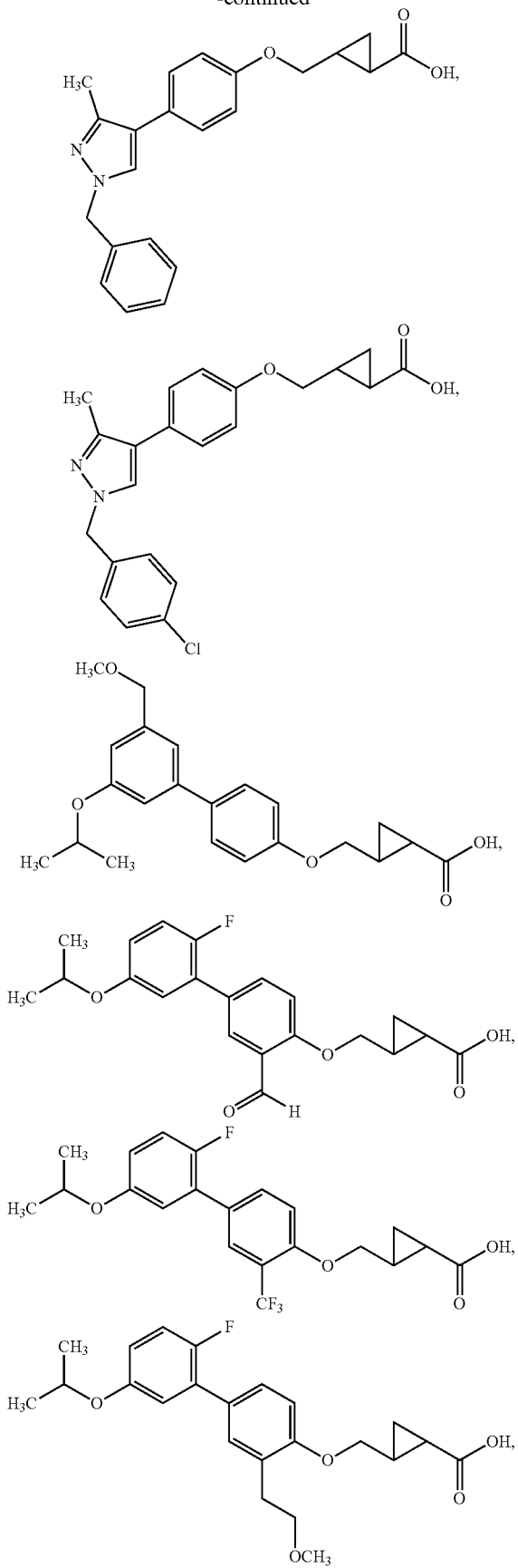
178
-continued
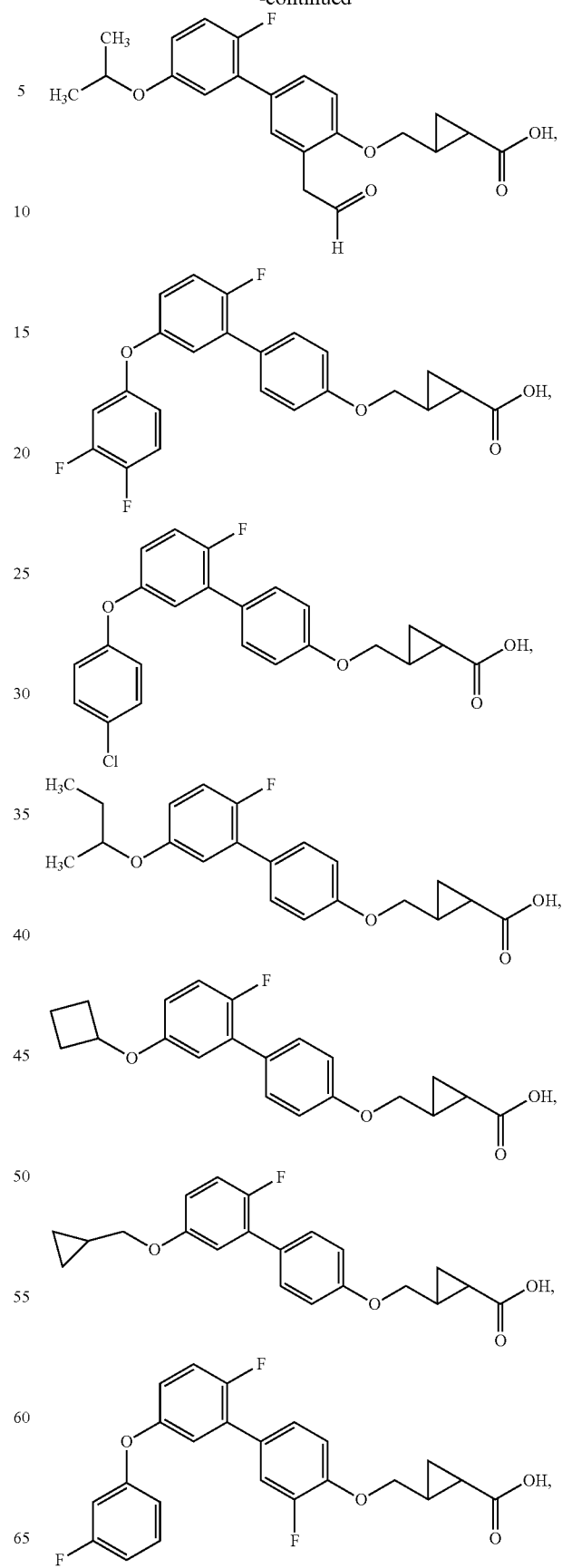

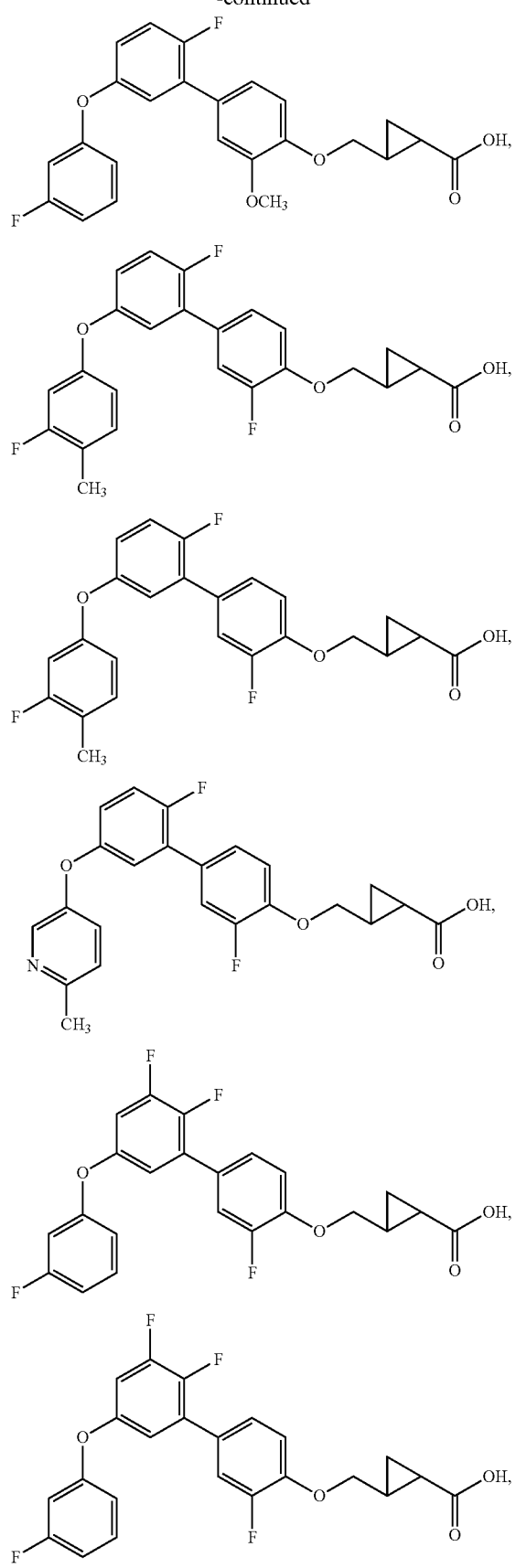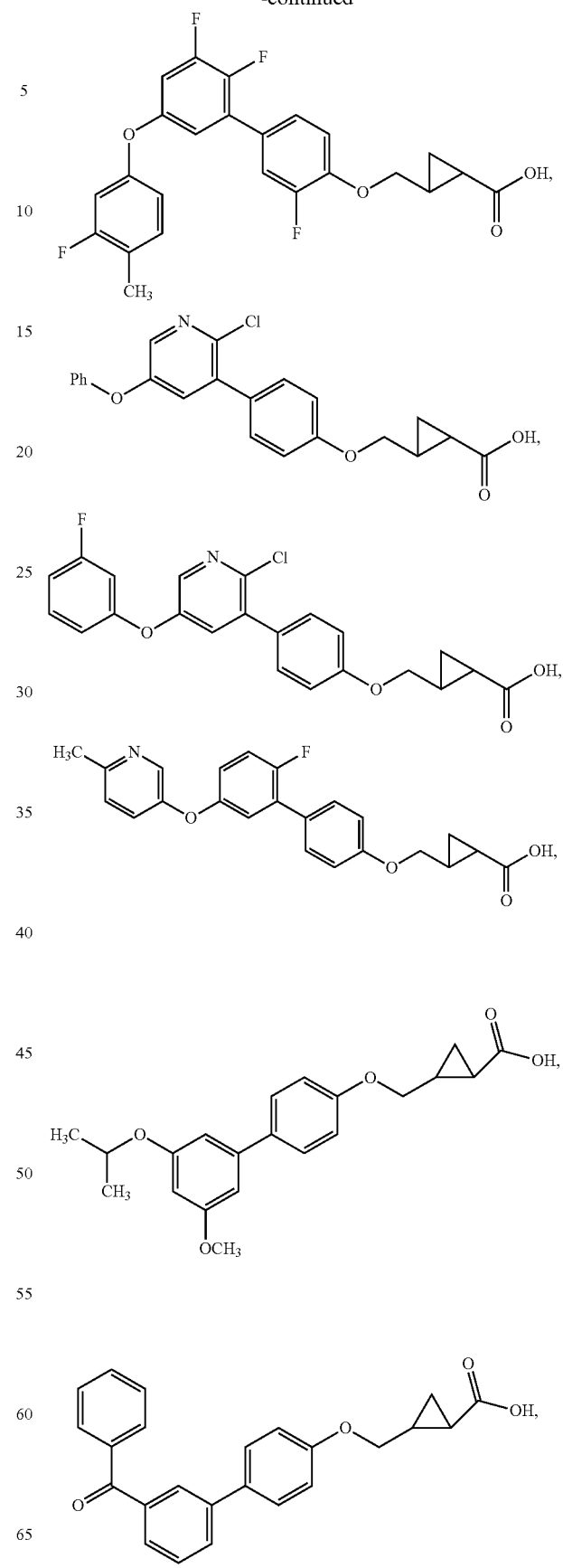

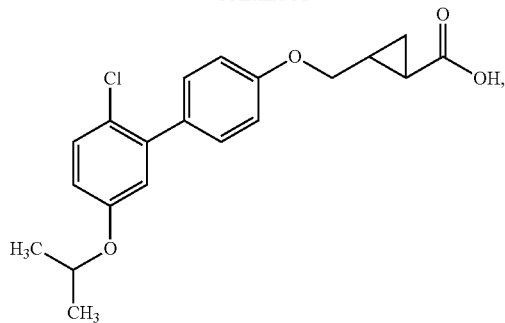 [SMILES: CC(C)Oc1ccc(Cl)c(-c2ccc(CCC3CC3C(=O)O)cc2)c1]
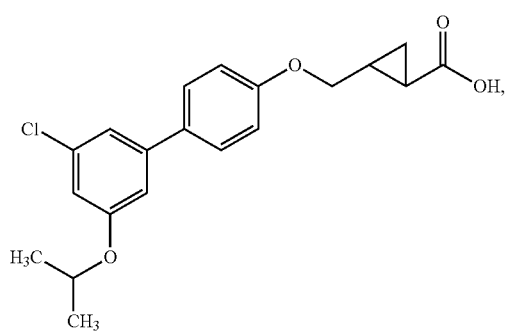
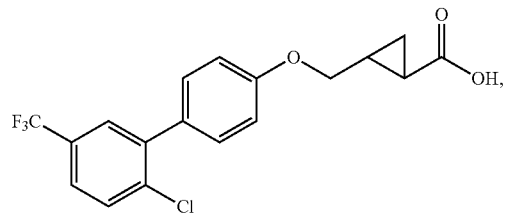
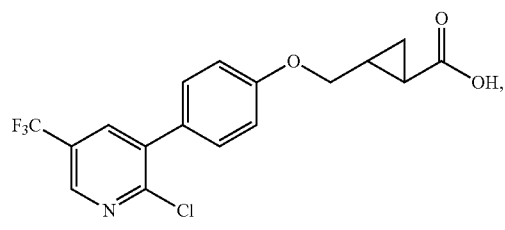
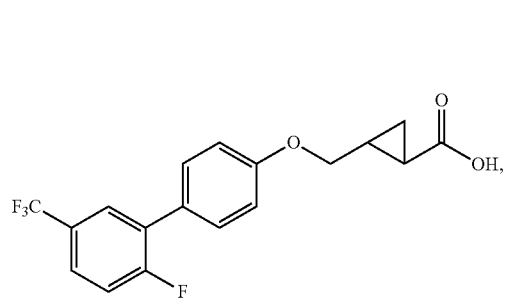
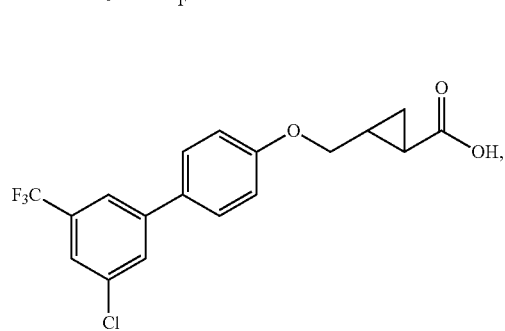
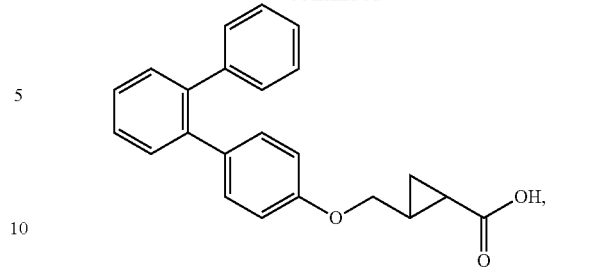
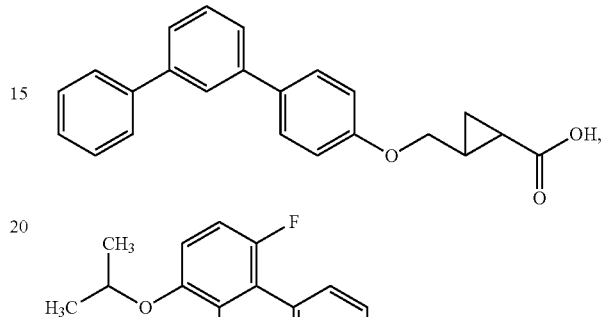
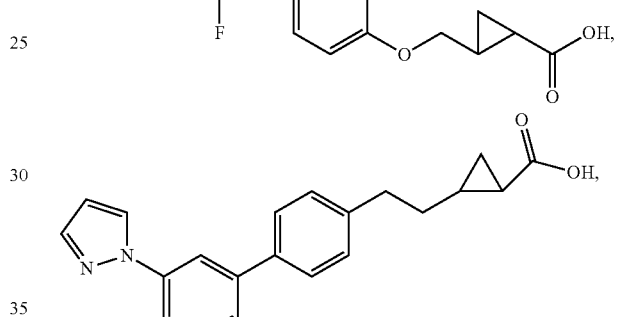
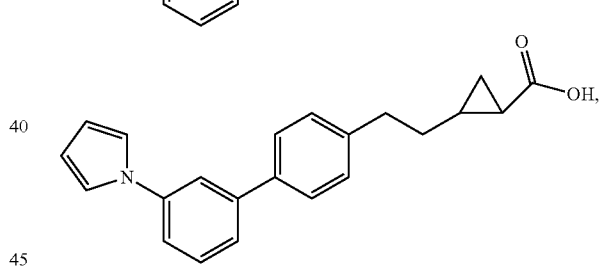
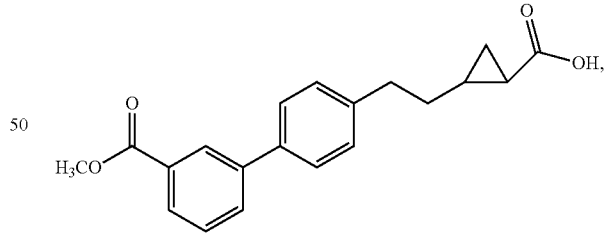
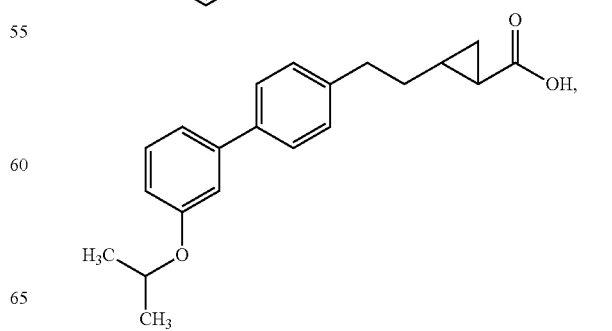

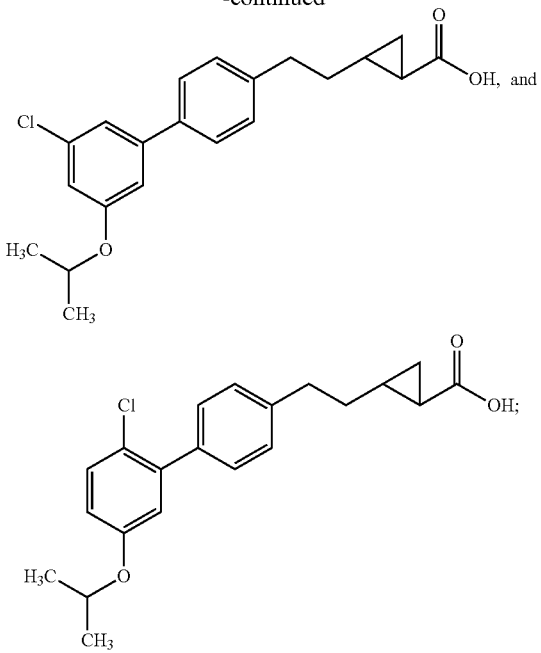

or a stereoisomer, or a pharmaceutically acceptable salt thereof.

10. A pharmaceutical composition, comprising a pharmaceutically acceptable carrier and a compound of claim 4, or a stereoisomer, a tautomer, or a pharmaceutically acceptable salt thereof.

11. The pharmaceutical composition according to claim 10, further comprising one or more other suitable therapeutic agents selected from: a dipeptidyl peptidase-IV inhibitor, a sodium-glucose transporter-2 inhibitor and a 11b-HSD-1 inhibitor.

12. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 4.

13. A pharmaceutical composition, comprising a pharmaceutically acceptable carrier and a compound of claim 5, or a stereoisomer, a tautomer, or a pharmaceutically acceptable salt thereof.

14. The pharmaceutical composition according to claim 13, further comprising one or more other suitable therapeutic agents selected from: a dipeptidyl peptidase-IV inhibitor, a sodium-glucose transporter-2 inhibitor and a 11b-HSD-1 inhibitor.

15. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 5.

16. A pharmaceutical composition, comprising a pharmaceutically acceptable carrier and a compound of claim 9, or a stereoisomer, a tautomer, or a pharmaceutically acceptable salt thereof.

17. The pharmaceutical composition according to claim 16, further comprising one or more other suitable therapeutic agents selected from: a dipeptidyl peptidase-IV inhibitor, a sodium-glucose transporter-2 inhibitor and a 11b-HSD-1 inhibitor.

18. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 9.

* * * * *

UNITED STATES PATENT AND TRADEMARK OFFICE
CERTIFICATE OF CORRECTION

PATENT NO. : 9,938,222 B2
APPLICATION NO. : 15/509214
DATED : April 10, 2018
INVENTOR(S) : Yan Shi et al.

It is certified that error appears in the above-identified patent and that said Letters Patent is hereby corrected as shown below:

In the Claims

Column 176
Line 10-21 Claim 9

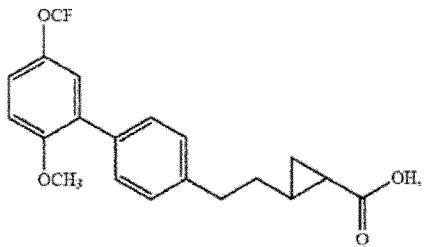 should read -- 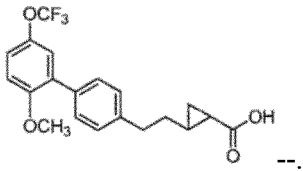 --.

Signed and Sealed this
Twenty-eighth Day of August, 2018

Andrei Iancu
*Director of the United States Patent and Trademark Office*